(12) United States Patent
Shelton, IV et al.

(10) Patent No.: US 11,974,744 B2
(45) Date of Patent: May 7, 2024

(54) STAPLING ADJUNCT ATTACHMENT

(71) Applicant: Ethicon LLC, Guaynabo, PR (US)

(72) Inventors: Frederick E. Shelton, IV, Hillsboro, OH (US); Jason L. Harris, Lebanon, OH (US); Michael J. Vendely, Lebanon, OH (US); Prudence Vulhop, Cincinnati, OH (US)

(73) Assignee: ETHICON LLC, Zug (CH)

( * ) Notice: Subject to any disclaimer, the term of this patent is extended or adjusted under 35 U.S.C. 154(b) by 600 days.

(21) Appl. No.: 17/183,712

(22) Filed: Feb. 24, 2021

(65) Prior Publication Data

US 2021/0177415 A1 Jun. 17, 2021

Related U.S. Application Data

(63) Continuation of application No. 16/931,759, filed on Jul. 17, 2020, which is a continuation of application
(Continued)

(51) Int. Cl.
*A61B 17/072* (2006.01)
*A61B 17/00* (2006.01)
*A61B 17/115* (2006.01)

(52) U.S. Cl.
CPC .. *A61B 17/07207* (2013.01); *A61B 17/07292* (2013.01); *A61B 2017/00004* (2013.01);
(Continued)

(58) Field of Classification Search
CPC ..... A61B 17/068–07292; A61B 17/115–1155; A61B 2017/1157
See application file for complete search history.

(56) References Cited

U.S. PATENT DOCUMENTS 3,595,187 A 7/1971 Gray
3,776,156 A 12/1973 Morgan
(Continued)

FOREIGN PATENT DOCUMENTS

EP 705570 A1 4/1996
EP 1621141 A2 2/2006
(Continued)

OTHER PUBLICATIONS

Ethicon Endo-Surgery, Inc. (2015) Echelon Flex: Engineering a Better Grip on Movement. [Brochure].
(Continued)

*Primary Examiner* — Kathleen S Holwerda
*Assistant Examiner* — Serenity A Miller
(74) *Attorney, Agent, or Firm* — Mintz, Levin, Cohn, Ferris, Glovsky and Popeo, P.C.

(57) ABSTRACT

Methods for applying one or more adjuncts to tissue are provided. In one embodiment, the method can include positioning an adjunct, e.g., using an adhesive, on one of first and second jaws of an end effector of a surgical stapler. In one embodiment, an attachment mechanism on the adjunct can prevent stretching of at least a portion of the adjunct. In other aspects, the adjunct can be maintained on the at least one jaw in a first state in which the adjunct is at least partially stretched over the at least one jaw, and actuation of the surgical stapler can cause the adjunct to transition from the first state to a second state such that the adjunct in the second state at least partially separates from the at least one jaw.

16 Claims, 101 Drawing Sheets

Related U.S. Application Data

No. 15/436,394, filed on Feb. 17, 2017, now Pat. No. 10,716,564.

(52) U.S. Cl.
CPC ............... *A61B 2017/00561* (2013.01); *A61B 2017/00893* (2013.01); *A61B 2017/00951* (2013.01); *A61B 2017/07257* (2013.01); *A61B 2017/07264* (2013.01); *A61B 2017/07271* (2013.01); *A61B 2017/07278* (2013.01); *A61B 17/1155* (2013.01)

(56) References Cited

U.S. PATENT DOCUMENTS

| | | | |
|---|---|---|---|
| 4,633,874 | A | 1/1987 | Chow et al. |
| 4,892,244 | A | 1/1990 | Fox et al. |
| 4,999,957 | A | 3/1991 | Kessler |
| 5,263,629 | A | 11/1993 | Trumbull et al. |
| 5,441,193 | A | 8/1995 | Gravener |
| 5,542,594 | A | 8/1996 | McKean et al. |
| 5,632,432 | A | 5/1997 | Schulze et al. |
| 5,702,409 | A | 12/1997 | Rayburn et al. |
| 5,752,965 | A | 5/1998 | Francis et al. |
| 6,273,897 | B1 | 8/2001 | Dalessandro et al. |
| 6,592,597 | B2 | 7/2003 | Grant et al. |
| 6,656,193 | B2 | 12/2003 | Grant et al. |
| 6,939,358 | B2 | 9/2005 | Palacios et al. |
| 7,143,925 | B2 | 12/2006 | Shelton, IV et al. |
| 7,453,904 | B2 | 11/2008 | Seto |
| 7,601,118 | B2 | 10/2009 | Smith et al. |
| 7,845,533 | B2 | 12/2010 | Marczyk et al. |
| 7,846,179 | B2 | 12/2010 | Belef et al. |
| 7,988,027 | B2 | 8/2011 | Olson et al. |
| 8,011,555 | B2 | 9/2011 | Tarinelli et al. |
| 8,028,883 | B2 | 10/2011 | Stopek |
| 8,256,654 | B2 | 9/2012 | Bettuchi et al. |
| 8,308,042 | B2 | 11/2012 | Aranyi |
| 8,317,070 | B2 | 11/2012 | Hueil et al. |
| 8,348,130 | B2 | 1/2013 | Shah et al. |
| 8,393,514 | B2 | 3/2013 | Shelton, IV et al. |
| 8,453,904 | B2 | 6/2013 | Eskaros et al. |
| 8,567,145 | B1 | 10/2013 | Chauncey |
| 8,584,920 | B2 | 11/2013 | Hodgkinson |
| 8,668,129 | B2 | 3/2014 | Olson |
| 8,814,025 | B2 | 8/2014 | Miller et al. |
| 8,899,464 | B2 | 12/2014 | Hueil et al. |
| 8,991,677 | B2 | 3/2015 | Moore et al. |
| 8,998,060 | B2 | 4/2015 | Bruewer et al. |
| 9,016,543 | B2 | 4/2015 | Stopek et al. |
| 9,050,084 | B2 | 6/2015 | Schmid et al. |
| 9,055,944 | B2 | 6/2015 | Hodgkinson et al. |
| 9,192,380 | B2 | 11/2015 | Racenet et al. |
| 9,282,962 | B2 | 3/2016 | Schmid et al. |
| 9,320,523 | B2 | 4/2016 | Shelton, IV et al. |
| 9,433,420 | B2 | 9/2016 | Hodgkinson |
| 9,693,772 | B2 | 7/2017 | Ingmanson et al. |
| 9,757,124 | B2 | 9/2017 | Schellin et al. |
| 9,833,241 | B2 | 12/2017 | Huitema et al. |
| 9,839,422 | B2 | 12/2017 | Schellin et al. |
| 9,839,423 | B2 | 12/2017 | Vendely et al. |
| 9,848,871 | B2 | 12/2017 | Harris et al. |
| 9,913,647 | B2 | 3/2018 | Weisenburgh, II et al. |
| 9,943,310 | B2 | 4/2018 | Harris et al. |
| 10,213,198 | B2 | 2/2019 | Aronhalt et al. |
| 10,265,074 | B2 | 4/2019 | Shelton, IV et al. |
| 10,307,160 | B2 | 6/2019 | Vendely et al. |
| 10,478,183 | B2 | 11/2019 | Hess et al. |
| 10,478,280 | B2 | 11/2019 | Vendely et al. |
| 10,485,544 | B2 | 11/2019 | Shelton, IV et al. |
| 10,555,734 | B2 | 2/2020 | Shelton, IV et al. |
| 10,575,850 | B2 | 3/2020 | Vendely et al. |
| 10,646,221 | B2 | 5/2020 | Shelton, IV et al. |
| 10,716,564 | B2 | 7/2020 | Shelton, IV et al. |
| 10,729,438 | B2 | 8/2020 | Vulhop et al. |
| 10,765,426 | B2 | 9/2020 | Shelton, IV et al. |
| 10,869,663 | B2 | 12/2020 | Shelton, IV et al. |
| 10,881,402 | B2 | 1/2021 | Shelton, IV et al. |
| 10,925,601 | B2 | 2/2021 | Shelton, IV et al. |
| 11,006,954 | B2 | 5/2021 | Landgrebe et al. |
| 11,141,150 | B2 | 10/2021 | Shelton, IV et al. |
| 11,202,632 | B2 | 12/2021 | Shelton, IV et al. |
| 2002/0122944 | A1 | 9/2002 | Ogle et al. |
| 2002/0161382 | A1 | 10/2002 | Neisz et al. |
| 2002/0165559 | A1 | 11/2002 | Grant et al. |
| 2002/0165562 | A1 | 11/2002 | Grant et al. |
| 2002/0165563 | A1 | 11/2002 | Grant et al. |
| 2003/0120284 | A1 | 6/2003 | Palacios et al. |
| 2005/0021026 | A1 | 1/2005 | Baily |
| 2005/0070929 | A1 | 3/2005 | Dalessandro et al. |
| 2005/0245966 | A1 | 11/2005 | Hammerslag et al. |
| 2005/0267325 | A1 | 12/2005 | Bouchier et al. |
| 2007/0027554 | A1 | 2/2007 | Biran et al. |
| 2007/0246505 | A1 | 10/2007 | Pace-Floridia et al. |
| 2008/0078804 | A1 | 4/2008 | Shelton et al. |
| 2008/0290134 | A1 | 11/2008 | Bettuchi et al. |
| 2009/0001122 | A1* | 1/2009 | Prommersberger ........................ A61B 17/07292 227/176.1 |
| 2009/0120994 | A1 | 5/2009 | Murray et al. |
| 2009/0134200 | A1 | 5/2009 | Tarinelli et al. |
| 2009/0206125 | A1 | 8/2009 | Huitema et al. |
| 2009/0206126 | A1 | 8/2009 | Huitema et al. |
| 2009/0255978 | A1 | 10/2009 | Viola et al. |
| 2009/0297582 | A1 | 12/2009 | Meyer et al. |
| 2010/0065606 | A1 | 3/2010 | Stopek |
| 2010/0081617 | A1 | 4/2010 | Okano et al. |
| 2010/0249805 | A1 | 9/2010 | Olson et al. |
| 2010/0252612 | A1 | 10/2010 | Viola |
| 2011/0087279 | A1 | 4/2011 | Shah et al. |
| 2012/0080336 | A1 | 4/2012 | Shelton, IV et al. |
| 2012/0080498 | A1 | 4/2012 | Shelton, IV et al. |
| 2012/0150176 | A1 | 6/2012 | Weizman |
| 2012/0187179 | A1* | 7/2012 | Gleiman ............... A61B 17/072 227/181.1 |
| 2012/0209319 | A1 | 8/2012 | Bianco-Peled et al. |
| 2012/0241492 | A1 | 9/2012 | Shelton, IV et al. |
| 2012/0241497 | A1 | 9/2012 | Mandakolathur Vasudevan et al. |
| 2012/0241499 | A1 | 9/2012 | Baxter, III et al. |
| 2012/0241503 | A1 | 9/2012 | Baxter, III et al. |
| 2012/0253298 | A1 | 10/2012 | Henderson et al. |
| 2012/0318844 | A1 | 12/2012 | Shelton, IV et al. |
| 2013/0068816 | A1 | 3/2013 | Mandakolathur Vasudevan et al. |
| 2013/0068820 | A1 | 3/2013 | Miller et al. |
| 2013/0105548 | A1 | 5/2013 | Hodgkinson et al. |
| 2013/0146642 | A1 | 6/2013 | Shelton, IV et al. |
| 2013/0161374 | A1 | 6/2013 | Swayze et al. |
| 2013/0214030 | A1 | 8/2013 | Aronhalt et al. |
| 2013/0221065 | A1 | 8/2013 | Aronhalt et al. |
| 2013/0256367 | A1* | 10/2013 | Scheib ............... A61B 17/07292 227/175.1 |
| 2013/0256373 | A1* | 10/2013 | Schmid ............ A61B 17/07207 227/176.1 |
| 2013/0256377 | A1 | 10/2013 | Schmid et al. |
| 2014/0021242 | A1 | 1/2014 | Hodgkinson et al. |
| 2014/0027490 | A1 | 1/2014 | Marczyk et al. |
| 2014/0048580 | A1 | 2/2014 | Merchant et al. |
| 2014/0103093 | A1 | 4/2014 | Koch, Jr. et al. |
| 2014/0131418 | A1 | 5/2014 | Kostrzewski |
| 2014/0151431 | A1 | 6/2014 | Hodgkinson et al. |
| 2014/0158741 | A1 | 6/2014 | Woodard, Jr. et al. |
| 2014/0158742 | A1 | 6/2014 | Stopek et al. |
| 2014/0166721 | A1 | 6/2014 | Stevenson et al. |
| 2014/0203061 | A1 | 7/2014 | Hodgkinson |
| 2014/0224686 | A1 | 8/2014 | Aronhalt et al. |
| 2014/0239046 | A1 | 8/2014 | Milliman |
| 2014/0291380 | A1 | 10/2014 | Weaner et al. |
| 2015/0041347 | A1 | 2/2015 | Hodgkinson |
| 2015/0076208 | A1 | 3/2015 | Shelton, IV |
| 2015/0122872 | A1 | 5/2015 | Olson et al. |
| 2015/0129634 | A1 | 5/2015 | Shelton, IV et al. |
| 2015/0133995 | A1 | 5/2015 | Shelton, IV et al. |
| 2015/0133996 | A1 | 5/2015 | Shelton, IV et al. |
| 2015/0134076 | A1 | 5/2015 | Shelton, IV et al. |

(56) References Cited

U.S. PATENT DOCUMENTS

| | | |
|---|---|---|
| 2015/0134077 A1 | 5/2015 | Shelton, IV et al. |
| 2015/0136831 A1 | 5/2015 | Baxter, III et al. |
| 2015/0201937 A1 | 7/2015 | Swayze et al. |
| 2015/0238185 A1 | 8/2015 | Schellin et al. |
| 2015/0238187 A1 | 8/2015 | Schellin et al. |
| 2015/0238188 A1 | 8/2015 | Vendely et al. |
| 2015/0272575 A1 | 10/2015 | Leimbach et al. |
| 2015/0277471 A1 | 10/2015 | Leimbach et al. |
| 2015/0282809 A1 | 10/2015 | Shelton, IV et al. |
| 2015/0297222 A1 | 10/2015 | Huitema et al. |
| 2015/0297235 A1 | 10/2015 | Harris et al. |
| 2015/0341758 A1 | 11/2015 | Aggarwal et al. |
| 2015/0351753 A1 | 12/2015 | Shelton, IV et al. |
| 2015/0351754 A1 | 12/2015 | Harris et al. |
| 2015/0351758 A1 | 12/2015 | Shelton, IV et al. |
| 2015/0351763 A1 | 12/2015 | Shelton, IV et al. |
| 2016/0015373 A1 | 1/2016 | Russo et al. |
| 2016/0030043 A1 | 2/2016 | Fanelli et al. |
| 2016/0058451 A1 | 3/2016 | Racenet et al. |
| 2016/0089142 A1 | 3/2016 | Harris et al. |
| 2016/0128694 A1 | 5/2016 | Baxter, III et al. |
| 2016/0270793 A1 | 9/2016 | Carter et al. |
| 2016/0278774 A1 | 9/2016 | Shelton, IV et al. |
| 2017/0055986 A1 | 3/2017 | Harris et al. |
| 2017/0056568 A1 | 3/2017 | Shelton, IV et al. |
| 2017/0086832 A1 | 3/2017 | Harris et al. |
| 2017/0086836 A1 | 3/2017 | Harris et al. |
| 2017/0086838 A1 | 3/2017 | Harris et al. |
| 2017/0086840 A1 | 3/2017 | Harris et al. |
| 2017/0086842 A1 | 3/2017 | Shelton, IV et al. |
| 2017/0086843 A1 | 3/2017 | Vendely et al. |
| 2017/0086844 A1 | 3/2017 | Vendely et al. |
| 2017/0086845 A1 | 3/2017 | Vendely et al. |
| 2017/0119380 A1 | 5/2017 | Dalessandro et al. |
| 2017/0367694 A1 | 12/2017 | Shelton, IV et al. |
| 2018/0168637 A1 | 6/2018 | Harris et al. |
| 2018/0235591 A1 | 8/2018 | Vendely et al. |
| 2018/0235612 A1 | 8/2018 | Shelton, IV et al. |
| 2018/0235613 A1 | 8/2018 | Shelton, IV et al. |
| 2018/0235615 A1 | 8/2018 | Landgrebe et al. |
| 2018/0235616 A1 | 8/2018 | Shelton, IV et al. |
| 2018/0235617 A1 | 8/2018 | Shelton, IV et al. |
| 2018/0235622 A1 | 8/2018 | Shelton, IV et al. |
| 2018/0235624 A1 | 8/2018 | Shelton, IV et al. |
| 2018/0235625 A1 | 8/2018 | Shelton, IV et al. |
| 2018/0235626 A1 | 8/2018 | Shelton, IV et al. |
| 2018/0235629 A1 | 8/2018 | Shelton, IV et al. |
| 2018/0235630 A1 | 8/2018 | Vulhop et al. |
| 2019/0038280 A1 | 2/2019 | Shelton, IV et al. |
| 2019/0290275 A1 | 9/2019 | Carter et al. |
| 2020/0008803 A1 | 1/2020 | Shelton, IV et al. |
| 2020/0345363 A1 | 11/2020 | Shelton, IV et al. |
| 2023/0043048 A1 | 2/2023 | Shelton, IV et al. |

FOREIGN PATENT DOCUMENTS

| | | |
|---|---|---|
| EP | 2245993 A2 | 11/2010 |
| EP | 2311386 A2 | 4/2011 |
| EP | 2630922 A1 | 8/2013 |
| EP | 2644125 A2 | 10/2013 |
| EP | 2837337 A1 | 2/2015 |
| EP | 2865344 A1 | 4/2015 |
| EP | 2939608 A1 | 11/2015 |
| EP | 3072457 A2 | 9/2016 |
| EP | 3072458 A2 | 9/2016 |
| EP | 3120781 A2 | 1/2017 |
| WO | WO-97/01989 A1 | 1/1997 |
| WO | WO-2012148669 A2 | 11/2012 |
| WO | WO-2013052435 A1 | 4/2013 |
| WO | WO-2013119365 A1 | 8/2013 |
| WO | WO-2015157459 A1 | 10/2015 |
| WO | WO-2016073538 A1 | 5/2016 |

OTHER PUBLICATIONS

European Search Report for Application No. 18157195.1, dated Jun. 18, 2018. (9 Pages).
Extended European Search Report fo EP App. No. 18157137.3 dated May 2, 2018 (8 pages).
Extended European Search Report for EP App. No. 18157118.3 dated May 8, 2018 (8 pages).
Extended European Search Report for EP App. No. 18157126.6 dated May 15, 2018 (11 pages).
Extended European Search Report for EP App. No. 18157185.2 dated Apr. 24, 2018 (8 pages).
Extended European Search Report for EP App. No. 18157186.0 dated Jun. 8, 2018 (12 pages).
Extended European Search Report for EP App. No. 18157194.4 dated May 4, 2018 (7 pages).
Extended European Search Report for EP App. No. 18157201.7 dated May 4, 2018 (10 pages).
Extended European Search Report for EP App. No. 18157205.8 dated Jul. 9, 2018 (6 pages).
Extended European Search Report for EP App. No. 18157212.4 dated May 2, 2018 (13 pages).
Extended European Search Report for EP App. No. 18157213.2 dated Aug. 14, 2018 (10 pages).
Extended European Search Report for EP App. No. 18157230.6 dated Jun. 13, 2018 (14 pages).
International Search Report and Written Opinion for International App. No. PCT/US2018/017757 dated May 23, 2018 (9 pages).
International Search Report for PCT/US2018/017747 dated Aug. 24, 2018 (7 pages).
U.S. Appl. No. 17/533,886, filed Nov. 23, 2021, Adjunct Material with Mating Features, Frederick E. Shelton, IV et al.
U.S. Appl. No. 17/969,313, filed Oct. 19, 2022, End Effector with Adjunct Materials, Frederick E. Shelton, IV et al.

* cited by examiner

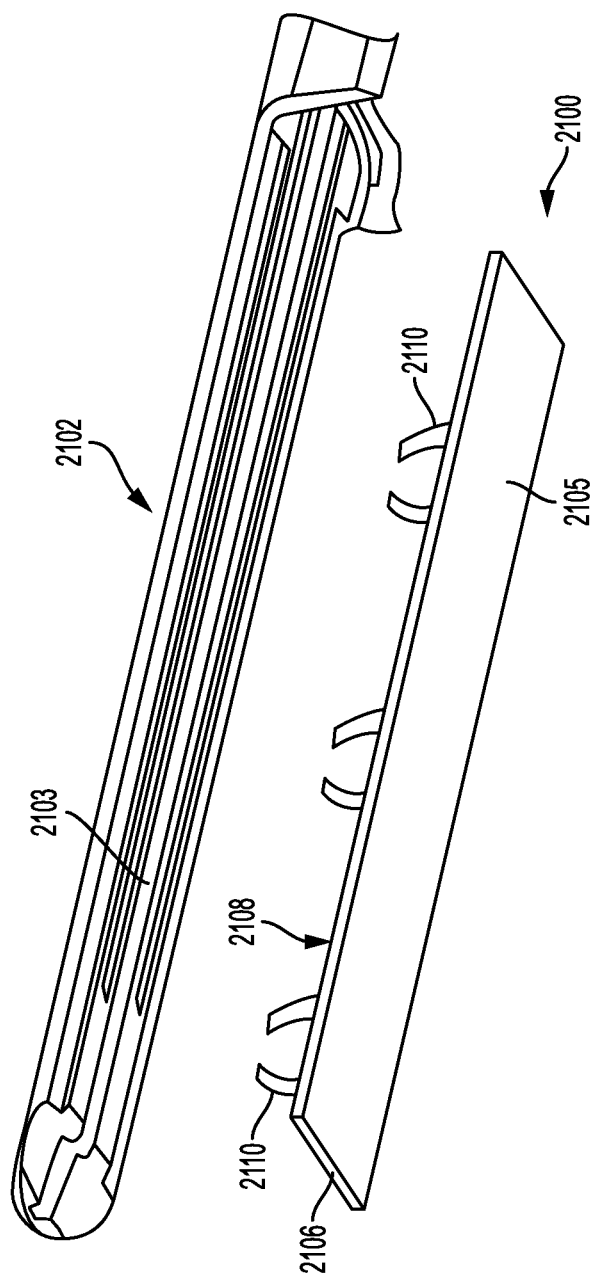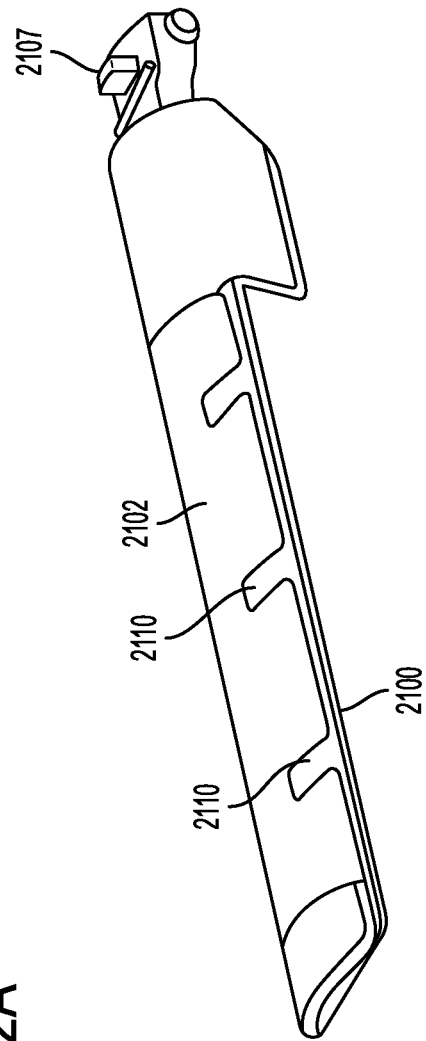
FIG. 12A
FIG. 12B

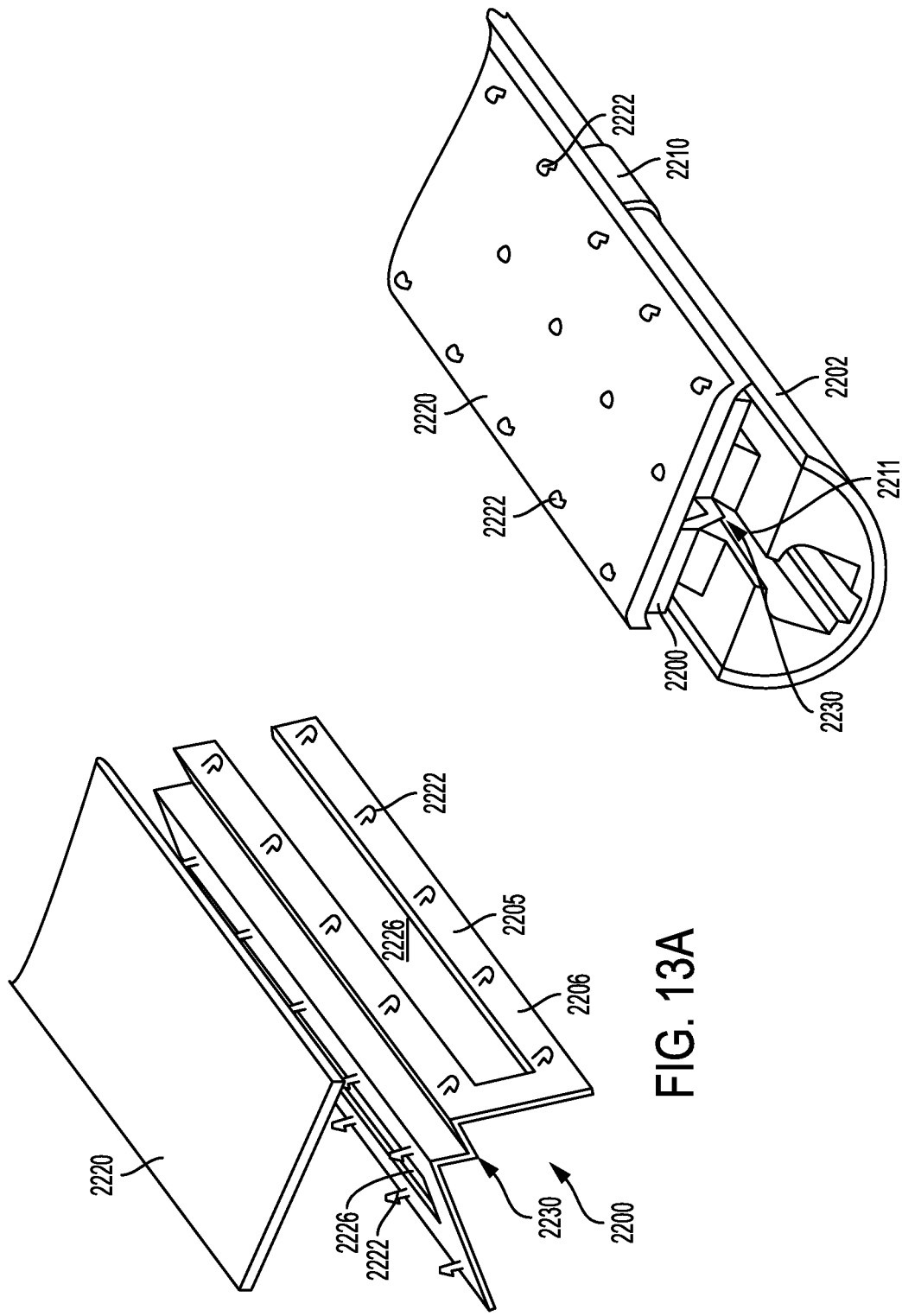

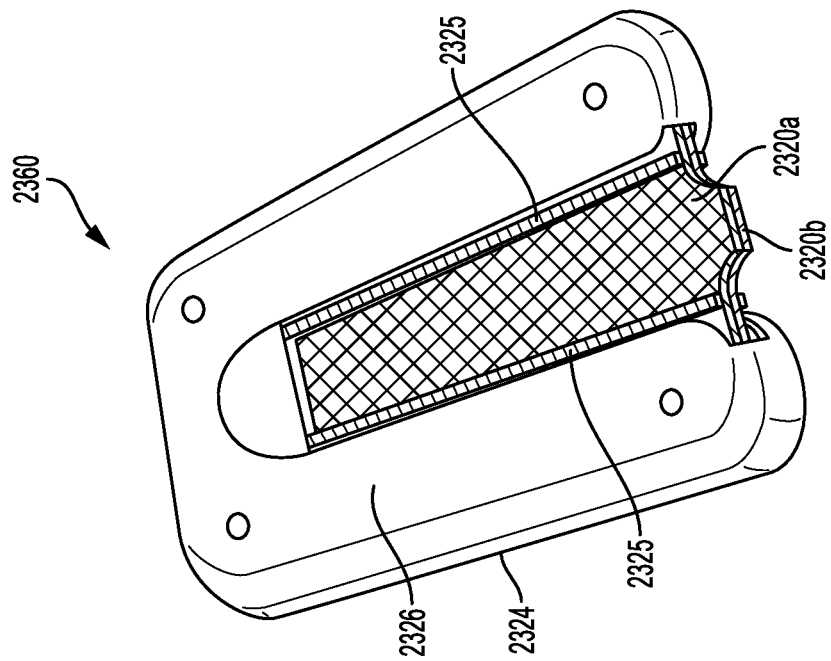
FIG. 14C
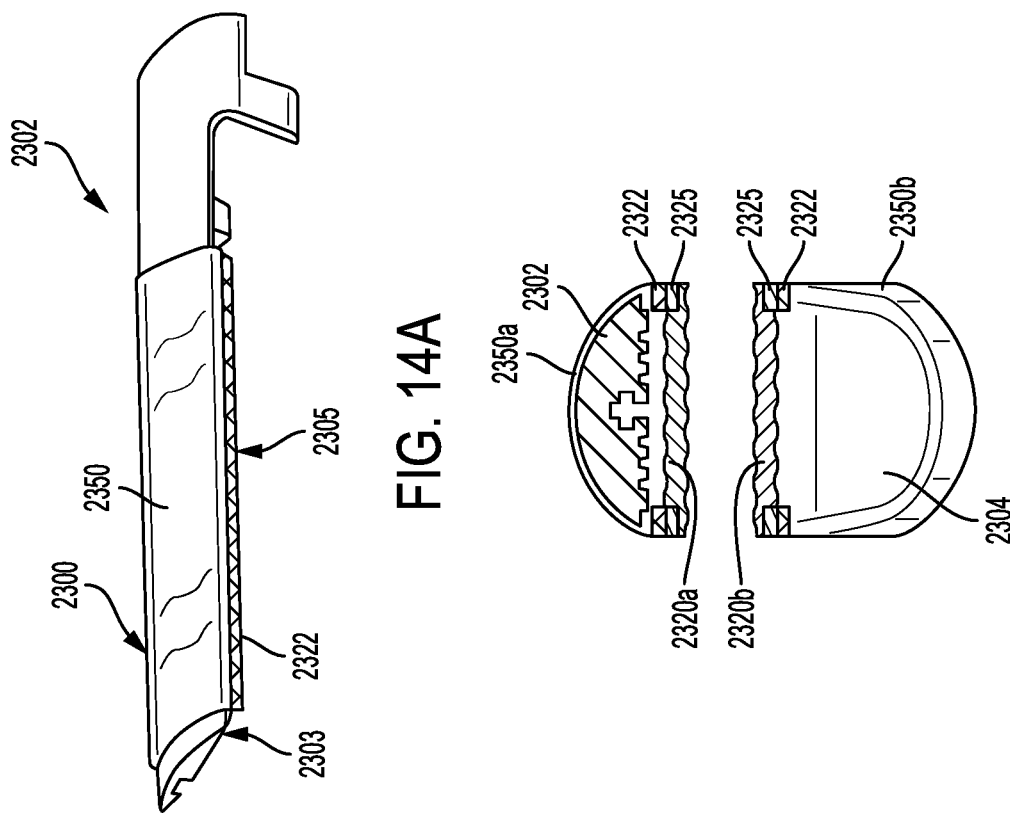
FIG. 14A
FIG. 14B

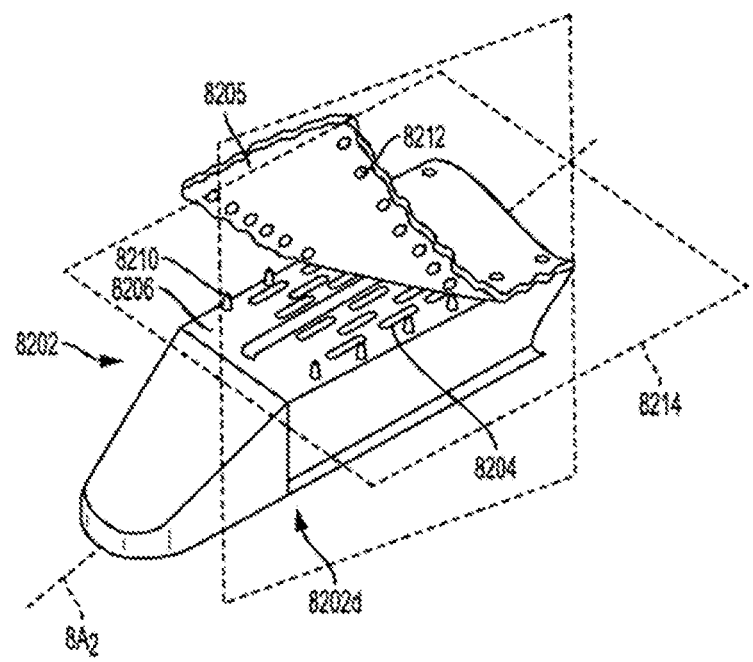
FIG. 61
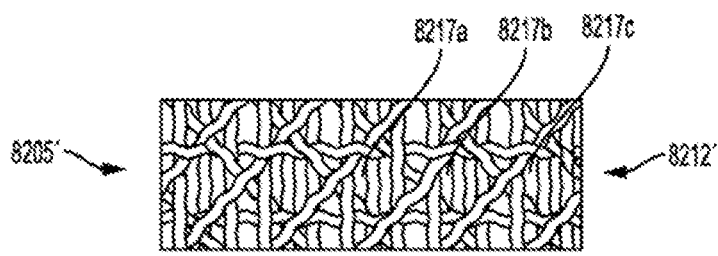
FIG. 62A
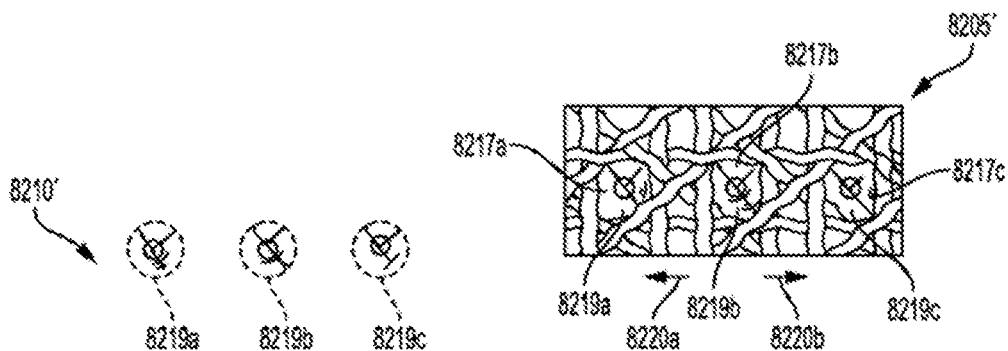
FIG. 62B
FIG. 62C

STAPLING ADJUNCT ATTACHMENT

CROSS REFERENCE TO RELATED APPLICATIONS

The present application is a continuation of U.S. patent application Ser. No. 16/931,759 filed on Jul. 17, 2020, entitled "Stapling Adjunct Attachment," which is a continuation of U.S. patent application Ser. No. 15/436,394, now U.S. Pat. No. 10,716,564, filed on Feb. 17, 2017, entitled "Stapling Adjunct Attachment," each of which is hereby incorporated by reference in its entirety.

FIELD

Methods and devices are provided for securing one or more adjunct materials to an end effector of a surgical instrument.

BACKGROUND

Surgical staplers are used in surgical procedures to close openings in tissue, blood vessels, ducts, shunts, or other objects or body parts involved in the particular procedure. The openings can be naturally occurring, such as passageways in blood vessels or an internal organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate shaft having an end effector with a pair of movable opposed jaws for engaging and stapling tissue. The staples are typically contained in a staple cartridge, which can house multiple rows of staples and that is often disposed in one of the jaws for ejection of the staples to the surgical site. In use, the jaws are positioned to engage tissue, and the device is actuated to eject staples through the tissue. Some staplers include a knife configured to travel between rows of staples in the staple cartridge to longitudinally cut the stapled tissue between the stapled rows.

While surgical staplers have improved over the years, a number of problems still present themselves. One common problem is that leaks can occur due to the staple forming holes when penetrating the tissue or other object in which it is disposed. Blood, air, gastrointestinal fluids, and other fluids can seep through the openings formed by the staples, even after the staple is fully formed. The tissue being treated can also become inflamed due to the trauma that results from stapling. Still further, staples, as well as other objects and materials that can be implanted in conjunction with procedures like stapling, generally lack some characteristics of the tissue in which they are implanted. For example, staples and other objects and materials can lack the natural flexibility of the tissue in which they are implanted. A person skilled in the art will recognize that it is often desirable for tissue to maintain as much of its natural characteristics as possible after staples are disposed therein.

Accordingly, there remains a need for improved devices and methods for stapling tissue, blood vessels, ducts, shunts, or other objects or body parts such that leaking and inflammation is minimized while substantially maintaining the natural characteristics of the treatment region.

SUMMARY

Methods for stapling tissue are provided. In one embodiment, the method can include positioning an adjunct on one of first and second jaws of an end effector of a surgical stapler. The adjunct can have an adhesive thereon that maintains the adjunct on the jaw. The method can also include positioning tissue between the first and second jaws, and actuating the surgical stapler to cause the first and second jaws to move from an open position to a closed position in which the tissue is engaged therebetween. A first attachment mechanism on the adjunct can prevent stretching of at least a portion of the adjunct.

In one embodiment, the first attachment mechanism can be at least one post formed on one of the adjunct and the jaw, and at least one bore formed on the other one of the adjunct and the jaw for receiving the post. In further aspects, a second attachment mechanism on the adjunct can prevent sliding of the adjunct relative to the jaw having the adjunct disposed thereon. The second attachment mechanism on the adjunct can prevent lateral sliding and/or longitudinal sliding of the adjunct relative to a longitudinal axis of the jaw. In other aspects, a second attachment mechanism on the adjunct can prevent curling of a distal-most end of the adjunct when the tissue is positioned between the first and second jaws.

In another embodiment, a method for stapling tissue is provided and includes positioning an adjunct on at least one jaw of first and second jaws of an end effector of a surgical stapler. The adjunct can be maintained on the at least one jaw in a first state in which the adjunct is at least partially stretched over the at least one jaw. The method can also include positioning tissue between the first and second jaws, and actuating the surgical stapler to cause the first and second jaws to move from an open position to a closed position in which the tissue is engaged therebetween. Actuation of the surgical stapler can cause the adjunct to transition from the first state to a second state such that the adjunct in the second state at least partially separates from the at least one jaw.

In certain embodiments, actuation of the surgical stapler can include causing a cutting element of the surgical stapler to move to thereby cut through at least a portion of the adjunct to cause the adjunct to transition from the first state to the second state. The cutting element can cut through at least a portion of the attachment feature as the cutting element moves. In further embodiments, actuation of the surgical stapler can cause staples to be deployed to thereby penetrate through at least a portion of the adjunct to cause the adjunct to transition from the first state to the second state.

BRIEF DESCRIPTION OF DRAWINGS

This invention will be more fully understood from the following detailed description taken in conjunction with the accompanying drawings, in which:

FIG. 12A is an exploded view of one embodiment of a frame configured to couple to an adjunct material and a jaw;

FIG. 12B is a perspective top view of the frame coupled to the jaw of FIG. 12A;

FIG. 13A is an exploded view of another embodiment of a frame configured to couple to a jaw and an adjunct material;

FIG. 13B is a perspective top view of the frame coupled to the jaw of FIG. 13A, with the adjunct material coupled to a tissue-facing surface of the frame;

FIG. 14A is a perspective view of yet another embodiment of a frame configured as an overlay extending around a jaw with a tissue facing surface of the overlay having two rows of retaining features;

FIG. 14B is a cross-sectional view of a portion of an end effector of FIG. 14A showing a first overlay coupled to the jaw and a second overlay coupled to another jaw with a first and second adjunct material, respectively, releasably coupled thereon;

FIG. 14C is a perspective view of an applicator member configured to apply the first and second adjunct materials to the first and second overlays of FIG. 14B;

FIG. 61 is a perspective view of a distal portion of an end effector having an adjunct material releasably mounted thereon in accordance with the described techniques;

FIG. 62A is a top view of a portion of an adjunct material having "non-retaining" female features used in accordance with the described techniques;

FIG. 62B is a top view of "non-retaining" male features that can be formed on a jaw for mating with the adjunct material of FIG. 62A, in accordance with the described techniques;

FIG. 62C is a top view of the adjunct material of FIG. 62A having its "non-retaining" female features encompassing the "non-retaining" male features of FIG. 62B;

FIG. 87 is a perspective view of one embodiment of an adjunct loader for use with a surgical stapler;

FIG. 88 is a top view of the adjunct loader of FIG. 87;

FIG. 89 is a cross-sectional side view of the adjunct loader of FIG. 87;

FIG. 90 is a perspective view of another embodiment of an adjunct loader for use with a surgical stapler;

FIG. 91 is a top view of the adjunct loader of FIG. 90;

FIG. 92 is a cross-sectional side view of the adjunct loader of FIG. 90;

FIG. 93 is a cross-sectional side view of another embodiment of an adjunct loader for use with a surgical stapler;

FIG. 94 is a cross-sectional side view of the adjunct loader of FIG. 93;

FIG. 95 is a cross-sectional side view of another embodiment of an adjunct loader for use with a surgical stapler;

FIG. 96 is a cross-sectional view of the adjunct loader of FIG. 95;

FIG. 97 is a perspective view of a jaw of an end effector having an adjunct material releasably mounted thereon using an attachment feature in accordance with the described techniques;

FIG. 98 is a perspective partial view of the jaw with the adjunct material of FIG. 97;

Figure 16:
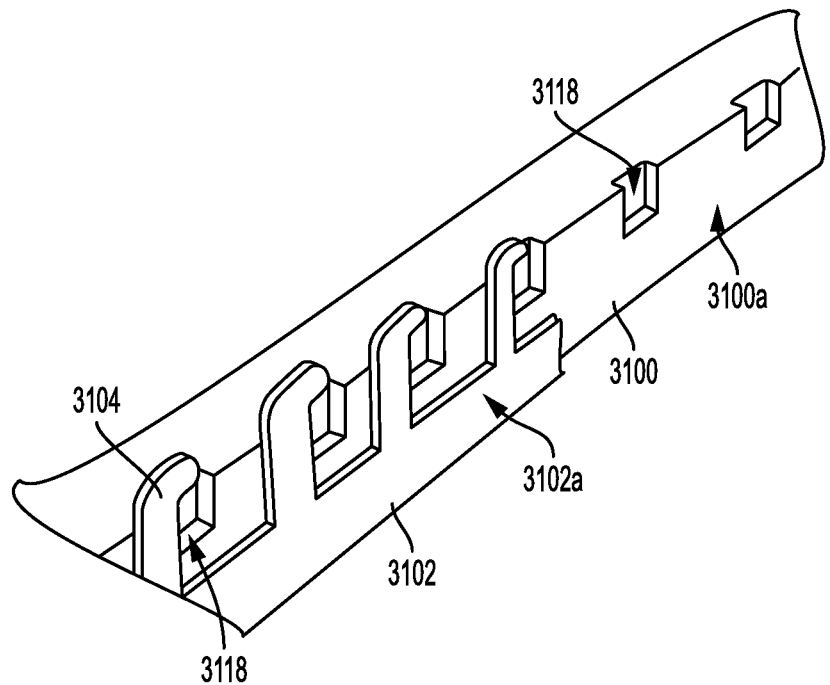
FIG. 16 is a perspective, partial cutaway view of a portion of the cartridge and retainer of FIG. 15.
Figure 97:
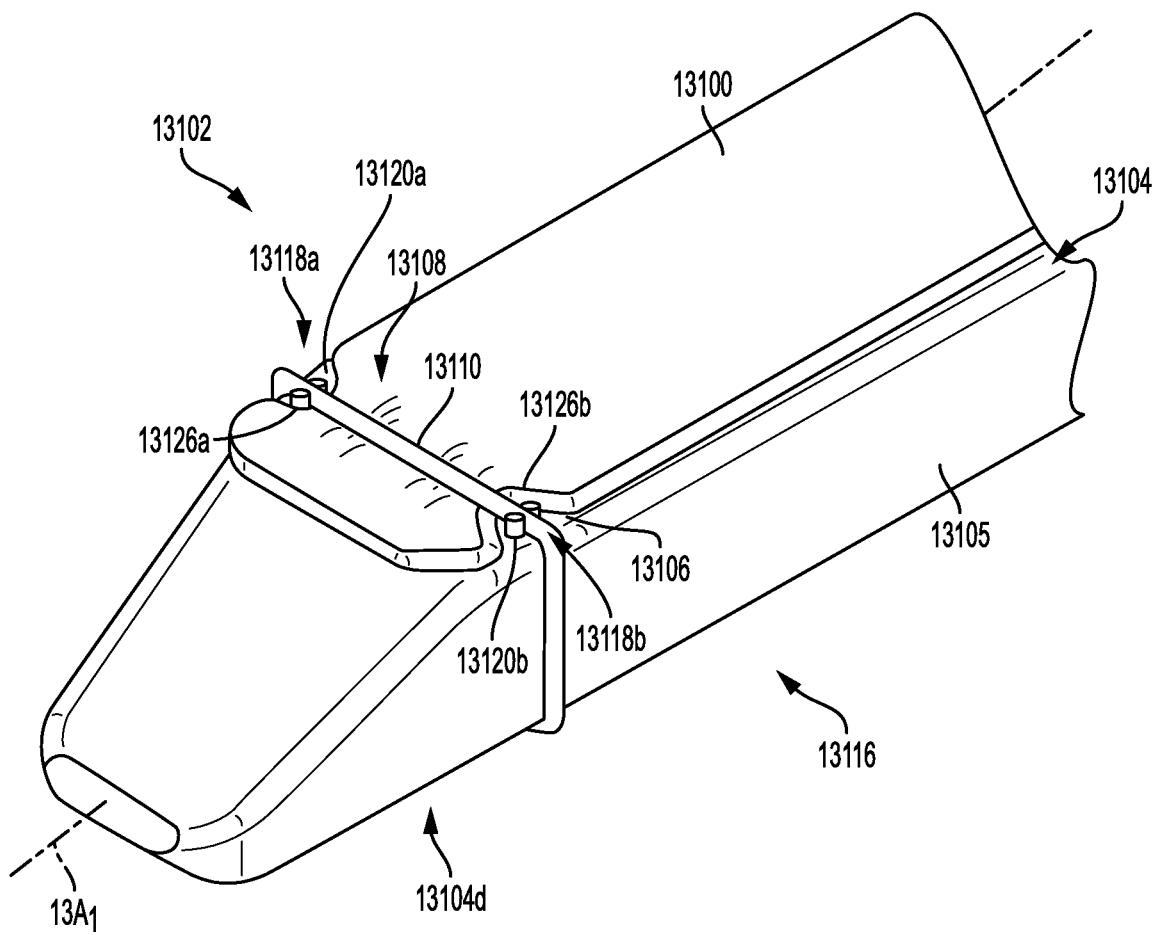
Figure 99:
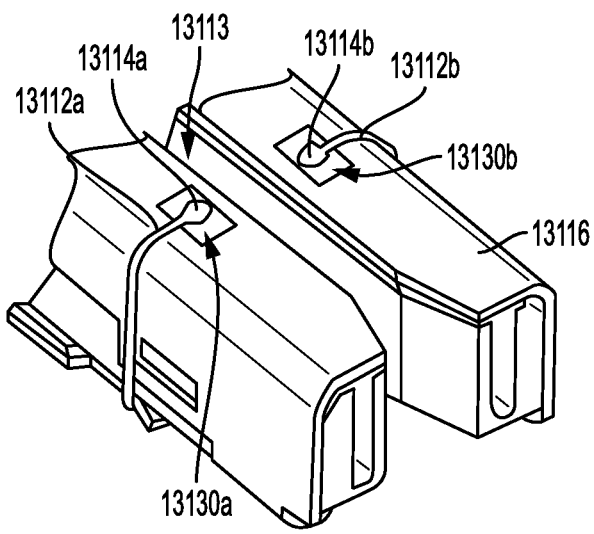
Figure 100:
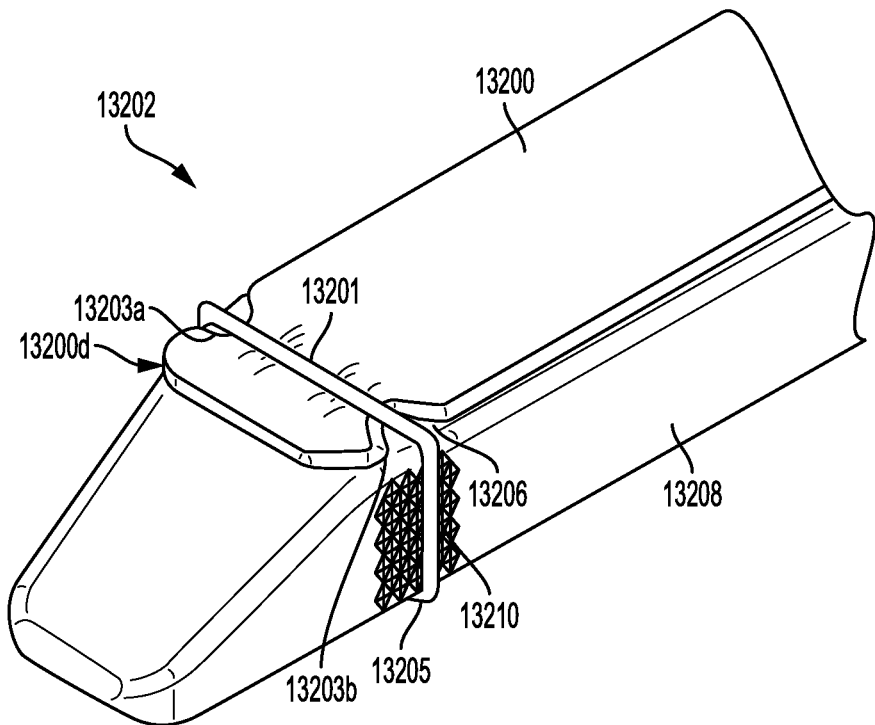
Figure 101:
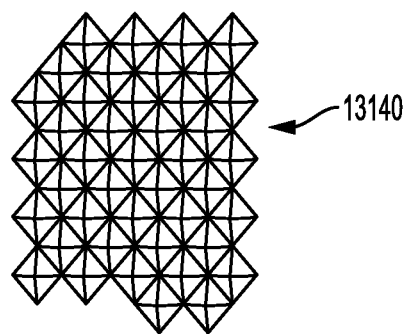
Figure 102:
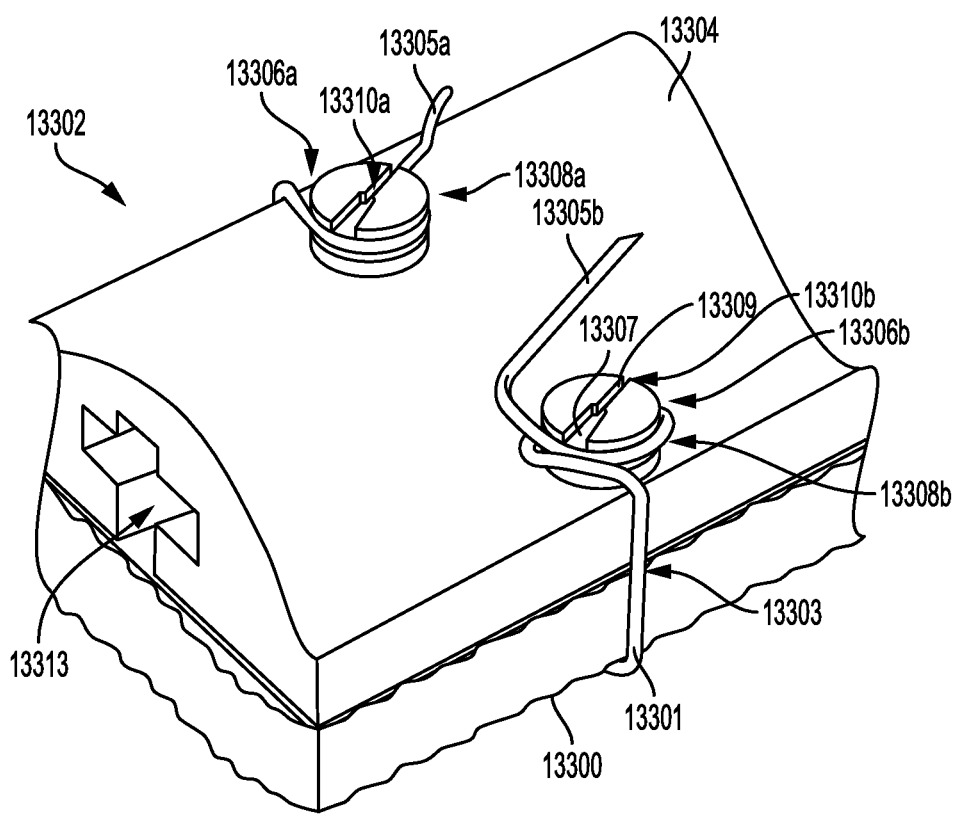
Figure 103:
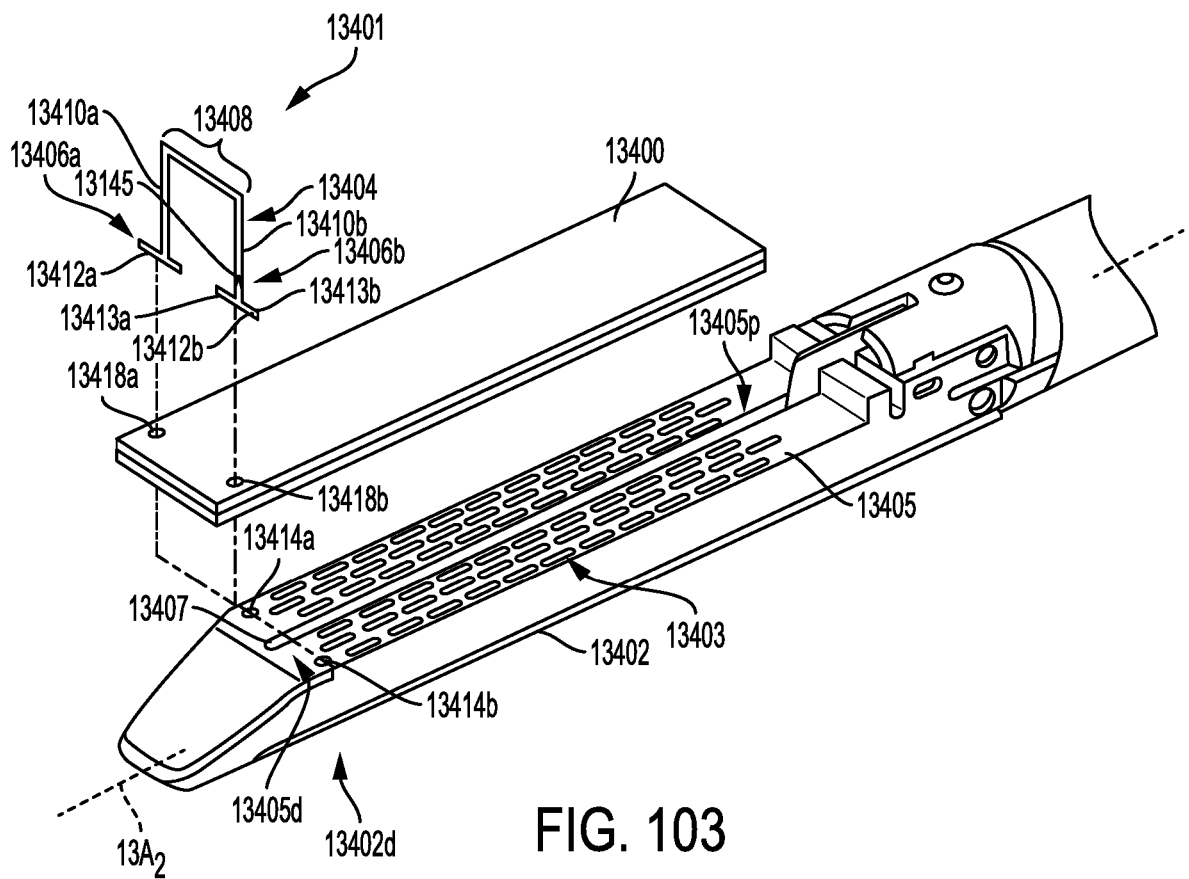
Figure 104:
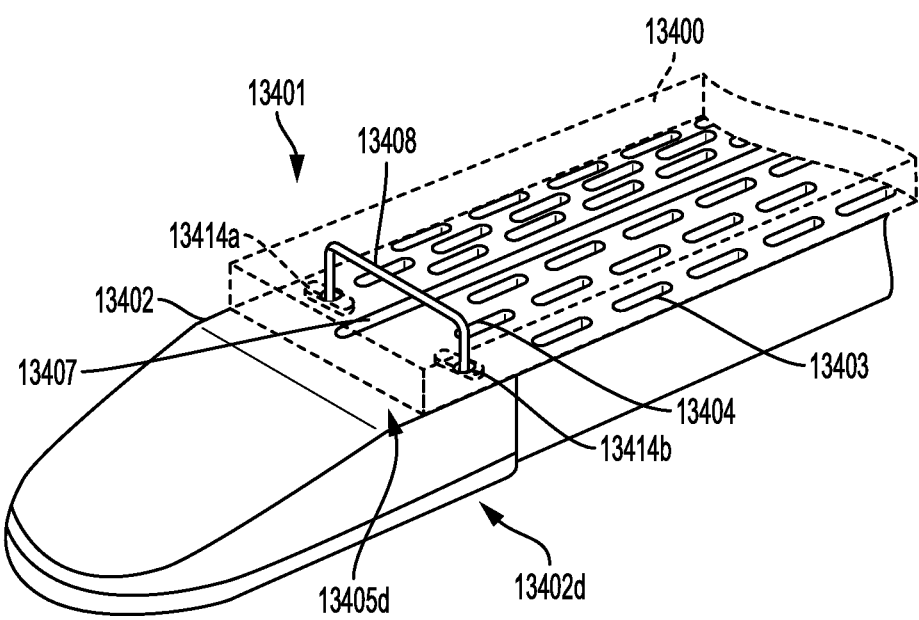
Figure 105:
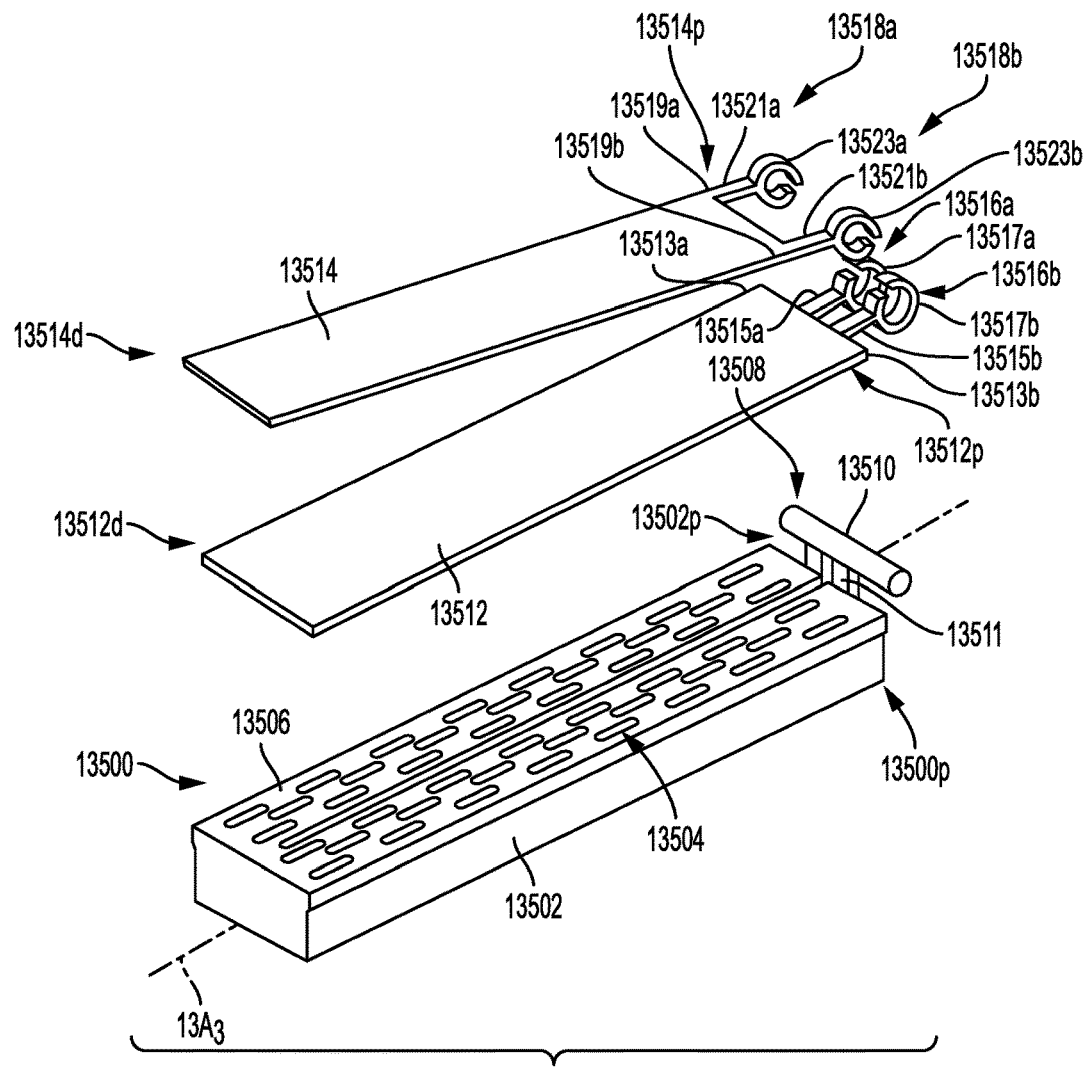
Figure 106:
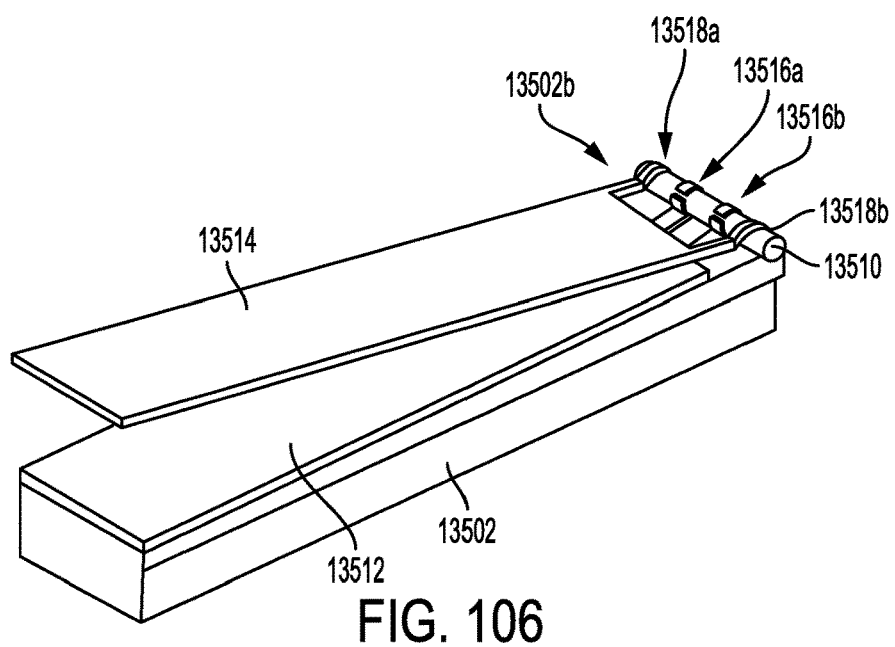
Figure 107:
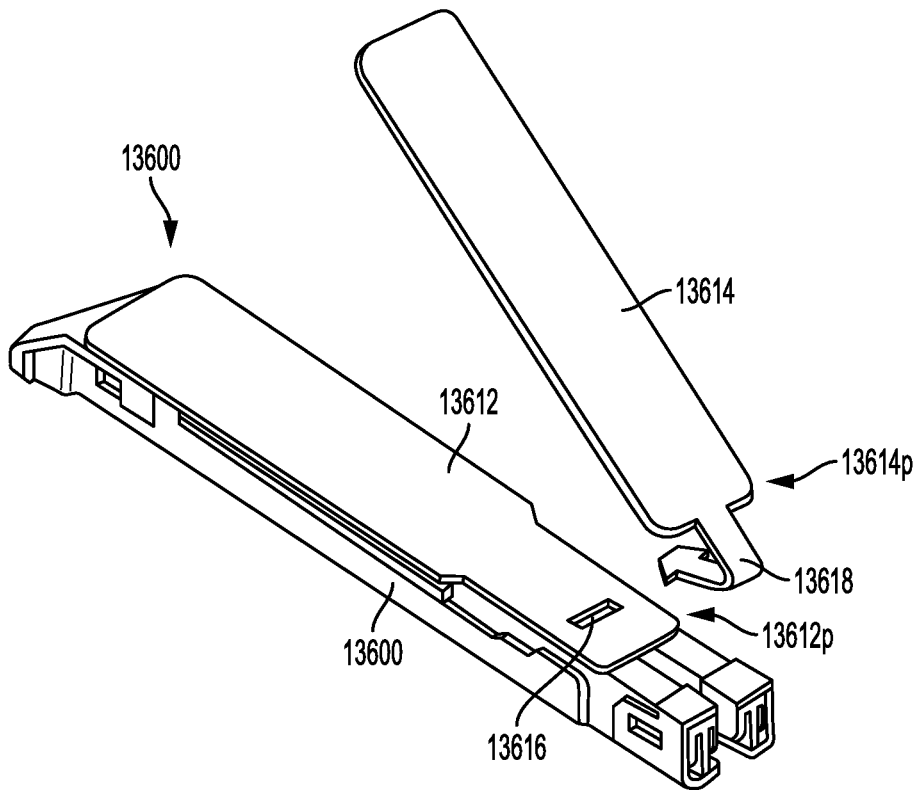
Figure 108:
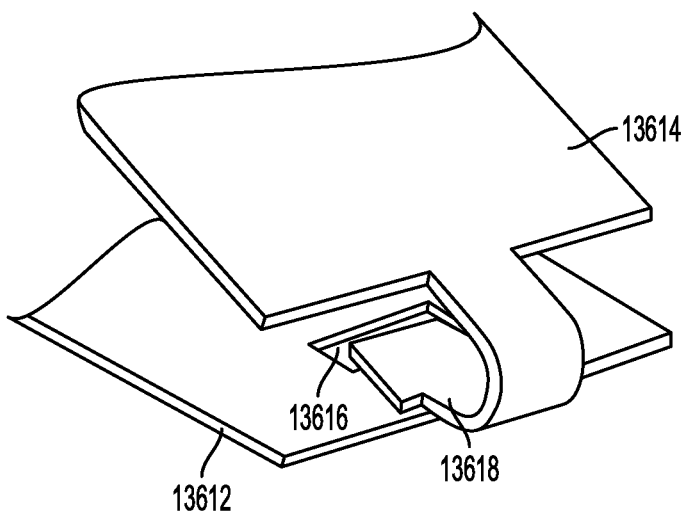
Figure 109:
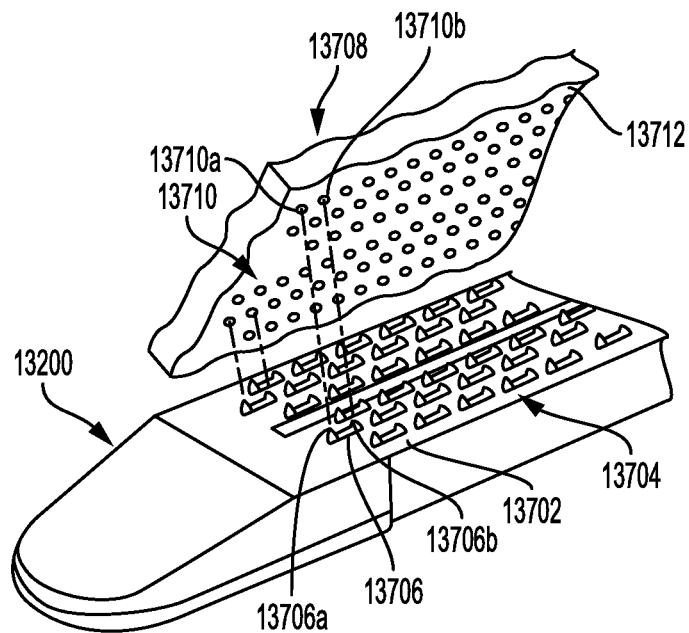
Figure 110A:
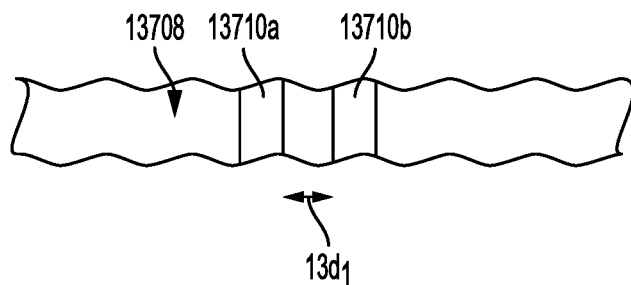
Figure 110B:
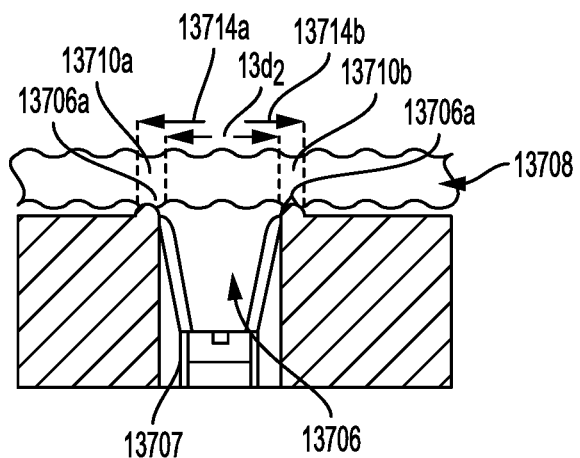
Figure 111:
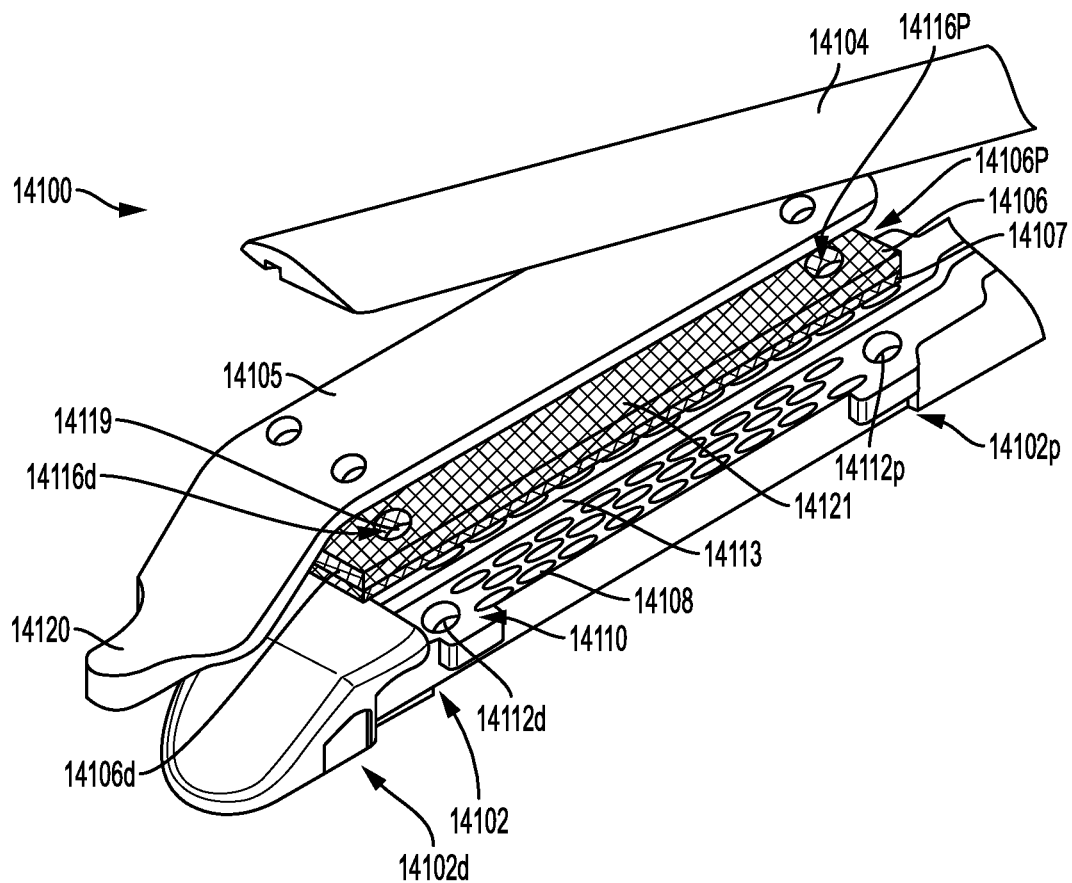
Figure 112:
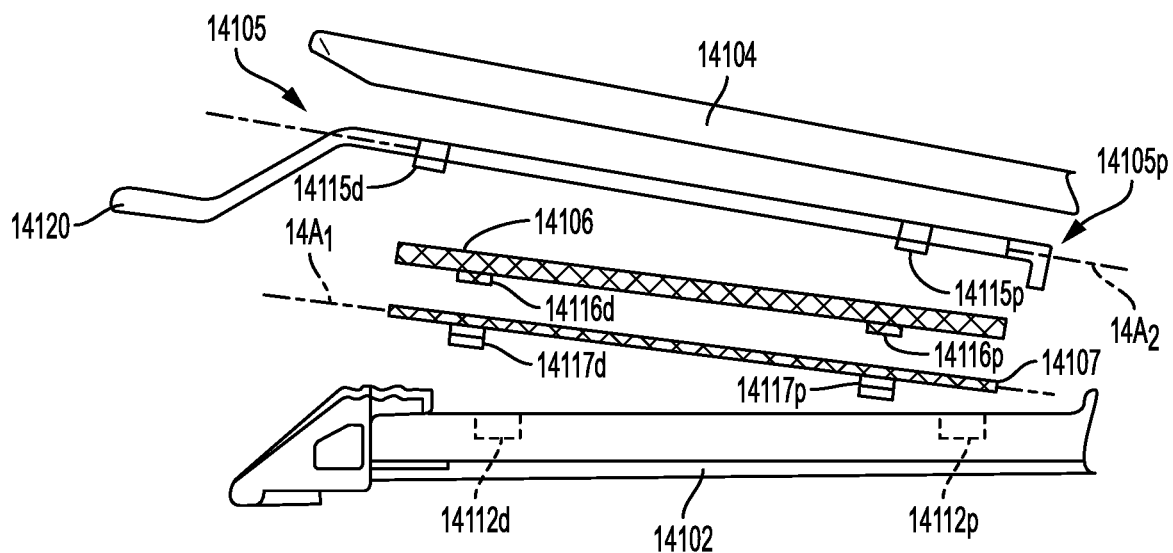
Figure 113A:
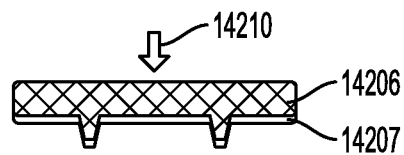
Figure 113B:
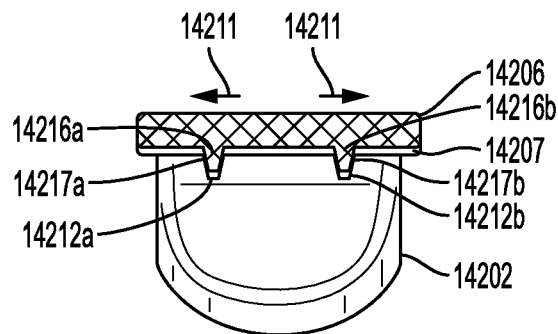
Figure 114:
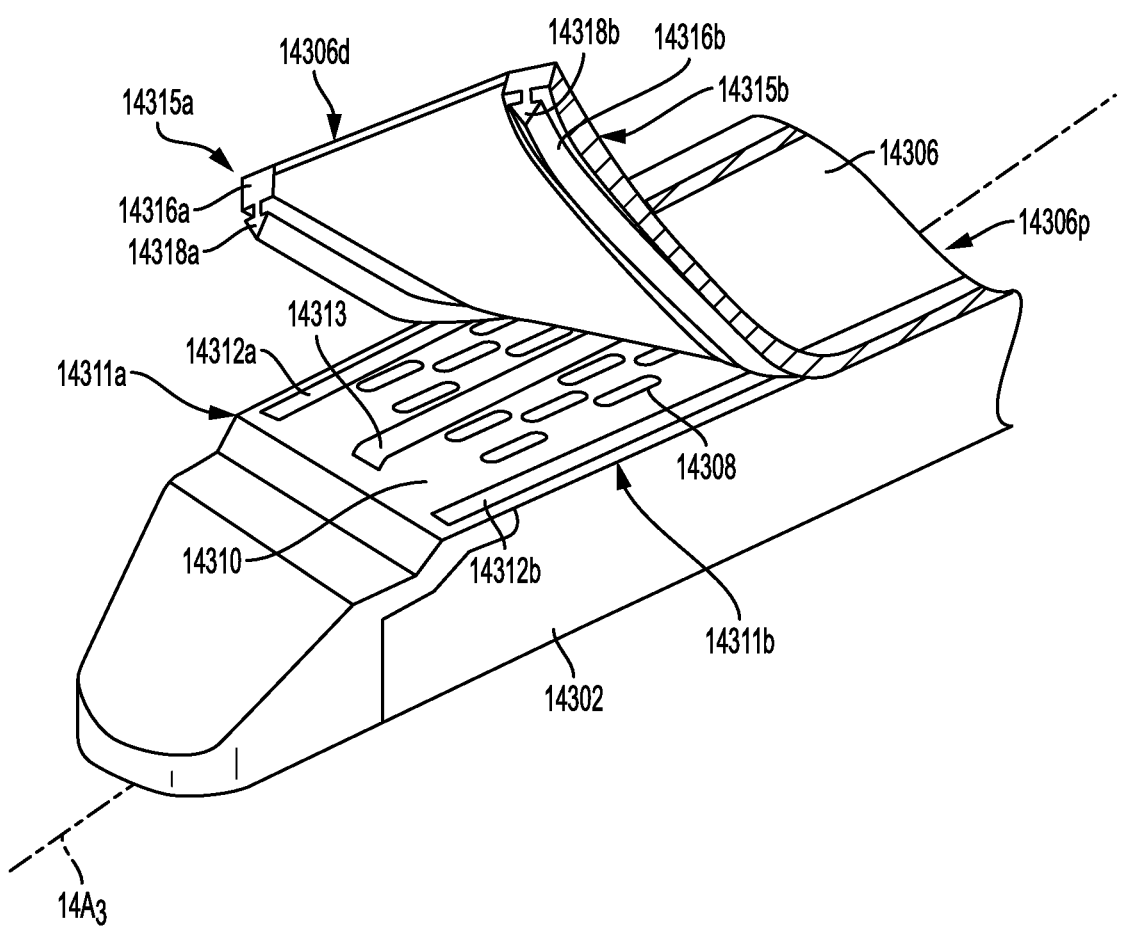
Figure 115:
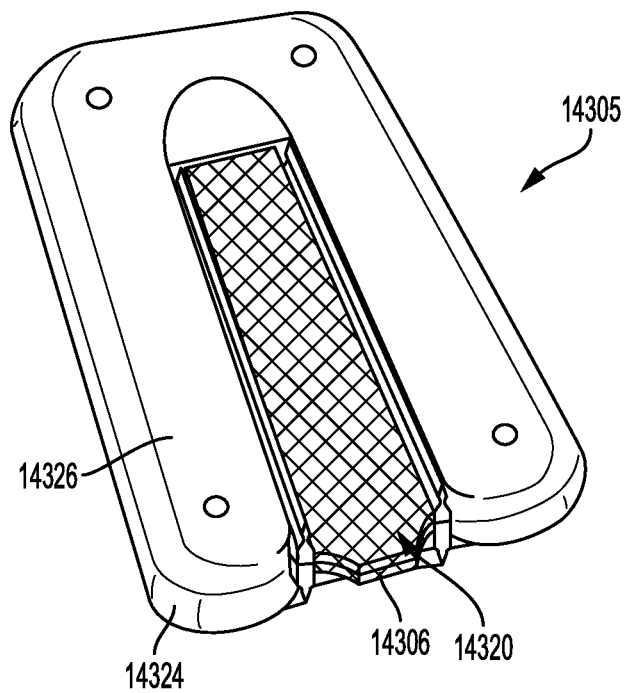
Figure 116:
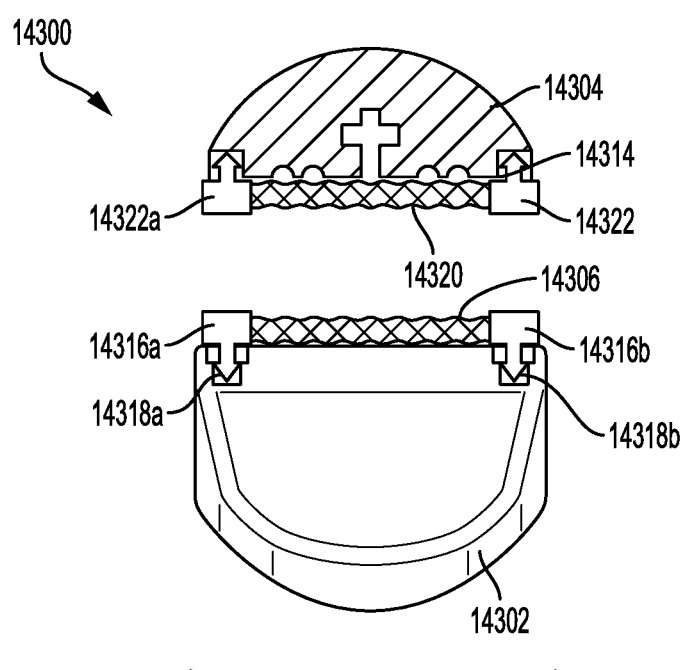
Figure 117:
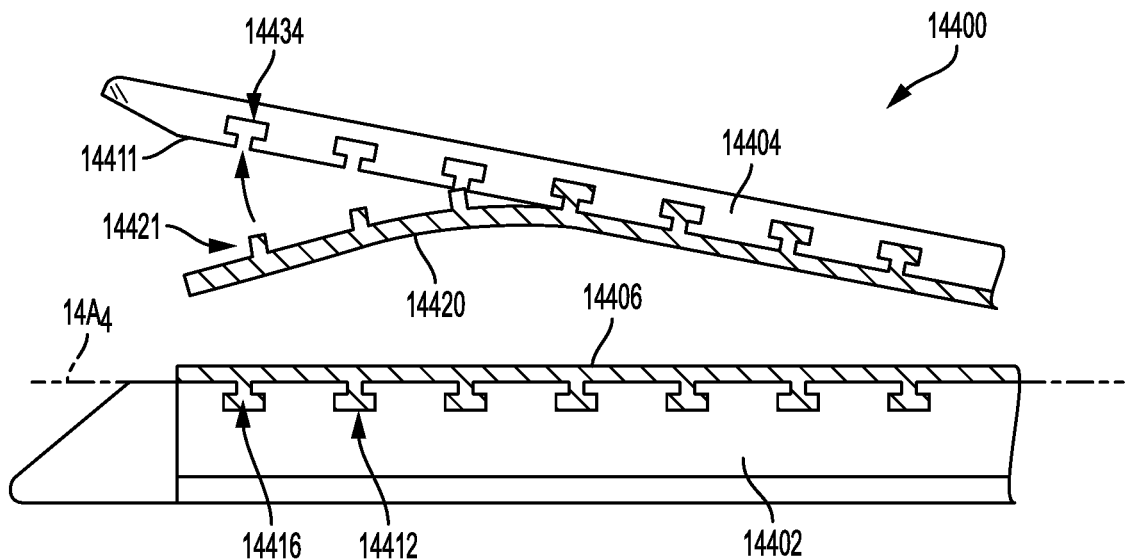
Figure 118:
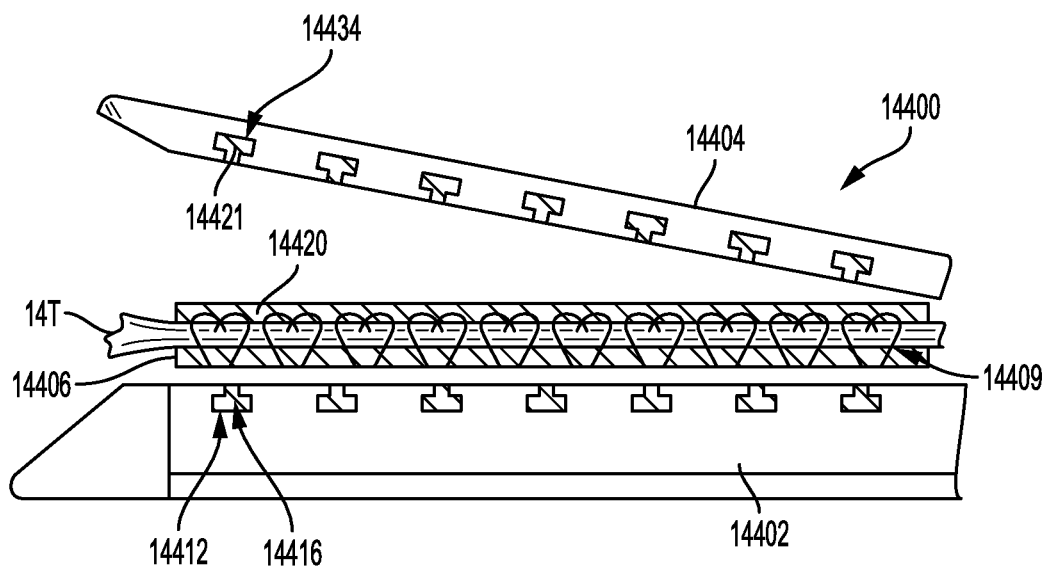
Figure 119:
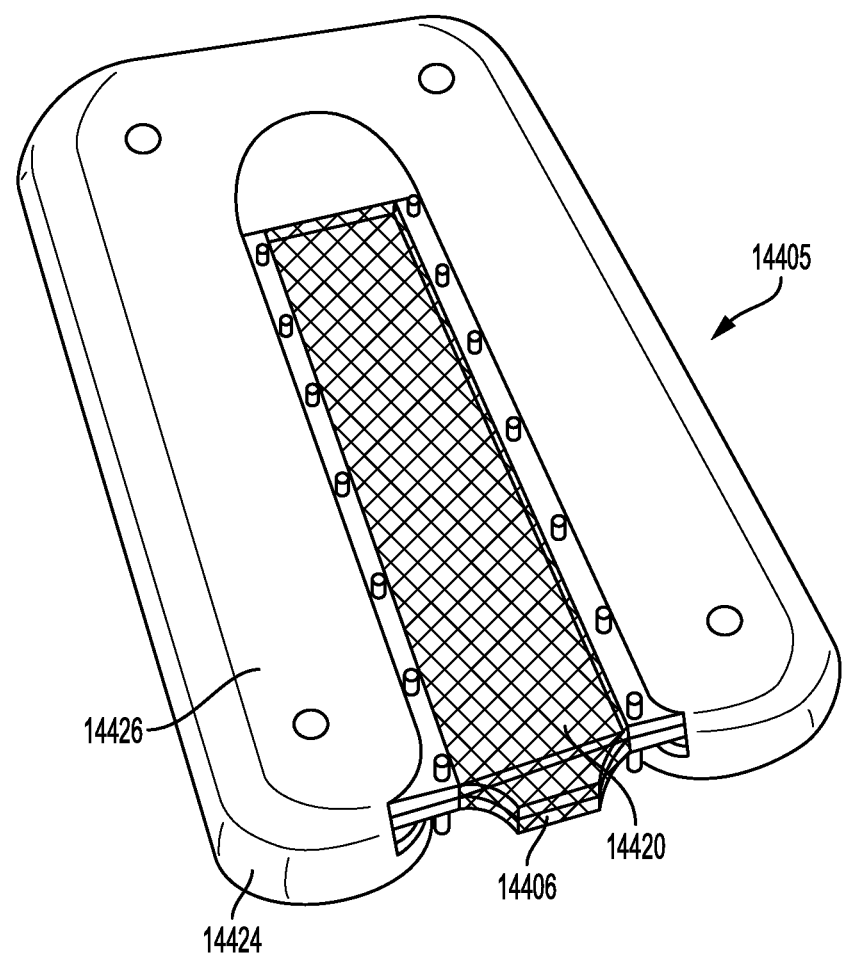
Figure 120:
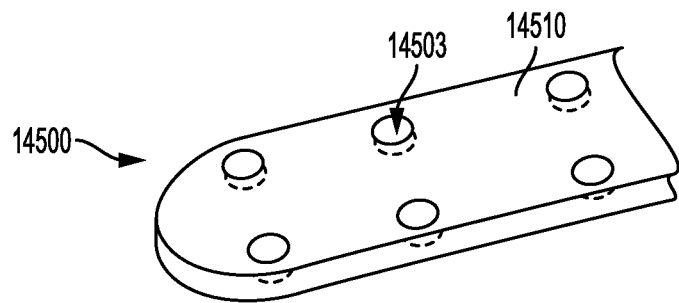
Figure 121:
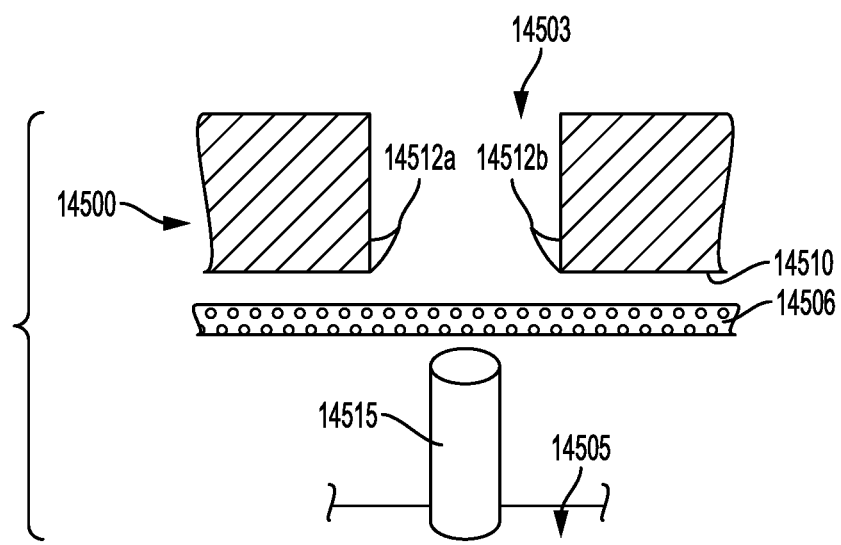
Figure 122:
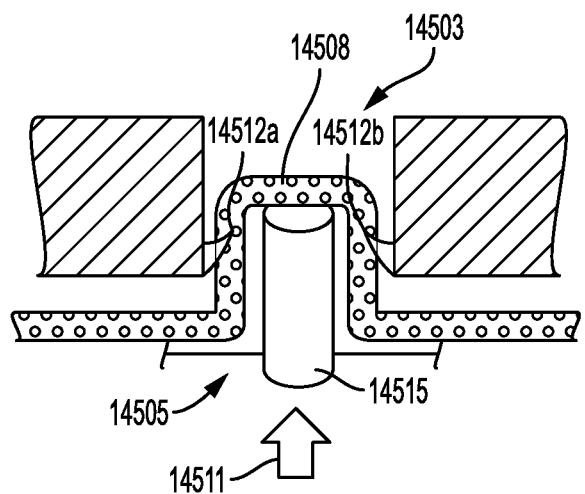
Figure 123:
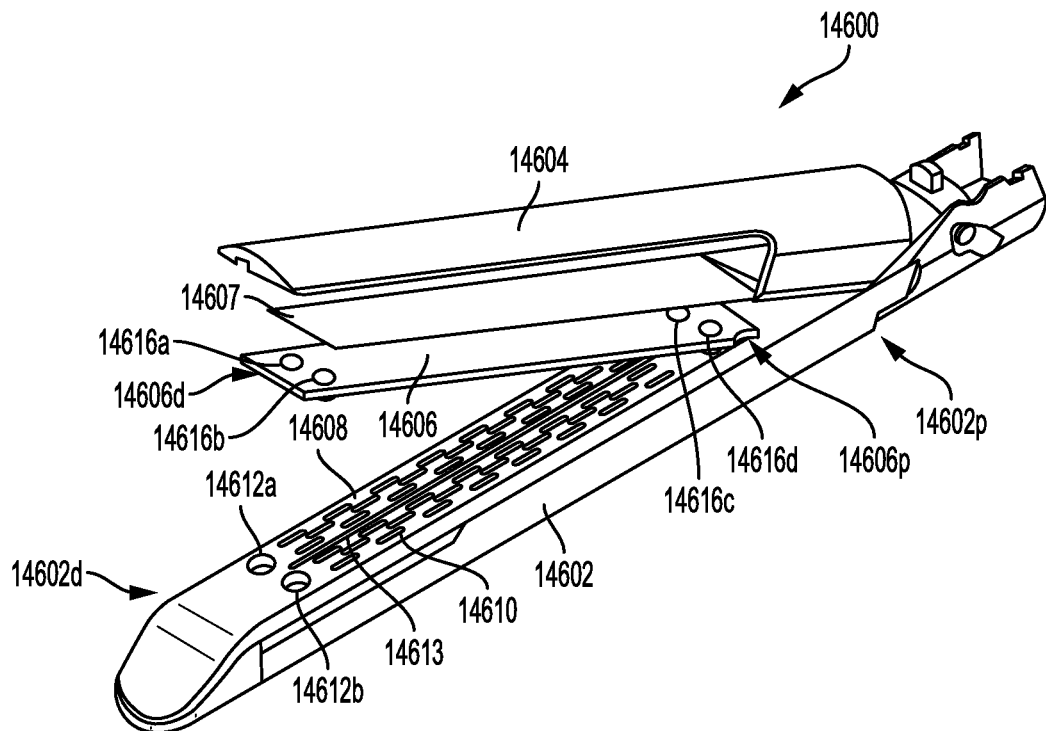
Figure 124:
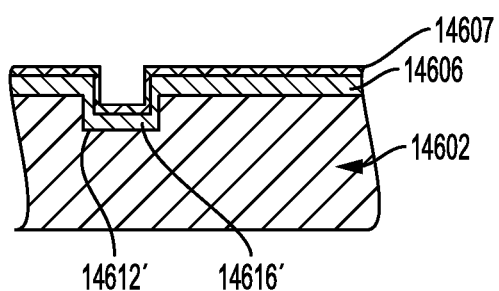
Figure 125:
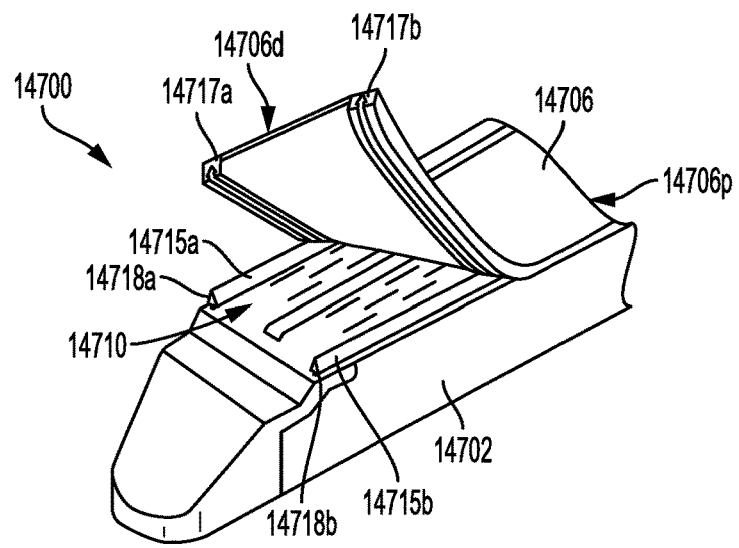
Figure 126:
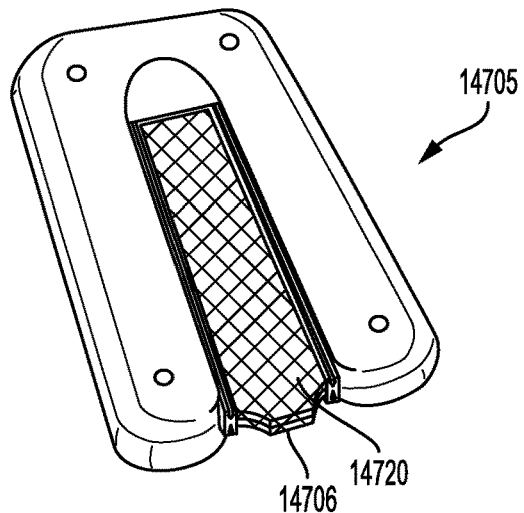
Figure 127:
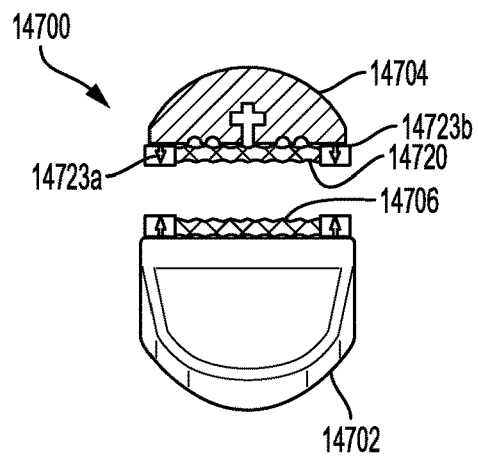
Figure 128A:
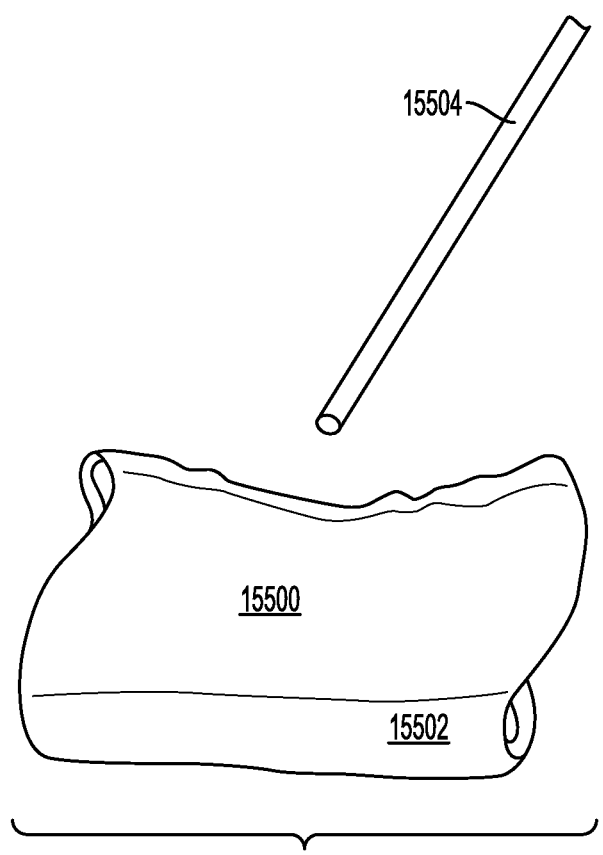
Figure 128B:
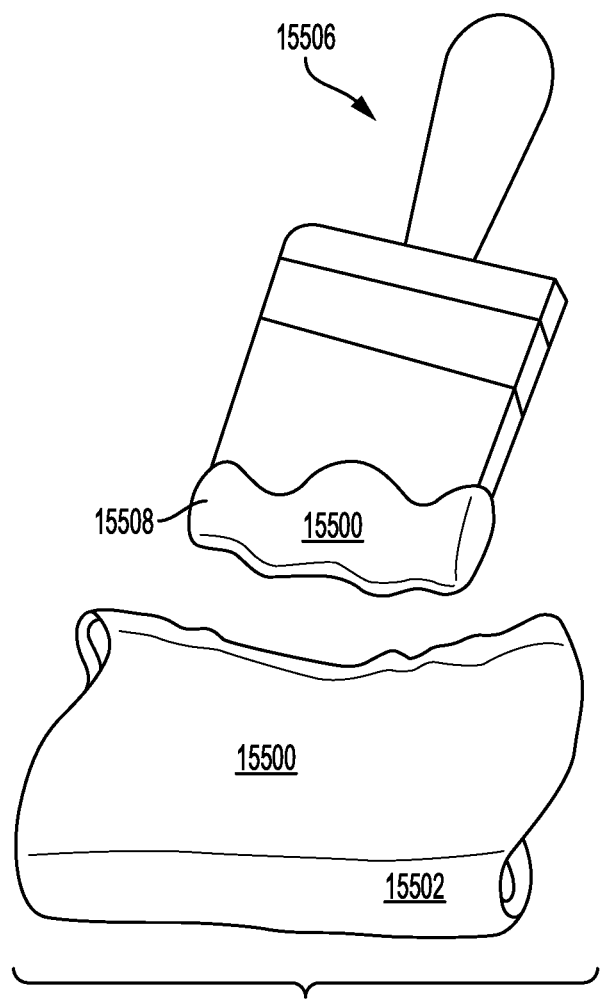
Figure 128C:
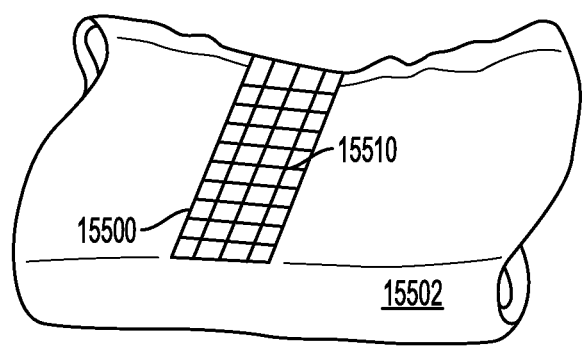
Figure 128D:
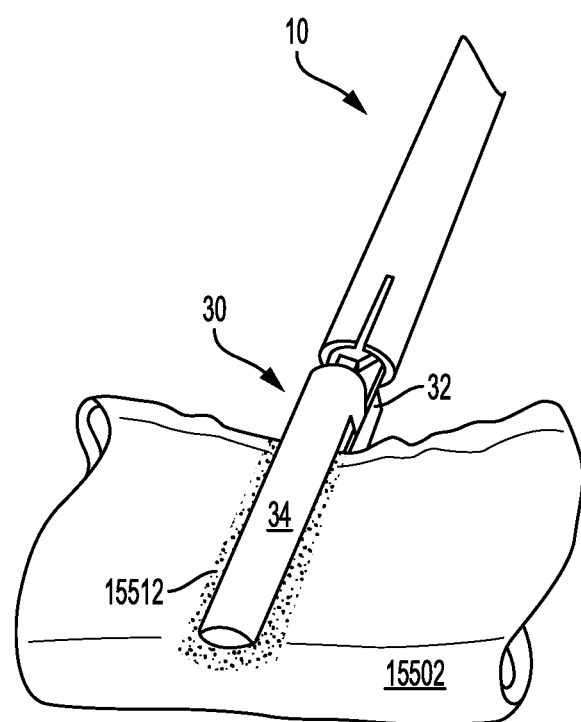
Figure 128E:
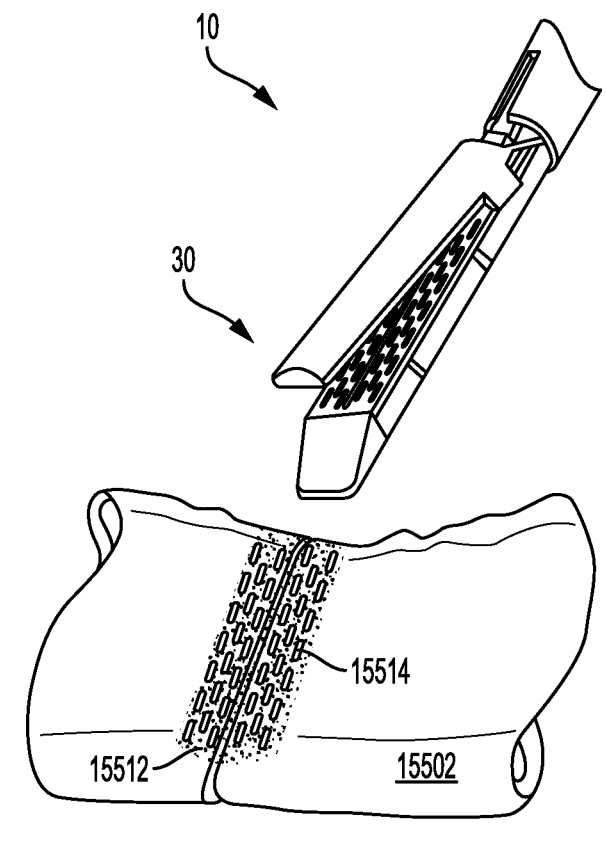
Figure 129A:
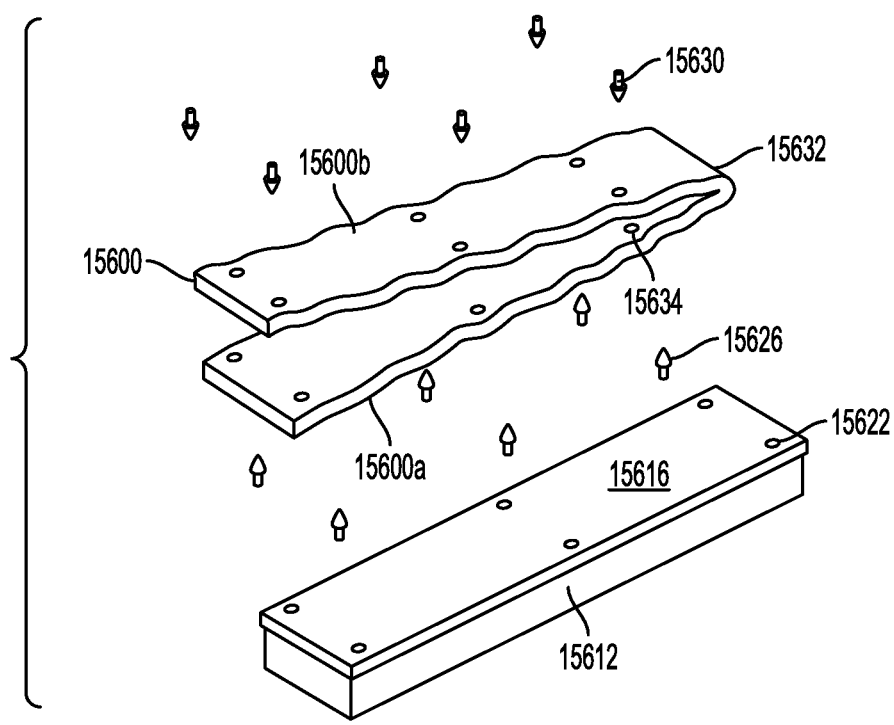
Figure 129B:
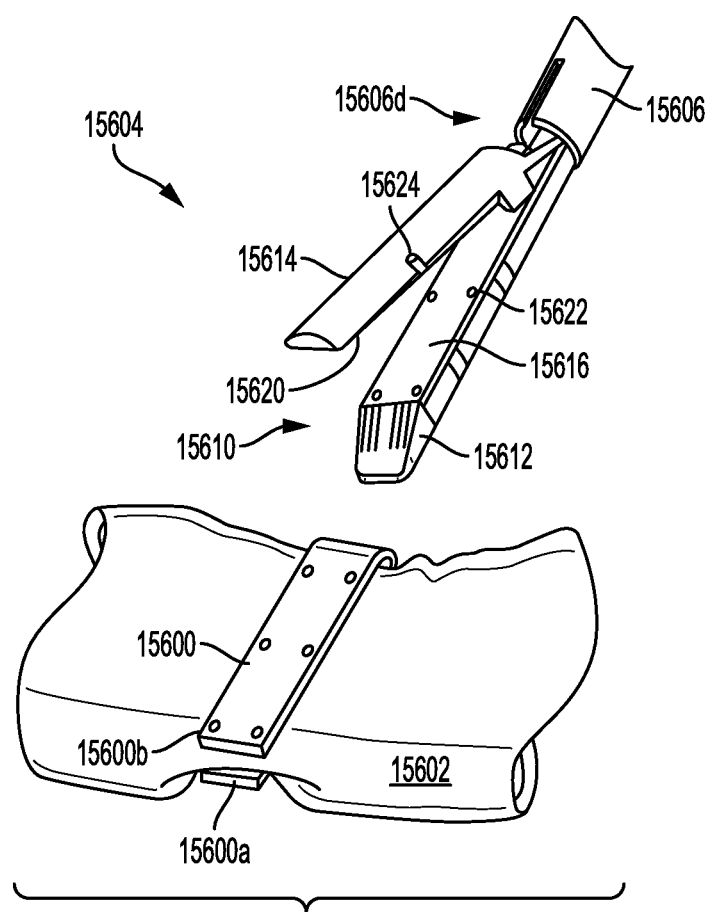
Figure 130A:
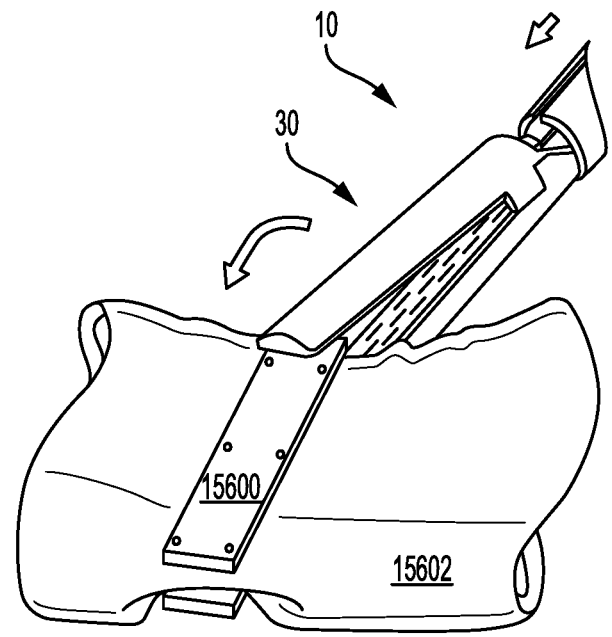
Figure 130B:
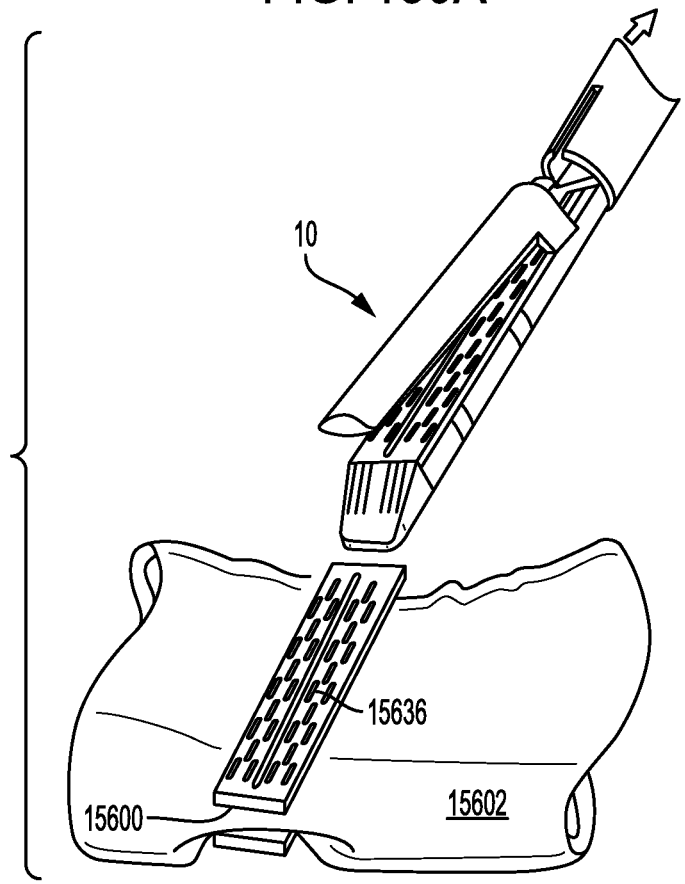
Figure 131A:
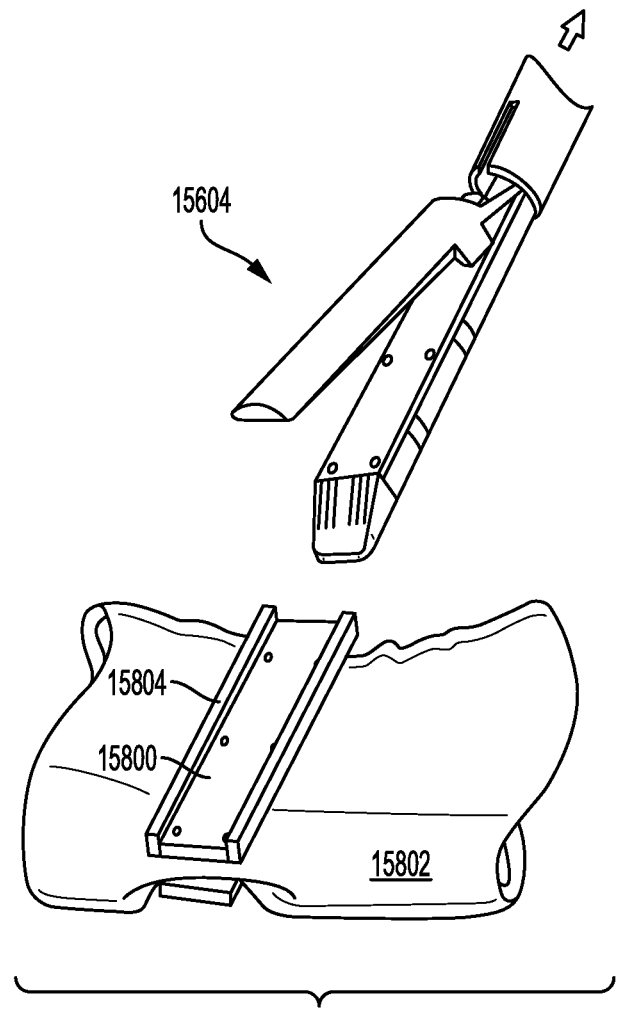
Figure 131B:
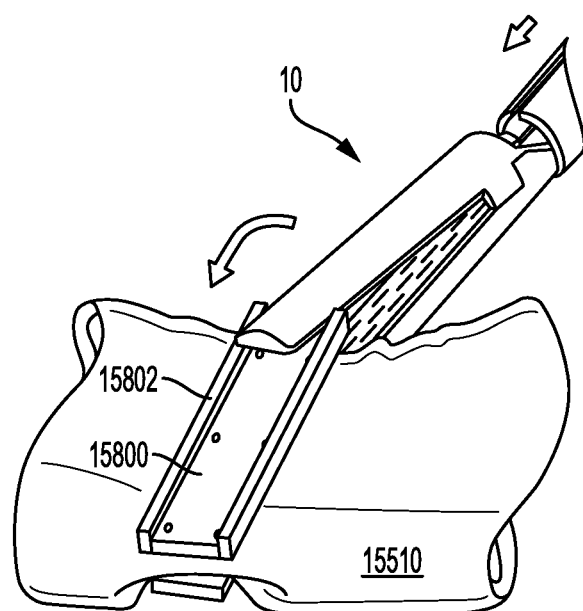
Figure 131C:
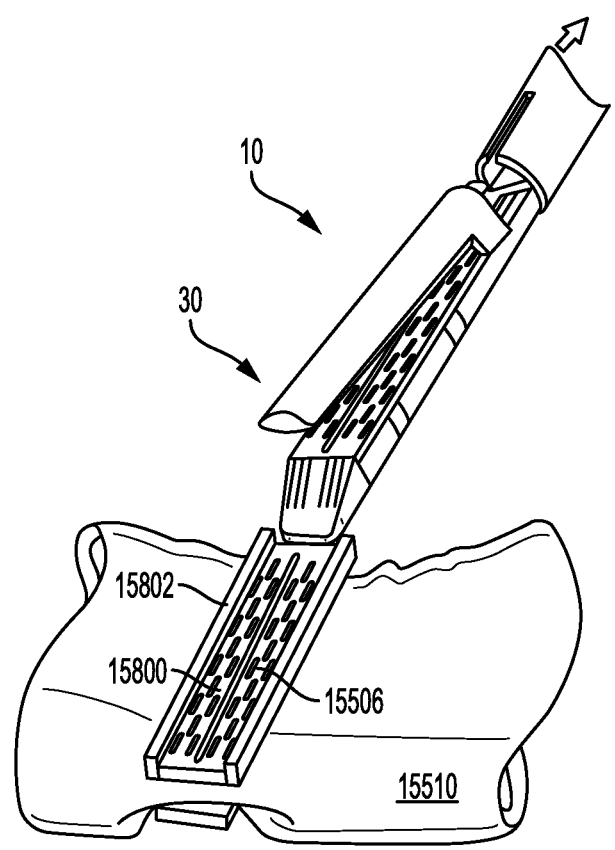
Figure 132A:
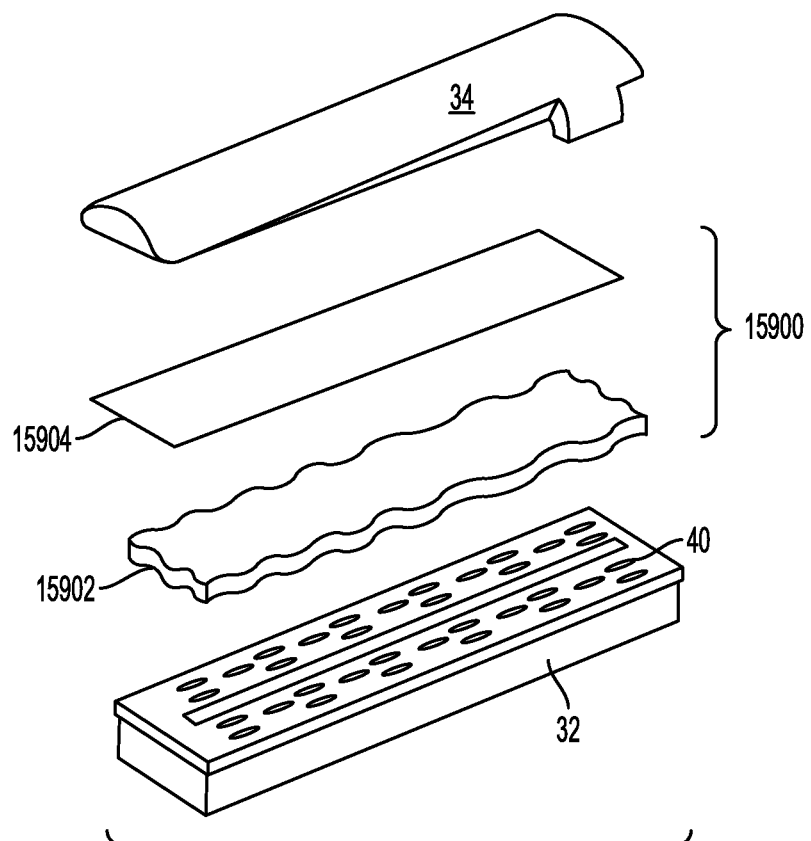
Figure 132B:
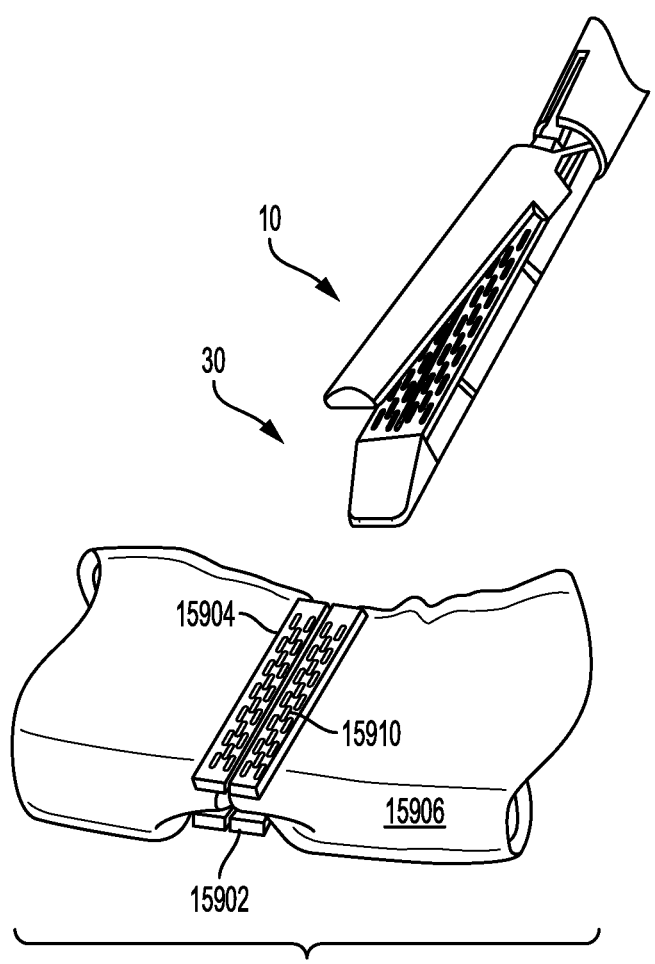

FIG. 99 is a perspective view of a side of the jaw of FIG. 97 that is opposed to a tissue-contacting side thereof, illustrating end features of the attachment feature;

FIG. 100 is another perspective view of a jaw of an end effector having an adjunct material releasably mounted thereon using an attachment feature in accordance with the described techniques;

FIG. 101 is a schematic diagram illustrating an example of a roughness portion that can be formed on the jaw of FIG. 97 and the jaw of FIG. 100;

FIG. 102 is a perspective view of an upper side of a jaw of an end effector having an adjunct material releasably mounted thereon using a spindle-type attachment feature in accordance with the described techniques;

FIG. 103 is a perspective view of a jaw of an end effector configured to releasably retain thereon an adjunct material using an attachment feature in accordance with the described techniques;

FIG. 104 is a perspective, partially transparent view of the jaw of FIG. 103, illustrating the attachment feature releasably retaining the adjunct material on the jaw;

FIG. 105 is a perspective view of a jaw of an end effector configured to releasably retain thereon first and second adjunct materials;

FIG. 106 is a perspective view of the jaw of FIG. 105, illustrating the first and second adjunct materials releasably retained on the jaw;

FIG. 107 is another perspective view of a jaw of an end effector configured to releasably retain thereon first and second adjunct materials;

FIG. 108 is a perspective view of a portion of the first and second adjunct materials of FIG. 16, illustrating a tab in one of the adjunct materials engaging with a slot in another one of the adjunct materials;

FIG. 109 is a perspective view of a jaw of an end effector configured to releasably retain thereon an adjunct material;

FIG. 110A is a schematic diagram illustrating a portion of the adjunct material of FIG. 109;

FIG. 110B is a schematic diagram illustrating the portion of the adjunct material of FIG. 110A in engagement with a portion of the jaw of FIG. 109;

FIG. 111 is a perspective, partially exploded view of an end effector having an adjunct material releasably mounted thereon in accordance with the described techniques;

FIG. 112 is a partially exploded side view of the end effector of FIG. 111;

FIG. 113A is a cross-sectional view of a portion of the adjunct material and a polymer layer material of FIG. 112;

FIG. 113B is a cross-sectional view of a portion of the end effector of FIG. 112 having the adjunct material with the polymer layer material releasably retained thereon;

FIG. 114 is a perspective view of an end effector having an adjunct material releasably mounted thereon in accordance with the described techniques;

FIG. 115 is a perspective view of an applicator member configured to apply the adjunct material to the end effector of FIG. 114;

FIG. 116 is a cross-sectional view of a portion of the end effector of FIG. 114 having the adjunct material releasably retained thereon;

FIG. 117 is a perspective, partially exploded view of an end effector having first and second adjunct materials releasably mounted thereon in accordance with the described techniques;

FIG. 118 is a perspective, partially exploded view of the end effector of FIG. 117, illustrating the first and second adjunct materials applied to a tissue in a patient;

FIG. 119 is a perspective view of an applicator member configured to apply the first and second adjunct materials to the end effector of FIG. 117;

FIG. 120 is a perspective, schematic view of a jaw of an end effector having recesses formed thereon that are configured to mate with portions of an adjunct material in accordance with the described techniques;

FIG. 121 is a perspective, schematic view of the jaw of FIG. 120 and of an applicator member configured to cause the portions of the adjunct material to be received in the recesses in the jaw;

FIG. 122 is a perspective, schematic view of the jaw of FIG. 120, illustrating the portions of the adjunct material received in the recesses in the jaw using the applicator member;

FIG. 123 is a perspective view of an end effector having an adjunct material releasably mounted thereon in accordance with the described techniques;

FIG. 124 is a cross-sectional view of a portion of the end effector of FIG. 123 having the adjunct material releasably retained thereon;

FIG. 125 is a perspective view of an end effector having an adjunct material releasably mounted thereon in accordance with the described techniques;

FIG. 126 is a perspective view of an applicator member configured to apply the adjunct material to the end effector of FIG. 125;

FIG. 127 is a cross-sectional view of a portion of the end effector of FIG. 125 having the adjunct material releasably retained thereon;

FIG. 128A is a perspective view of one embodiment of an applicator delivering a flowable adjunct precursor to a tissue;

FIG. 128B is a perspective view of another embodiment of an applicator delivering a flowable adjunct precursor to a tissue;

FIG. 128C is a perspective view of a mesh employed in combination with a flowable adjunct precursor delivered to a tissue;

FIG. 128D is a perspective view of a stapler engaging tissue having an adjunct formed from any of the adjunct precursor of FIGS. 128A-128C;

FIG. 128E is a perspective view illustrating the tissue and adjunct of FIG. 128D after delivery of a plurality of staples therethrough and the tissue is cut through the adjunct;

FIG. 129A is an expanded perspective view of another embodiment of an adjunct and a portion of an end effector of an adjunct delivery device configured to deliver the adjunct to a tissue treatment site;

FIG. 129B is a perspective view of a tissue after deposition of the adjunct thereon by the adjunct delivery device of FIG. 129A;

FIG. 130A is a perspective view of one embodiment of a stapler engaging the tissue and adjunct of FIG. 129B;

FIG. 130B is a perspective view of the tissue and adjunct of FIG. 129B after delivery of a plurality of staples therethrough;

FIG. 131A is a perspective view of a tissue and an alternative embodiment of an adjunct including a plurality of lateral flanges configured to guide a stapler with respect to the adjunct;

FIG. 131B is a perspective view of a stapler engaging the adjunct and the tissue of FIG. 131A;

FIG. 131C is a perspective view the adjunct and tissue of FIG. 8B after delivery of the plurality of staples therethrough and the tissue is cut through the adjunct;

FIG. 132A is an expanded perspective view of another embodiment of an adjunct system configured for use with a surgical stapler; and FIG. 132B is a perspective view of the adjunct system of FIG. 132A positioned on a tissue after delivery of a plurality of staples therethrough and the tissue is cut through the adjunct system.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

It can be desirable to use one or more biologic materials and/or synthetic materials, collectively referred to herein as "adjuncts" or "buttresses," in conjunction with surgical instruments to help improve surgical procedures. While a variety of different surgical end effectors can benefit from the use of adjuncts, in some exemplary embodiments the instrument can be a surgical stapler. When used in conjunction with a surgical stapler, the adjunct(s) can be disposed between and/or on jaws of the stapler, incorporated into a staple cartridge disposed in the jaws, or otherwise placed in proximity to the staples. When staples are deployed, the adjunct(s) can remain at the treatment site with the staples, in turn providing a number of benefits. For example, the adjunct(s) may reinforce tissue at the treatment site, preventing tearing or ripping by the staples at the treatment site. Tissue reinforcement may be needed to keep the staples from tearing through the tissue if the tissue is diseased, is healing from another treatment such as irradiation, medications such as chemotherapy, or other tissue property altering situation. In some instances, the adjunct(s) may minimize tissue movement in and around the staple puncture sites that can occur from tissue deformation that occurs after stapling (e.g., lung inflation, gastrointestinal tract distension, etc.). It will be recognized by one skilled in the art that a staple puncture site may serve as a stress concentration and that the size of the hole created by the staple will grow when the tissue around it is placed under tension. Restricting the tissues movement around these puncture sites can minimize the size the holes may grow to under tension. In some instances, the adjunct(s) can be configured to wick or absorb beneficial fluids, e.g., sealants, blood, glues, that further promote healing, and in some instances, the adjunct(s) can be configured to degrade to form a gel, e.g., a sealant, that further promotes healing. In some instances, the adjunct(s) can be used to help seal holes formed by staples as they are implanted into tissue, blood vessels, and various other objects or body parts. The adjunct(s) may also affect tissue growth through the spacing, positioning and/or orientation of any fibers or strands associated with the adjunct(s). Furthermore, in some circumstances, an adjunct can be useful in distributing pressure applied by the staple thereby reducing the possibility of a staple pulling through a tissue (which can be friable) and failing to fasten the tissue as intended (so-called "cheese wiring"). Additionally, the adjunct can be at least partially stretchable and can thus allow at least partial natural motion of the tissue (e.g., expansion and contraction of lung tissue during breathing) In some embodiments, a staple line can be flexible as described, for example, in U.S. Pat. Pub. No. 2016/0089142 entitled "Method for Creating a Flexible Staple Line," filed on Sep. 26, 2014, which is hereby incorporated by reference herein in its entirety.

Coupling an adjunct material to one or both jaws of an end effector can be tedious and time consuming for a user, which can undesirably prolong surgical procedures. Furthermore, surgical procedures can be prolonged when more than one adjunct material is applied to a jaw, such as for consecutive stapling with an adjunct material. As such, various adjunct frame embodiments are described herein that are configured to releasably attach an adjunct material thereto and to efficiently couple to a jaw of an end effector of a surgical instrument. The adjunct frames can thus provide an efficient way to couple an adjunct material to a jaw. The adjunct frames are also configured to release the adjunct material when desired, such as after the adjunct material has been cut by a knife of the end effector and/or after firing of staples by the end effector. The adjunct frames can release the adjunct material while maintaining coupling between the adjunct frame and the respective jaw. This can ensure that the frame is not left at the surgical site, which would require additional procedure time to retrieve the frame and could result in complications. Instead, the user can retract the end effector with the adjunct frame still attached, thereby allowing the user to reload the adjunct frame with another adjunct material or decouple the adjunct frame from the jaw.

Surgical Stapling Instruments

A variety of surgical instruments can be used in conjunction with the adjunct(s) and/or medicant(s) disclosed herein. "Adjuncts" are also referred to herein as "adjunct materials." The surgical instruments can include surgical staplers. A variety of surgical staplers can be used, for example linear surgical staplers and circular staplers. In general, a linear stapler can be configured to create longitudinal staple lines and can include elongate jaws with a cartridge coupled thereto containing longitudinal staple rows. The elongate jaws can include a knife or other cutting element capable of creating a cut between the staple rows along tissue held within the jaws. In general, a circular stapler can be configured to create annular staple lines and can include circular jaws with a cartridge containing annular staple rows. The circular jaws can include a knife or other cutting element capable of creating a cut inside of the rows of staples to define an opening through tissue held within the jaws. The staplers can be used in a variety of tissues in a variety of different surgical procedures, for example in thoracic surgery or in gastric surgery.

Figure 1:
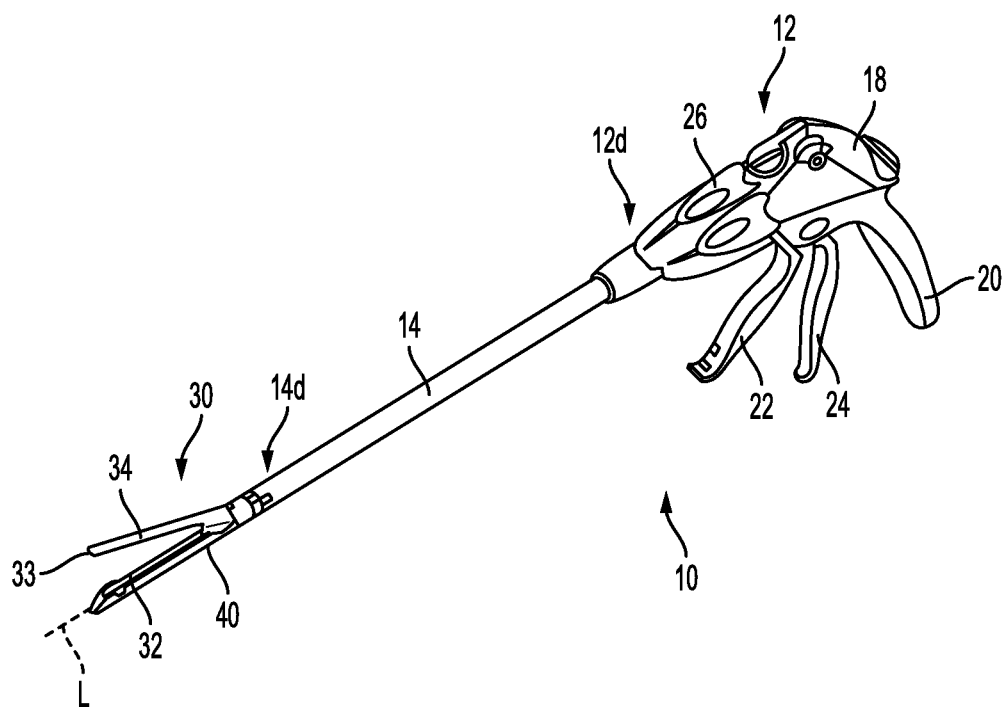
FIG. 1 is a perspective view of one embodiment of a surgical stapler.
Figure 2:
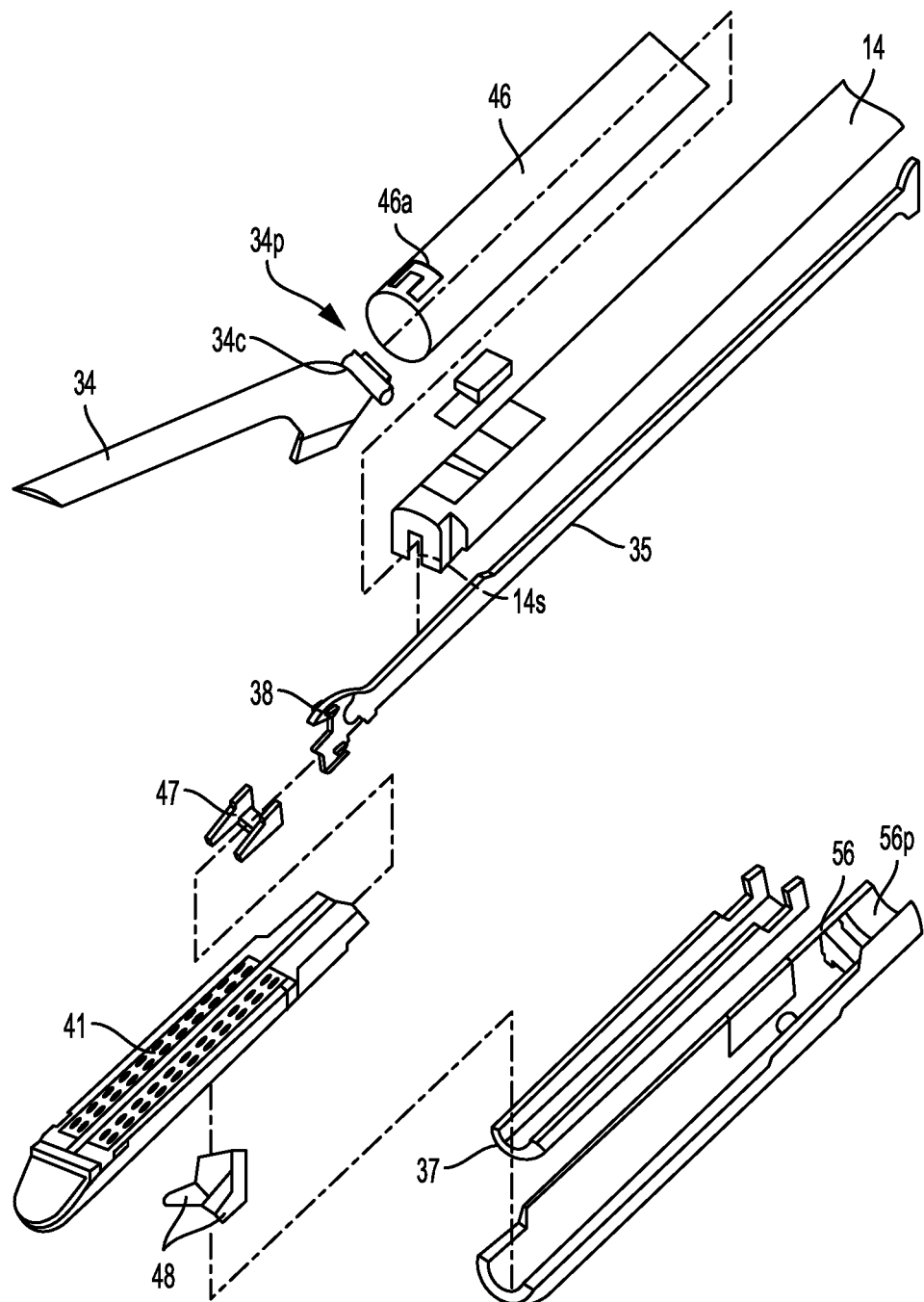
FIG. 2 is an exploded view of a distal portion of the surgical stapler of FIG. 1.

FIG. 1 illustrates one example of a linear surgical stapler 10 suitable for use with one or more adjunct(s) and/or medicant(s). The stapler 10 generally includes a handle assembly 12, a shaft 14 extending distally from a distal end 12d of the handle assembly 12, and an end effector 30 at a distal end 14d of the shaft 14. The end effector 30 has opposed lower and upper jaws 32, 34, although other types of end effectors can be used with the shaft 14, handle assembly 12, and components associated with the same. As shown in FIG. 2, the lower jaw 32 has a staple channel 56 (see FIG. 2) configured to support a staple cartridge 40, and the upper jaw 34 has an anvil surface 33 that faces the lower jaw 32 and that is configured to operate as an anvil to help deploy staples of the staple cartridge 40 (the staples are obscured in FIGS. 1 and 2). At least one of the opposed lower and upper jaws 32, 34 is moveable relative to the other lower and upper jaws 32, 34 to clamp tissue and/or other objects disposed therebetween. In some implementations, one of the opposed lower and upper jaws 32, 34 may be fixed or otherwise immovable. In some implementations, both of the opposed lower and upper jaws 32, 34 may be movable.

Components of a firing system can be configured to pass through at least a portion of the end effector 30 to eject the staples into the clamped tissue. In various implementations a knife blade 36 (see FIG. 3) or other cutting element can be associated with the firing system to cut tissue during the stapling procedure. The cutting element can be configured to cut tissue at least partially simultaneously with the staples being ejected. In some circumstances, it may be advantageous if the tissue is cut after the staples have been ejected and the tissue is secured. Thus, if a surgical procedure requires that a tissue captured between the jaws be severed, the knife blade 36 is advanced to sever the tissue grasped between the jaws after the staples have been ejected from the staple cartridge 40.

Operation of the end effector 30 can begin with input from a user, e.g., a clinician, a surgeon, etc., at the handle assembly 12. The handle assembly 12 can have many different configurations designed to manipulate and operate the end effector 30 associated therewith. In the illustrated example, the handle assembly 12 has a pistol-grip type housing 18 with a variety of mechanical and/or electrical components disposed therein to operate various features of the instrument 10. For example, the handle assembly 12 can include a rotation knob 26 mounted adjacent the distal end 12d thereof which can facilitate rotation of the shaft 14 and/or the end effector 30 with respect to the handle assembly 12 about a longitudinal axis L of the shaft 14. The handle assembly 12 can further include clamping components as part of a clamping system actuated by a clamping trigger 22 and firing components as part of the firing system that are actuated by a firing trigger 24. The clamping and firing triggers 22, 24 can be biased to an open position with respect to a stationary handle 20, for instance by a torsion spring. Movement of the clamping trigger 22 toward the stationary handle 20 can actuate the clamping system, described below, which can cause the jaws 32, 34 to collapse towards each other and to thereby clamp tissue therebetween. Movement of the firing trigger 24 can actuate the firing system, described below, which can cause the ejection of staples from the staple cartridge 40 disposed therein and/or the advancement the knife blade 36 to sever tissue captured between the jaws 32, 34. A person skilled in the art will recognize that various configurations of components for a firing system, mechanical, hydraulic, pneumatic, electromechanical, robotic, or otherwise, can be used to eject staples and/or cut tissue.

As shown in FIG. 2, the end effector 30 of the illustrated implementation has the lower jaw 32 that serves as a cartridge assembly or carrier and the opposed upper jaw 34 that serves as an anvil. The staple cartridge 40, having a plurality of staples therein, is supported in a staple tray 37, which in turn is supported within a cartridge channel of the lower jaw 32. The upper jaw 34 has a plurality of staple forming pockets (not shown), each of which is positioned above a corresponding staple from the plurality of staples contained within the staple cartridge 40. The upper jaw 34 can be connected to the lower jaw 32 in a variety of ways, although in the illustrated implementation the upper jaw 34 has a proximal pivoting end 34p that is pivotally received within a proximal end 56p of the staple channel 56, just distal to its engagement to the shaft 14. When the upper jaw 34 is pivoted downwardly, the upper jaw 34 moves the anvil surface 33 and the staple forming pockets formed thereon move toward the opposing staple cartridge 40.

Various clamping components can be used to effect opening and closing of the jaws 32, 34 to selectively clamp tissue therebetween. As illustrated, the pivoting end 34p of the upper jaw 34 includes a closure feature 34c distal to its pivotal attachment with the staple channel 56. Thus, a closure tube 46, whose distal end includes a horseshoe aperture 46a that engages the closure feature 34c, selectively imparts an opening motion to the upper jaw 34 during proximal longitudinal motion and a closing motion to the upper jaw 34 during distal longitudinal motion of the closure tube 46 in response to the clamping trigger 22. As mentioned above, in various implementations, the opening and closure of the end effector 30 may be effected by relative motion of the lower jaw 32 with respect to the upper jaw 34, relative motion of the upper jaw 34 with respect to the lower jaw 32, or by motion of both jaws 32, 34 with respect to one another.

Figure 3:
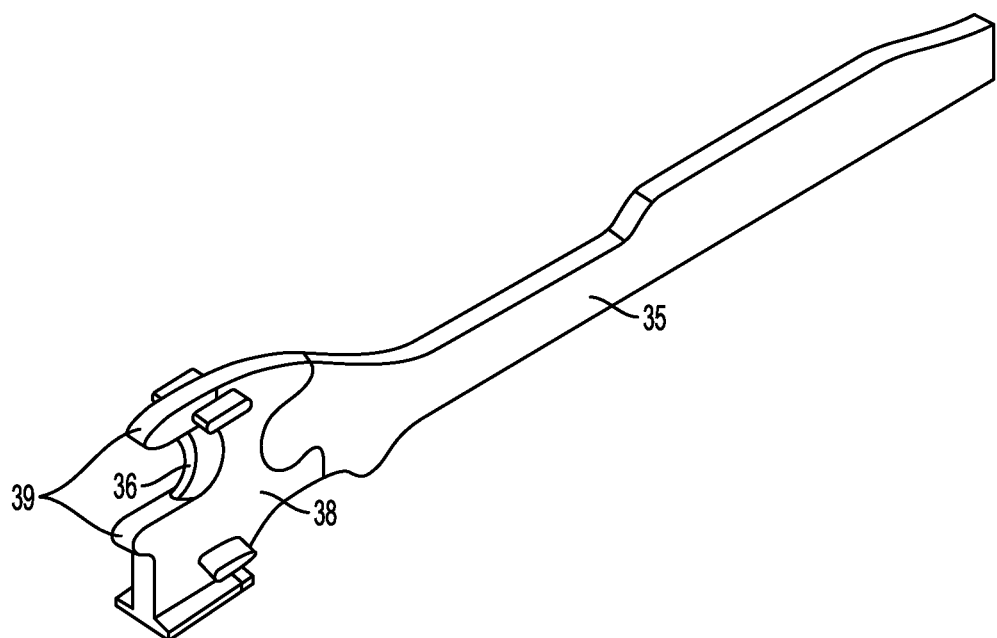
FIG. 3 is a perspective view of a firing bar of the surgical stapler of FIG. 1.

The firing components of the illustrated implementation includes a firing bar 35, as shown in FIG. 3, having an E-beam 38 on a distal end thereof. The firing bar 35 is encompassed within the shaft 14, for example in a longitudinal firing bar slot 14s of the shaft 14, and guided by a firing motion from the handle 12. Actuation of the firing trigger 24 can affect distal motion of the E-beam 38 through at least a portion of the end effector 30 to thereby cause the firing of staples contained within the staple cartridge 40. As illustrated, guides 39 projecting from a distal end of the E-Beam 38 can engage a wedge sled 47, shown in FIG. 2, which in turn can push staple drivers 48 upwardly through staple cavities 41 formed in the staple cartridge 40. Upward movement of the staple drivers 48 applies an upward force on each of the plurality of staples within the cartridge 40 to thereby push the staples upwardly against the anvil surface 33 of the upper jaw 34 and create formed staples.

In addition to causing the firing of staples, the E-beam 38 can be configured to facilitate closure of the jaws 32, 34, spacing of the upper jaw 34 from the staple cartridge 40, and/or severing of tissue captured between the jaws 32, 34. In particular, a pair of top pins and a pair of bottom pins can engage one or both of the upper and lower jaws 32, 34 to compress the jaws 32, 34 toward one another as the firing bar 35 advances through the end effector 30. Simultaneously, the knife 36 extending between the top and bottom pins can be configured to sever tissue captured between the jaws 32, 34.

In use, the surgical stapler 10 can be disposed in a cannula or port and disposed at a surgical site. A tissue to be cut and stapled can be placed between the jaws 32, 34 of the surgical stapler 10. Features of the stapler 10 can be maneuvered as desired by the user to achieve a desired location of the jaws 32, 34 at the surgical site and the tissue with respect to the jaws 32, 34. After appropriate positioning has been achieved, the clamping trigger 22 can be pulled toward the stationary handle 20 to actuate the clamping system. The clamping trigger 22 can cause components of the clamping system to operate such that the closure tube 46 advances distally through at least a portion of the shaft 14 to cause at least one of the jaws 32, 34 to collapse towards the other to clamp the tissue disposed therebetween. Thereafter, the firing trigger 24 can be pulled toward the stationary handle 20 to cause components of the firing system to operate such that the firing bar 35 and/or the E-beam 38 are advanced distally through at least a portion of the end effector 30 to effect the firing of staples and optionally to sever the tissue captured between the jaws 32, 34.

Figure 4:
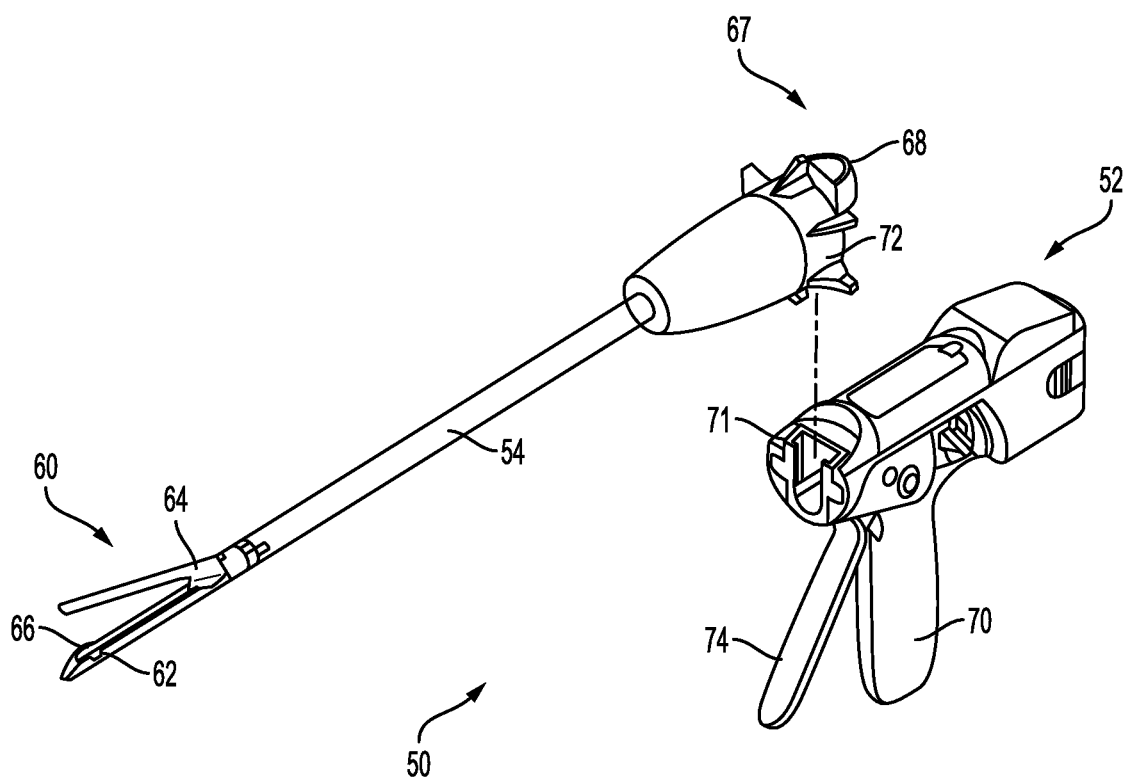
FIG. 4 is a perspective view of another embodiment of a surgical stapler having a modular shaft.

Another example of a surgical instrument in the form of a linear surgical stapler 50 is illustrated in FIG. 4. The stapler 50 can generally be configured and used similar to the stapler 10 of FIG. 1. Similar to the surgical instrument 10 of FIG. 1, the surgical instrument 50 includes a handle assembly 52 with a shaft 54 extending distally therefrom and having an end effector 60 on a distal end thereof for treating tissue. Upper and lower jaws 64, 62 of the end effector 60 can be configured to capture tissue therebetween, staple the tissue by firing of staples from a cartridge 66 disposed in the lower jaw 62, and/or to create an incision in the tissue. In this implementation, an attachment portion 67 on a proximal end of the shaft 54 can be configured to allow for removable attachment of the shaft 54 and the end effector 60 to the handle assembly 52. In particular, mating features 68 of the attachment portion 67 can mate to complementary mating features 71 of the handle assembly 52. The mating features 68, 71 can be configured to couple together via, e.g., a snap fit coupling, a bayonet type coupling, etc., although any number of complementary mating features and any type of coupling can be used to removably couple the shaft 54 to the handle assembly 52. Although the entire shaft 54 of the illustrated implementation is configured to be detachable from the handle assembly 52, in some implementations, the attachment portion 67 can be configured to allow for detachment of only a distal portion of the shaft 54. Detachable coupling of the shaft 54 and/or the end effector 60 can allow for selective attachment of a desired end effector 60 for a particular procedure, and/or for reuse of the handle assembly 52 for multiple different procedures.

The handle assembly 52 can have one or more features thereon to manipulate and operate the end effector 60. By way of non-limiting example, a rotation knob 72 mounted on a distal end of the handle assembly 52 can facilitate rotation of the shaft 54 and/or the end effector 60 with respect to the handle assembly 52. The handle assembly 52 can include clamping components as part of a clamping system actuated by a movable trigger 74 and firing components as part of a firing system that can also be actuated by the trigger 74. Thus, in some implementations, movement of the trigger 74 toward a stationary handle 70 through a first range of motion can actuate clamping components to cause the opposed jaws 62, 64 to approximate toward one another to a closed position. In some implementations, only one of the opposed jaws 62, 24 can move to move the jaws 62, 64 to the closed position. Further movement of the trigger 74 toward the stationary handle 70 through a second range of motion can actuate firing components to cause the ejection of the staples from the staple cartridge 66 and/or the advancement of a knife or other cutting element (not shown) to sever tissue captured between the jaws 62, 64.

Figure 5:
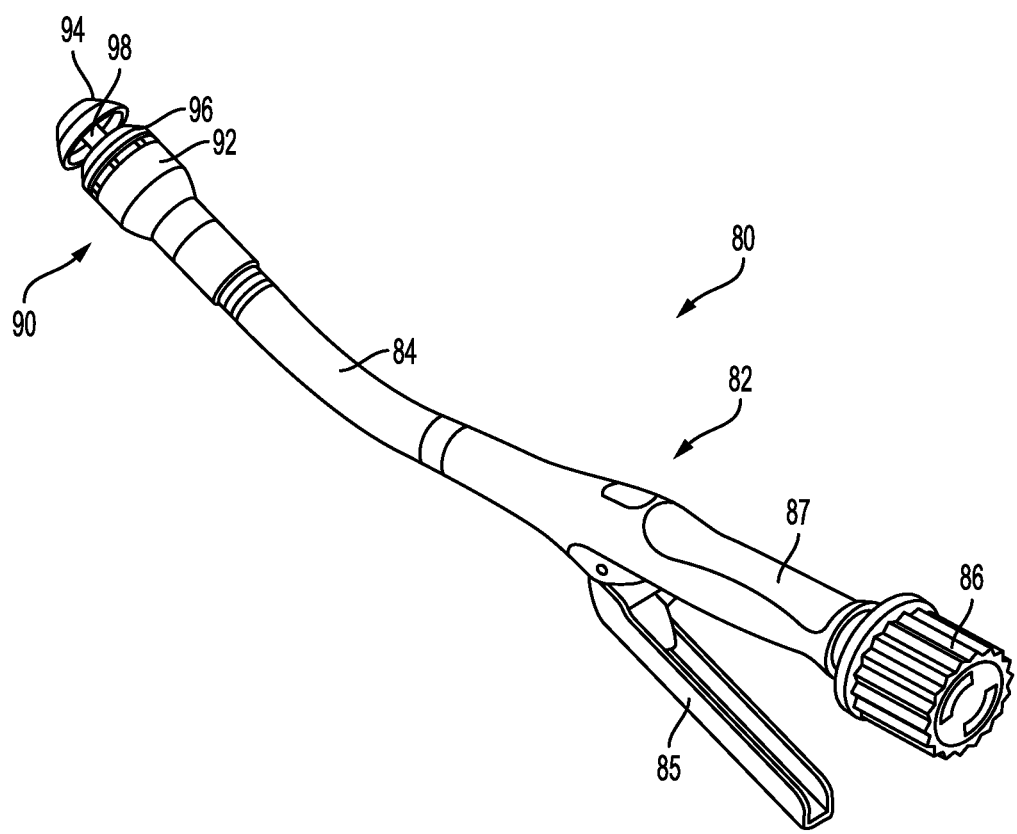
FIG. 5 is a perspective view of an embodiment of a circular surgical stapler.

One example of a surgical instrument in the form of a circular surgical stapler 80 is illustrated in FIG. 5. The stapler 80 can generally be configured and used similar to the linear staplers 10, 50 of FIGS. 1 and 4, but with some features accommodating its functionality as a circular stapler. Similar to the surgical instruments 10, 50, the surgical instrument 80 includes a handle assembly 82 with a shaft 84 extending distally therefrom and having an end effector 90 on a distal end thereof for treating tissue. The end effector 90 can include a cartridge assembly 92 and an anvil 94, each having a tissue-contacting surface that is substantially circular in shape. The cartridge assembly 92 and the anvil 94 can be coupled together via a shaft 98 extending from the anvil 94 to the handle assembly 82 of the stapler 80, and manipulating an actuator 85 on the handle assembly 82 can retract and advance the shaft 98 to move the anvil 94 relative to the cartridge assembly 92. The anvil 94 and cartridge assembly 92 can perform various functions and can be configured to capture tissue therebetween, staple the tissue by firing of staples from a cartridge 96 of the cartridge assembly 92 and/or can create an incision in the tissue. In general, the cartridge assembly 92 can house a cartridge containing the staples and can deploy staples against the anvil 94 to form a circular pattern of staples, e.g., staple around a circumference of a tubular body organ.

In one implementation, the shaft 98 can be formed of first and second portions (not shown) configured to releasably couple together to allow the anvil 94 to be detached from the cartridge assembly 92, which may allow greater flexibility in positioning the anvil 94 and the cartridge assembly 92 in a body of a patient. For example, the first portion of the shaft 98 can be disposed within the cartridge assembly 92 and extend distally outside of the cartridge assembly 92, terminating in a distal mating feature. The second portion of the shaft 98 can be disposed within the anvil 94 and extend proximally outside of the cartridge assembly 92, terminating in a proximal mating feature. In use, the proximal and distal mating features can be coupled together to allow the anvil 94 and cartridge assembly 92 to move relative to one another.

The handle assembly 82 of the stapler 80 can have various actuators disposed thereon that can control movement of the stapler. For example, the handle assembly 82 can have a rotation knob 86 disposed thereon to facilitate positioning of the end effector 90 via rotation, and/or the trigger 85 for actuation of the end effector 90. Movement of the trigger 85 toward a stationary handle 87 through a first range of motion can actuate components of a clamping system to approximate the jaws, i.e. move the anvil 94 toward the cartridge assembly 92. Movement of the trigger 85 toward the stationary handle 87 through a second range of motion can actuate components of a firing system to cause the staples to deploy from the staple cartridge assembly 92 and/or cause advancement of a knife to sever tissue captured between the cartridge assembly 92 and the anvil 94.

The illustrated examples of surgical stapling instruments 10, 50, 80 provide only a few examples of many different configurations, and associated methods of use, that can be used in conjunction with the disclosures provided herein. Although the illustrated examples are all configured for use in minimally invasive procedures, it will be appreciated that instruments configured for use in open surgical procedures, e.g., open linear staplers as described in U.S. Pat. No. 8,317,070 entitled "Surgical Stapling Devices That Produce Formed Staples Having Different Lengths" and filed Feb. 28, 2007, can be used in conjunction with the disclosures provided herein. Greater detail on the illustrated examples, as well as additional examples of surgical staplers, components thereof, and their related methods of use, are provided in U.S. Pat. Pub. No. 2015/0277471 entitled "Systems And Methods For Controlling A Segmented Circuit" and filed Mar. 26, 2014, U.S. Pat. Pub. No. 2013/0256377 entitled "Layer Comprising Deployable Attachment Members" and filed Feb. 8, 2013, U.S. Pat. No. 8,393,514 entitled "Selectively Orientable Implantable Fastener Cartridge" and filed Sep. 30, 2010, U.S. Pat. No. 8,317,070 entitled "Surgical Stapling Devices That Produce Formed Staples Having Different Lengths" and filed Feb. 28, 2007, U.S. Pat. No. 7,143,925 entitled "Surgical Instrument Incorporating EAP Blocking Lockout Mechanism" and filed Jun. 21, 2005, U.S. Pat. Pub. No. 2015/0134077 entitled "Sealing Materials For Use In Surgical Stapling" and filed Nov. 8, 2013, entitled "Sealing Materials for Use in Surgical Procedures, and filed on Nov. 8, 2013, U.S. Pat. Pub. No. 2015/0134076, entitled "Hybrid Adjunct Materials for Use in Surgical Stapling," and filed on Nov. 8, 2013, U.S. Pat. Pub. No. 2015/0133996, entitled "Positively Charged Implantable Materials and Method of Forming the Same," and filed on Nov. 8, 2013, U.S. Pat. Pub. No. 2015/0129634, entitled "Tissue Ingrowth Materials and Method of Using the Same," and filed on Nov. 8, 2013, U.S. Pat. Pub. No. 2015/0133995, entitled "Hybrid Adjunct Materials for Use in Surgical Stapling," and filed on Nov. 8, 2013, U.S. Pat. Pub. No. 2015/0272575, entitled "Surgical Instrument Comprising a Sensor System," and filed on Mar. 26, 2014, and U.S. Pat. Pub. No. 2015/0351758, entitled "Adjunct Materials and Methods of Using Same in Surgical Methods for Tissue Sealing," and filed on Jun. 10, 2014, which are hereby incorporated by reference herein in their entireties.

Implantable Adjuncts

As indicated above, various implantable adjuncts are provided for use in conjunction with surgical stapling instruments. The adjuncts can have a variety of configurations, and can be formed from various materials. In general, an adjunct can be formed from one or more of a film, a foam, an injection molded thermoplastic, a vacuum thermoformed material, a fibrous structure, and hybrids thereof. The adjunct can also include one or more biologically-derived materials and one or more drugs. Each of these materials is discussed in more detail below.

An adjunct can be formed from a foam, such as a closed-cell foam, an open-cell foam, or a sponge. An example of how such an adjunct can be fabricated is from animal derived collagen, such as porcine tendon, that can then be processed and lyophilized into a foam structure. Gelatin can also be used and processed into a foam. Examples of various foam adjuncts are further described in previously mentioned U.S. Pat. No. 8,393,514 entitled "Selectively Orientable Implantable Fastener Cartridge" and filed Sep. 30, 2010.

An adjunct can also be formed from a film formed from any suitable material or combination thereof discussed below. The film can include one or more layers, each of which can have different degradation rates. Furthermore, the film can have various regions formed therein, for example, reservoirs that can releasably retain therein one or more medicants in a number of different forms. The reservoirs having at least one medicant disposed therein can be sealed using one or more different coating layers which can include absorbable or non-absorbable polymers. The film can be formed in various ways. For example, it can be an extruded or a compression molded film. The medicants can also be absorbed onto the film or bound to the film via non-covalent interactions such as hydrogen bonding.

An adjunct can also be formed from injection molded thermoplastic or a vacuum thermoformed material. Examples of various molded adjuncts are further described in U.S. Pat. Pub. No. 2013/0221065 entitled "Fastener Cartridge Comprising A Releasably Attached Tissue Thickness Compensator" and filed Feb. 8, 2013, which is hereby incorporated by reference in its entirety. The adjunct can also be a fiber-based lattice which can be a woven fabric, knitted fabric or non-woven fabric such as a melt-blown, needle-punched or thermal-constructed loose woven fabric. An adjunct can have multiple regions that can be formed from the same type of lattice or from different types of lattices that can together form the adjunct in a number of different ways. For example, the fibers can be woven, braided, knitted, or otherwise interconnected so as to form a regular or irregular structure. The fibers can be interconnected such that the resulting adjunct is relatively loose. Alternatively, the adjunct can include tightly interconnected fibers. The adjunct can be in a form of a sheet, tube, spiral, or any other structure that can include compliant portions and/or more rigid, reinforcement portions. The adjunct can be configured such that certain regions thereof can have more dense fibers while others have less dense fibers. The fiber density can vary in different directions along one or more dimensions of the adjunct, based on an intended application of the adjunct.

The adjunct can be formed from woven, knitted, or otherwise interconnected fibers, which allows the adjunct to be stretched. For example, the adjunct can be configured to stretch in a direction along its longitudinal axis and/or in a lateral direction that is perpendicular to the longitudinal axis. While being stretchable in at least two dimensions (e.g., X and Y directions), the adjunct can provide reinforcement along its thickness (e.g., a Z direction) such that it stretches but resists tearing and pull-through by the staples. Non-limiting examples of adjuncts that are configured to be implanted such that they can stretch with the tissue are described in the above-mentioned U.S. Pat. Pub. No. 2016/0089142 entitled "Method for Creating a Flexible Staple Line," filed on Sep. 26, 2014, which is hereby incorporated by reference herein in its entirety.

The adjunct can also be a hybrid construct, such as a laminate composite or melt-locked interconnected fiber. Examples of various hybrid construct adjuncts are further described in U.S. Pat. No. 9,282,962 entitled "Adhesive Film Laminate" and filed Feb. 8, 2013, and in U.S. Pat. No. 7,601,118 entitled "Minimally Invasive Medical Implant And Insertion Device And Method For Using The Same" and filed Sep. 12, 2007, which are hereby incorporated by reference in their entireties.

The adjuncts in accordance with the described techniques can be formed from various materials. The materials can be used in various embodiments for different purposes. The materials can be selected in accordance with a desired therapy to be delivered to tissue so as to facilitate tissue ingrowth. The materials can include bioabsorbable and biocompatible polymers, including homopolymers and copolymers. Bioabsorbable polymers can be absorbable, resorbable, bioresorbable, or biodegradable polymers.

An adjunct can also include active agents, such as active cell culture (e.g., diced autologous tissue, agents used for stem cell therapy (e.g., Biosutures and Cellerix S.L.), hemostatic agents, and tissue healing agents.

The adjuncts can releasably retain therein at least one medicant that can be selected from a large number of different medicants. Medicants include, but are not limited to, drugs or other agents included within, or associated with, the adjunct that have a desired functionality. The medicants include, but are not limited to, for example, antimicrobial agents such as antibacterial and antibiotic agents, antifungal agents, antiviral agents, anti-inflammatory agents, growth factors, analgesics, anesthetics, tissue matrix degeneration inhibitors, anti-cancer agents, hemostatic agents, and other agents that elicit a biological response. The adjuncts can also be made from or include agents that enhance visibility during imaging, such as, for example, echogenic materials or radio-opaque materials.

Examples of various adjuncts and various techniques for releasing medicants from adjuncts are further described in U.S. patent application Ser. No. 14/840,613 entitled "Medicant Eluting Adjuncts and Methods of Using Medicant Eluting Adjuncts" and filed Aug. 31, 2015, which is hereby incorporated by reference in its entirety.

Surgical End Effector Adjunct Attachment

Various exemplary devices, systems and methods for releasably retaining an adjunct material on an end effector of a surgical instrument are described herein. In a typical surgical stapler end effector, the anvil has a preconfigured set of staple pockets formed therein and configured to receive and form staples fired from the cartridge. As a result, the end effector can only be used with staple cartridges having staple cavities that align with the anvil. Accordingly, in an exemplary embodiment, various anvil plates are provided having varying staple pocket configurations for use with different staple cartridges. The anvil plate can mate to the upper jaw of an end effector, and a cartridge designed for use with that particular anvil plate can be inserted into the lower jaw of the end effector. As such, the end effector can create a variety of staple configurations by switching out the anvil assembly and/or cartridge. Furthermore, adjunct materials can be releasably secured to either the cartridge or anvil plate using one or more restraining elements. For example, the adjunct materials can be pre-attached to the anvil plate and/or the cartridge (e.g., during manufacturing) and can be released from the anvil plate and/or cartridge during firing of the end effector (e.g., advancing a knife along the end effector to fire staples and cut tissue, adjunct material, and any restraining elements), as will be described in greater detail below.

Figure 6:
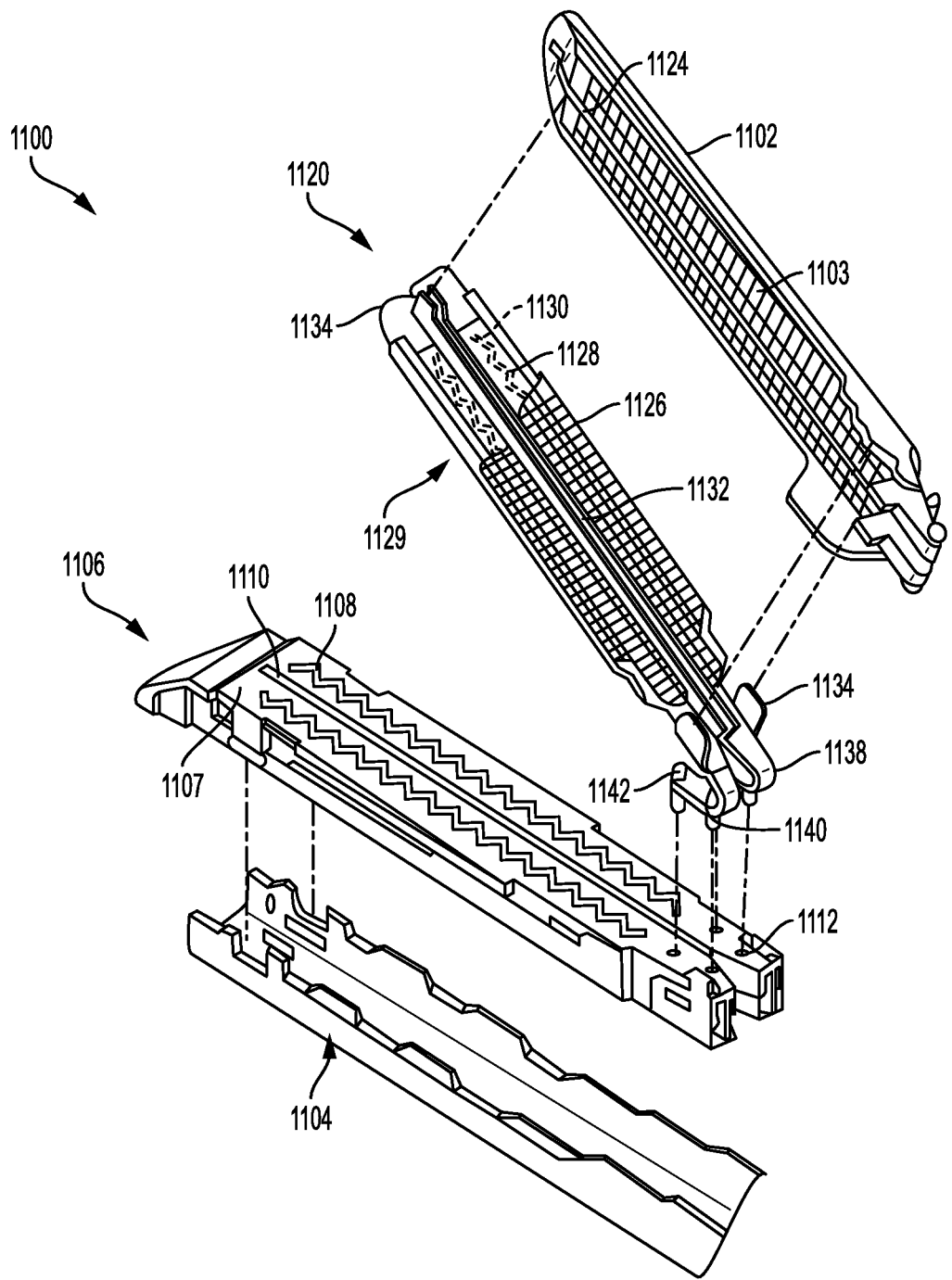
FIG. 6 is a partially exploded view of an end effector including a pair of opposed jaws and a cartridge.

FIG. 6 illustrates one embodiment of an end effector 1100 including upper and lower jaws 1102, 1104, respectively, that can pivot between open and closed configurations. As shown in FIG. 6, a staple cartridge 1106 can be configured to releasably couple to the lower jaw member 1104, and can include staple cavities 1108 having staples disposed therein. The upper jaw 1102 can be in the form of an anvil having staple pockets 1103 formed therein and configured to receive and form staples fired from the cartridge 1106. Both the upper jaw 1102 and cartridge 1106 can include knife slots 1124, 1110, respectively, configured to allow a knife to advance therealong.

As shown in FIG. 6, an anvil assembly 1120 can be configured to releasably couple to an inward tissue-facing surface 1107 of the cartridge 1106 and/or an inward-facing surface 1103 of the upper jaw 1102. The anvil assembly 1120 can include an anvil plate 1128 having a rectangular shape that can extend along either the upper jaw 1102 or cartridge 1106. The anvil plate 1128 can include an anvil adapter 1126 along an outward-facing surface of the anvil plate 1128. The anvil adapter 1126 can include plate features configured to mate with jaw features along the inward-facing surface 1103 of the upper jaw 1102 (see, for example, FIG. 11) thereby assisting with securing the alignment between the anvil plate 1128 and the upper jaw 1102. The anvil plate 1128 can further include staple pockets 1130 (shown as imprints along an outward-facing surface of the anvil plate 1128) that are recessed along an inward tissue-facing surface 1129 of the anvil plate 1128. The staple pockets 1130 can be arranged along the anvil plate 1128 such that each staple pocket 1130 corresponds to a staple cavity 1108 of the cartridge 1106 for assisting with forming the staples (e.g., stapling tissue together and/or adjunct to tissue). The anvil plate 1128 can include a knife channel 1132 that extends longitudinally along the anvil plate 1128 and that is configured to allow a knife to advance therealong.

In some embodiments, the anvil plate 1128 can include one or more alignment features 1134 that can assist with maintaining alignment between the anvil plate 1128 and the upper jaw 1102. For example, as shown in FIG. 6, the anvil plate 1128 can include proximal and distal alignment features 1134 that extend upward from the outward-facing surface of the anvil plate 1128 toward the upper jaw 1102. The alignment features 1134 can be configured as tabs that mate with one or more recesses, slots, through-holes, etc., in the upper jaw 1102. Depending on the configuration of the upper jaw 1102, the alignment features 1134 may slide longitudinally within the recesses, slots, through holes, etc., of the upper jaw 1102 as the jaw members move between the open and closed positions thus maintaining alignment between the anvil plate 1128 and the upper jaw 1102 during opening and closing of the jaws. Additionally, the alignment features 1134 can function to maintain alignment between the anvil plate 1128 and the cartridge 1106. Proper alignment between the anvil plate 1128 and the cartridge 1106 ensures that staples contact staple pockets 1130, and form properly, when fired from the cartridge 1106.

As shown in FIG. 6, the anvil assembly 1120 can also include one or more attachment features 1138 for coupling the anvil plate 1128 to the cartridge 1106, such as to the inward tissue-facing surface 1107 of the cartridge 1106. In some embodiments, as shown in FIG. 6, the attachment features 1138 can include at least one bracket. The bracket can extend between the anvil plate 1128 and cartridge 1106 and can allow the anvil plate 1128 to pivot (e.g., along with the upper jaw) between an open and closed configuration relative to the cartridge 1106. In some embodiments, the attachment features 1138 can function as a hinge and biasing element that biases the anvil plate 1128 to the open configuration thereby allowing the anvil plate 1128 to pivot and follow the upper jaw 1102 when the jaws open.

The attachment features 1138 of the anvil assembly 1120, and the inward tissue-facing surface 1107 of the cartridge 1106, can include coupling features 1140, 1112, respectively. The coupling features 1140, 1112 can be in the form of through-holes that enable, for example, pins 1142, rivets, or similar features, to extend therethrough and connect the coupling features 1140 of the anvil assembly 1120 to the coupling features 1112 on the cartridge 1106. This configuration allows the anvil plate 1128 and cartridge 1106 to be releasably coupled together thereby allowing the end effector to provide various stapling configurations by switching out either the cartridge 1106 or anvil plate 1128. As such, the replaceable cartridge 1106 and anvil assembly 1120 can provide an advantage over end effectors that are, for example, limited to the configuration of the staple pockets in the anvil.

Furthermore, it can be desirable for an end effector to include features and/or components that facilitate releasable attachment of an adjunct to the end effector. For example, an adjunct can be attached, including pre-attached during manufacturing or prior to a surgical procedure, to the end effector using a restraining element, such as a suture. In one embodiment, the suture can be elongated and made out of, for example, a thermoplastic such as polydioxanone (PDS), an elastic material, and/or any other biocompatible material suitable for securing the adjunct to the end effector. In some embodiments, the restraining element can be continuous or non-continuous with opposing ends of the restraining element anchored to a part of the anvil assembly and/or cartridge. When the stapler is fired, staples can fire through the tissue and adjunct toward the anvil to be formed. A knife can travel through knife channels in the cartridge, anvil plate, and upper jaw thereby cutting the restraining element and releasing the adjunct from the end effector to allow the adjunct to remain at the surgical site.

Figure 7:
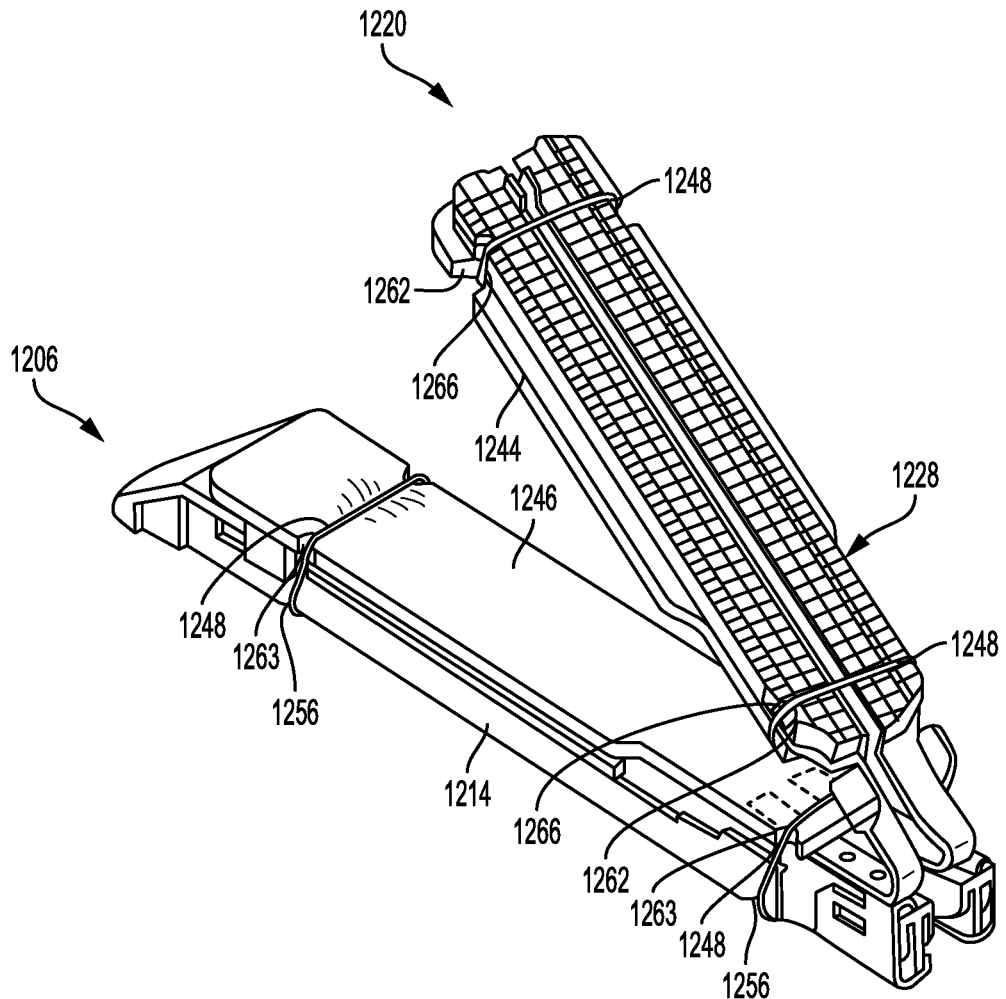
FIG. 7 is a perspective view of another embodiment of an end effector having an anvil assembly coupled to a cartridge with an adjunct secured to the anvil assembly and an adjunct secured to the cartridge.

FIG. 7 illustrates an anvil assembly 1220 releasably coupled to a cartridge 1206 with a first adjunct material 1244 coupled to an inward tissue-facing surface of an anvil plate 1228 of an anvil assembly 1220, and a second adjunct material 1246 coupled to an inward tissue-facing surface of the cartridge 1206. The first and second adjuncts 1244, 1246 can each be secured to the anvil assembly 1220 and cartridge 1206, respectively, using one or more restraining elements or sutures 1248. Each suture 1248 can extend around the first adjunct 1244 and anvil plate 1228 or around the second adjunct 1246 and cartridge 1206, thereby securing the first or second adjuncts 1244, 1246 to the respective anvil plate 1228 or cartridge 1206.

As shown in FIG. 7, the cartridge 1206 and/or a cartridge pan 1214 (coupled to the cartridge 1206) can include one or more cartridge notches 1256, and the anvil plate 1228 of the anvil assembly 1220 can include one or more anvil notches 1266. For example, the notches 1256, 1266 can be shaped as curved recesses and can be configured to allow a part of the suture 1248 to sit therein for maintaining a position of the suture 1248 relative to either the anvil plate 1228 or cartridge 1206. The notches 1256, 1266 can thus assist with preventing the suture 1248 from slipping and unsecuring a position of either the first or second adjunct 1244, 1246 relative to the anvil plate or cartridge, respectively.

For example, the first adjunct 1244 can be secured to an inward tissue-facing surface of the anvil plate 1228 by a pair of sutures 1248 (e.g., one suture 1248 positioned adjacent at a distal end of the anvil plate 1228 and one suture 1248 positioned adjacent a proximal end of the anvil plate 1228) that wrap around the first adjunct 1244 and anvil plate 1228. As shown in FIG. 7, portions of the proximally and distally positioned sutures 1248 can be positioned in anvil notches 1266 along a side of the anvil plate 1228. The notches 1266 can prevent the sutures 1248 from shifting or slipping longitudinally along the anvil plate 1228, thereby ensuring that the sutures 1248 secure the first adjunct to the anvil plate 1228.

Similarly, the second adjunct 1246 can be secured to an inward tissue-facing surface of the cartridge 1206 by a pair of sutures 1248 (e.g., one suture 1248 positioned adjacent a distal end of the cartridge 1206 and one suture 1248 positioned adjacent a proximal end of the cartridge 1206) that wrap around the second adjunct 1246 and cartridge 1206. As shown in FIG. 7, portions of the proximally and distally positioned sutures 1248 can be positioned in cartridge notches 1256 along a side of the cartridge 1206 and/or cartridge pan 1214. The cartridge notches 1256 can prevent the sutures 1248 from shifting or slipping longitudinally along the cartridge 1206 thereby ensuring that the sutures 1248 secure the second adjunct 1246 to the cartridge 1206.

As shown in FIG. 7, the first adjunct 1244 can include first adjunct notches 1262 along opposing sides of the first adjunct 1244, and the second adjunct 1246 can include second adjunct notches 1263 along opposing sides of the second adjunct 1246. The first and second adjuncts 1244, 1246 can be made of the same material, or they can be made of different materials. The first adjunct notches 1262 can be positioned along the first adjunct 1244 such that first adjunct notches 1262 align with the anvil notches 1266 when the first adjunct 1244 is properly aligned with the anvil plate 1228 (e.g., the adjunct surface area of the first adjunct covers the inward tissue-facing surface of the anvil plate 1228). As such, when the suture 1248 extends around the first adjunct 1244 and anvil plate 1228 and along the first adjunct notches 1262 and anvil notches 1266, the suture 1248 secures a desired positioning between the first adjunct 1244 and the anvil plate 1228. Similarly, the second adjunct notches 1263 can be positioned along the second adjunct 1246 such that the second adjunct notches 1263 align with the cartridge notches 1256 when the second adjunct 1246 is properly aligned with the cartridge 1206 (e.g., the second adjunct surface area of the second adjunct covers the inward tissue-facing surface of the cartridge 1206). As such, when the suture 1248 extends around the second adjunct 1246 and cartridge 1206 and along the second adjunct notches 1263 and cartridge notches 1256, the suture 1248 secures a desired positioning between the second adjunct 1246 and the cartridge 1206. Each of the sutures 1248 can be made of the same material, or one or more of the sutures 1248 can be made of a different material.

Although the cartridge notches 1256, anvil notches 1266, and first and second adjunct notches 1262, 1263 are shown as U-shaped cutouts, any one of the cartridge notches 1256, anvil notches 1266, and first and second adjunct notches 1262, 1263 can have any number of shapes and/or sizes that allow a part of suture to extend therealong for securing the suture in position relative to either the anvil plate 1228 or cartridge 1206. For example, any one of the cartridge notches 1256, anvil notches 1266, and first and second adjunct notches 1262, 1263 can be V-shaped, squared, or any other geometry. Furthermore, any number of notches (e.g., cartridge notches 1256, anvil notches 1266, and first and second adjunct notches 1262, 1263) and lengths of suture 1248 can be used to secure the position of either the first or second adjuncts 1244, 1246. Alternatively, rather than notches 1256, 1266, the cartridge 1206, cartridge pan 1214, and/or the anvil plate 1228, can include holes through which sutures 1248 can be threaded. Similarly, the adjuncts 1244, 1246 can include holes that align with holes on the cartridge 1206, cartridge pan 1214, and/or anvil plate 1228. Sutures can be threaded through the holes in the adjuncts 1244, 1246 and through the holes in the cartridge 1206, cartridge pan 1214, and/or the anvil plate 1228, to retain the adjuncts 1244, 1246 on inward tissue-facing surfaces of the cartridge 1206 and the anvil plate 1228.

In some embodiments, it can be desirable to angle a suture extending around the adjunct material and cartridge to ensure that the adjunct is detached from the cartridge after at least one staple has been deployed (e.g., thereby securing the adjunct to the tissue).

Figure 8:
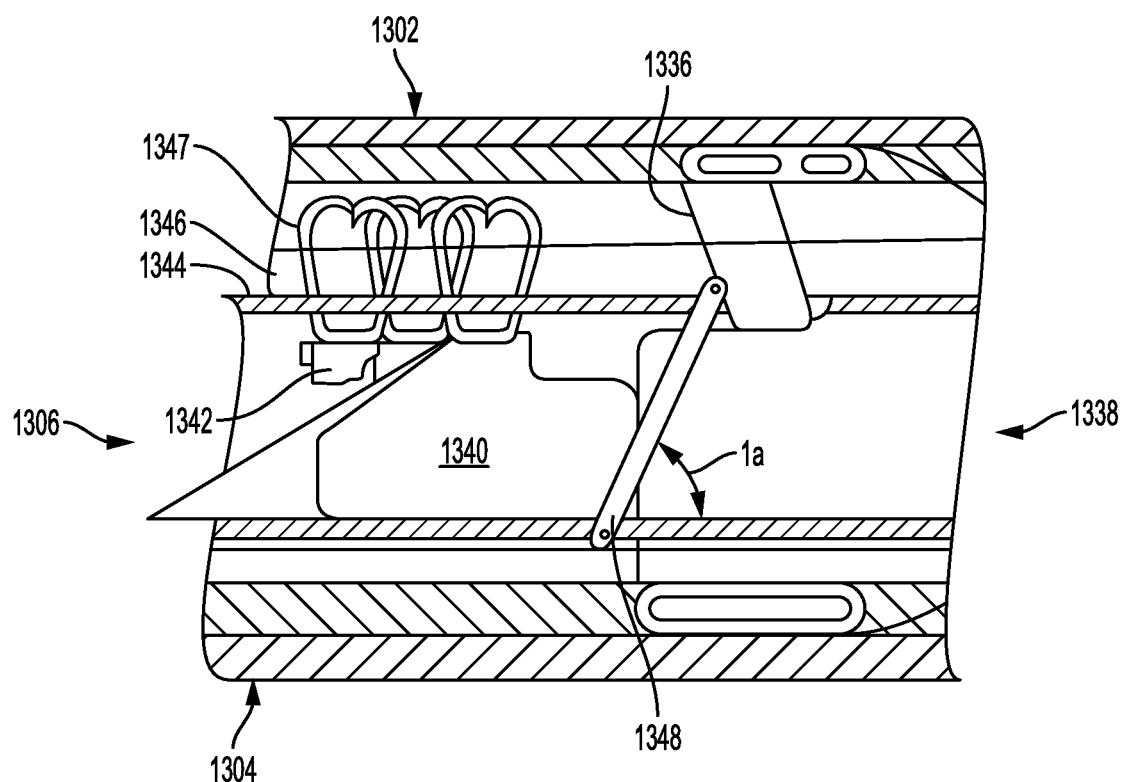
FIG. 8 is a cross-sectional view of one embodiment of an end effector having an adjunct material secured to a cartridge with a suture that extends around the cartridge.

FIG. 8 illustrates upper and lower jaws 1302, 1304 in a closed configuration, clamped around tissue 1346, with an adjunct 1344 secured to an inward tissue-facing surface of a cartridge 1306 that is seated within the lower jaw 1304. As shown in FIG. 8, the adjunct 1344 is secured to the cartridge 1306 using a suture 1348 that extends around the adjunct 1344 and cartridge 1306 at an angle (la). For example, the suture 1348 can extend along the adjunct 1344 at a location proximal to the location at which the suture 1348 extends around the back side of the cartridge 1306. As such, as shown in FIG. 8, a side view of the suture 1348 extending around the adjunct 1344 and cartridge 1306 shows the suture 1348 extending at an angle (la) across the side of the cartridge 1306. As illustrated in FIG. 8, a knife 1338 can be configured to advance along the cartridge 1306 to cut the tissue 1346, suture, 1348, and adjunct 1344, using a knife blade 1336. The knife 1338 can also be configured to drive staples 1347 from the cartridge 1306 as it advances along the cartridge 1306. As the knife advances along the length of the cartridge 1306, it can push a wedge sled 1340, which can push staple drivers 1342 that hold staples 1347 in a tissue-facing direction to form the staples 1347. The angling of the suture 1348 can ensure that the suture 1348 is in a position to be cut without being stapled to the tissue 1346. The angled suture 1348 can be positioned such that the knife blade 1336 is the first part of the knife 1338 that contacts the suture 348 in order to cause the angled suture 1348 to be cut approximately upon contact with the knife 1338.

Alternatively or in addition to using continuous restraining elements, such as continuous sutures or lengths of suture that couple end to end, one or more non-continuous restraining elements that anchor opposing ends of the restraining elements to components of the cartridge and/or anvil assembly can be used.

Figure 9A:
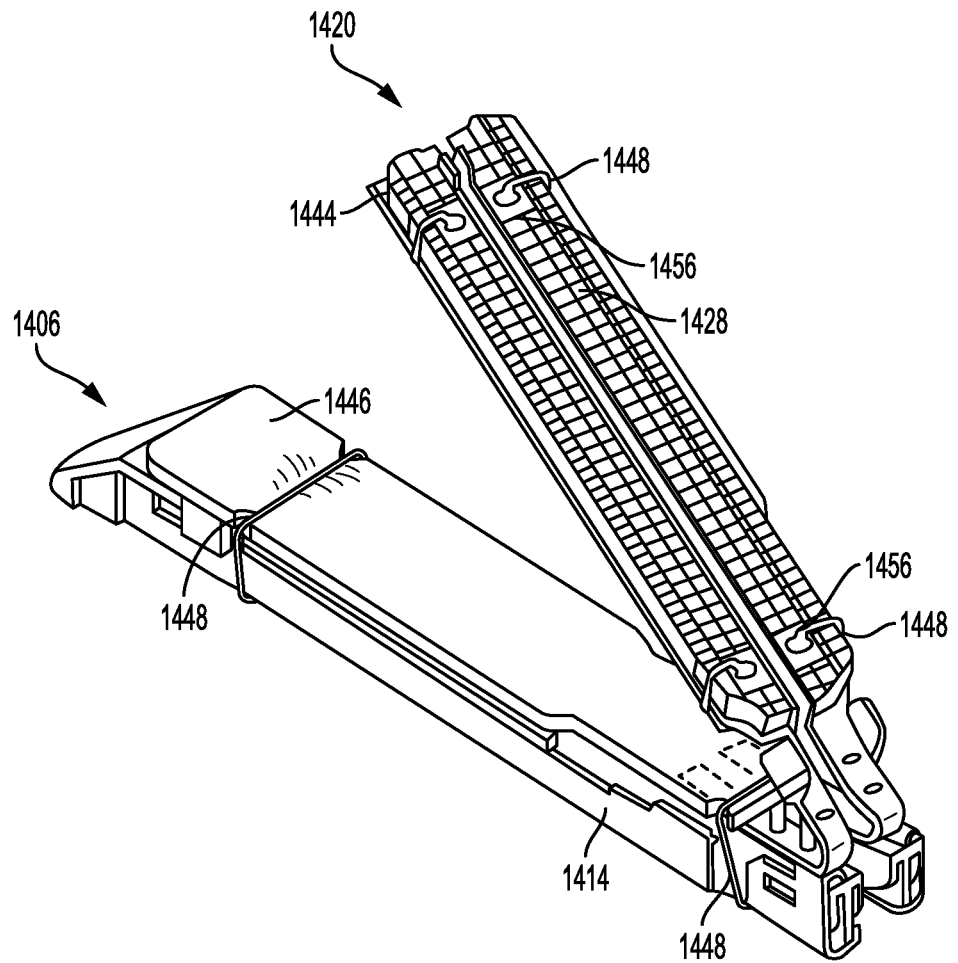
FIG. 9A is a perspective view of another embodiment of an end effector having an anvil assembly coupled to a cartridge with an adjunct secured to an anvil plate of the anvil assembly and an adjunct secured to the cartridge using at least one suture.
Figure 9B:
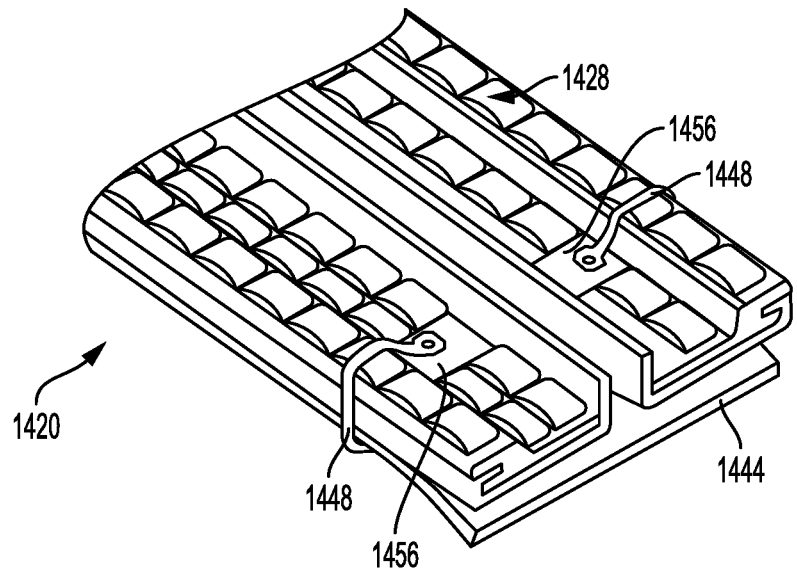
FIG. 9B is a top perspective view of a portion of the anvil plate of FIG. 9A showing suture attachment points along the top surface of the anvil plate.
Figure 9C:
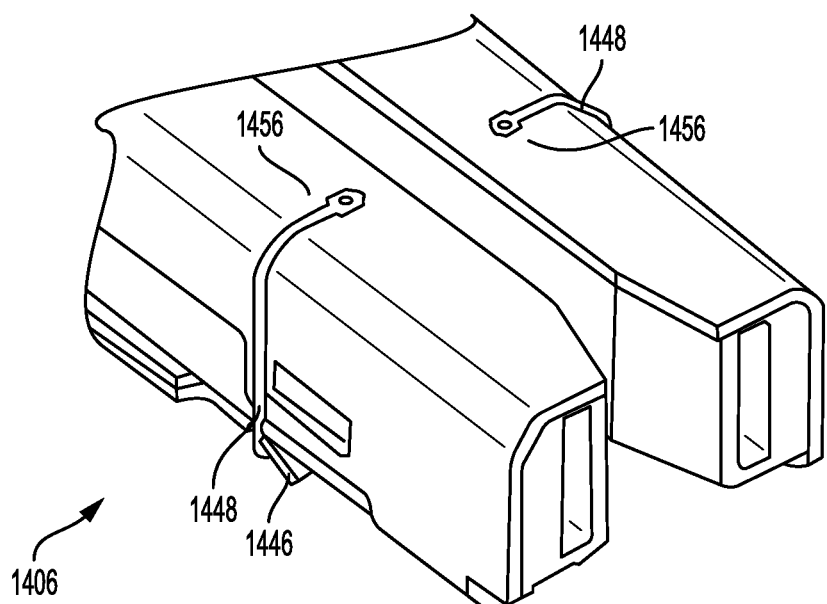
FIG. 9C is a bottom perspective view of a portion of the cartridge of FIG. 9A showing the suture attachment points along the underside of the cartridge.

FIGS. 9A-9C illustrate another embodiment of an anvil assembly 1420 releasably coupled to a cartridge 1406 with a cartridge pan 1414 coupled to a bottom side of the cartridge 1406. As shown in FIGS. 9A-9C, a first adjunct material 1444 can be coupled to an inward tissue-facing surface of the anvil plate 1428 of the anvil assembly 1420 and a second adjunct material 1446 can be coupled to an inward-tissue facing surface of the cartridge 1406. The first and second adjuncts 1444 and 1446 can be secured to the anvil assembly 1420 and cartridge 1406 with one or more sutures 1448. Furthermore, the anvil assembly 1420 and/or cartridge 1406 can include one or more suture attachment sites 1456 that are configured to couple a part (e.g., opposing ends) of the suture 1448 thereto. As shown in FIGS. 9B and 9C, at least one pair of attachments sites 1456 can be positioned along an outward-facing surface of the anvil plate 1428 of the anvil assembly 1420 (as shown in FIGS. 9A and 9B), and another pair of attachment sites 1456 can be positioned along an outward-facing surface of the cartridge 1406 and/or an outward-facing surface of the cartridge pan 1414 (as shown in FIG. 9C).

The suture 1448, and more particularly each of the opposing ends of the suture 1448, can be heat staked, welded, or otherwise adhered to the attachment sites 1456. In some implementations, the attachment site 1456 can include a texture that assists with securing the suture 1448 to the attachment site. For example, the attachment site 1456 can be roughened or otherwise made to include a textured surface. The cartridge 1406 and/or anvil assembly 1420 can include one or more attachment site 1456, and each attachment site 1456 can include any of a variety of sized and shaped surface areas. For example, the attachment sites 1456 can have various shapes, such as circular, triangular, or any other shaped surface area. Additionally, some attachment sites 1456 can be coated with a material that improves the attachment of the suture 1448. Alternatively or in addition, small posts, barbs or hooks can be used at the attachment sites 1456 to secure the suture 1448 in place. Although two sutures 1448 and two pairs of attachment sites 1456 are used to secure each adjunct 1444, 1446 in FIGS. 9A-9C, any number of sutures and attachment sites can be used to secure the adjuncts to the anvil plate and/or cartridge.

Figure 10A:
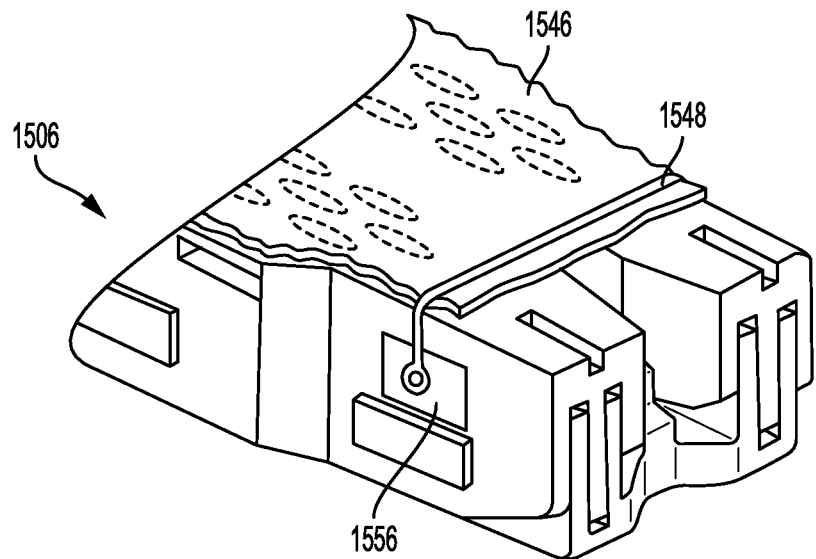
FIG. 10A is a perspective view of a portion of a cartridge having suture attachment points on opposed sides of the cartridge according to another embodiment.
Figure 10B:
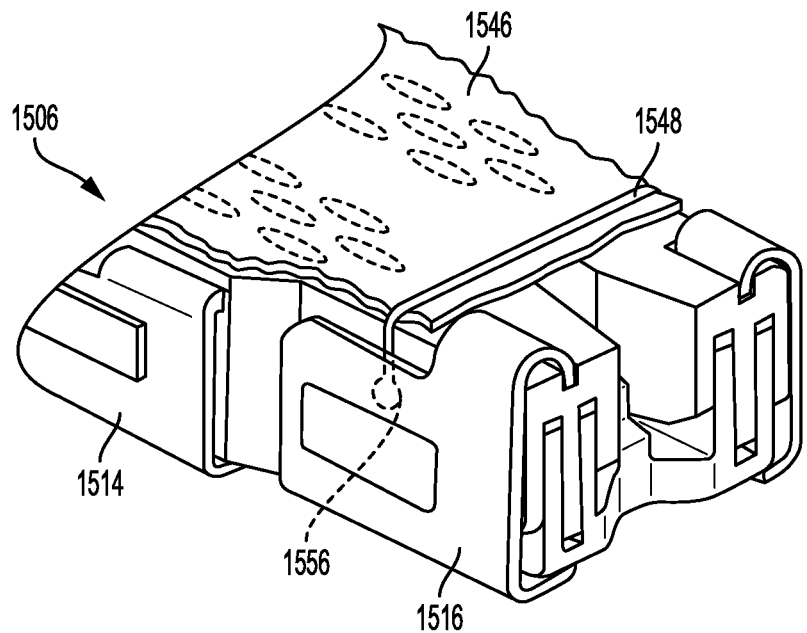
FIG. 10B is a perspective view of the portion of the cartridge of FIG. 10A showing a pan coupled to the cartridge and positioned over the suture attachment points.

FIGS. 10A-10B illustrate another embodiment of a suture 1548 extending across a second adjunct 1546 for securing the second adjunct 1546 to a cartridge 1506. As shown in FIG. 10A, opposed ends of the suture can be secured to attachment sites 1556 positioned along opposed sides of the cartridge 1506. More than one suture 1548 can be secured across the second adjunct and secured to attachment sites 1556 positioned on opposed sides of the cartridge 1506 or lower jaw 1514. Similarly, opposed ends of suture can be secured to attachment sites positioned along opposed sides of the anvil plate or other part of the anvil assembly.

Additionally or alternatively, as shown in FIG. 10B, a pan 1516 can be releasably coupled to the cartridge 1506 such that an inner surface of the pan 1516 can provide a compressive force against the ends of the suture 1548, thereby further securing the coupling between the ends of the suture 1548 and the attachment sites 1556. The pan 1516 can also protect the ends of the suture 1548 from being dislodged from the cartridge 1506 as the cartridge 1506 is inserted into a channel of a lower jaw of an end effector. Various other components can be coupled to either the cartridge and/or anvil plate for providing additional securing forces at the point of attachment between the suture and attachment sites, which are within the scope of the is disclosure.

Figure 11:
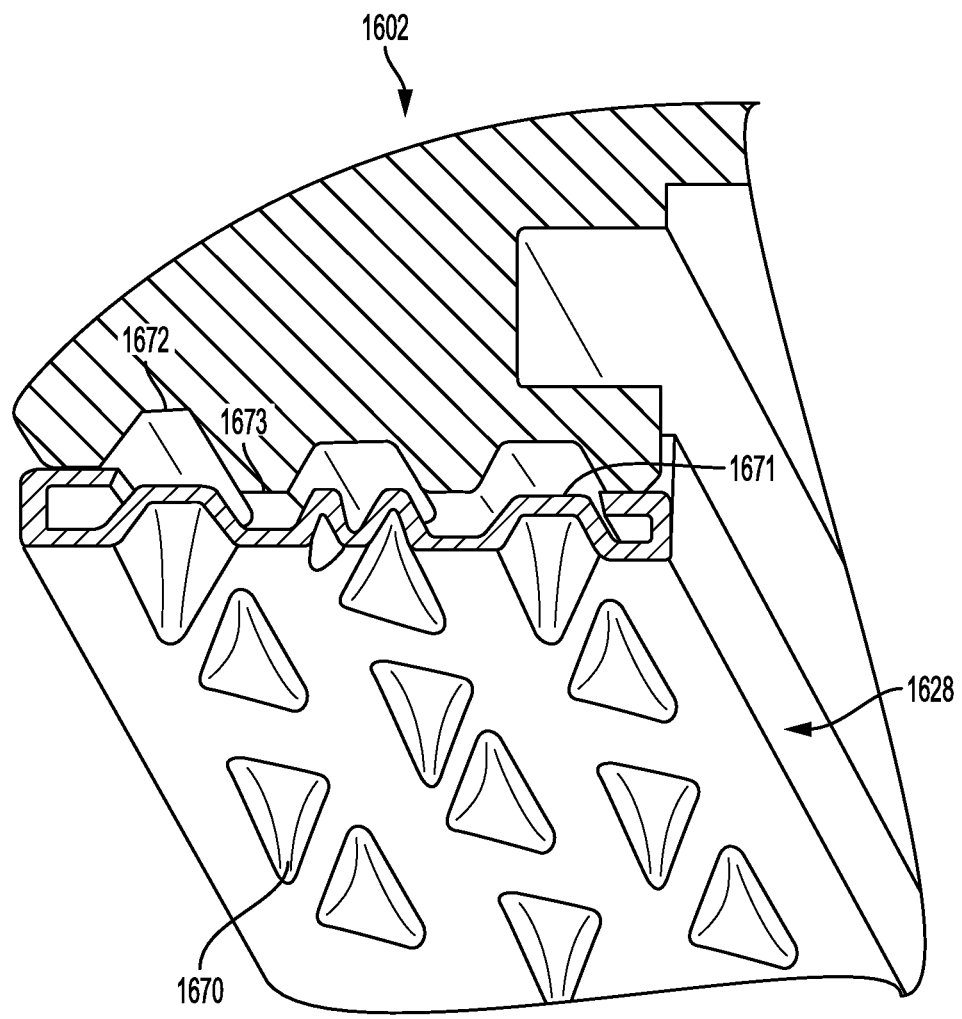
FIG. 11 is a cross-sectional view of an anvil plate having anvil surface features that mate with upper jaw cavities along an upper jaw member of an end effector according to yet another embodiment.

FIG. 11 illustrates anvil features 1670 that can extend from an outward-facing surface 1671 of the anvil plate 1628 and that are configured to mate with jaw features 1672 (e.g., cavities) that extend into an inward-facing surface 1673 of the upper jaw 1602. The anvil features 1670 can have a similar shape as the jaw features 1672 such that, when mated, the outward-facing surface of the anvil plate 1628 can be restricted from sliding against the inward-facing surface of the upper jaw 1602, thereby assisting with maintaining a preferred alignment between the anvil plate 1628 and the upper jaw 1602. The anvil features 1670 and/or jaw features 1672 can include stamped metal and/or elastomer and can have any number of a variety of shapes and sizes. Furthermore, it is within the scope of this disclosure for the cartridge and/or lower jaw to include features that mate with corresponding features along the lower jaw for assisting with maintaining a desired position of the cartridge relative to the lower jaw.

Surgical End Effector Adjunct Attachment

Various exemplary devices, systems and methods are provided for releasably retaining a frame with an adjunct to a jaw of an end effector of a surgical instrument. In certain exemplary embodiments, the frame can include retaining features for coupling an adjunct to a tissue-facing surface of the frame, thereby releasably coupling the adjunct material to the jaw of the end effector. In some implementations, the frame can include a plurality of retaining features that are configured to engage the adjunct material thereby creating a tension in the adjunct material, which can further assist with securing the frame to the jaw. The frame can also include various attachment features (e.g., attachment arms) that are configured to assist with releasably coupling the frame to the jaw.

In other embodiments, a removable applicator can be member provided for retaining at least one adjunct material and for aligning and coupling the adjunct material to a frame that is already secured to the jaw. Thus, in some implementations the jaws can be manipulated to engage the adjunct material retained by the applicator member, thereby mounting the adjunct onto the end effector. In particular, a force applied to the applicator member can cause the applicator member to release the at least one adjunct material and to transfer the at least one adjunct material to at least one respective frame secured to a jaw of the end effector.

FIGS. 12A and 12B illustrate one exemplary embodiment of a frame 2100 that is configured to releasably couple to an upper jaw 2102 of an end effector and to releasably retain an adjunct material (not shown) on a tissue-facing surface 2105 of the frame 2100. As shown, the frame 2100 can be in the form of an elongated body 2106 having an outward facing surface 2108 that can mate to and extend along an anvil surface 2103 of an anvil of the upper jaw 2102. One or more pairs of attachment arms 2110 can extend from the elongated body 2106, with each pair of attachment arms 2110 extending from opposing sides of the elongated body 2106 and arching towards a longitudinal axis of the elongated body 2106. The attachment arms 2110 can have a shape that is similar to an outer profile of the outward facing surface of the upper jaw 2102, thereby allowing the attachment arms to extend around a part of the outward facing surface of the upper jaw 2102 for securing the frame 2110 to the upper jaw 2102. Although the frame 2110 is shown and described as being configured for releasably securing to the upper jaw 2102, the frame 2100 can be configured for releasably securing to the upper jaw and/or lower jaw without departing from the scope of this disclosure.

Some embodiments of the attachment arms 2110 can be made out of a compliant and or elastic material that allows the attachment arms 2110 to deform or spread apart. The compliant and/or elastic attachment arms 2110 can assist with coupling the frame 2100 to the upper jaw 2102, as well as provide a compressive force against the outward facing surface of the upper jaw 2102 thereby securing the attachment and position of the frame 2100 to the upper jaw 2102. For example, the frame 2100 can be coupled to the upper jaw 2102 by guiding a distal end of the upper jaw 2102 through a space created by the attachment arms 2110 and/or spreading the attachment arms 2110 to allow the upper jaw 2102 to be positioned within the arcs of the attachment arms 2110.

The frame 2100 can be made out of one or more of a variety of materials, including compliant and/or elastic materials. For example, the frame can be made out of any number of materials (e.g., surgical grade), such as metals and polymers, without departing the scope of this disclosure.

In some embodiments, the upper jaw 2102 and/or frame 2100 can include a locking mechanism that assists with releasably securing the frame 2100 to the upper jaw 2102. For example, the upper jaw 2102 can include a locking feature at a proximal end that interacts and locks the frame 2100 to the upper jaw 2102 when the frame 2100 is loaded onto the upper jaw 2102. Furthermore, the upper jaw 2102 and/or frame 2100 can include a release feature (e.g., shown as a tab 2107 in FIG. 12B) that is configured to force or allow the release of the frame 2100 from the upper jaw 2102 when acted upon (e.g., pushed or pivoted).

As discussed above, the tissue facing surface 2105 of the frame 2100 can be configured to releasably secure an adjunct material thereto for allowing the adjunct material to be stapled to tissue and to remain at a surgical site. The frame 2100 can be configured such that the adjunct material can be secured to the frame 2100, however, the adjunct material can also be uncoupled from the frame 2100 thereby allowing the adjunct material, and not the frame 2100, to remain at the surgical site. Various attachment techniques can be utilized to mate an adjunct to the frame, such as an adhesive, fasteners, or any other chemical or mechanical attachment techniques.

FIGS. 13A-13E illustrate another embodiment of a frame 2200 that can be releasably coupled to a jaw of an end effector, such as an upper jaw 2202. The frame 2200 can be configured to releasably retain an adjunct material 2220 to thereby releasably secure the adjunct material 2220 to the upper jaw 2202. Similar to the embodiment above, the frame 2200 can be coupled to either the upper and/or lower jaw without departing from the scope of this disclosure. As shown in FIGS. 13B-13E, the frame 2200 can include attachment arms 2210 that extend from an elongated body 2206 of the frame 2200 and that can be shaped to conform to an outward facing surface of the upper jaw 2202. As such, the attachment arms 2210 can assist with securing the position of the frame 2200 and adjunct 2220 relative to the upper jaw 2202, such as before and during firing of staples.

As shown, the tissue facing surface 2205 of the frame 2200 can include a plurality of retaining features 2222 positioned along the length of the elongated body 2206. The plurality of retaining features 2222 can be configured to releasably secure the adjunct material 2220 to the frame 2200 such that the adjunct material 2220 can remain securely coupled to the frame 2200 at least until firing of a knife along the end effector thereby cutting the adjunct material 2220. The retaining features 2222 can be shaped and engaged with the adjunct material 2220 such that they allow the adjunct material 2220 to release attachment from the frame 2200 after the adjunct material 2220 has been cut and as the end effector moves away from the surgical site after firing of the staples. The frame 2200 can remain coupled to the end effector, such as the upper jaw, as the adjunct is released. A user can subsequently decouple the frame 2200 from the jaw or load another adjunct material 2220 onto the frame 2200. As such, the frame 2200 is configured such that the adjunct material 2220 is allowed to remain at the surgical site and the frame 2200 remains attached to the end effector so that the frame 2200 is not left at the surgical site and can either be reused or disposed of.

As shown in FIG. 13A, the frame 2200 can include at least one slot or opening 2226 that extends along a length of the elongate body 2206. Each opening 2226 can be configured to allow staples to pass therethrough and into the adjunct and tissue engaged between the jaws, thereby stapling the adjunct material 2220 to adjacent tissue. The openings 2226 can be shaped such that they surround the staple cavities of the cartridge and/or staple forming cavities of the anvil surface thereby allowing the firing of the staples without the frame 2200 interfering or getting stapled to tissue.

Figure 13C:
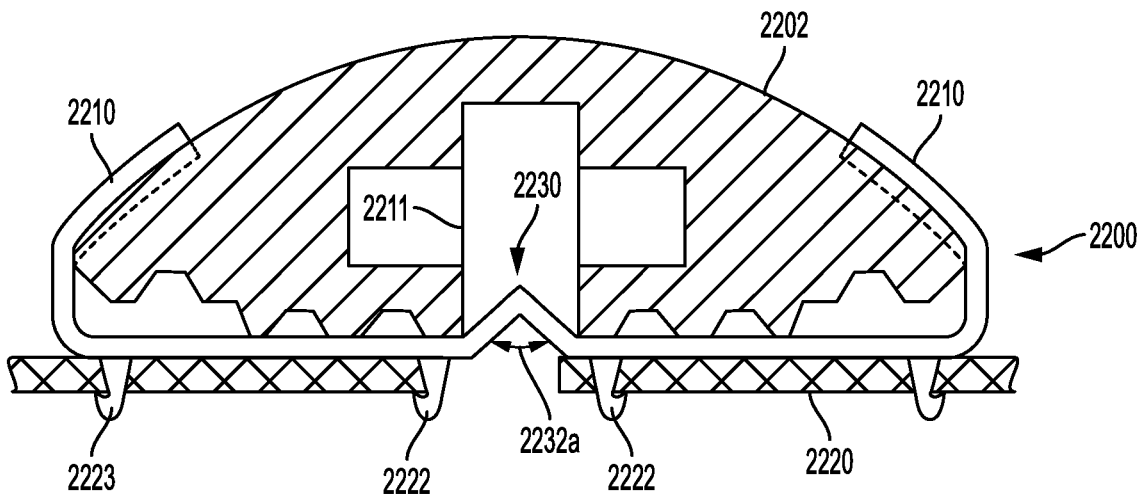
FIG. 13C is a cross section view of the frame coupled to the jaw of FIG. 13B, with the frame having a plurality of retaining features that secure the adjunct material to the tissue-facing surface of the frame.
Figure 13D:
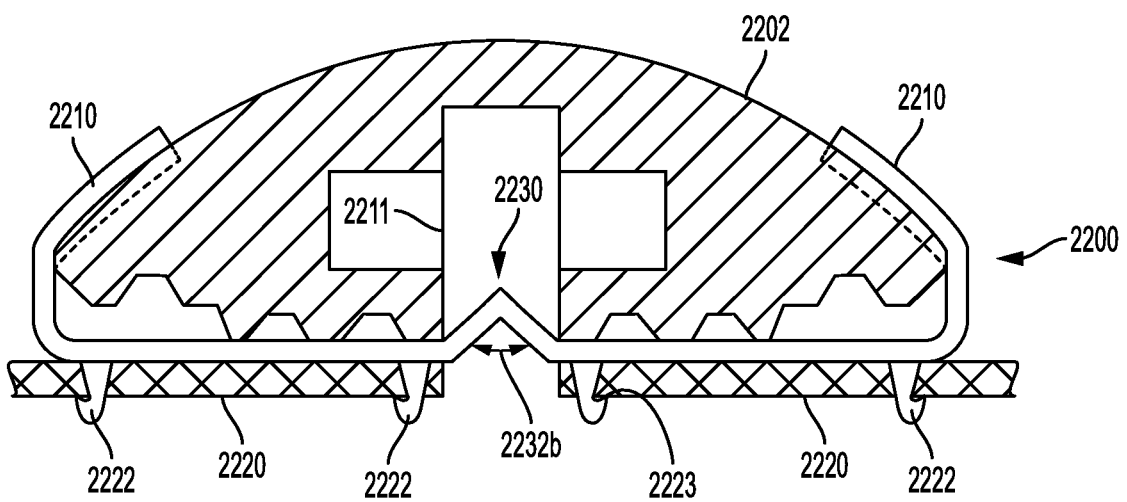
FIG. 13D is a cross section view of the frame coupled to the jaw of FIG. 13B.

The frame 2200 can also include a hinge 2230 along a length of the elongate body 2206 that allows the elongate body 2206 to apply tension to the adjunct. As shown in FIG. 13A, the hinge 2230 can extend along a longitudinal axis of the elongated body 2206 and can include a V-shaped profile. The V-shaped hinge 2230 can be configured to extend a distance within a knife slot 2211 of the upper jaw 2202 when the frame is coupled to the upper jaw, as shown in FIGS. 13C-13D. This can allow a knife to advance along the knife slot 2211 and cut the adjunct material 2220 without interference from the frame 2200. In an exemplary embodiment, however, the hinge 2230 can be formed from a material that can be cut by the knife as it is advanced through the knife slot 2211. Cutting of the hinge 2230 can assist with releasing the adjunct from the frame 2200, as will be discussed in more detail below.

FIGS. 13C-13D illustrate the frame 2200 coupled to the upper jaw, with the hinge 2230 extending into the knife slot 2211. The adjunct material 2220 is also shown coupled to a plurality of retaining features 2222. The retaining features 2222 can be made out of a rigid, semi-rigid, or flexible material and can include a hook or securing feature 2223 that extends outward away from the longitudinal axis of the elongate body 2206. This configuration of the retaining features 2222 can allow a first side of the adjunct material 2220 to be secured to a plurality of retaining features 2222 positioned on a first side of the hinge 2230. The adjunct material 2220 can then be pulled so that it is under tension before securing a second side of the adjunct material 2220 to the retaining features 2222 positioned on a second side of the hinge 2230, as shown in FIG. 13C. The retaining features 2222 on the first side of the hinge 2230 can thus pull in an opposite direction from the retaining features 2222 on the second side of the hinge 2230 thereby placing the adjunct material under tension. The retaining features 2222 can also deform or bend when the adjunct material 2220 is under tension thereby further securing the adjunct material 2220 to the frame 2200. Furthermore, having the retaining features engage the adjunct material 2220 under tension can pull opposing sides of the elongate body 2206 closer together thereby allowing the hinge 2230 to form a first angle 2232a and further securing the frame 2200 to the upper jaw 2202.

As mentioned above, a knife can be advanced along the knife slot 2211 thereby cutting the adjunct material 2220 as well as cutting at least part of the hinge 2230. By cutting the adjunct material 2220 positioned adjacent the knife slot 2211, the tension in the adjunct material 2220 caused by the retaining features 2222 pulling on the adjunct material from opposing sides of the knife slot 2211 can be released. When this tension along the adjunct material 2220 is released, the retaining features 2222 can reform (e.g., straighten) thereby allowing the adjunct material 2220 to be pulled off of the frame, such as after being stapled. The opposing sides of the elongate body to 2205 can also move further apart when the tension along the adjunct material 2220 is released, which can allow the hinge 2230 to form a second angle 2232b (see FIG. 13D). The second angle 2232b can be larger than the first angle 2232a thereby allowing the opposing sides of the elongate body 2206 to move further apart from each other, such as for allowing a user to decouple the frame 2200 from the upper jaw 2202. Similarly, if a part of the hinge 2230 is cut, the opposing sides of the elongate body 2206 can move further apart to allow a user to decouple the frame from the upper jaw 2202. In some embodiments, the frame can include an adhesive and/or one or more features that can couple to a part of the knife slot to further assist in securing the frame to the upper jaw 2202.

Figure 13E:
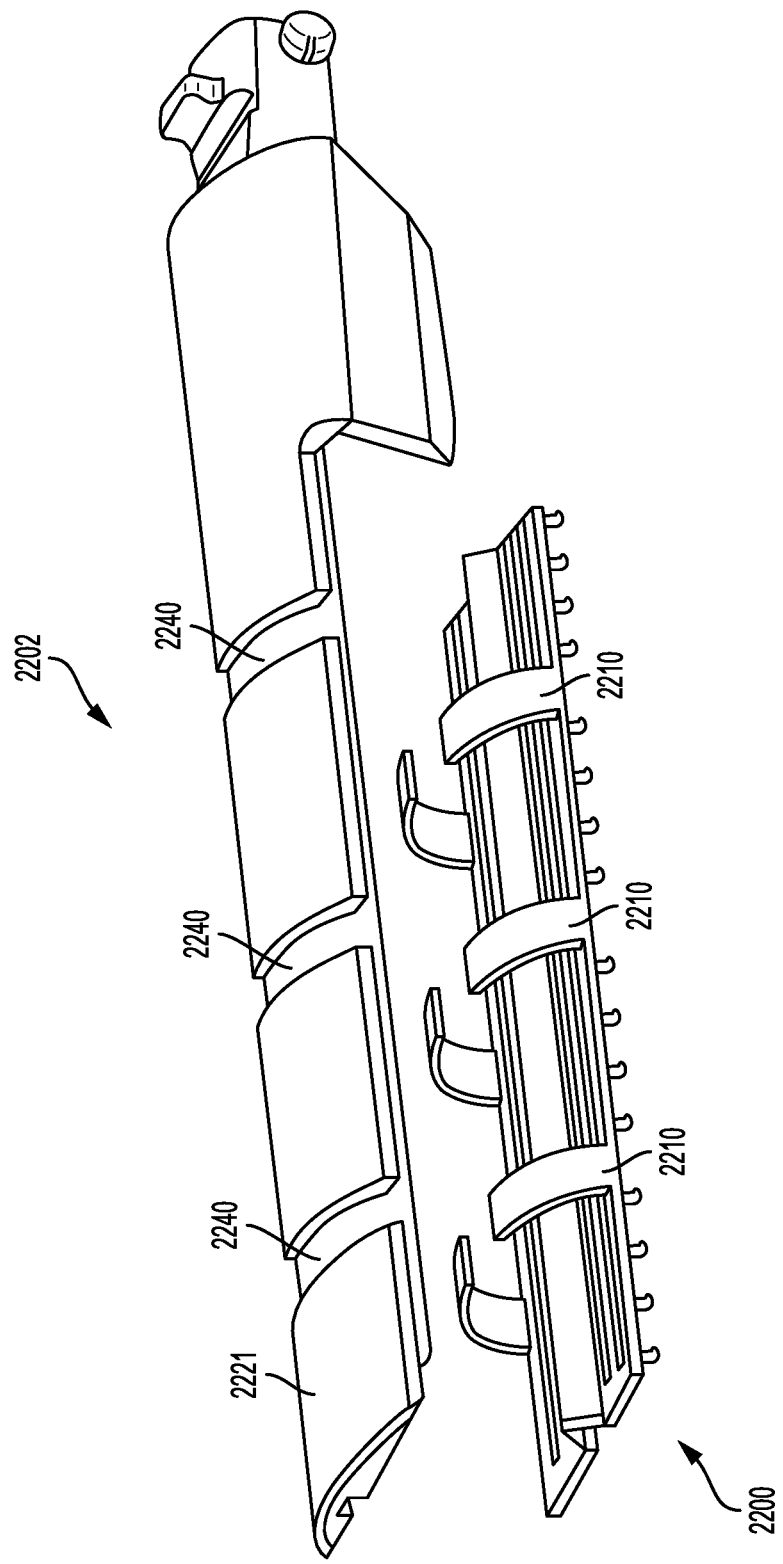
FIG. 13E is an exploded view of the frame of FIG. 13A and the jaw showing an outward facing surface of the jaw having attachment arm features.

FIG. 13E illustrates the outward facing surface 2221 of the upper jaw 2202 having attachment arm coupling features 2240 therealong that are configured to prevent attachment arms 2210 of the frame 2200 from moving relative to a length of the upper jaw 2202, such as when the frame 2200 is coupled to the upper jaw 2202. As shown, each attachment arm coupling feature 2240 can include a recess that has a shape and depth that allows an attachment arm 2210 to be seated therein to prevent the attachment arm 2210 from sliding out of the attachment arm coupling features 2240 and/or along the length of the upper jaw 2202. For example, the attachment arm coupling feature 2240 can be in the form of a recessed band that extends at an arc perpendicular to the longitudinal axis of the upper jaw.

Because the attachment arm coupling features 2240 can prevent the frame 2200 from sliding along the upper jaw 2202 even during loading of the frame 2200 onto the upper jaw 2202, the frame 2200 can be snapped on by deforming (e.g., elastically) the attachment arms 2210 to allow the upper jaw 2202 to fit within the confines of the attachment arms 2210. The attachment arms can be aligned with the attachment arm coupling features 2240 such that each of the attachment arms 2210 can spring towards the outward facing surface and into a corresponding attachment arm coupling feature 2240. Once coupled, the attachment arms 2210 and attachment arm coupling features 2240 can prevent the frame 2200 from sliding along the upper jaw 2202 thereby ensuring a desired positioning of the adjunct material 2220 relative to the upper jaw 2202.

As mentioned above, the frames 22100, 2200 can be configured to mate to either the upper and/or lower jaws. In addition, a frame can be coupled or mounted to a jaw of an end effector prior to having an adjunct coupled to the frame. As such, a user may need to align and mount an adjunct material to the frame when the frame is coupled to the jaw. Some frames can be reusable such that more than one adjunct can be used with a single frame. FIGS. 14A-14B illustrate a reusable frame that can be coupled to either the upper or lower jaw of the end effector and, as shown in FIG. 14C, an applicator member can be used to position and assist with mounting at least one adjunct material onto a respective frame coupled to either the upper or lower jaw.

FIG. 14A illustrates an embodiment of a frame 2300 including an overlay 2350 that is configured to extend along a part of an upper jaw 2302. In some embodiments, the overlay 2350 can include a flexible elongated tubular member that can slide over the upper jaw 2302 thereby covering an anvil surface 2303 of the upper jaw 2302. In some embodiments, the overlay 2350 can include an elongated surface that can cover the anvil surface 2303 and can further include edges that wrap around one or more sides of the upper jaw to thereby secure the overlay to the upper jaw. The overlay 2350 can further include an adhesive material that can assist with securing the position of the overlay 2350 relative to the upper jaw 2302. A tissue facing surface 2305 of the overlay 2350 can include at least one row of retaining features 2322 that are configured to assist with coupling an adjunct material 2320 thereto. For example, the tissue facing surface 2305 of the overlay 2350 can include two rows of retaining features 2322 with each row positioned along opposing sides of the anvil surface 2303 when the overlay 2350 is coupled to the upper jaw 2302.

FIG. 14B illustrates the upper and lower jaws 2302, 2304 each having an overlay 2350a, 2350b covering an outer surface thereof. As shown in FIG. 14B, an adjunct material 2320 can be releasably mated to both of the upper and lower jaws 2302, 2304. The adjunct material 2320 can include at least one row of complimentary retaining features 2325 that are configured to engage and releasably secure to at least one row of retaining features 2322 along the overlay 2350. For example, the adjunct material 2320 can include two rows of complimentary retaining features 2325, with each row positioned along opposing sides of the adjunct material 2320 such that they align with the two rows of retaining features 2322 along the overlay 2350, as shown in FIG. 14B. As such, the adjunct material 2320 can be coupled to an overlay 2350 by aligning the rows of retaining features 2322 along the overlay 2350 with the rows of complimentary retaining features 2325 along the adjunct material 2320. Once aligned, the retaining features 2322 and complimentary retaining features 2325 can be engaged thereby releasably securing the adjunct material 2320 to the overlay 2350. The engagement between the retaining features 2322 and complimentary retaining features 2325 can be strong enough to maintain the position of the adjunct material 2320 relative to the overlay 2350 prior to firing of staples, while allowing the adjunct material 2320 to uncouple and remain stapled at the surgical site after firing of the staples. The retaining features 2322 and/or complimentary retaining features 2325 can have various configurations, such as hook and loop members, various self-adhering materials, snap-fit features, etc. Furthermore, although the retaining features 2322 and complimentary retaining features 2325 are shown and described as being formed into rows along the overlay and adjunct material 2320, respectively, the retaining features 2322 and complimentary retaining features 2325 can have any number of shapes and configurations. For example, positioning retaining features 2322 and complimentary retaining features 2325 along opposing sides of the anvil surface 2203 (when the overlay 2350 is coupled to the upper jaw) allows the retaining features 2322 and complimentary retaining features 2325 to not interfere with either the advancing of the knife and/or firing of staples, however, other configurations can also achieve this.

One or both of the adjunct materials 2320 can be releasably retained on the overlays 2350a, 2350b coupled to the upper and lower jaws 2302, 2304, respectively, using an applicator member 2360 shown in FIG. 14C. The applicator member 2360 can be in the form of a frame-like holder configured to releasably retain one or both of the adjunct materials 2320a, 2320b. In the illustrated example, the applicator member 2360 is in the form of first (e.g., bottom) and second (e.g., top) generally rectangular housings 2324, 2326 coupled to one another as shown in FIG. 14C. As also shown in FIG. 14C, the first and second housing 2324, 2326 can engage edges of the long sides of the adjunct materials 2320a, 2320b therebetween. In other words, the applicator member 2360 can be in the shape of a generally U-shaped frame that surrounds an outer perimeter of at least two sides (e.g., long sides) of one or two adjunct materials. In particular, as shown in FIG. 14C, the applicator member 2360 can expose the complimentary retaining features 2325 thereby allowing the complimentary retaining features 2325 to align with and couple to the retaining features 2322 along the overlay 2350. It should be appreciated that the adjunct materials 2320a, 2320b and the first and second housings 2324, 2326 of the applicator member 2360 encompassing them can be symmetrical. Thus, either of the adjunct materials 2320a, 2320b can be applied to either overlay 2350a, 2350b coupled to the upper or lower jaw 2302, 2304, respectively.

The applicator member 2360 can be formed from any suitable material (e.g., plastic), and its walls can be relatively thin and it can be disposable. In use, to transfer the adjunct materials 2320a, 2320b to the overlays 2350a, 2350b, respectively, the upper or lower jaws 2302, 2304 can be clamped together into the opening in the applicator member 2360, with the complimenting retaining features 2325 of the adjunct materials 2320a, 2320b aligned with the retaining features 2322 along the overlays 2350a, 2350b. In this way, force applied by the jaws 2302, 2304 can cause the adjunct materials 2320a, 2320b to separate from the applicator member 2360 and to be engaged with the overlays 2350a, 2350b. In particular, in this example, as force is applied to the applicator member 2360 by the jaws 2302, 2304 of the end effector, the complimentary retaining features 2325 of the adjunct materials 2320a, 2320b are securely coupled to the retaining features 2322 along the overlays 2350a, 2350b.

After the adjunct materials 2320a, 2320b are transferred to the overlays positioned over the upper and lower jaws 2302, 2304, the jaws can be opened and the applicator member 2360 can be separated from the end effector. The overlays 2350a, 2350b attached to the upper and lower jaws

2302, 2304 can thus be mated with their respective adjunct materials 2320a, 2320b, as shown in FIG. 14B, and can then be used as desired in a surgical procedure.

It should be appreciated that the applicator member 2360 is shown to releasably retain two adjunct materials 2320a, 2320b by way of example only, and the applicator member 2360 or a similar component configured to releasably hold at least one adjunct material 2320 can be used to transfer an adjunct material 2320 only to a single frame or overlay coupled to the end effector. Moreover, the applicator member can be used to attach one or more adjuncts to any of the frames and/or jaws disclosed herein.

Surgical Adjunct Retaining Mechanism

An adjunct can be releasably retained on an end effector of a surgical tool, such as a surgical stapler, using a plurality of retaining elements. The retaining elements can be configured to retain the adjunct to the end effector with a mechanical force until a force is applied to the adjunct that overcomes the mechanical force, thereby allowing release of the adjunct from the end effector and into a patient's body where it may provide any number of benefits, as discussed above. The force can be applied to the adjunct in the normal course of use of the surgical tool, such as in the course of deploying staples from the end effector, which may facilitate ease of use since a user need not take any special action to release the adjunct. The retaining elements can be configured to releasably retain the adjunct to the end effector without using an adhesive, which may make the system easier to assemble, may facilitate release of the adjunct from the end effector since adhesive may require application of a higher force to release an adjunct, and/or may prevent staple cavities or other components of a surgical tool from being clogged by or otherwise compromised in function by the adhesive. The retaining elements can be on a retainer releasably coupled to the end effector. Existing end effectors may be retrofitted with a retainer and/or existing staple cartridges may be coupled to the retainer. Existing end effectors that include a metal pan may have the pan modified to include the features of a retainer as described herein.

Figure 15:
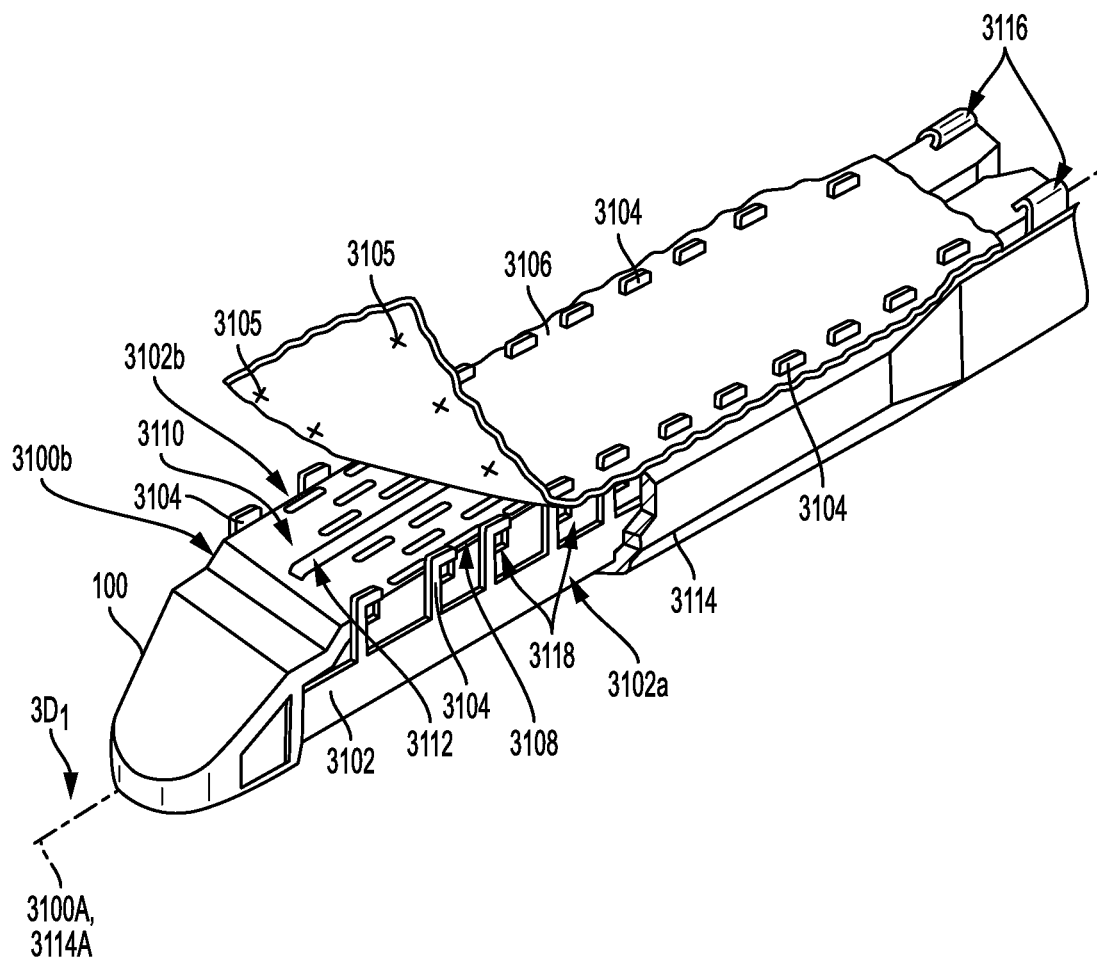
FIG. 15 is a perspective, partial cutaway view of one embodiment of a cartridge having an adjunct releasably retained thereon via a retainer.

FIG. 15 illustrates one embodiment of a staple cartridge 3100 coupled to a retainer 3102 including a plurality of retaining elements 3104 configured to releasably retain an adjunct 3106 to the staple cartridge 3100. The staple cartridge 3100 is generally configured and used similar to the staple cartridge 40 of FIGS. 1 and 2, e.g., has a plurality of staple cavities 3108 in a tissue-facing surface 3110 thereof that each seat a staple therein (the staples are obscured in FIG. 15), is configured to have a sled moved therethrough to push the staples out of the staple cavities 3108, has a longitudinal slot 3112 through which a knife or other cutting element can translate to cut tissue, etc. The staple cartridge 3100 is releasably seated in a lower jaw 3114 of an end effector of a surgical tool. The cartridge 3100 is seated in the retainer 3102, which is seated in a channel in the lower jaw 3114. The sled that translates along the cartridge 3100 can thus translate along an inner bottom surface of the retainer 3102. The lower jaw 3114 includes a coupling mechanism 3116 that couples the lower jaw 3114 to an upper jaw of the end effector that is configured to cooperate with the lower jaw 3114 to engage and staple tissue, as discussed above.

The retainer 3102 in this illustrated embodiment is in the form of a pan or tray that has a bottom with opposed sidewalls extending upwardly therefrom. The cartridge 3100 is fixedly seated in the retainer 3102 in this illustrated embodiment, e.g., is not removable from the retainer 3102. The cartridge 3100 and the retainer 3102 are thus configured to be removably and replaceably seated in the lower jaw 3114 as a unit. The cartridge 3100 being fixed to the retainer 3102 may help ensure that the retaining elements 3104 are in a desirable location relative to the cartridge 3100, which may help the adjunct 3102 be desirably positioned over the cartridge's tissue-facing surface 3110 and/or may help ensure alignment of the retaining elements 3104 with cutouts or pockets 3118 formed in the cartridge 3100, which are also shown in FIG. 16 and are discussed further below. In other embodiments, a cartridge can be releasably retained in a retainer, which may allow for re-use of the retainer with different staple cartridges. The retainer in such embodiments is configured to be seated in an end effector's lower jaw either before or after the cartridge is seated in the retainer.

The retainer 3102 can be formed from any of a variety of materials. In an exemplary embodiment, the retainer 3102 is formed from a metal, such as stainless steel, titanium, or a shape memory metal such as Nitinol.

The retaining elements 3104 are longitudinally aligned and are positioned along opposed longitudinal sides 3102a, 3102b of the retainer 3102. The retaining elements 3104 are thus positioned along opposed longitudinal sides 3100a, 3100b of the cartridge 3100. In an exemplary embodiments, a first number of the retaining elements 3104 are on one side 3102a (e.g., left side) of the retainer 3102 and a second number of the retaining elements 3104 are on the other side 3102b (e.g., right side) of the retainer 3102. The first and second numbers of the retaining elements 3104 can be equal, as in this illustrated embodiment in which there are eleven retaining element 3104 on each side 3102a, 3102b of the retainer 3102 for a total or twenty-two retaining elements 3104. Having an equal number of retaining elements 3104 on opposed sides 3102a, 3102b of the retainer 3102 may help provide even securing of the adjunct 3106 to the cartridge 3100. However, the first and second numbers of the retaining elements 3104 can vary. In an exemplary embodiment there are at least three retaining elements 3104 on each side 3102a, 3102b of the retainer 3102. For example, one retaining element 3104 can be near a proximal end thereof for releasable attachment to the adjunct 3100 near a proximal end thereof, one retaining element 3104 can be near a distal end thereof for releasable attachment to the adjunct 3100 near a distal end thereof, and one retaining element 3104 can be near a middle thereof for releasable attachment to the adjunct 3100 near a middle thereof. Any additional retaining elements 3104 can be located between the proximal retaining element and the middle retaining element and/or between the distal retaining element and the middle retaining element. Regardless of a number of retaining elements 3104 on each side 3102a, 3102b of the retainer 3102, the retaining elements 3104 can be equidistantly spaced therealong, as in this illustrated embodiment, which may help evenly secure the adjunct 3106 to the cartridge 3100.

The retaining elements 3104 extend upwardly from the retainer 3102, e.g., in a direction toward the upper jaw (e.g., the anvil) coupled to the lower jaw 3114. The retaining elements 3104 thus extend in a direction 3D1 substantially perpendicular to a longitudinal axis 3100A of the cartridge 3100 and a longitudinal axis 3114A of the lower jaw 3114. The retaining elements 3104 extending upwardly may help prevent lateral movement of the adjunct 3106 engaged therewith relative to the cartridge 3100, which may help ensure that all of the staples in the cartridge 3100 are deployed through the adjunct 3106, e.g., that each of the staples pierces the adjunct 3106, which may facilitate release the adjunct 3106 from the retaining elements 3104 and the cartridge 3100. The retaining elements 3104 each extend a distance above the tissue-facing surface 3110 of the cartridge 3100, which allows the adjunct 3106 engaged by the retaining elements 3104 to be seated on and be substantially flat on the tissue-facing surface 3110 of the cartridge 3100. A person skilled in the art will appreciate that although the adjunct 3106 may not be precisely flat it can nevertheless be considered to be substantially flat due to any number of factors, such as flexibility of the adjunct material and/or manufacturing tolerance at the adjunct's surface.

Each of the retaining elements 3104 in this illustrated embodiment is in the form of a hook. Each of the hooks is angled or oriented in a same proximal direction. The hooks are thus angled or oriented in a direction that is opposite to the distal direction that the sled translates along the cartridge 3100 and lower jaw 3114. As the sled translates distally along the cartridge 3100 and lower jaw 3114 to eject the staples, the upward movement of the staples out of the staple cavities 3108 exerts a force, e.g., an upward force in a direction of the upper jaw against which the staples are pushed, on the adjunct 3106. The adjunct 3106 is thus urged upwardly away from the cartridge 3100, which causes the adjunct 3106 to be released from the retaining elements 3104 by being pushed thereof. The retaining elements 3104 can experience deformation during the release of the adjunct 3106 therefrom in response to the upward force. In other words, the pushing of the adjunct 3106 off the retaining elements 3104 may cause the hooks to bend upwardly. The force exerted by the staples being ejected through the adjunct 3106 can thus be enough to overcome the mechanical force that the retaining elements 3104 exert to hold the adjunct 3106 thereto. In other embodiments, retaining elements in the form of hooks can each be angled or oriented in a same distal direction so as to be angled in the same direction that the sled translates along the cartridge and lower jaw. In this way, the sled's distal movement can help urge disengagement of the adjunct from the retaining elements as the sled travels in a distal direction to drive staples from the cartridge. The hooks in such an embodiment would be less likely to experience plastic deformation than hooks oriented proximally and may not deform at all.

The retaining elements 3104 on the retainer 3102 can be integrally formed with the retainer 3102, as in this illustrated embodiment, such as with a stamping process. The retaining elements 3104 can thus also, in an exemplary embodiment, be formed from a metal. The retaining elements 3104 can be very thin, as in this illustrated embodiment, in which case the retaining elements 3104 will have some degree of flexibility even if formed from a rigid material such as metal. This flexibility can result in plastic deformation of the retaining elements 3104 during release of the adjunct 3106 therefrom, e.g., one or more of the retaining elements 3104 may be irreversibly bent during release of the adjunct 3106, such as by being bent upwardly during staple deployment as discussed above. In other embodiments, instead of being integral with the retainer 3102, the retaining elements 3104 can be separate members attached thereto, such as by welding, adhesive, press fit, etc.

In at least some embodiments, one or more of the retaining elements 3104 can include a gripping feature thereon configured to facilitate gripping of the adjunct 3106. The gripping feature may help prevent premature release of the adjunct 3106 from the cartridge 3100. For example, the gripping feature can be a textured surface on the retaining element 3104 that increases friction between the retaining element 3104 and the adjunct 3106. For another example, the gripping feature can be an enlarged tip of the retaining element 3104, such as a bulb or ball at the retaining element's tip, which may help prevent the adjunct 3106 from prematurely sliding off the retaining element 3104 since passing over the enlarged tip will be made more difficult, e.g., require a higher force to be released therefrom.

The cartridge 3100 has a plurality of cut-outs or pockets 3118 formed therein. The cut-outs 3118 are longitudinally aligned and are positioned along the opposed longitudinal sides 3100a, 3100b of the cartridge 3100. The cut-outs 3118 are aligned with the retaining elements 3114 such that each of the cut-outs 3118 has an associated retaining element 3114. The cut-outs 3118 are each configured to seat a portion of the adjunct 3106 therein, as shown in FIG. 15, when the retaining elements 3104 are holding the adjunct 3106 on the cartridge 3100. The cut-outs 3118 may thus help prevent buckling of the adjunct 3106, which may allow the staples to more evenly advance through the adjunct 3106. The cut-outs 3118 each have a square shape in this illustrated embodiment but can have other shapes, e.g., rectangular, semi-circular, etc.

Figure 17:
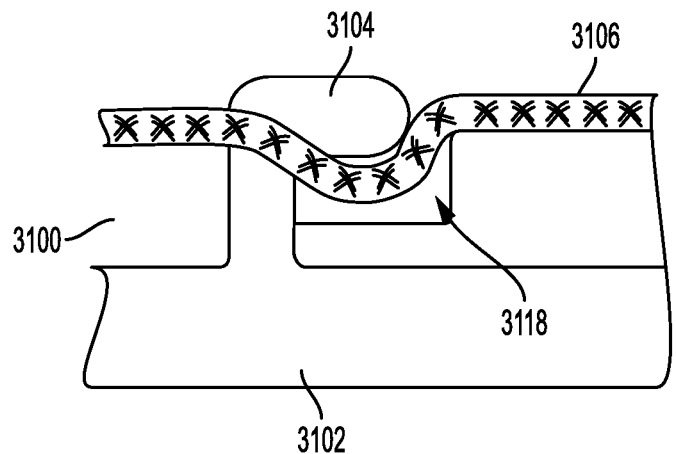
FIG. 17 is a side view of a portion of the cartridge, retainer, and adjunct of FIG. 15.

The adjunct 3106 in this illustrated embodiment is a fibrous structure that includes a plurality of fibers. As shown in FIGS. 15 and 17, the retaining elements 3104 can extend through the adjunct 3106 so as to hook the adjunct 3106 thereto. The fibers can separate to allow the retaining elements 3104 to extend therethrough at points 3105 where the adjunct 3106 engages the retaining elements 3104, although depending on various factors such as the tightness of the fiber's lattice structure, whether the retaining element's tips are blunted or pointed (the tips are blunted in this illustrated embodiment), and the strength of the retaining elements 3104, the retaining elements 3104 can pierce through the fibrous structure so as to form holes therein at any one or more of the points 3105. The retaining elements 3104 pierce through the adjunct 3106 in this illustrated embodiment. The adjunct 3106 may have pre-formed holes therein at locations where the retaining elements 3104 will extend through the adjunct 3106, which may help the retaining elements 3104 all pass through the adjunct 3106 both during loading of the adjunct 3106 onto the retaining elements 3104 and during release of the adjunct 3106 from the retaining elements 3104.

In some embodiments, the adjunct 3106 can be releasably coupled to the retaining elements 3104 in manufacturing such that the cartridge 3100, retainer 3102, and adjunct 3106 can be provided to a user as an assembled unit. Providing such an assembled unit may save user time since the assembly is pre-performed and/or may help ensure that the adjunct 3106 is properly secured to the cartridge 3100 and retainer 3102. In other embodiments, the adjunct 3106 can be provided to a user as a separate element from the retainer 3102 and cartridge 3100, which as mentioned above may be separate elements or may be fixed together as a unit. The adjunct 3106 in such embodiments can thus be configured to be coupled to the retainer 3102 and cartridge 3100 by a user. The adjunct 3106 can be coupled to the retainer 3102 and cartridge 3100 in any of a variety of ways. For example, the adjunct 3106 can be manually engaged with the retaining elements 3104 by being pressed or slid thereon by hand. For another example, an applicator tool can be configured to have the adjunct 3106 loaded thereon, and the applicator tool can be configured to engage the adjunct 3106 with the retaining elements 3104 by sliding or pressing the adjunct 3106 thereon. Use of the applicator tool may allow for more predictable engagement of the adjunct 3106 with the retaining elements 3104 than application by hand.

Figure 18:
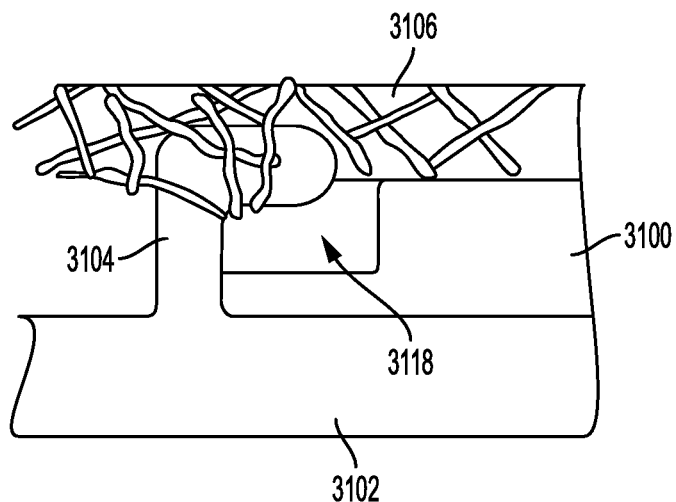
FIG. 18 is another side view of a portion of the cartridge, retainer, and adjunct of FIG. 15.

FIG. 18 illustrates another embodiment of the retaining elements 3104 engaging the adjunct 3106. In this illustrated embodiment, the retaining elements 3104 catch various ones of interlaced fibers of the adjunct 3106 to hold the adjunct 3106 thereto. Some or all of the retaining elements 3104 may therefore not extend above the adjunct 3106, as with the retaining element 3104 illustrated in FIG. 18.

In other embodiments, the adjunct releasably engaged with the retaining elements 3104 can have a configuration other than a fibrous structure. For example, the adjunct can be a film, and the retaining elements 3104 can extend through the film so as to hook the adjunct thereto. The film may have pre-formed holes therein at locations where the retaining elements 3104 will extend therethrough.

Figure 19:
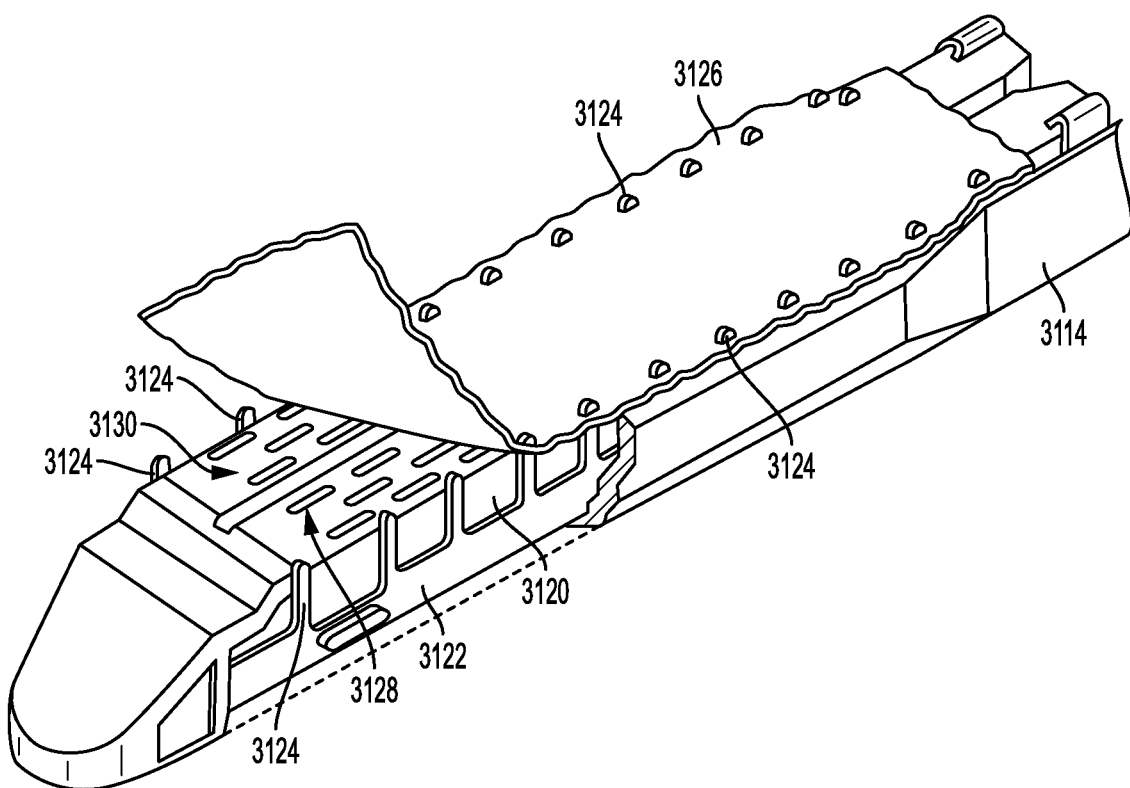
FIG. 19 is a perspective, partial cutaway view of another embodiment of a cartridge having an adjunct releasably retained thereon via a retainer.

FIG. 19 illustrates another embodiment of a staple cartridge 3120 coupled to a retainer 3122 including a plurality of retaining elements 3124 configured to releasably retain an adjunct 3126 to the staple cartridge 3120. The staple cartridge 3120 is generally configured and used similar to the staple cartridge 40 of FIGS. 1 and 2, e.g., has a plurality of staple cavities 3128 in a tissue-facing surface 3130 thereof that each seat a staple therein (the staples are obscured in FIG. 19), is configured to have a sled moved therethrough to push the staples out of the staple cavities 3128, has a longitudinal slot 3122 through which a knife or other cutting element can translate to cut tissue, etc. The staple cartridge 3120 is releasably seated in the lower jaw 3114 of FIG. 15 but can be similarly seated in other types of jaws. The cartridge 3120 in this illustrated embodiment does not have any cut-outs or pockets formed therein, but in other embodiments may have a plurality of cuts-outs similar to the cut-outs 3118 of the cartridge 3100 of FIG. 15. The adjunct 3126 is a fibrous structure similar to the adjunct 3106 of FIG. 15 but can have other configurations.

The retainer 3122 is generally configured and used similar to the retainer 3102 of FIG. 15. The retainer 3122 in this illustrated embodiment is in the form of a pan or tray that has a bottom with opposed sidewalls extending upwardly therefrom. The cartridge 3120 is fixedly seated in the retainer 3122, which is seated in a channel in the lower jaw 3114, but can instead be releasably seated in the retainer 3122.

The retaining elements 3124 are also generally configured and used similar to the retaining elements 3114 of FIG. 15, e.g., are longitudinally aligned along opposed sides of the retainer 3122 and along opposed sides of the cartridge 3120, extend upwardly toward the upper jaw coupled to the lower jaw 3114, etc. However, in this illustrated embodiment, the retaining elements 3124 are in the form of pegs that extend upwardly from the retainer 3122. The adjunct 3126 is configured to be coupled with the retaining elements 3124 by being pushed straight down thereon, such as by hand or with an applicator tool. Such loading may be easier than with retaining elements in the form of hooks, since an adjunct may need to be loaded onto hooks at an angle that may generally be less intuitive than a straight down motion. The retaining elements 3124 are integrally formed with the retainer 3122, but similar to that discussed above, can be otherwise attached thereto. In at least some embodiments, one or more of the retaining elements 3124 can include a gripping feature thereon configured to facilitate gripping of the adjunct 3126, similar to that discussed above.

Figure 20:
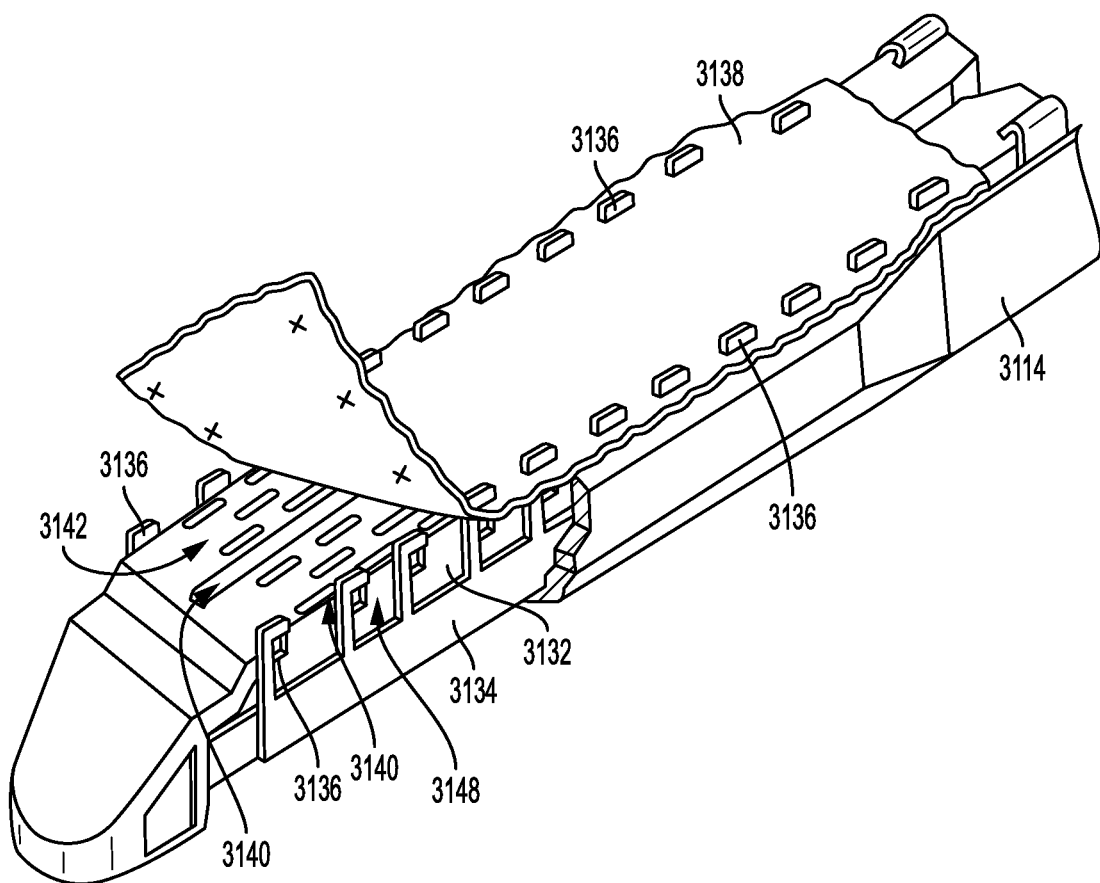
FIG. 20 is a perspective, partial cutaway view of yet another embodiment of a cartridge having an adjunct releasably retained thereon via a retainer.
Figure 21:
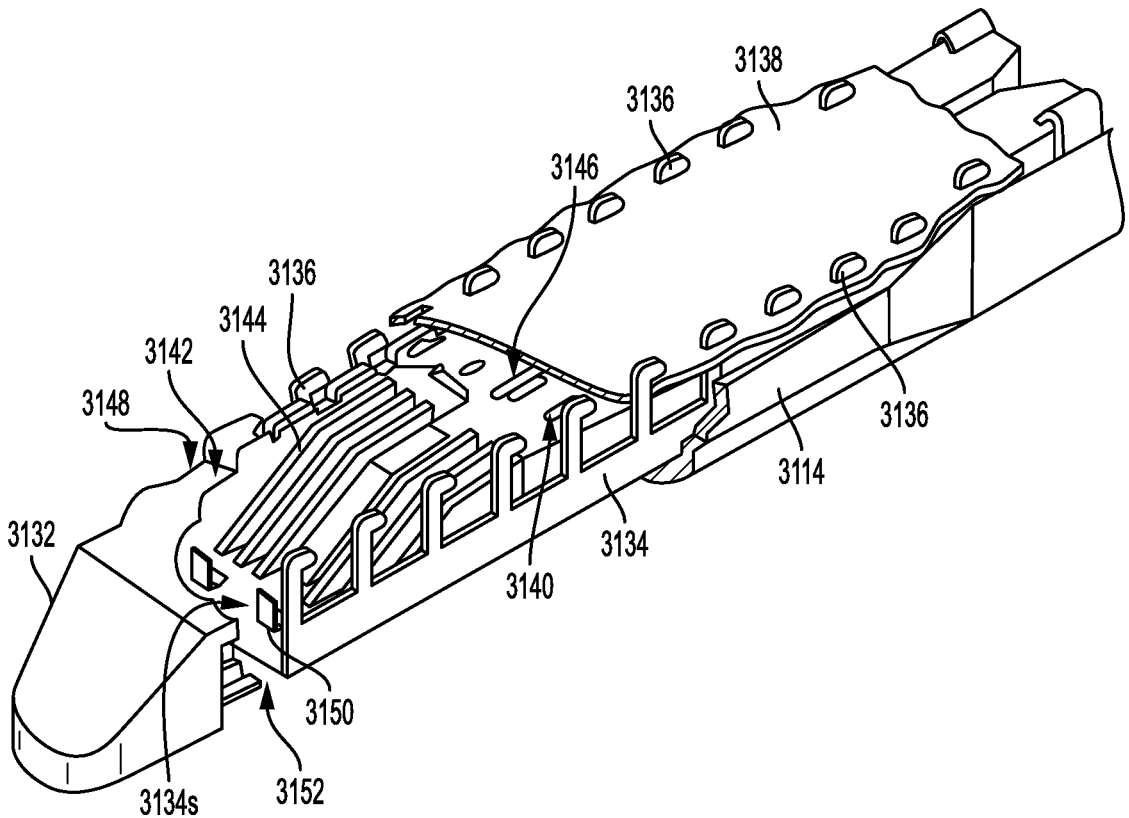
FIG. 21 is another perspective, partial cutaway view of the cartridge, retainer, and adjunct of FIG. 20.

FIGS. 20 and 21 illustrate another embodiment of a staple cartridge 3132 coupled to a retainer 3134 including a plurality of retaining elements 3136 configured to releasably retain an adjunct 3138 to the staple cartridge 3132. The staple cartridge 3132 is generally configured and used similar to the staple cartridge 40 of FIGS. 1 and 2, e.g., has a plurality of staple cavities 3140 in a tissue-facing surface 3142 thereof that each seat a staple therein (the staples are obscured in FIG. 20 and have already been deployed in FIG. 21), is configured to have a sled 3144 moved therethrough to push the staples out of the staple cavities 3140, has a longitudinal slot 3146 through which a knife or other cutting element can translate to cut tissue, etc. The sled 3144 is shown in a distal position in FIG. 21 after it has slid distally a partial distance along an inner bottom surface 3134s of the retainer 3134 to deploy staples from the cartridge 3132, prior to release of the adjunct 3138, which is discussed further below. The adjunct 3138 is a fibrous structure similar to the adjunct 3106 of FIG. 15 but can have other configurations. The retaining elements 3136 are also generally configured and used similar to the retaining elements 3114 of FIG. 15, e.g., are longitudinally aligned along opposed sides of the retainer 3134 and along opposed sides of the cartridge 3132, extend upwardly toward the upper jaw coupled to the lower jaw 3114, are in the form of hooks angled proximally, etc.

Figure 22:
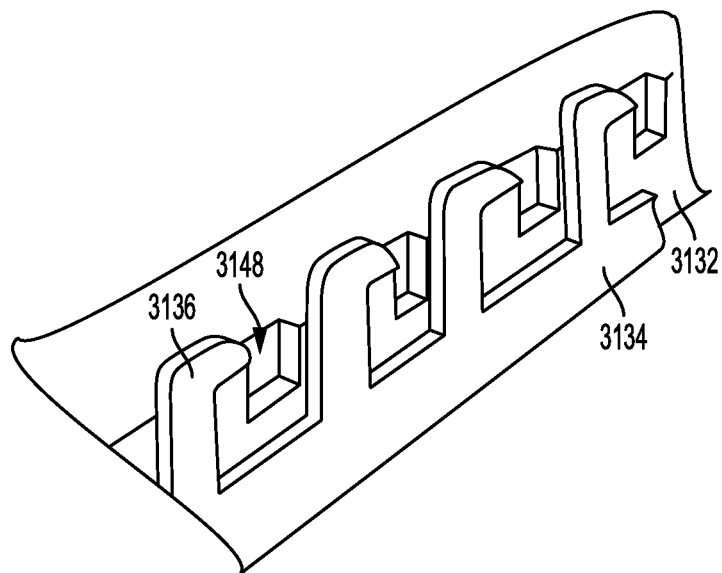
FIG. 22 is a side view of a portion of the cartridge and retainer of FIG. 20.

The staple cartridge 3132 is releasably seated in the lower jaw 3114 of FIG. 15 but can be similarly seated in other types of jaws. The cartridge 3132 has a plurality of cut-outs or pockets 3148 formed therein, as also shown in FIG. 22, that are similar to the cut-outs 3118 of the cartridge 3100 of FIG. 15.

The retainer 3134 in this illustrated embodiment is in the form of a pan or tray that has a bottom with opposed sidewalls extending upwardly therefrom. The retainer 3134 is generally configured and used similar to the retainer 3102 of FIG. 15, but the retainer 3134 in the illustrated embodiment of FIGS. 20-22 is movably seated in the lower jaw 3114. The retainer 3134 is configured to move relative to the cartridge 3132 and the lower jaw 3114 to facilitate release of the adjunct 3138. The retainer 3134 is configured to move from a locked or engaged configuration, which is shown in FIGS. 20 and 21, to an unlocked or unengaged configuration, which is shown in FIG. 22. In the locked configuration, the retaining elements 3136 each releasably engage the adjunct 3136, e.g., "lock" the adjunct 3136 to the cartridge 3132. In the unlocked configuration, the retaining elements 3136 are each disengaged from the adjunct 3136, e.g., the adjunct 3136 is "unlocked" from the cartridge 3132.

The retainer 3134 includes a release element 3150 configured to facilitate movement of the retainer 3134 from the locked configuration to the unlocked configuration. The release element 3150 is located in a distal portion of the retainer 3134 either at the retainer's distal edge or, as in this illustrated embodiment, just proximal to the retainer's distal edge. In this illustrated embodiment, the release element 3150 includes a pair of tabs extending upwardly from the retainer's inner bottom surface 3134s, although there can be another number of release elements. The release element can have other configurations, such as a semi-spherical protrusion on the retainer's inner bottom surface 3134s, a raised elongate bar on the retainer's inner bottom surface 3134s, an elongate bar located above the retainer's inner bottom surface 3134s and extending between opposed inner sides of the retainer 3134, etc.

The release element 3150 is configured to engage the sled 3144 to move the retainer 3134 from the locked configuration to the unlocked configuration. As discussed above, the sled 3144 is configured to slide distally along the cartridge 3134 and lower jaw 3114 on the retainer's inner bottom surface 3134s to deploy the staples through the staple cavities 3140. The staples pierce through the adjunct 3138 as they are deployed, as also discussed above. The sled 3144 will contact or abut the release element 3150 as its nears the end of its distal translation along the cartridge 3134 and lower jaw 3114. Continued distal movement of the sled 3144 with the sled 3144 contacting or abutting the release element 3150 pushes the retainer 3134 distally relative to the cartridge 3134 and lower jaw 3114. The retaining elements 3136 attached to the retainer 3134 will thus also move distally. The distal movement of the retaining elements 3136 causes the retaining elements 3136 to slide free of the adjunct 3138 so as to release the adjunct 3138 therefrom. Thus, unlike the embodiments of the retaining elements 3104, 3124 of FIGS. 15, 18, and 19 that are configured to sequentially release the adjunct coupled thereto in a proximal to distal direction, the retaining elements 3136 are configured to simultaneous release the adjunct 3138.

As shown in FIGS. 20 and 21, the retaining elements 3134 are aligned with the cartridge's cut-outs 3148 when the retainer 3134 is in the locked configuration. As shown in FIG. 22, the retaining elements 3134 are not aligned with the cartridge's cut-outs 3148 when the retainer 3134 is in the unlocked configuration. The adjunct 3136 is thus free to exit the cut-outs 3148 when the retainer 3134 is in the unlocked configuration.

The cartridge 3132 can include open space 3152 in a distal portion thereof, as shown in FIG. 21. The retainer 3134 is configured to move into the open space 3152 when the retainer 3134 moves distally to move from the locked configuration to the unlocked configuration.

The cartridge 3132 can include a stop element in the distal portion thereof configured to contact or abut the retainer 3134 in its locked configuration. The stop element can be configured to stop the distal movement of the retainer 3134 relative to the cartridge 3132 and lower jaw 3114. The stop element can have a variety of configurations, such as one or more tabs extending upwardly from an inner bottom surface of the cartridge 3132, a semi-spherical protrusion on the cartridge's inner bottom surface, a raised elongate bar on the cartridge's inner bottom surface, an elongate bar located above the cartridge's inner bottom surface and extending between opposed inner sides of the cartridge 3132, etc.

In an exemplary embodiment, the adjunct 3138 is releasably coupled to the retaining elements 3136 in manufacturing, which may help ensure that the retainer 3134 is in a proper location relative to the cartridge 3132 prior to staple deployment so the retainer 3134 can appropriately slide distally to release the adjunct 3138. The adjunct 3138 can, however, instead be manually applied to the retaining elements 3136 by a user.

In another embodiment, instead of the sled 3144 contacting or abutting the release element 3150 to push the retainer 3134 distally relative to the cartridge 3132 and lower jaw 3114, an E-beam that advances distally along the cartridge 3132 and lower jaw 3114 can contact or abut the release element 3150 to push the retainer 3134 distally relative to the cartridge 3132 and lower jaw 3114. In yet another embodiment, both the sled 3144 and an E-beam can contact or abut the release element 3150 to push the retainer 3134 distally relative to the cartridge 3132 and lower jaw 3114.

In another embodiment, instead of the retainer 3134 including the release element 3150, the cartridge 3132 can include the release element 3150. The retainer can include an opening for the release element to extend through, e.g., one opening for each of a pair of tabs extending upwardly from the cartridge. The opening and the release element are configured to cooperate to help hold the retainer in position relative to the cartridge until the sled and/or the E-beam contact or abut the release element and push the retainer distally. The release element extending from the cartridge can have elasticity to allow the release element to bend during the distal advancement of the retainer so the retainer can at least partially slide over the release element.

In another embodiment, instead of the sled 3144 (and/or the E-beam) contacting or abutting the release element 3150 to push the retainer 3134 distally relative to the cartridge 3132 and lower jaw 3114, the sled 3144 (and/or the E-beam) contacting or abutting the release element 3150 can move the retainer 3134 in a downward direction such that the retaining elements 3136 move downward and out of engagement with the adjunct 3138. The cartridge's bottom surface can slope downward distal to an initial position of the retainer to guide this downward movement of the retainer.

Figure 23:
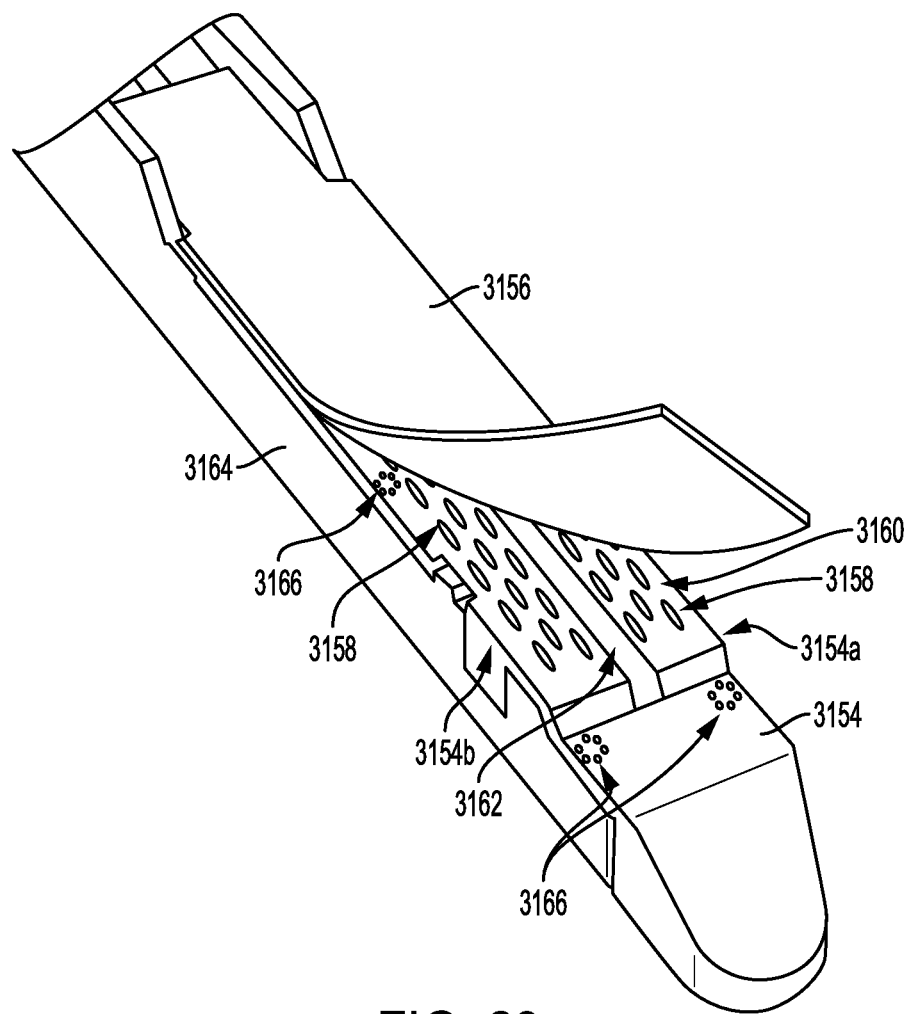
FIG. 23 is a perspective, partial cutaway view of another embodiment of a cartridge having an adjunct releasably retained thereon.

FIG. 23 illustrates another embodiment of a staple cartridge 3154 configured to releasably retain an adjunct 3156. The staple cartridge 3154 is generally configured and used similar to the staple cartridge 40 of FIGS. 1 and 2, e.g., has a plurality of staple cavities 3158 in a tissue-facing surface 3160 thereof that each seat a staple therein (the staples are obscured in FIG. 23), is configured to have a sled moved therethrough to push the staples out of the staple cavities 3158, has a longitudinal slot 3162 through which a knife or other cutting element can translate to cut tissue, etc. The staple cartridge 3154 is releasably seated in a lower jaw 3164 of an end effector that is generally configured and used similar to the lower jaw 3114 of FIG. 15.

In this illustrated embodiment, the cartridge 3154 includes a plurality of retaining elements 3166 configured to releasably retain the adjunct 3156 to the cartridge 3154. The retaining elements 3166 are in the form of pegs, similar to the retaining elements 3124 of FIG. 19, that extend upwardly from the tissue-facing surface 3160 of the cartridge 3154. The retaining elements 3166 are arranged in clusters that are longitudinally aligned along opposed sides 3154a, 3154b of the cartridge 3154. The number of retaining elements 3166 in each cluster can vary, but in an exemplary embodiment there are at least three retaining elements 3166 in each cluster. In an exemplary embodiment there are at least three clusters of retaining elements 3166 on each side 3154a, 3154b of the cartridge 3154. For example, one cluster can be near a proximal end of the cartridge 3154 for releasable attachment to the adjunct 3156 near a proximal end thereof, one cluster can be near a distal end of the cartridge 3154 for releasable attachment to the adjunct 3156 near a distal end thereof, and one cluster can be near a middle of the cartridge 3154 for releasable attachment to the adjunct 3156 near a middle thereof. Any additional clusters can be located between the proximal cluster and the middle cluster and/or between the distal cluster and the middle cluster. Regardless of a number of clusters on each side 3154a, 3154b of the cartridge 3154, the clusters can be equidistantly spaced therealong, as in this illustrated embodiment, which may help evenly secure the adjunct 3156 to the cartridge 3154. In some embodiments, instead of clusters of retaining elements 3166, the retaining elements 3166 can be individual members aligned longitudinally along the cartridge 3154.

The retaining elements 3166 are integrally formed with the cartridge 3154 in this illustrated embodiment, such as by being molded therewith. In other embodiments, instead of being integral with the cartridge 3154, the retaining elements 3166 can be separate members attached thereto, such as by welding, adhesive, press fit, etc.

Figure 24:
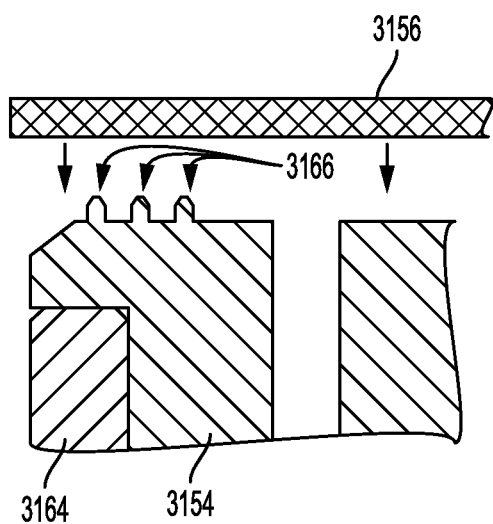
FIG. 24 is a side view of a portion of the cartridge and adjunct of FIG. 23 pre-assembly.

The adjunct 3156 in this illustrated embodiment is a fibrous structure that is configured to transition from an original, non-contracted configuration to a contracted configuration under application of heat. FIG. 24 illustrates the adjunct 3156 in the non-contracted configuration, and FIG.

Figure 25:
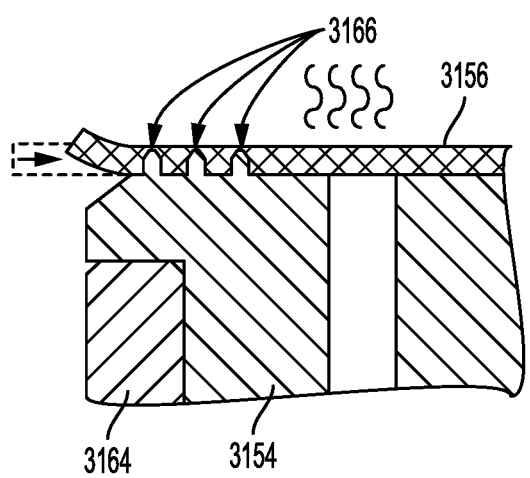
FIG. 25 is a side view of the portion of the assembled cartridge and adjunct of FIG. 24.

25 illustrates the adjunct 3156 in the contracted configuration. In general, the adjunct 3156 can be positioned on the cartridge's tissue-facing surface 3160 and heated at least in the areas where the retaining elements 3166 are located. The fibers of the adjunct 3156 can separate to allow the retaining elements 3166 to extend into the adjunct 3156. The application of heat to the adjunct 3156 is configured to cause the adjunct 3156 to transition from the non-contracted configuration to the contracted configuration. The contraction of the adjunct 3156 urges the fibers thereof together to grip the retaining features 3166 and help hold the adjunct 3156 thereto. The contraction of the adjunct 3156 can cause the retaining elements 3166 to deform, as shown in FIG. 25 in which the retaining elements 3166 have become bent from their straight configuration shown in FIG. 24. The deformation of the retaining elements 3166 may help grip the adjunct 3156 and thereby help hold the adjunct 3156 on the cartridge 3154 and/or may facilitate release of the adjunct 3156 since heating the adjunct 3156 can make the adjunct 3156 non-flexible. Exemplary embodiments of contractable adjuncts and of releasably coupling the adjunct to a member such as a staple cartridge or anvil are further described in U.S. application Ser. No. 15/435,891 entitled "Methods And Systems For Mating Constrictable Adjunct Materials With End Effectors" filed on even date herewith.

The adjuncts 3106, 3126, 3138, 3156 of FIGS. 15, 18-20, and 23 are releasably coupled to a staple cartridge and a lower jaw that seats the staple cartridge. In other embodiments, an adjunct can be releasably coupled to an anvil at an upper jaw of a surgical tool.

Figure 26:
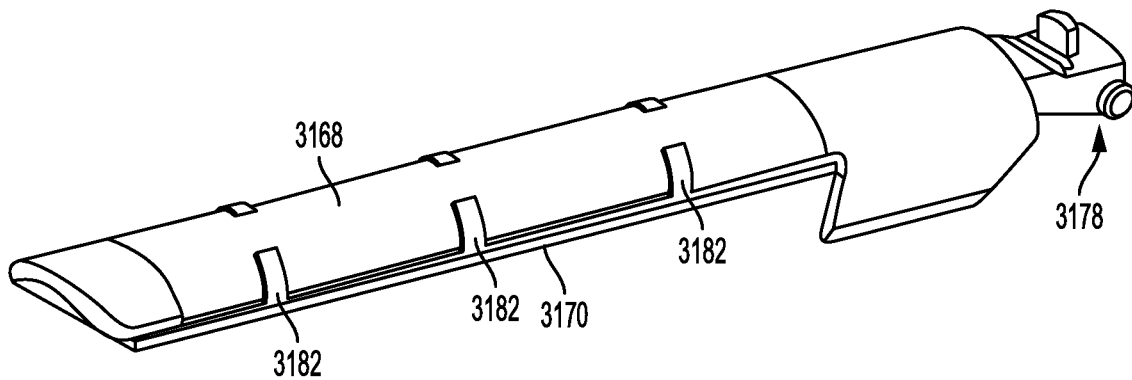
FIG. 26 is a perspective view of an embodiment of an anvil and a retainer coupled thereto.
Figure 27:
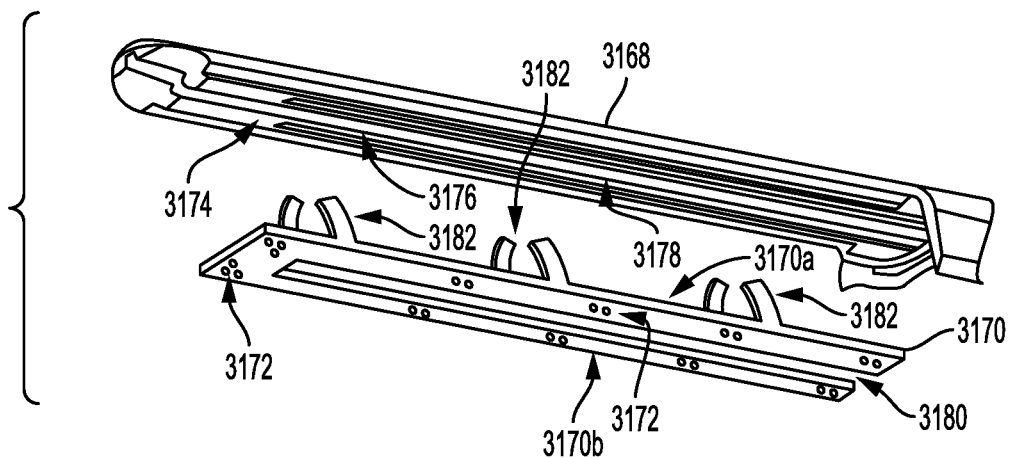
FIG. 27 is an exploded view of the anvil and retainer of FIG. 26.

FIG. 26 illustrates one embodiment of an upper jaw or anvil 3168 coupled to a retainer 3170 including a plurality of retaining elements 3172 configured to releasably retain an adjunct to the anvil 3168. FIG. 27 illustrates the anvil 3168 and the retainer 3170 prior to their coupling. The anvil 3168 is generally configured and used similar to the upper jaw 34 of FIGS. 1 and 2, e.g., has a tissue-facing surface 3174 with staple forming pockets 3176 formed thereon, has a longitudinal slot 3178 through which a knife or other cutting element can translate to cut tissue, etc. The anvil 3168 includes a coupling mechanism 3178 that couples the upper jaw 3168 to a lower jaw of the end effector that is configured to cooperate with the upper jaw 3168 to engage and staple tissue, as discussed above.

The retainer 3170 in this illustrated embodiment is in the form of a plate. The retainer 3170 has a longitudinal slot 3180 through which a knife or other cutting element can translate to cut tissue, etc. The slot 3180 is open at a proximal end thereof to allow the knife or other cutting elements to slide therein. The slot 3180 is thus configured to be aligned with the anvil's longitudinal slot 3178 when the retainer 3170 is coupled to the anvil 3168. The slot 3180 extends along a partial longitudinal length of the retainer 3170 to allow the retainer 3170 to be a singular element, e.g., with a connected distal end. In other embodiments, the retainer 3170 can be a two-piece element with left and right sides providing a space therebetween through which the knife or other cutting element can translate to cut tissue, etc.

The retainer 3170 can be formed from any of a variety of materials. In an exemplary embodiment, the retainer 3170 is formed from a plastic or polymer such that the retainer 3170 has elasticity.

The retainer 3170 is configured to releasably couple to the anvil 3168 so as to be positioned over the anvil's tissue-facing surface 3174, as shown in FIG. 26. The slot 3180 can be wide enough to not obscure any of the staple forming pockets 3176 on the anvil's tissue-facing surface 3174 such that staples can be deployed from a lower jaw coupled to the upper jaw 3168, pierce through the adjunct, and be formed by the staple forming pockets 3176.

The retainer 3170 includes at least one attachment mechanism 3182 configured to releasably attach the retainer 3170 to the anvil 3168. The retainer 3170 being releasably coupled to the anvil 3168 may allow for re-use of the retainer 3170 with different anvils and/or may facilitate cleaning of the retainer 3170 and/or anvil 3168 since the retainer 3170 can be removed from the anvil 3168 prior to cleaning of one or both of the retainer 3170 and anvil 3168. In other embodiments, the retainer 3170 can be fixed to the anvil 3168, which may help ensure that the retaining elements 3172 are in a desirable location relative to the anvil 3168, which may help the adjunct be desirably positioned over the anvil's tissue-facing surface 3174. The attachment mechanism 3182 in this illustrated embodiment includes a pair of arms. The retainer 3170 in this illustrated embodiment including three pairs of arms, but can have another number of pairs in other embodiments. The arms are configured to snap around an exterior of the anvil 3168, as shown in FIG. 26.

The attachment mechanism 3182 is integrally formed with the retainer 3170 in this illustrated embodiment. The attachment mechanism 3182 can thus also, in an exemplary embodiment, have elasticity. The attachment mechanism 3182 having elasticity may help the attachment mechanism 3182 snap around the anvil 3168. In other embodiments, instead of being integral with the retainer 3170, the attachment mechanism 3182 can be a separate member attached thereto.

The retaining elements 3172 are in the form of pegs, similar to the retaining elements 3124 of FIG. 19, and extend downwardly from the tissue-facing surface 3174 of the anvil 3168 in a direction toward the lower jaw coupled to the upper jaw 3168. The retaining elements 3172 are arranged in clusters that are longitudinally aligned along opposed sides 3170a, 3170b of the retainer 3170, similar to the clusters of the retaining elements 3166 of FIG. 23 discussed above. Each of the clusters has two retaining elements 3172 but can have another number. The retainer 3170 has five clusters along each side 3170a, 3170b of the retainer 3170 but can have another number.

Figure 28:
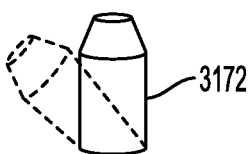
FIG. 28 is a perspective view of a retaining element of the retainer of FIG. 27.

The retaining elements 3172 are integrally formed with the retainer 3170 in this illustrated embodiment. The retaining elements 3172 can thus also, in an exemplary embodiment, have elasticity. FIG. 28 illustrates flexing of the retaining element 3172 allowed by the elasticity, with the retaining element 3172 in phantom showing the retaining element 3172 bent. In other embodiments, instead of being integral with the retainer 3170, the retaining elements 3172 can be separate members attached thereto. Also, in other embodiments, the retaining elements 3172 can be integrally formed with the anvil 3168 or be separate members attached thereto such that a retainer is not used.

The adjunct releasably coupled to the anvil 3168 can have a variety of configurations, as discussed above. In an exemplary embodiment, the adjunct is a fibrous structure or a film.

Figure 29:
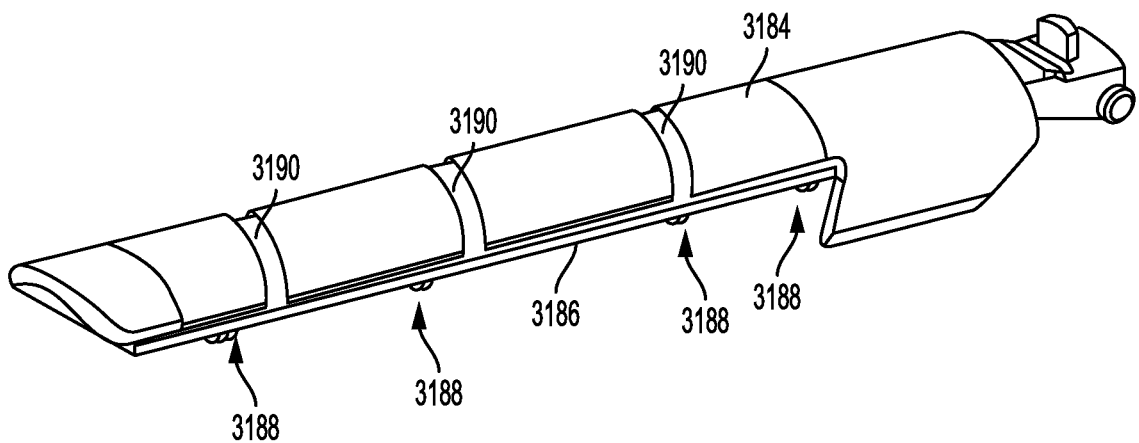
FIG. 29 is a perspective view of another embodiment of an anvil and a retainer coupled thereto.
Figure 30:
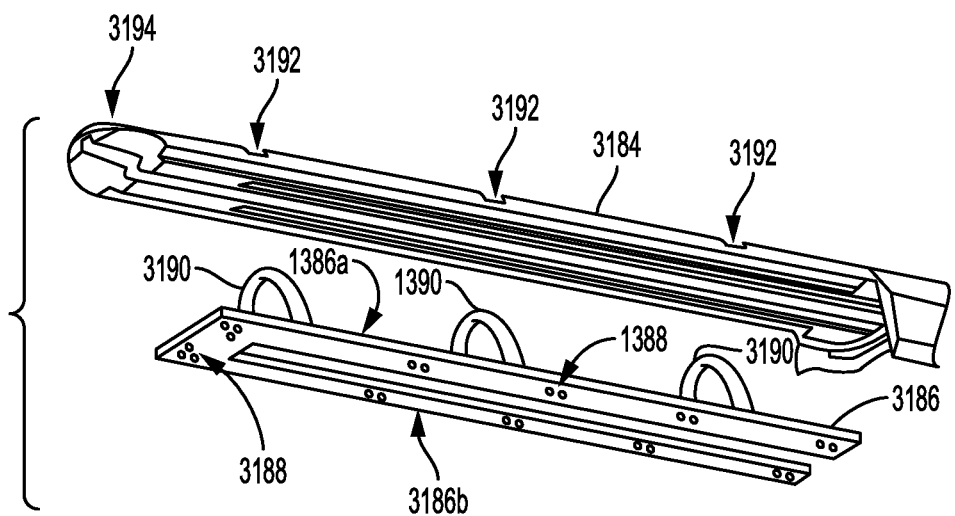
FIG. 30 is an exploded view of the anvil and retainer of FIG. 29.

FIG. 29 illustrates another embodiment of an upper jaw or anvil 3184 coupled to a retainer 3186 including a plurality of retaining elements 3188 configured to releasably retain an adjunct to the anvil 3190. FIG. 30 illustrates the anvil 3184 and the retainer 3186 prior to their coupling. The retaining elements 3188 are configured and used similar to the retaining elements 3172 of FIG. 27 except that in this illustrated embodiment the proximal-most clusters on either side 3186a, 3186b of the anvil 3184 have three retaining elements 3188 each while a remainder of the clusters have two retaining elements 3188 each.

The retainer 3186 is generally configured and used similar to the retainer 3170 of FIG. 27 except that in this illustrated embodiment the retainer's attachment mechanism 3190 includes a frame. The retainer 3186 in this illustrated embodiment including three frames, but can have another number of frames in other embodiments. The frames are configured to slide around an exterior of the anvil 3184 and be seated in recesses 3192 formed in the anvil's exterior surface. A distal end 3194 of the anvil 3184 can be advanced in a distal direction through a proximal-most one of the frames and continue advancing distally until the frames each align with respective ones of the recesses 3192, thereby coupling the anvil 3184 and the retainer 3186 together. The anvil 3184 can be moved in a proximal direction relative to the retainer 3186 to remove the anvil 3184 from the retainer 3186. The attachment mechanism 3190 can have elasticity, as discussed above, which may facilitate seating thereof in the recesses 3190 as well as facilitate removal of the anvil 3168 from the retainer 3186. The anvil 3184 is generally configured and used similar to the anvil 3168 of FIG. 27 except that the anvil 3184 in this illustrated embodiment includes the recesses 3192 that extend radially around its outer surface.

The adjunct releasably coupled to the anvil 3184 can have a variety of configurations, as discussed above. In an exemplary embodiment, the adjunct is a fibrous structure or a film.

Adjunct Release for Surgical Staplers

Various exemplary devices, systems, and methods for releasably retaining an adjunct material on an end effector of a surgical instrument are described herein. In some implementations, an adjunct material can be releasably retained on a jaw of an end effector in a manner that reduces or prevents the adjunct material from prematurely slipping off the jaw. In this way, the adjunct can be securely coupled to the end effector while a surgeon manipulates the end effector during a surgical procedure. The adjunct material can be coupled to an end effector in a variety of ways, for example by inserting portions of the adjunct into connection cavities on a tissue-facing surface of the jaw. In some embodiments, the adjunct can have tags or protrusions that extend from an outward facing surface such that the tags can be configured to be received in cavities on the tissue-facing surface of the jaw. In other implementations, the adjunct can be coupled to the tissue-facing surface of the jaw using an adhesive. The adjunct can remain coupled to the end effector until it is separated from the end effector and transferred to a treatment site in a patient, for example by a release mechanism that includes features and/or components that are configured for releasably attaching an adjunct thereto. A variety of release mechanisms can be used, such as staple deployment members and/or a cutting element that causes the adjunct to separate from the end effector. The release mechanism can thus allow a user to securely attach an adjunct to an end effector and allow the user to rapidly deploy the adjunct when desired.

Figure 31:
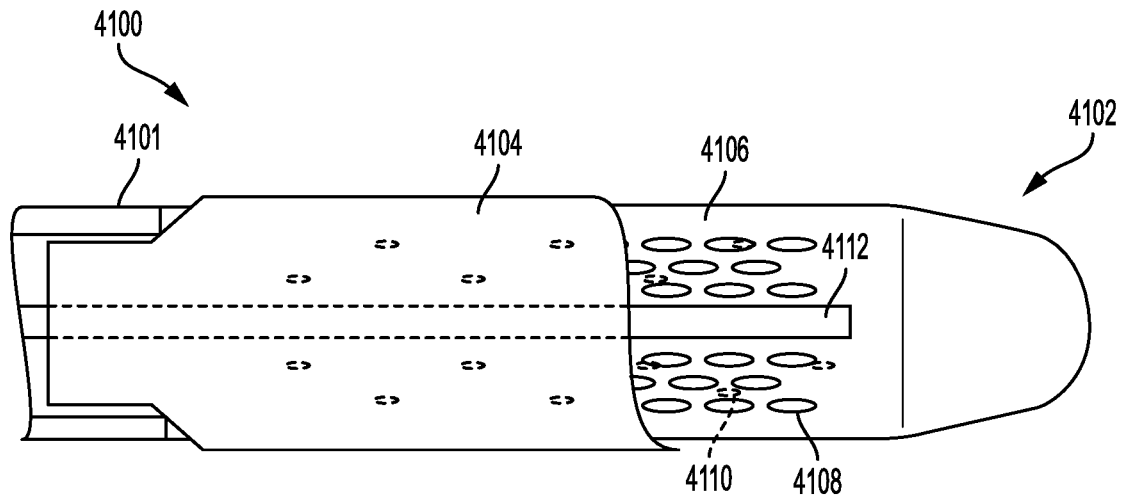
FIG. 31 is a top view of a lower jaw member of a surgical stapler showing a portion of an adjunct disposed thereon.
Figure 32:
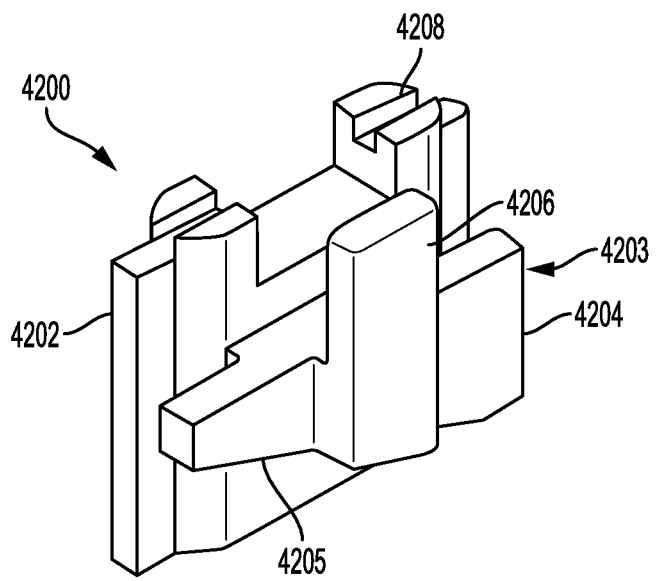
FIG. 32 is a perspective view of a single staple driver with an adjunct releasing mechanism.
Figure 33:
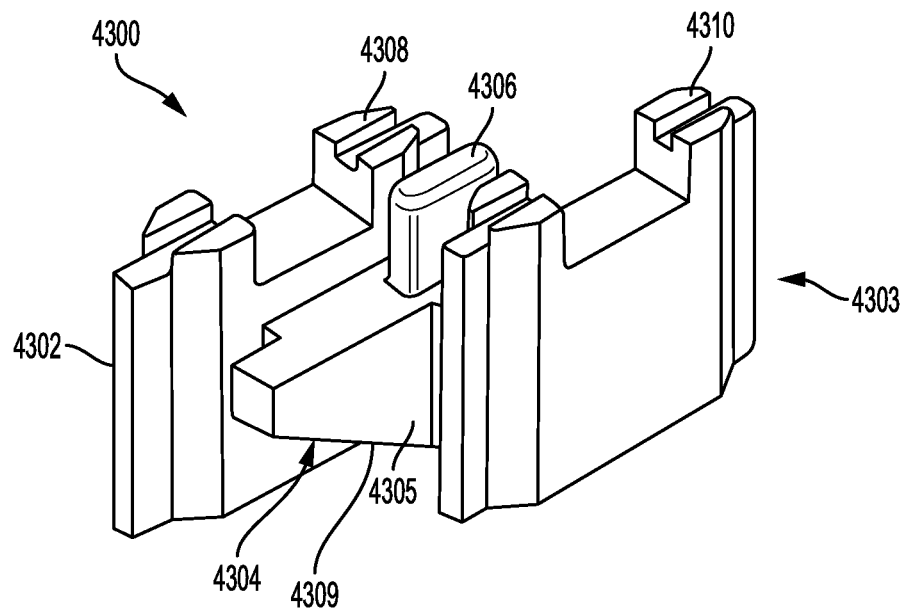
FIG. 33 is a perspective view of a double staple driver with an adjunct releasing mechanism.

Attaching an adjunct to and releasing an adjunct from an end effector can be achieved through a variety of techniques. FIGS. 31-33 illustrate one embodiment of an end effector 4100 having an adjunct releasing mechanism. FIG. 31 illustrates a portion of a lower jaw 4101 of the end effector 4100, which can be disposed on a distal end of a surgical instrument, such as surgical staplers 10, 50 discussed above. The lower jaw 4101 can have a cartridge 4102 disposed thereon, similar to the staple cartridge 40, that has a tissue-facing surface 4106 with an adjunct 4104 (only a portion of the adjunct 4104 is shown) disposed thereon, such as one or more of the buttresses, adjuncts, and/or medicants discussed above.

The cartridge 4102 can have staples disposed in staple cavities 4108 which are formed in the tissue-facing surface 4106. The tissue-facing surface 4106 can also have a channel 4112 configured to receive a cutting element, similar to the knife blade 36, as it moves distally therethrough. One or more connection cavities 4110 can extend between and connect the staple cavities 4108 for attaching an adjunct to the cartridge 4102. The connection cavities 4110 can be in the form of recesses or bores, and can have a variety of configurations and shapes. For example, the connection cavities 4110 can be roughly oval in shape and smaller than the staple cavities 4108. In other embodiments, the cavities can be circular, square, rectangular, 3-dimensional shapes, etc., and they can be larger than, equal in size to, or a combination of sizes relative to the staple cavities 4108. The cavities 4110 can be disposed between rows of the staple cavities 4108. However, the connection cavities 4110 can have any number of configurations, such as each staple cavity 4108 having a connection cavity 4110 adjacent thereto. While the connection cavities 4110 are formed adjacent to the staple cavities 4108 on the tissue-facing surface 4106, they can be formed elsewhere. For example, the cavities can be formed at the interface of the cartridge and a tray, similar to tray 37, such that some portion of the inner surface of the cavity is a surface of the cartridge, and another portion is a surface of the tray. Furthermore, connection cavities for attaching and detaching an adjunct need not be limited to the tissue-facing surface of the cartridge. For example, connection cavities can be formed along the edge of the tissue-facing surface of the cartridge such that when the end effector is assembled, a portion of the connection cavity will be formed by a staple tray similar to staple tray 37. Alternatively, rather than connection cavities, a channel can be formed between the tissue-facing surfaces of the cartridge and the tray. Portions of the adjunct can be tucked into the channel, or adhered to the tissue-facing surface at locations proximal to the channel, during manufacturing or at any time prior to use. In such an embodiment, drivers near the outermost edge of the tissue-facing surface of the cartridge can have an adjunct releasing mechanism such that portions of the adjunct are pushed out of the channel, and/or break the adhesive bond along the channel between the adjunct and the cartridge during firing.

The adjunct 4104 can be configured to be releasably retained on the tissue-facing surface 4106. The adjunct 4104 can have protrusions or tabs disposed on a surface that contacts the tissue-facing surface 4106, and the protrusions can be configured to extend into and engage with the connection cavities 4110. The adjunct 4104 can be configured to engage the tissue-facing surface 4106 through a variety of means. For instance, protrusions on the adjunct can be received in the connection cavities and securely attaching due to a friction fit attachment. In such an example, an adjunct can be created by extruding a film such that it has protrusions in predefined locations that correspond to locations of the connection cavities on a tissue-facing surface of a cartridge. In other embodiments, the adjunct can be made from a VICRYL® (polyglactin 910) material, and can include one or more backing layers made of polydioxanone (PDS). The one or more PDS layers can be fused to the VICRYL® material, and the one or more PDS layers can include protrusions that can be configured to extend into and mate with the connection cavities. In addition or alternatively, the adjunct can engage the tissue-facing surface through use of an adhesive, such as cyanoacrylate.

The cartridge 4102 can have one or more staple drivers 4200, 4300 movably disposed therein, similar to staple drivers 48. The staple drivers 4200, 4300 can be configured to move upward through the staple cavities 4108 to apply an upward force on each of the plurality of staples within the cartridge 4102. The staple driver 4200 illustrated in FIG. 32 can have a staple portion 4202 that can have a staple channel 4208 formed on an upper end thereon and that can be configured to seat a staple therein, similar to the staple driver 48. The driver 4200 can also have an adjunct releasing mechanism 4203 attached to a side of the staple portion 4202 and having a generally L-shaped configuration. The adjunct releasing mechanism 4203 can have a connecting element 4204 that connects the staple portion 4202 to the adjunct releasing mechanism 4203. A post 4206 can be attached to the connecting element 4204 and it can extend upward in the same direction as the staple channel 4208 of the staple portion 4202. The connecting element 4204 can have an upward-angled bottom 4205 that is configured to contact a wedge sled, similar to the wedge sled 47, to allow upward movement of the driver 4200 and firing of the staples. The post 4206 can have a variety of shapes, such as a rectangular shape as illustrated in FIG. 32, a cylindrical shape, a square, etc. In an exemplary embodiment, the post 4206 has a shape that corresponds to a shape of the connection cavity 4110 such that the post 4206 can be received in the connection cavity 4110.

FIG. 33 illustrates another embodiment of a staple driver 4300 that can be configured similar to the staple driver 4200. However, staple driver 4300 can have first and second staple portions 4302, 4303 similar to the staple portion 4202 with staple channels 4308, 4310 disposed on upper ends of the staple portions 4302, 4303, respectively. Each staple channel 4308, 4310 can be configured to seat a staple therein, and the staple driver 4300 can be configured to fire two staples simultaneously. The first and second staple portions 4302, 4303 can have an adjunct releasing mechanism 4304 coupled therebetween. The adjunct releasing mechanism 4304 can include a connecting element 4305 and a post 4306. The connecting element 4305 extends between and connects the two staple portions 4302, 4303, and it has an upward-angled bottom 4309 that is configured to contact a wedge sled, similar to the wedge sled 47, to allow upward movement of the driver 4300 and firing of the staples. The post 4306 is attached to the connecting element 4305 and extends upward in the same direction as the staple channels 4308, 4310. The post 4306 can have a variety of shapes, such as a rectangular shape as illustrated in FIG. 32, a cylindrical shape, a square, etc. In an exemplary embodiment, the post 4306 has a shape that corresponds to a shape of the connection cavity 4110 such that the post 4306 can be received in the connection cavity 4110.

While the illustrated staple drivers 4200, 4300 have connecting elements between the staple portions and the adjunct releasing mechanisms, a variety of connections can be used to connect multiple staple drivers. For example, two connecting elements can be used to connect three staple drivers. One skilled in the art will appreciate that a connecting element can include multiple adjunct releasing mechanisms, that multiple connecting elements can be used in parallel or in series to connect multiple staple drivers, and that the adjunct releasing mechanisms can have any number of geometries. For example, the adjunct releasing mechanisms can be curved, or can have cross-sections that are square, circular, triangular, etc. Additionally, it is possible that not all of the adjunct releasing mechanisms are uniform. The adjunct releasing mechanisms can have sharp features, as well. For example, the detachment features can be sharpened such that they can cut away a small portion of the adjunct to detach the rest from a tissue-facing surface of a cartridge.

In use, the staple drivers 4200 and/or 4300 can be disposed in the cartridge 4102 and aligned with the staple cavities 4108 and the connection cavities 4110 such that the staple channels 4208, 4308, 4310 are aligned with the staple cavities 4108 and the posts 4206, 4306 are aligned with the connection cavities 4110. The cartridge 4102 can be loaded with staples. The adjunct 4104 can be retained on the tissue-facing surface 4106 by, for example, having a plurality of protrusions friction fit within the connection cavities 4110. The adjunct 4104 can be applied to the tissue-facing surface 4106 any time before use, such as during manufacture or during preparation for use, and can be applied through a variety of techniques, such as by use of an applicator.

A surgeon can maneuver the surgical stapler into position and clamp tissue between jaws of the end effector 4100 thereon. The surgeon can then fire the surgical stapler, causing a sled, similar to wedge sled 47, to move distally through the cartridge 4102 of the end effector 4100. The sled can push one or more of the staple drivers 4200, 4300 upwardly through the staple cavities 4108 in the staple cartridge 4102. Upward movement of the staple drivers 4200, 4300 applies an upward force on each of the plurality of staples within the cartridge 4102 to thereby push the staples upwardly through the adjunct 4104 and tissue and against an anvil surface of an upper jaw of the end effector 4100 to form the staples. Upward movement of the staple drivers 4200, 4300 also moves the posts 4206, 4306 upwards. The posts 4206, 4306 apply an upward force on the protrusions of the adjunct 4104, forcing the protrusions out of the connection cavities 4110 as distal ends of the posts 4206, 4306 enter the cavities 4110. Forcing the protrusions from the cavities 4110 releases the adjunct 4104 from the tissue-facing surface 4106, and the adjunct can be secured by staples to the tissue grasped by the end effector 4100. In other embodiments, the posts 4206, 4306 can be configured to force the protrusions only partially out of the connection cavities 4110, which can be sufficient to loosen the adjunct 4104 from the tissue-facing surface 4106 enough such that the staples will remove the adjunct 4104 entirely upon firing. In various embodiments, firing the surgical stapler can also cause a cutting element to translate through the cartridge 4102 along the channel 4112 to tissue while staples are fired and the adjunct 4104 is released.

Figure 34:
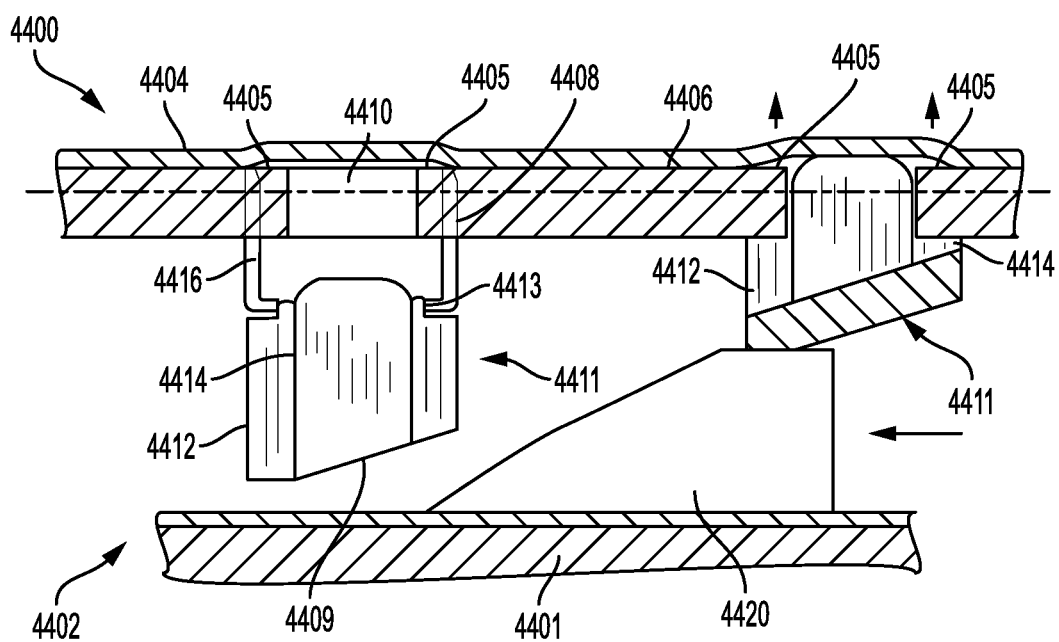
FIG. 34 is a cross-sectional side view of another embodiment of a portion of a lower jaw member of a surgical stapler with an adjunct releasing mechanism.

While the adjunct 4104 can be attached to the cartridge 4102 by protrusions, as noted above, adjuncts can be attached to a cartridge of a surgical stapler through a variety of means. For example, FIG. 34 illustrates an end effector 4400 with a cartridge 4402 and an adjunct 4404 secured thereto by an adhesive. The end effector 4400 can generally function and include components similar to end effector 4100. For example, the end effector 4400 can include an upper jaw having an anvil (not shown) and a lower jaw 4401 with the cartridge 4402 engaged thereon.

The cartridge 4402 can have staples 4416 disposed in a plurality of staple cavities 4408 and a plurality of connection cavities 4410 formed in a tissue-facing surface 4406. The connection cavities 4410 can have a variety of configurations and shapes. For example, the connection cavities 4410 can be roughly oval in shape and smaller than the staple cavities 4408. In other embodiments, the connection cavities 4410 can be circular, square, rectangular, etc., and they can be larger than, equal in size to, or a combination of sizes relative to the staple cavities 4408. The connection cavities 4410 can be disposed between rows of the staple cavities 4408. However, the connection cavities 4410 can have any number of configurations.

The adjunct 4404 can be configured to be releasably retained on the tissue-facing surface 4406, and the adjunct 4404 can be any of the adjuncts discussed herein. The adjunct 4404 can have adhesive disposed on a surface that contacts the tissue-facing surface 4406. For example, there can be adhesive points 4405 between the adjunct 4404 and the tissue-facing surface 4406 around outer edges of the connection cavities 4410 that can be configured to retain the adjunct 4404 on the cartridge 4402. However, a variety of different placements of the adhesive points 4405 is possible, such as in a grid pattern. Additionally, the adhesive can be spread uniformly on the tissue-facing surface 4406. A variety of adhesives can be used, such as cyanoacrylate.

When the adjunct is attached to the cartridge with an adhesive, it can be desirable in various embodiments to prevent the adhesive from spilling into the cartridge, for example into a cutting element channel or into the staple cavities. Various adjuncts can be configured to include features that prevent or inhibit adhesive from spilling into the cartridge and/or specifically the cutting element channel of the cartridge during the attachment process. As an example, the adhesive points 4405 can be formed by including small circular molded features on a surface of the adjunct 4404 that contacts the tissue-facing surface 4406 of the cartridge 4404. The circular molded features can act as reservoirs to form adhesive droplet attachment point insuring the adhesive, such as cyanoacrylate, does not enter the cartridge 4402 and/or the cutting element channel during attachment. In other embodiments, the adhesive can be housed within the adjunct itself, or reservoirs for adhesive can be part of an applicator used to apply the adjunct to the cartridge. For example, the reservoirs can be broken as part of clamping or pulling an activation lever on the applicator.

The cartridge 4402 can have one or more staple drivers 4411 movably disposed therein, similar to staple drivers 4200, 4300, that can be configured to move upward through staple cavities 4408 to apply an upward force on each of the plurality of staples 4416 within the cartridge 4402. Each staple driver 4411 can have a staple portion 4412 that can have a staple channel 4413 formed on an upper end thereof that is configured to seat a staple 4416 therein. The driver 4411 can also have an adjunct releasing mechanism attached to a side of the staple portion 4412 and having a post 4414 that is attached to the staple portion 4412 and that extends upward in the same direction as the staple channel 4413 of the staple portion 4412. The staple driver 4411 can have an upward-angled bottom 4409 that is configured to receive a wedge sled 4420, similar to the wedge sled 47, to allow upward movement of the driver 4200 and firing of the staple. The post 4414 can have a variety of shapes, such as a rectangular shape, a cylindrical shape, a square shape, etc., and the post 4406 can be configured to be received in the connection cavities 4410.

In use, the cartridge 4402 can have a plurality of the staple drivers 4411 disposed therein and loaded with staples 4416. The adjunct 4404 can be retained on the tissue-facing surface 4406 by, for example, having a plurality of adhesive points 4405 between the adjunct 4404 and the tissue-facing surface 4406 around the outer edges of the connection cavities 4410. The adjunct 4404 can be applied to the tissue-facing surface 4406 any time before use, such as during manufacture or during preparation for use, and can be applied through a variety of techniques, such as by use of an applicator. A surgeon can maneuver the surgical stapler into position and clamp tissue between jaws of the end effector 4400 thereon. The surgeon can then fire the surgical stapler, causing the sled 4420 to move distally through the cartridge 4402 of the end effector 4400. The sled 4420 can push one or more of the staple drivers 4411 upwardly through the staple cavities 4408 in the staple cartridge 4402. Upward movement of the staple drivers 4411 applies an upward force on each of the plurality of staples 4416 within the cartridge 4402 to thereby push the staples upwardly through the adjunct 4404 and tissue and against an anvil surface of the upper jaw of the end effector 4400 to form the staples. Upward movement of the staple drivers 4411 also moves the posts 4414 upwards. The posts 4414 can apply an upward force on the adjunct 4404, forcing the adjunct 4404 to move upwards and breaking the adhesive points 4405 once the posts 4414 move sufficiently through the connection cavities 4411. For example, the adhesive points 4405 can hold firm until a distalmost end of the posts 4414 crosses a plane of the tissue-facing surface 4406. Breaking, cracking, or separating the adhesive points 4405 from between the adjunct 4404 and the tissue-facing surface 4406 releases the adjunct 4404 from the tissue-facing surface 4406, and the adjunct 4404 can be secured by the staples 4416 to the tissue grasped by the end effector 4400. Although a distalmost end of the posts 4414 can cross a plane of the tissue-facing surface 4406, the posts 4414 can be configured such that they only extend even with, or below, the tissue-facing surface 4406. In some embodiments, firing the surgical stapler can also cause a cutting element to translate through the cartridge 4402, cutting tissue while the staples 4416 are fired and the adjunct 4404 is released.

While an adjunct can be attached to a lower jaw as illustrated above, an adjunct can also be attached to components of the upper jaw, such as the anvil. The upper jaw can be similar to that shown in FIGS. 1-2, but can include features and/or components for attaching and detaching an adjunct. For example, the upper jaw can be configured to include connection cavities and drivers that are driven by an E-beam to cause the adjunct to detach from the jaw. In various embodiments, when stapling is initiated, the components of the lower jaw can function to drive staples through tissue and the adjunct, while the drivers in the upper jaw can function to detach the adjunct from the anvil.

End Effector Having Extension Features for Mating with Adjuncts

Various exemplary techniques for releasably retaining an adjunct material on one or both jaws of an end effector of a surgical instrument are described herein. One or both of the opposed jaws can have extension elements formed thereon that extend beyond a nominal perimeter of that jaw. The extension elements are formed outside an area of the jaw's tissue-contacting and treating surface having staple-holding cavities (if the jaw is a cartridge body) or a tissue-contacting surface having staple-forming cavities (if the jaw is an anvil). An adjunct material configured to be releasably retained on the jaw can have a shape complementary to that of the jaw.

In some implementations, an end effector for a surgical instrument has first and second jaws, at least one of which is movable relative to the other one between open and closed positions. For example, the first jaw can have a cartridge body having on a tissue-contacting surface thereof a plurality of staple cavities configured to seat staples therein. The first jaw can have a generally rectangular nominal perimeter defining a regular perimeter around outer rows of the plurality of staple cavities. The second jaw can have or can be an anvil with a plurality of staple forming cavities formed on a tissue-contacting surface thereof. The second jaw can also have a generally rectangular nominal perimeter opposed to the nominal perimeter of the first jaw.

At least one of the first and second jaws can have a plurality of attachment features formed thereon on extension elements extending beyond the nominal perimeter of the at least one jaw. Each of the extension elements can have at least one attachment feature formed thereon. For example, the attachment feature can be a projection extending from the corresponding extension element. The attachment feature is configured to mate with a corresponding mating feature formed on an adjunct material that has a shape complementary to a shape of the jaw.

FIGS. 35, 36, 37, and 38 illustrate an example of an end effector 5100 of a surgical instrument configured to be coupled to a distal end of an elongate shaft of the surgical instrument (not shown). The end effector 5100 has a first jaw in the form a cartridge body 5102 and a second opposed jaw in the form of an anvil 5104 that are configured to clamp tissue therebetween. At least one of the cartridge body 5102 and the anvil 5104 is movable relative to the other between open and closed positions. In some embodiments, the cartridge body 5102 can seat therein a removable and replaceable cartridge. Furthermore, in some embodiments, the cartridge body 5102 can be part of a disposable loading unit coupled distally to an elongate shaft of a surgical instrument. One or both of the jaws of the end effector can have an implantable adjunct material releasably retained thereon. For example, the cartridge body 5102 can have an adjunct material 5101 shown in FIG. 38 releasably retained thereon as discussed in more detail below.

Figure 35:
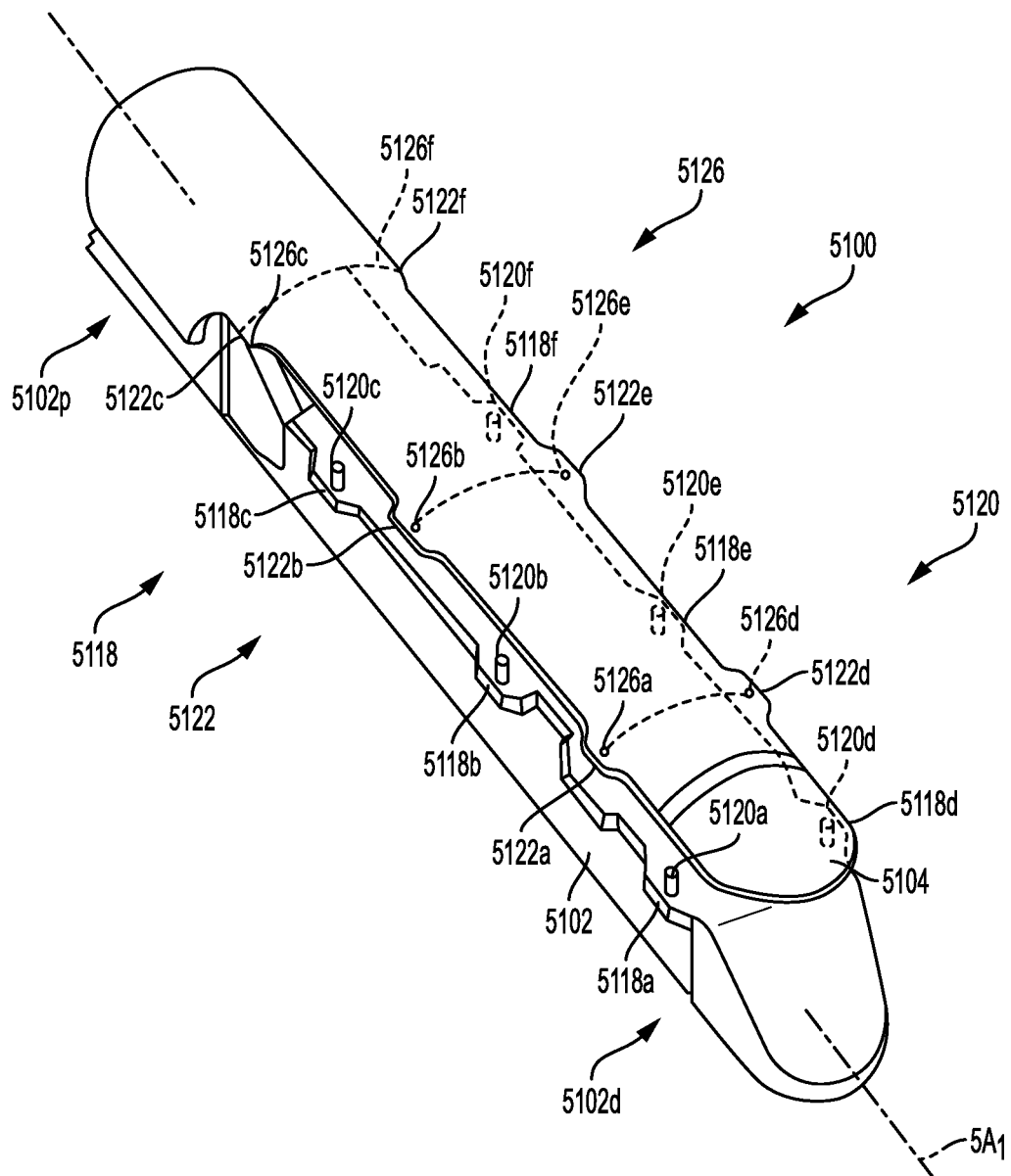
FIG. 35 is a perspective view of one embodiment of an end effector in accordance with the described techniques.
Figure 36:
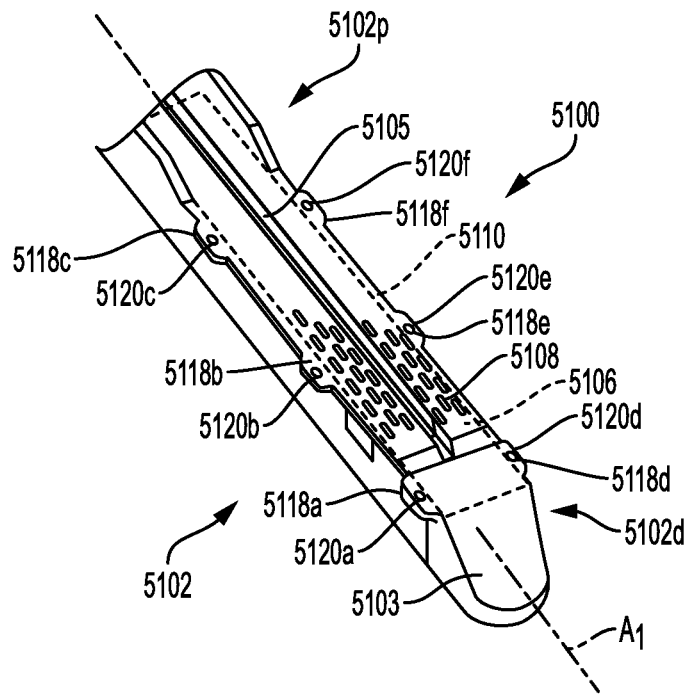
FIG. 36 is a perspective view of the cartridge body of the end effector of FIG. 35.

The cartridge body 5102 has a tissue-contacting surface 5106 having a plurality of staple cavities 5108 (shown partially in FIGS. 36 and 37) configured to seat staples therein. The tissue-contacting surface 5106 can have an adjunct material disposed thereon and may therefore not directly contact tissue. Moreover, the tissue-contacting surface 5106 is also a tissue-treating surface. The anvil 5104 has a plurality of staple forming cavities formed on a tissue-contacting (and treating) surface thereof, which are obscured in FIG. 35. In this example, both the cartridge body 5102 and the anvil 5104 are generally rectangular. As schematically shown in FIG. 36, the cartridge body 5102 has a longitudinal axis 5A1 and a generally rectangular nominal perimeter 5110 defining a regular perimeter around outer rows of the plurality of staple cavities 5108. The nominal perimeter 5110 has long sides 5112a, 5112b extending along the longitudinal axis 5A and short sides 5114a, 5114b. The anvil 5104 can also have a generally rectangular nominal perimeter opposed to the nominal perimeter 5114 of the cartridge body 5102.

In the example illustrated, the cartridge body 5102 has multiple extension elements 5118 extending beyond the nominal perimeter 5110. In particular, as shown in FIG. 35, the extension elements 5118 protrude from the cartridge body 5102 such that they extend beyond the side walls of the cartridge body 5102, such as a sidewall 5115 in FIGS. 35-37. As shown, the extension elements 5118 are formed outside the area of the cartridge body 5102 having the staple holding cavities 5108. In this example, six extension elements 5118a, 5118b, 5118c, 5118d, 5118e, 5118f are shown formed on the cartridge body 5102. As shown in FIG. 36, the extension elements 5118 are formed along at least one of the long sides 5112a, 5112b of the nominal perimeter 5114, in the plane of the tissue-contacting surface 5106 of the cartridge body 5102. In embodiments in which the cartridge body 5102 is in the form of a channel configured to removably and replaceably sit therein a cartridge with staples, the extension elements are formed on a body of the channel. In embodiments in which the entire cartridge body 5102 is removable and replaceable (e.g., as part of a disposable loading unit), the extension elements are formed on the cartridge body 5102.

As shown, the distal-most extension elements 5118a, 5118d are formed on opposite sides from a knife channel 5105 (FIG. 36) at a distal end 5102d of the cartridge body 5102, adjacent to a distal tip 5103. The extension elements 5118b, 5118e are formed more proximally on both sides of the knife channel 5105, and the extension elements 5118d, 5118f are the closest to the proximal end 5102p of the cartridge body 5102. In this example, the pairs of extension elements formed at opposed sides from the knife channel 5105 (e.g., the extension elements 5118a, 5118d) can be disposed along the same axis, which can be perpendicular to the longitudinal axis 5A1 of the jaw 5102. The extension elements formed along the same side of the jaw can be spaced equidistantly from one another along the side of the jaw, or one or more of the extension elements can be spaced differently from other extension elements.

The extension elements 5118 can have a number of different configurations. In the example illustrated, the extension elements 5118 have a trapezoidal shape (e.g., of an isosceles trapezoid) with its longer base being the closest to the nominal perimeter of the cartridge body 5102. However, it should be appreciated that the extension elements formed on the cartridge body can be rectangular, square, semi-circular, or they can have any other suitable shape(s), including regular and irregular shapes. Also, the cartridge body can have extension elements of two or more different configurations and/or sizes.

Furthermore, six extension elements 5118a, 5118b, 5118c, 5118d, 5118e, 5118f are shown by way of example only, as any suitable number of extension elements can extend beyond the nominal perimeter of the cartridge body. For example, one, two, three, four, five, or greater than six extension elements can be formed. Also, a different number of extension elements can be formed on one long side 5112a of the cartridge body 5102 as compared to the cartridge body's another long side 5112b.

Figure 37:
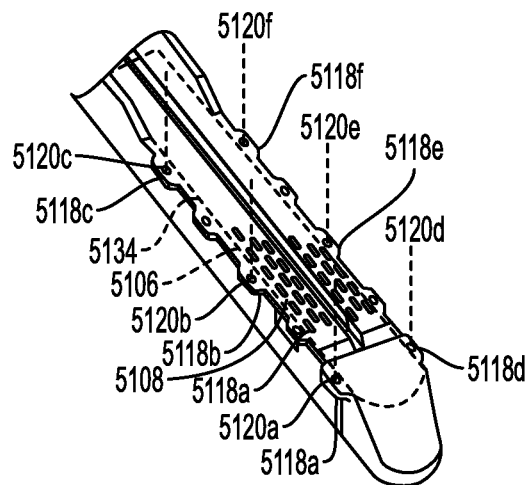
FIG. 37 is another perspective view of the cartridge body of the end effector of FIG. 35.

As in the implementation shown in FIGS. 35-37, the extension elements can be formed in the plane that is parallel to the tissue-contacting surface 5106 of the cartridge body 5102. However, in other implementations, one or more of the extension elements can have at least a portion thereof formed at an angle to the tissue-contacting surface 5106 of the cartridge body 5102, in a manner that does not interfere with proper operation of the end effector. The extension elements 5118a, 5118b, 5118c, 5118d, 5118e, 5118f can be formed monolithically and/or integrally with the cartridge body 5102. Furthermore, in some embodiments, the extension elements can be separate features coupled to the cartridge body 5102 in a suitable way.

The cartridge body 5102 and the extension elements 5118 have a size such that the cartridge body 5102 with the cartridge body 5102 with the extension elements 5118 extending therefrom fit within a trocar providing access to a surgical site. For example, in the illustrated embodiments, the cartridge body 5102 with the extension elements 5118 is sized such that the end effector 5100 has an overall diameter smaller than 12.8 mm. As a person skilled in the art will appreciate, regardless of the specific configuration of the cartridge body or anvil, the extension elements are formed thereon such that the end effector can fit within a suitable surgical site access instrument.

As shown in FIGS. 35-37, the extension elements 5118a, 5118b, 5118c, 5118d, 5118e, 5118f have respective attachment features 5120 formed thereon. In this example, each of the extension elements 5118a, 5118b, 5118c, 5118d, 5118e, 5118f has a respective one of the attachment features 5120a, 5120b, 5120c, 5120d, 5120e, 5120f formed thereon. Each of the attachment features can be in the form of a post or a projection extending from a respective extension element perpendicular to the longitudinal axis 5A1 of the cartridge body 5102. The projection can have a rounded tip or a tip having other suitable configuration. However, it should be appreciated that the attachment features formed on the extension elements 5118 can have any other various configurations. Also, in some implementations, the jaw (e.g., the cartridge body 5102) can have attachment features of more than one type formed thereon.

One or both of the cartridge body 5102 and anvil 5104 can have an adjunct material (or "adjunct") releasably retained thereon. In the illustrated implementation, the adjunct material has a shape complementary to a shape of the jaw on which it is mounted and the adjunct material is configured to releasably mate with the attachment features formed on the extension elements of the jaw. Thus, the adjunct has a generally rectangular nominal perimeter with discrete extension elements that extend beyond the nominal perimeter in a plane parallel to a surface of the adjunct configured to contact tissue. The extension elements can be formed on the adjunct such that at least two extension elements are formed along each of long sides of the adjunct's nominal perimeter. Each of the extension elements can have at least one mating feature configured to mate with a respective attachment features formed on the jaw.

Figure 38:
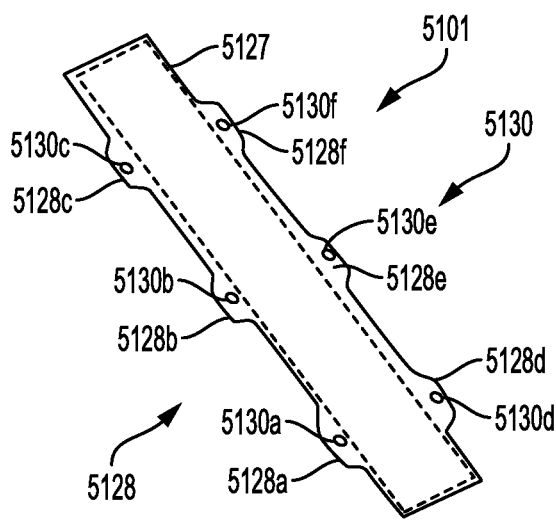
FIG. 38 is a perspective view of the adjunct material releasably retained on at least one jaw of the end effector of FIG. 35.

FIG. 38 shows the adjunct material 5101 that can be releasably retained on the tissue-contacting surface 5106 of the cartridge body 5102. As shown in FIG. 38, the adjunct material 5101 has a shape that corresponds to the shape of the cartridge body 5102—extension elements 5128, such as elements 5128a, 5128b, 5128c, 5128d, 5128e, 5128f are formed that extend beyond a nominal perimeter 5127 in a plane parallel to a surface of the adjunct 5101 configured to contact tissue. The extension elements 5128 can be formed integrally with the adjunct material 5101 or they can be separate elements coupled to the adjunct 5101 along the nominal perimeter 5127 thereof in a suitable manner.

The extension elements 5128a, 5128b, 5128c, 5128d, 5128e, 5128f are configured to be disposed over the respective extension elements 5118a, 5118b, 5118c, 5118d, 5118e, 5118f extending beyond the nominal perimeter 5110 of the cartridge body 5102. Thus, the shape of the adjunct 5101 is such that it "traces" the shape of the cartridge body 5102. The size of the adjunct material 5101 also corresponds to the size of the cartridge body 5102. In this way, the adjunct material 5101 is aligned with the cartridge body 5102 when the adjunct 5101 is disposed thereon.

The adjunct material 5101 can be configured to mate with the cartridge body 5102 in a variety of different ways. In the example illustrated, as shown in FIG. 38, the adjunct material 5101 has a plurality of mating features 5130, such as mating features 5130a, 5130b, 5130c, 5130d, 5130e, 5130f that are complementary to the attachment features 5120a, 5120b, 5120c, 5120d, 5120e, 5120f formed on the cartridge body 5102 and are configured to releasably mate with the attachment features 5120a, 5120b, 5120c, 5120d, 5120e, 5120f. In the illustrated implementation, the mating features are in the form of through openings formed in the adjunct material 5101. The openings are configured so as to receive the projections therein, such that the adjunct material can be released from the engagement with the jaw when staples are ejected from staple cavities.

The mating features 5130a, 5130b, 5130c, 5130d, 5130e, 5130f are formed on the adjunct's extension elements 5128a, 5128b, 5128c, 5128d, 5128e, 5128f as shown in FIG. 38, at locations on these extension elements corresponding to the locations of the cartridge's attachment features 5120a, 5120b, 5120c, 5120d, 5120e, 5120f. In this way, when the adjunct material 5101 is superimposed over the cartridge body 5102, the mating features 5130a, 5130b, 5130c, 5130d, 5130e, 5130f align with the cartridge's attachment features 5120a, 5120b, 5120c, 5120d, 5120e such that each opening receives therein a corresponding projection. The cartridge's attachment features and adjunct's mating features can releasably mate via a friction fit or in other ways.

As shown in FIG. 35 illustrating a partially transparent view of the anvil 5104, the anvil 5104 can also have extension elements 5122, such as elements 5122a, 5122b, 5122c, 5122d, 5122e, 5122f, formed thereon that beyond the nominal perimeter 5124 thereof. Each of the extension elements 5122 can have a shape and size similar to that of the extension elements 5118 formed on the cartridge body 5102. For example, as illustrated, the extension elements 5122 can be generally trapezoidal, though they can have other shapes, as the described techniques are not limited in this respect. Similar to the cartridge body 5102, each of the extension elements 5122 can have a respective attachment feature 5126 thereon for mating with an adjunct to be releasably retained on the anvil 5104. FIG. 35 illustrates that each of the extension elements 5122a, 5122b, 5122c, 5122d, 5122e, 5122f can have a respective one of the attachment features 5126a, 5126b, 5126c, 5126d, 5126e, 5126f formed thereon.

In the illustrated implementation, the extension elements 5122 are formed on the anvil 5104 in a manner such that they do not overlap with the extension elements 5118 formed on the cartridge body 5102. Thus, as shown in FIG. 35 and additionally in FIG. 37 (where a shadow or footprint 5134 of the anvil 5104 is schematically shown superimposed over the cartridge body 5102), the extension elements 5122 are staggered with respect to the extension elements 5118.

Figure 39:
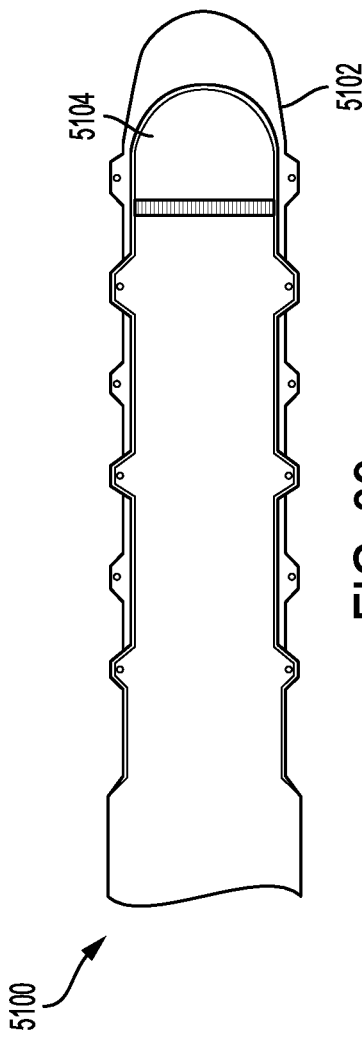
FIG. 39 is a top view of the end effector of FIG. 35, showing the jaws of the end effector in a closed position.

In the described embodiments, the respective extension elements are formed on the cartridge body 5102 and the anvil 5104 such that, when the end effector 5100 is in the closed position, the cartridge body's extension elements 5118 extend beyond the nominal perimeter of the anvil 5104 and the anvil's extension elements 5122 extend beyond the nominal perimeter of the cartridge body 5102. For example, FIG. 39, showing the end effector 5100 in a closed configuration, illustrates that the footprint of the cartridge body 5102 is outside the footprint of the anvil 5104 and that the extension elements 5122a, 5122b, 5122c, 5122d, 5122e, 5122f are staggered with respect to the extension elements 5118a, 5118b, 5118c, 5118d, 5118e, 5118f. However, it should be appreciated that, in some implementations, all or some of the cartridge's and anvil's extension elements are not staggered with respect to one another. For example, the cartridge's and anvil's extension elements can be formed symmetrical, such that at least one of the anvil's extension elements overlaps with at least one of the cartridge's extension elements.

Figure 40:
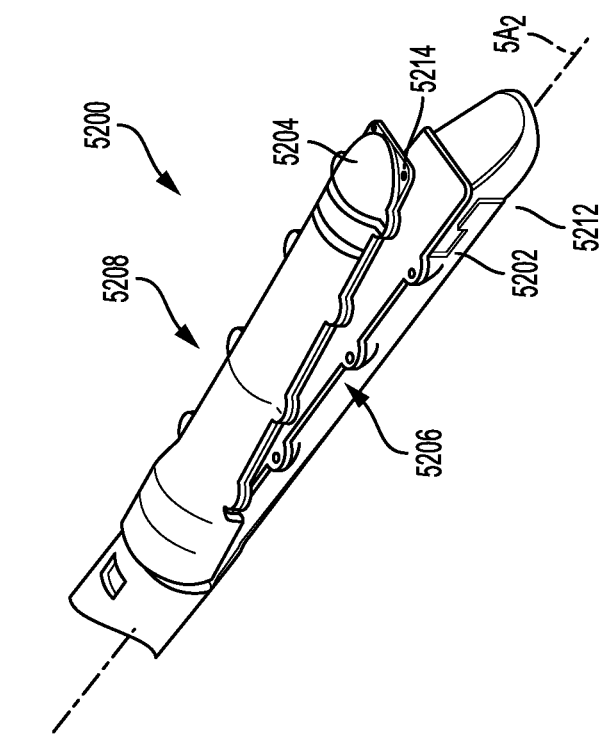
FIG. 40 is a perspective view of another embodiment of an end effector in accordance with the described techniques.

FIG. 40 additionally illustrates an end effector 5200 having a longitudinal axis 5A2, which can have a configuration similar to that of the end effector 5100 (FIGS. 35-37 and 39). Thus, similar to the end effector 5199, the end effector 5200 has extension elements formed, in the example of FIG. 40, on both of the jaws 5202 (cartridge body) and 5204 (anvil). The extension elements formed on the cartridge body 5202 and anvil 5204 are collectively identified as extension elements 5206, 5208, respectively. In this example, each of the cartridge body 5202 and anvil 5204 releasably retain thereon respective adjunct materials 5212, 5214 that are separately shown in FIGS. 41 and 42. The cartridge's extension elements 5206 and anvil's extension elements 5208 have attachment features, such as projections, configured to mate with corresponding mating features (e.g., openings) formed on adjunct materials 5212, 5214, respectively.

Figure 41:
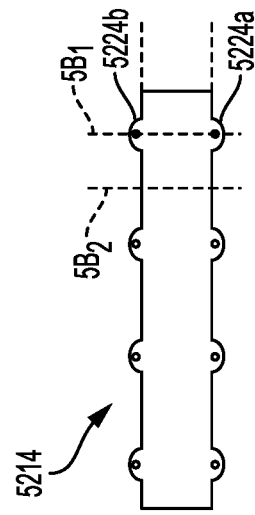
FIG. 41 is a top view of the adjunct material releasably retained on the anvil of the end effector of FIG. 40.
Figure 42:
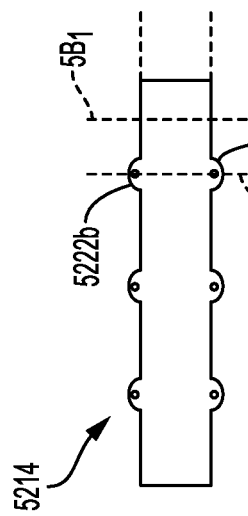
FIG. 42 is a top view of the adjunct material releasably retained on the cartridge of the end effector of FIG. 40.

As shown in FIGS. 40-42, the adjunct materials 5212, 5214 have shapes complementary to shapes of the cartridge body 5202 and anvil 5204, respectively. In this example, the extension elements 5206 formed on the cartridge body 5202 are staggered with respect to the extension elements 5208 formed on the anvil 5204. In a similar manner, the extension elements of the adjunct material 5212 are staggered with respect to the extension elements the adjunct material 5214. Thus, FIGS. 41 and 42 illustrate that, while the anvil's adjunct material 5214 has extension features 5224a, 5224b along an axis 5B1 (also shown in FIG. 40), the cartridge body's adjunct material 5212 does not have any extension elements formed along the axis 5B1. However, the cartridge body's adjunct material 5212 has extension elements 5222a, 5222b formed along an axis 5B2 (also shown in FIG. 40), whereas the anvil's adjunct material 5214 does not have extension elements formed along the axis 5B2.

An implantable adjunct configured to be releasably retained over a jaw of an end effector can be made from a variety of different materials described herein. For example, as discussed above, the adjunct can be formed from one or more of a film, foam, an injection molded thermoplastic, a vacuum thermoformed material, a fibrous structure, and hybrids thereof. The adjunct can also include one or more biologically-derived materials and one or more drugs. Furthermore, in the described implementations, one or more portions of the adjunct can have different properties. For example, the areas configured to be superimposed over the extensions features formed on a jaw can be configured differently from other areas of the adjunct.

A jaw (such as a cartridge body or an anvil) having extension elements and an adjunct material having a shape complementary to that jaw can have other features formed thereon for mating between these components. For example, in some implementations, the jaw can have attachment features in the form of recesses, through openings, or other types of features formed in the corresponding extension elements of the jaw and configured to mate with respective features formed on the adjunct material.

In some implementations, the opposed jaws of the end effector can have different types of adjunct materials releasably retained thereon. Furthermore, the same or different types of adjunct materials can be coupled to the opposed jaws using the same or different techniques. For example, one adjunct material can be attached to one of the jaws via mechanical features (e.g., projections on the jaw and openings on the adjunct, as discussed above), whereas another adjunct material can be attached to the opposed jaw using a suitable adhesive material.

In some embodiments, a cartridge body (e.g., part of a reloadable unit) can have an adjunct material attached thereon via an adhesive material, while another adjunct material can be attached to the anvil using mechanical feature, such as the projections on the jaw and openings on the adjunct. The cartridge body can be manufactured with a suitable adjunct material already retained thereon. At the same time, an adjunct material can be attached to the anvil of an end effector during surgery.

In some implementations, the anvil of an end effector can have mating features in the form of female features formed on the extensions of the anvil extending beyond the anvil's nominal perimeter. The female features, configured to mate with complementary features formed in an adjunct material configured to be releasably retained on the anvil, can be shaped as openings, pockets, cleats, etc. The adjunct material's mating features can be, for example, hooks, snaps, barbs, features having expandable elements (e.g., tree- or umbrella-like features) that can releasably mate with the pocket-type openings in the anvil. Furthermore, in some implementations, the anvil can have one or more three-dimensional pockets that allow an overmold feature of the adjunct to be releasably retained thereon. The overmold feature can be, for example, a projection molded into the three-dimensional pocket. It should be appreciated that at least on of the jaws of the end effector and an adjunct configured to releasably mate with that jaw can also have these features additionally or alternatively to the features described in connection with FIGS. 35-42.

Figure 43:
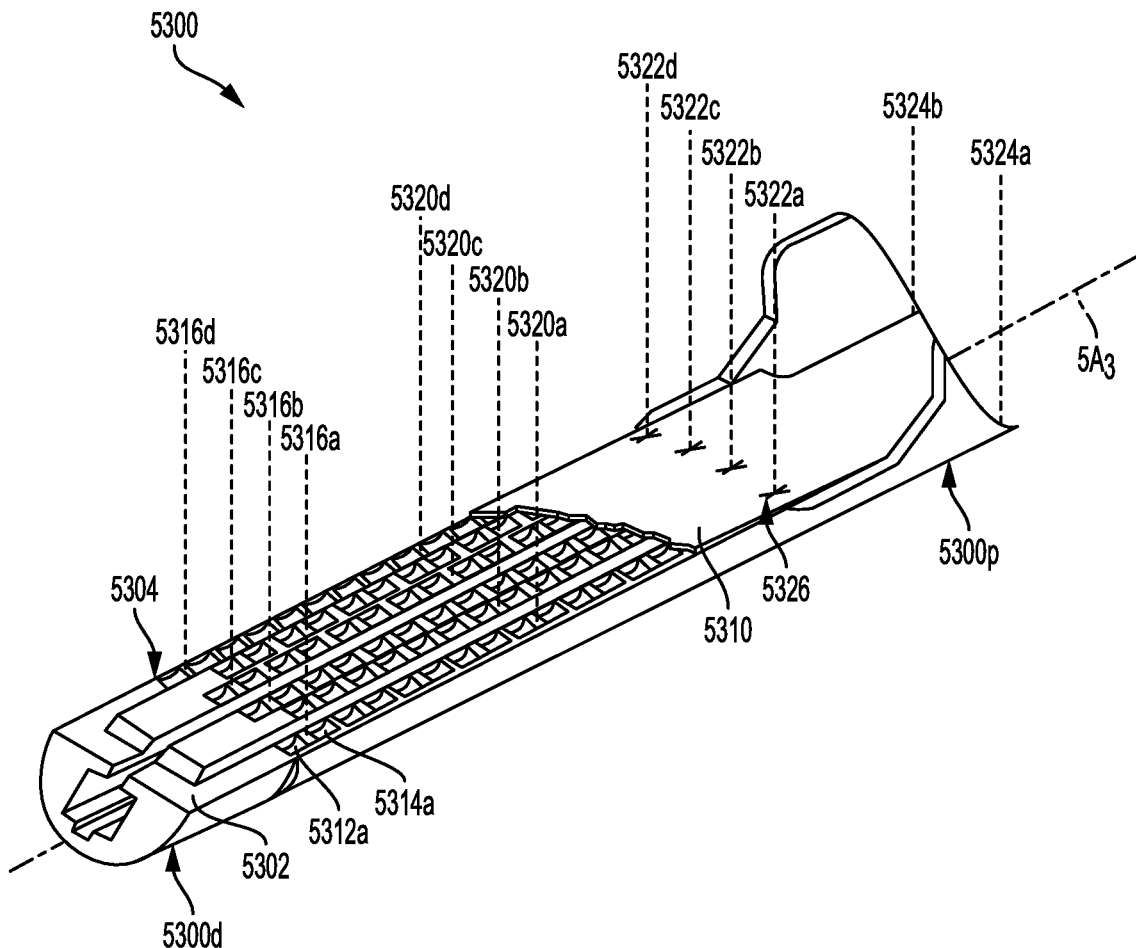
FIG. 43 is a perspective, partially cut-away view of one embodiment of an anvil of an end effector in accordance with the described techniques.
Figure 44:
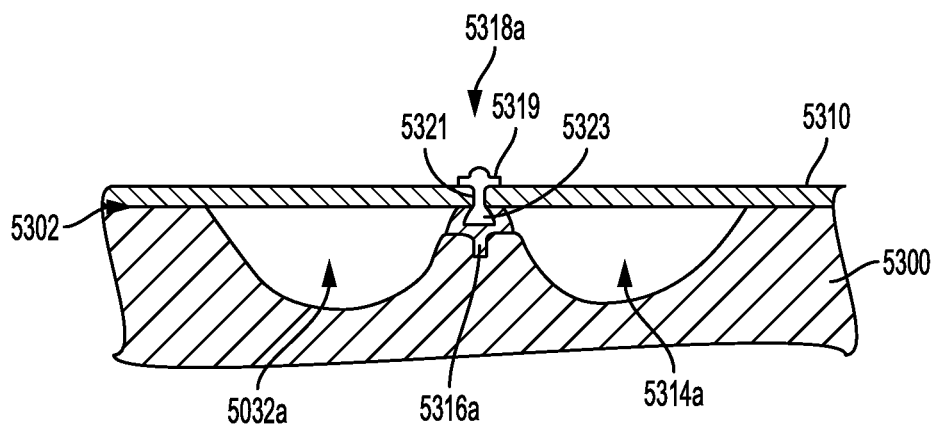
FIG. 44 is a side view of a portion of the anvil of FIG. 43.

Furthermore, in some embodiments, one or both of the jaws of the end effector may not have extension features formed thereon. In such embodiments, attachment features can be formed on an end effector's jaw within a nominal perimeter of the jaw. FIGS. 43 and 44 illustrate an example of such an embodiment providing an anvil 5300 of an end effector having female features formed thereon for mating with an adjunct material 5310 that has corresponding mating features. The anvil 5300 has a tissue-contacting surface 5302 having a plurality of staple-forming pockets or cavities 5304. The staple-forming cavities 5304 can form various patterns on the tissue-contacting surface 5302. In this example, the staple-forming cavities 5304 are arranged in six rows extending along a longitudinal axis 5A3 of the anvil 5300. As shown in FIG. 43, the tissue-contacting surface 5302 has attachment features 5316a, 5316b, 5316c, 5316d formed at a distal end 5300d of the anvil 5300 between adjacent staple-forming cavities. As shown, in this example, the attachment features 5316a, 5316b, 5316c, 5316d are formed in a row that is generally perpendicular to a longitudinal axis 5A3 of the anvil 5300.

FIG. 44 illustrates by way of example two adjacent staple-forming cavities 5312a, 5314a having the attachment feature 5316a therebetween, which is in the form of an overmold cleat or pocket. Thus, the attachment feature 5316a and other similar attachment features are formed on the anvil's tissue-contacting surface 5302 by overmolding a suitable polymeric material (or a polymer blend or a copolymer) between adjacent staple-forming cavities at selected locations on the tissue-contacting surface 5302. The attachment features 5316b, 5316c, 5316d, as well as other attachment features formed on the tissue-contacting surface 5302, can be formed in a similar manner and are not shown in detail.

FIG. 44 also illustrates that the adjunct material 5310 (which is shown partially in FIG. 43) has a mating feature 5318a configured to be received within the pocket 5316a. The mating feature 5318a can be in the form of an expandable (e.g., umbrella-like) mating feature extending through a thickness of the adjunct 5310 and a portion of which expands upon being inserted into the pocket 5316a. The pocket 5316a and the mating feature 5318a are configured to mate such that, when staples are ejected from a cartridge and formed against the staple-forming cavities, the mating features 5318a are caused to be disengaged from the pocket 5316a.

As shown in FIG. 44, the mating feature 5318a can be associated with the adjunct such that its top portion 5319 seats on one side above the surface of the adjunct 5310, its mid-portion 5321 penetrates through the adjunct's surface and extends toward the opposite side of the adjunct that comes in contact with the anvil's tissue-contacting surface 5302, and its expandable bottom portion 5323 is disposed on the opposite side of the adjunct, within the pocket 5316a. The expandable portion 5323 of the mating feature 5318a can have one or more portions (e.g., arms, wings, prongs, snaps, etc.) that are configured to expand when load is applied to the top portion 5319.

In use, the adjunct material 5310 is brought in proximity to the tissue-contacting surface 5302 and force can be applied to the adjunct material 5310 to cause the mating feature 5318a to be received within the pocket 5316a such that the expandable portion 5323 is received within the pocket 5316a and expands to thereby releasably retain the adjunct 5310 over the tissue-contacting surface 5302. It should be appreciated that the mating feature 5318a can have other configurations that allow this feature to be used to releasably retain the adjunct on the jaw. The adjunct's mating features can have a changeable configuration, e.g., such that at least a portion of the feature expands, as the exemplary mating feature 5318a in FIG. 44. As another variation, the mating feature can be in the form of a hook or other non-expandable feature configured to be received within a recess in a jaw. The load can be applied to the adjunct 5310 manually, or using a loader or applicator member which can be removably coupled to the end effector or removably coupled to the adjunct 5310. In some embodiments, the adjunct 5310 can have an applicator (e.g., in the form of a frame of a suitable configuration disposed over the adjunct) for applying load thereto to be coupled to the adjunct 5310. During a surgical procedure, such applicator can be utilized to cause the adjunct 5310 to be releasably retained over the jaw.

FIG. 43 shows that, besides the attachment features 5316a, 5316b, 5316c, 5316d, the tissue-contacting surface 5302 also has attachment features 5320a, 5320b, 5320c, 5320d formed at a mid-portion 5300m of the anvil 5300. The tissue-contacting surface 5302 also has attachment features 5322a, 5322b, 5322c, 5322d formed at a proximal portion 5300p of the anvil 5300, the locations of which are shown schematically in FIG. 43 as these features are obscured by the adjunct 5310. Additionally, the tissue-contacting surface 5302 has proximal-most attachment features 5324a, 5324b (obscured by the adjunct 5310), which locations are shown in FIG. 43. The attachment features 5324a, 5324b are disposed at opposite sides of an anvil knife channel 5308 extending between distal and proximal ends 5300d, 5300p of the anvil 5300.

The mid-portion attachment features 5320a, 5320b, 5320c, 5320d and the proximal attachment features 5322a, 5322b, 5322c, 5322d are arranged in two respective rows generally perpendicular to the longitudinal axis 5A3 of the anvil 5300. As in this example, the attachment features can be located symmetrically with respect to the anvil knife channel 5108. Regardless of its specific location, each of the attachment features is configured to releasably mate with at least one mating feature formed on the adjunct material. Thus, FIG. 43 schematically shows that the proximal attachment features 5322a, 5322b, 5322c, 5322d (obscured in FIG. 43) are configured to mate with respective adjunct's mating feature collectively indicated as features 5326. These mating features can be configured similar to the feature 5318a shown in FIG. 44, or in another way.

It should be appreciated that the attachment features in FIG. 43 are shown to form three rows by way of example only, as attachment features can be formed on a tissue-contacting surface of a jaw at any desired locations, so as to form various patterns. Also, eight attachment features are shown by way of example, as any number of the attachment features can be formed on the jaw's tissue-contacting surface. Furthermore, although the anvil 5300 is shown in FIGS. 43 and 44, in some implementations, features similar to those shown in FIGS. 43 and 44 can be formed on a cartridge body of an end effector. Also, the cartridge body and the anvil of an end effector can have respective adjuncts releasably coupled thereto via different techniques. For example, the cartridge body can have extension elements with attachment features as shown in FIGS. 35-37 (and in FIGS. 39 and 40), whereas the anvil can have openings or pockets as shown in FIGS. 43 and 44, or vice versa.

Methods and Systems for Mating Constructible Adjunct Materials with End Effectors Various exemplary devices, systems, and methods for releasably retaining an adjunct material on one or both jaws of an end effector of a surgical instrument are described herein. One or both of the opposed jaws can have retaining members formed thereon that are configured to mate with an adjunct material.

In some implementations, an adjunct material can be releasably retained on a jaw of an end effector in a secure manner, such that a possibility of the adjunct material prematurely slipping off the jaw is decreased or eliminated. In this way, the adjunct is securely coupled to the jaw while a surgeon manipulates the end effector during a surgical procedure. The adjunct remains coupled to the jaw until it is separated from the jaw and transferred to a treatment site in a patient, for example, when staples are deployed and/or when movement of a cutting element causes the adjunct to separate from the jaw. In such implementations, the adjunct material can be coupled to a jaw of an end effector using one or more contractible attachment features. The contractible attachment features, which are configured to couple the adjunct material with retaining members or other features of the jaw, can be features formed separately from the adjunct material. Additionally or alternatively, the contractible attachment features can be interwoven into or otherwise coupled to adjunct material.

In some embodiments, the contractible attachment feature can be in the form of one or more strands of a shrinkable polymer. The strands can be disposed on the adjunct material and/or they can be passed through the adjunct material in one or more locations. Furthermore, in some embodiments, the attachment feature can be in the form of a plurality of polymer strands interwoven into the adjunct material. The attachment features can be formed from any suitable material(s). For example, in some implementations, they can be formed from polydioxanone (PDO) or from other material(s) having a melting temperature that is lower than that of the adjunct material.

Regardless of the specific configuration of the contractible attachment features and the materials from which they are formed, each attachment feature can be configured to be transitioned from an original, non-contracted configuration to a contracted configuration under application of heat. The attachment feature can be engaged with the adjunct material, and contraction of the attachment feature is effective to couple the adjunct material with retaining members formed on the jaw. Adjunct materials can be releasably coupled to one or both jaws of an end effector of a surgical instrument using the contractible attachment features described herein.

Figure 45:
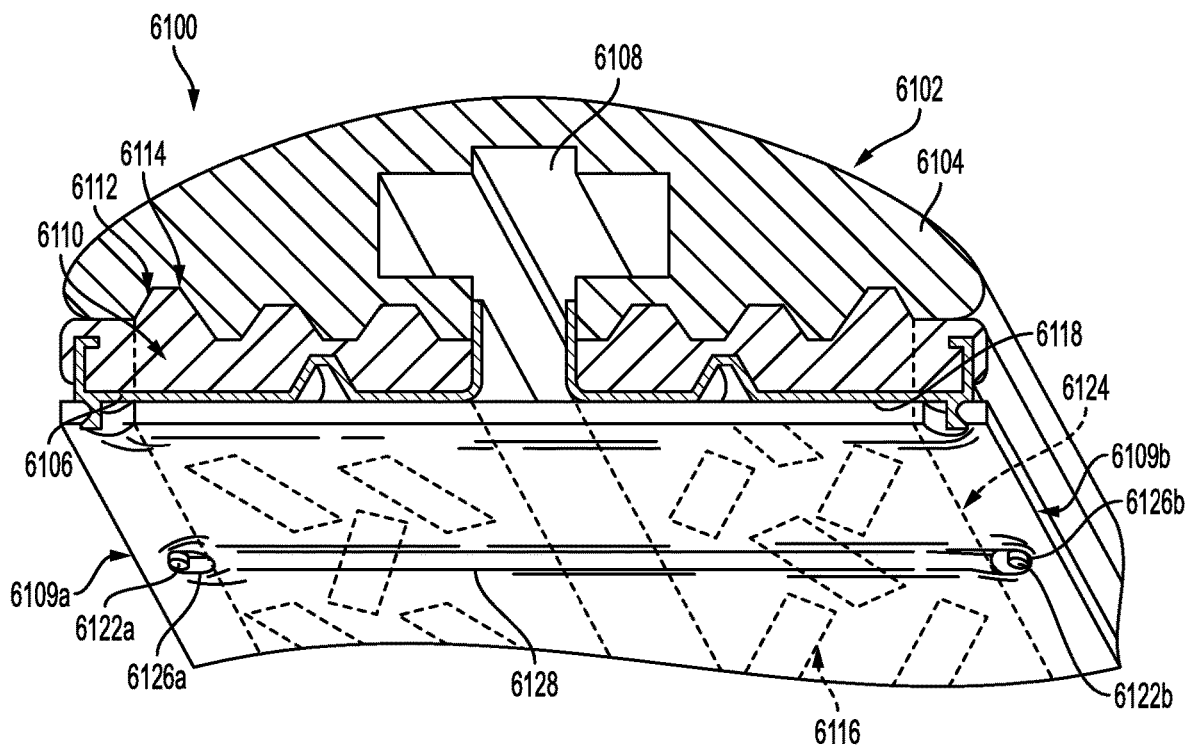
FIG. 45 is a perspective view of a jaw of an end effector that has an adjunct material releasably secured thereto.

FIG. 45 illustrates an example of a jaw of an end effector that has an adjunct material releasably secured thereto using contractible attachment features. FIG. 45 shows a portion of an end effector 6100 of a surgical instrument configured to be coupled to a distal end of an elongate shaft of the surgical instrument (not shown). The end effector 6100 can generally include components similar to those described with regard to FIGS. 1-4, and can also include features and/or components that enable adjuncts to be releasably attached thereto. Thus, similar to surgical staplers 10 (FIG. 1) and 50 (FIG. 4), the end effector 6100 includes an upper jaw having an anvil and an lower jaw having a cartridge body (not shown), with only the upper jaw 6102 being shown in FIG. 45. The lower jaw can generally include a staple cartridge that has a plurality of staple-holding cavities configured to seat staples therein, the staple-holding cavities opening on a tissue-facing surface of the cartridge.

As shown in FIG. 45, the upper jaw 6102 having an anvil 6104 can have an adjunct material 6124 (shown partially transparent) releasably retained on a tissue-facing surface 6118 of the anvil 6104 using one or more contractible attachment features 6128, as discussed in more detail below. As schematically shown in FIG. 45, the anvil 6104 has staple-forming cavities 6116 formed on the tissue-facing surface 6118 thereof. As also shown, the tissue-facing surface 6118 has a knife channel 6108 configured to receive a cutting element (e.g., a knife) as it moves distally therethrough.

In the example illustrated, the anvil 6104 is shown in the form of a modular jaw that includes an anvil plate 6106 releasably attached to the anvil 6104 via an adapter 6110. The anvil plate 6106 is a substantially rigid surface against which staples can be formed. In the illustrated example, the adapter 6110 can include mating features 6112 configured to mate with corresponding anvil features 6114 formed along a side of the anvil 6104 facing the opposed jaw, thereby ensuring an alignment between the anvil plate 6106 and the cartridge-facing surface of the anvil 6104. The adapter 6110 can be, e.g., an elastomer or other compliant member, and it can be overmolded, adhered to, or otherwise coupled to the anvil plate. The adapter 6110 can be used to releasably couple the anvil plate 6106 to the anvil 6104 in a variety of ways. For example, the adapter 6110 can snap into the jaw 6102. The modular configuration can allow interchangeably using anvil plates having different staple-forming features with the same jaw. The described techniques can be used in conjunction with various end effectors having modular jaws. For example, such end effectors are described in U.S. patent application Ser. No. 15/435,986 entitled "Surgical End Effector Adjunct Attachment," filed on even date herewith, and U.S. patent application Ser. No. 15/385,953 entitled "Methods of Stapling Tissue" filed on Dec. 21, 2016, the entire contents of which are incorporated by reference herein.

In the example of FIG. 45, the tissue-facing surface 6118 is in the form of the surface of the anvil plate 6106 facing the adjunct material 6124. However, it should be appreciated that the modular anvil 6104 having the anvil plate 6106 is shown by way of example only, and that the described techniques can be used to releasably couple an adjunct material to any type of a jaw, including a jaw having a tissue-facing surface non-removably coupled thereto.

Regardless of its particular configuration, the tissue-facing surface 6118 of the anvil 6104 has at least first and second retaining members 6122a, 6122b that are configured to couple the adjunct material 6124 to the anvil 6104. The first retaining member 6122a is disposed at one side of the tissue-facing surface 6118 in proximity to one edge 6109a of the tissue-facing surface 6118, and the second retaining member 6122b is disposed at another, opposed side of the tissue-facing surface 6118 in proximity to another, opposed edge 6109b thereof. In this way, the first and second retaining members 6122a, 6122b are disposed at opposed sides of the knife channel 6108.

The retaining members 6122a, 6122b can have a variety of different configurations. In the example illustrated, they are in the form of generally cylindrical posts extending from the tissue-facing surface 6118. However, the retaining members 6122a, 6122b can have other shapes, as the described implementations are not limited in this respect. For example, the retaining members can have an hour glass shape, a bulbous or widened end region, or any other shape. Additionally or alternatively, the retaining members can be curved and/or angled in any suitable manner. For example, as shown in FIG. 45, the retaining members 6122a, 6122b can be slightly angled away from one another towards respective edges 6109a, 6109b of the tissue-facing surface 6118. Such configuration can assist in engaging the one or more attachment features 6128 with the retaining members 6122a, 6122b, as discussed below. The retaining members can be configured in any other manner and have any other retaining features, such as, for example, one or more teeth, notches, grooves, undercuts, roughness areas, etc., that can facilitate retention of the attachment features 6128 at the retaining members.

Although two retaining members 6122a, 6122b are shown in FIG. 45, the tissue-facing surface 6118 can have any other number of retaining members (e.g., one or greater than two) configured to couple an adjunct thereto. Furthermore, the retaining members can be formed at various locations on the tissue-facing surface 6118 of the anvil 6104. For example, in some embodiments, two or more retaining members can be formed along each edge 6109a, 6109b of the tissue-facing surface 6118. The retaining members can be formed at any suitable distance from one another that allows securely retaining the adjunct material on the jaw's tissue-facing surface. In addition, the retaining members can be disposed symmetrically with respect to the knife channel 6108 or other features of the tissue-facing surface 6118, or they can be formed at various other ways on the surface 6118.

As shown in FIG. 45, in the example illustrated, each of the retaining members 6122a, 6122b is formed outside of the area of the tissue-facing surface 6118 having the staple-forming cavities 6116. However, in some implementations, one or more of the retaining members can be formed within the area having the staple-forming cavities 6116.

As mentioned above, the adjunct material 6124 is configured to releasably couple with the anvil 6104 using at least one contractible attachment feature 6128 configured to be transitioned from an original, non-contracted configuration to a contracted configuration under application of heat, as discussed in more detail below. The adjunct material 6124 can couple with the anvil 6104 in a secure manner, which helps ensure that the adjunct material 6124 remains coupled to the anvil 6104 while the end effector 6100 is manipulated as desired using a surgical procedure. The adjunct 6124 is held in engagement with the anvil 6104 until an action, such as an activation of the end effector 6100 to release staples from its cartridge and/or an activation of a cutting element, is taken that causes the separation of the adjunct 6124 from the anvil 6104.

To accommodate a contraction of the at least one contractible attachment feature 6128 that occurs as a result of heating, the adjunct material 6124 can be configured such that it assumes an appropriate shape and size once heating has occurred so as to couple the adjunct material 6124 to the jaw 6102. For example, the adjunct material 6124 can be sized such that it extends beyond the perimeter of the tissue-facing surface 6118 of the anvil 6104 prior to heating, and adopts the appropriate size once heating has occurred.

The first and second retaining members 6122a, 6122b are configured to mate with respective mating features of the adjunct material 6124. In particular, in the described implementation, the adjunct material 6124 includes openings 6126a, 6126b configured to receive the retaining members 6122a, 6122b, respectively. In this example, the through openings 6126a, 6126b in the adjunct 6124 are generally round, though it should be appreciated that the openings 6126a, 6126b can have any other suitable shapes.

The openings 6126a, 6126b can have various sizes and configurations, and they can be disposed at various locations of the adjunct 6124. For example, the openings 6126a, 6126b can be formed at locations of the adjunct material 6124 that correspond to the locations of the retaining members 6122a, 6122b formed on the anvil plate 6106.

In the described implementations, as mentioned above, the retaining members 6122a, 6122b couple the adjunct 6124 to the anvil 6104 by engaging one or more contractible attachment features 6128 configured to be transitioned from an original, non-contracted configuration to a contracted configuration under application of heat. The contractible attachment features 6128 can be in the form of one or more strands of a shrinkable polymer, which can be coupled to the adjunct material 6124 at one or more locations. The adjunct material 6124 and the at least one contractible attachment feature 6128 can be made from a variety of materials. For example, in at least some embodiments, the adjunct 6124 can be made from VICRYL® (polyglactin 910) material, whereas the contractible attachment feature 6128 can be in the form of one or more PDO strands that can be bioabsorbable and/or biodegradable. Any other materials can be used additionally or alternatively. One or more of the strands can be coupled (e.g., removably) to the adjunct material 6124. The PDO has a relatively low melting temperature, which is advantageous for its use in conjunction with adjuncts and attachment features. For example, the PDO has a melting temperature of 105 C°. Heat can be applied for, for example, from 30 seconds to several minutes to cause the attachment feature 6128 to transition into the contracted configuration.

Referring to FIG. 45, the contractible attachment features 6128 can be engaged with the adjunct material, and contraction of the contractible attachment feature 6128 is effective to couple the adjunct material 6124 with the retaining members 6122a, 6122b. For example, the adjunct material 6124 can be disposed over the tissue-facing surface 6118 of the jaw 6102 such that adjunct's openings 6126a, 6126b receive the retaining members 6122a, 6122b. In some embodiments, the adjunct material 6124 can be applied to the jaw using a loader member, as discussed below. Further, the adjunct material 6124 is associated with the at least one contractible attachment feature 6128 which can be disposed over the adjunct material 6124 such that the attachment feature 6128 is engaged with the retaining members 6122a, 6122b. The attachment feature 6128 can be coupled to the adjunct material 6124—e.g., it can be in the form of one or more strands of a shrinkable polymer, one or more of which are passed through at least one portion of the adjunct 6124. Heat can be applied to cause at least a portion of the attachment feature 6128 to contract to thereby cause the adjunct material 6124 to couple with the retaining members 6122a, 6122b using the attachment feature 6128. In particular, the attachment feature 6128 can be caused to transition from the original, non-contracted configuration to the contracted configuration such that, in the contracted configuration, the attachment feature 6128 is coupled to retaining members 6122a, 6122b and thereby retains the adjunct material 6124 in secure (albeit releasable) engagement with the retaining members 6122a, 6122b and thus with the anvil 6104.

It should be appreciated that the adjunct materials can be attached to an end effector using various other approaches. For example, the U.S. Pat. App. No. 614/871,078 entitled "Tubular Absorbable Constructs" filed on Sep. 30, 2015, which is incorporated by reference herein in its entirety, describes another approach.

Figure 46A:
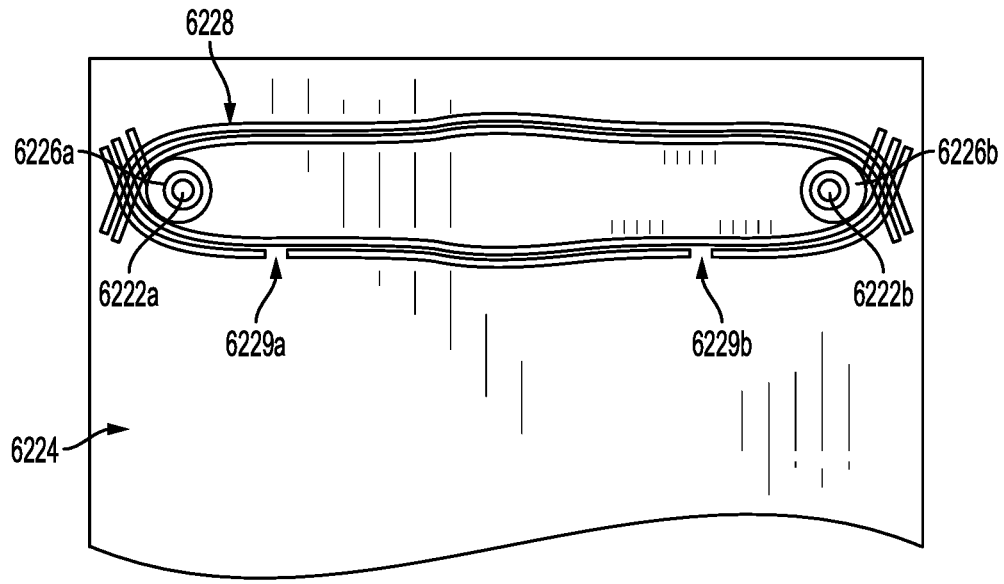
FIG. 46A is a perspective view an adjunct that has contractible attachment features disposed on a jaw of an end effector before the adjunct is coupled to the jaw.
Figure 46B:
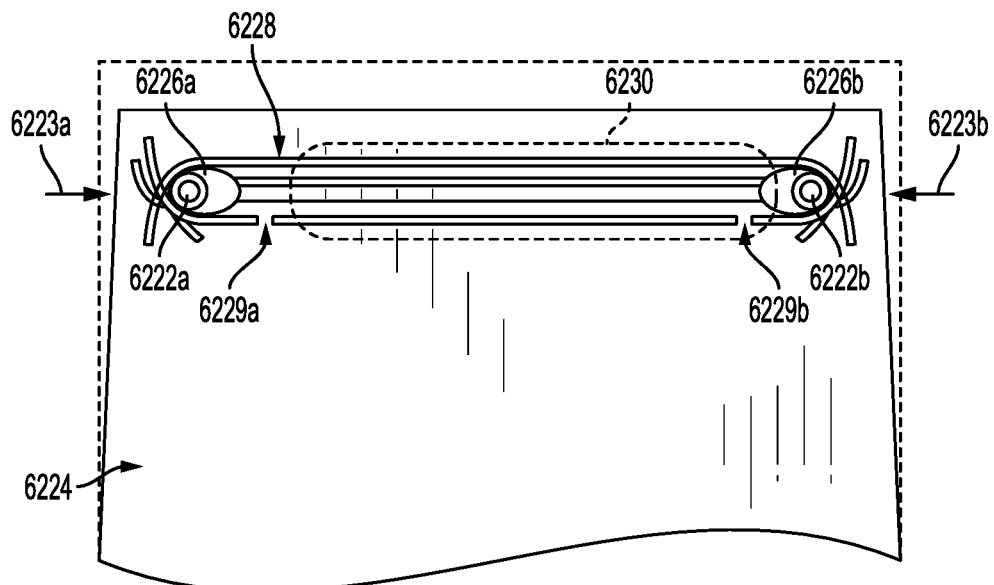
FIG. 46B is a perspective view of the adjunct of FIG. 47A, illustrating the adjunct coupled to the jaw by application of heat.

FIGS. 46A and 46B illustrate an embodiment of an adjunct material or adjunct 6224 that can be disposed on a tissue facing surface of a jaw (not shown), such as a jaw having an anvil (e.g., anvil 6104 in FIG. 45). It should be appreciated that the jaw can also be a jaw having a cartridge. In this example, the adjunct 6224 has a plurality of attachment features 6228 associated therewith.

The attachment features 6228 can be in the form of two or more attachment features. The attachment features 6228 can be, for example, strands of a shrinkable polymer, such as PDO strands that can pass through at least one portion of the adjunct material, at one or more points. For example, the PDO strands can be woven, knitted, braded into the adjunct 6224, or otherwise associated with the adjunct 6224. As shown by way of example, one or more of the attachment features 6228 can be coupled to the adjunct 6224 at points 6229a, 6229b, though it should be appreciated that the attachment feature 6228 can be coupled to the adjunct 6224 at any number of points at any locations in the adjunct 6224. In some cases, the adjunct 6224 can be manufactured such that the attachment features 6228 are created during the manufacturing process and are thus part of the adjunct 6224. In other embodiments, however, some or all of the attachment features 6228 can be separate threads coupled to the adjunct 6224.

In use, the adjunct 6224 can be mated with the jaw via retaining members 6222a, 6222b formed on the jaw and mating with openings 6226a, 6226b in the adjunct 6224. As shown in FIG. 46A, before the adjunct 6224 is securely and releasably coupled to the jaw, the attachment features 6228 are in a non-contracted configuration such that they form one or more loops that encompass both of the retaining members 6222a, 6222b. As shown, the loops can be disposed in a relatively loose manner around the retaining members 6222a, 6222b. As discussed above, the attachment features 6228 can be associated with the adjunct in a variety of ways. For example, they can be passed through one or more portions of the adjunct 6224. Additionally or alternatively, the attachment features can be disposed over, and coupled to the adjunct using, e.g., an adhesive.

As illustrated schematically in FIG. 46B, the adjunct 6224 can be secured to the jaw by applying heat to a region 6230 that encompasses a portion of the attachment features 6228. Under the application of heat, the attachment features 6228 transition from the non-contracted configuration (shown in FIG. 46A) to a contracted configuration as shown in FIG.

46B. In the contracted configuration, the attachment features 6228 can be arranged such that one or more loops are engaged around the retaining members 6222a, 6222b and thereby releasably retain the adjunct material 6224 over the jaw. In this way, in the contracted configuration, the loops of the attachment features 6228 are held in tension more tightly around the retaining members 6222a, 6222b than in the non-contracted configuration. Also, as mentioned above, the retaining members 6222a, 6222b are configured to have retaining features that facilitate engagement of the attachment features 6228 therewith.

In the example shown in FIG. 46B, when heat is applied to a region encompassing a portion of the attachment features 6228, the portions of the attachment features 6228 in that region contract. The heat can be applied to the attachment features 6228 in a variety of ways, as discussed in more detail below. The contraction results in the attachment features 6228 and the through openings 6226a, 6226b being tensioned around the retaining members 6222a, 6222b which thus releasably retain the adjunct 6224 over the jaw. Thus, FIGS. 46A and 46B illustrate that the area of the adjunct 6224 is reduced to some degree after the heat has been applied. FIGS. 46A and 46B also illustrate that a shape of the openings 6226a, 6226b formed the adjunct 6224 changes when the adjunct 6224 is in the contracted configuration. In particular, the openings 6226a, 6226b become more stretched as the material from which the adjunct 6224 is formed as pulled towards the middle of the adjunct 6224 due to the contraction of the attachment features 6228, which is also shown by arrows 6223a, 6223b in FIG. 46B. When the staples are fired and a cutting element (e.g., a knife) is activated, the attachment features 6228 are cut, thus allowing the adjunct 6224 to separate from the jaw.

It should be appreciated that the implementation in FIGS. 46A and 46B is shown by way of example only. Thus, the attachment features 6228 can be wrapped around the retaining members in many various ways. For example, as in the example illustrated, the attachment features 6228 can form one or more loops in a substantially oval pattern. As another example, the attachment features can be arranged in a figure-eight pattern around the retaining members, or they can be arranged such that one or more portions form one or more crisscross patterns over the adjunct. Also, the attachment feature(s) can be arranged around the retaining members in a substantially random way. As mentioned above, one or more of the attachment features can be coupled to (e.g., woven through) the adjunct at one or more locations. Moreover, in some implementations, one or more of the attachment features can be coupled to or interconnected with one another.

Furthermore, in some embodiments, the attachment features are not engaged with the retaining members. For example, the adjunct can have openings formed around its perimeter some or all of which can be engaged with (e.g., receive therethrough) the retaining members of the jaw. The contractible attachment features, which can be coupled to the adjunct in any suitable manner (e.g., passed through the adjunct one or more times, attached used an adhesive, etc.), can be disposed in a certain way, e.g., across the middle of the adjunct, such that, when they are exposed to heat, they constrict and cause the two sides of the adjunct to be pulled together. Depending on the configuration of the adjunct and the attachment features, the adjunct will constrict or deform as a result of the application of heat in a suitable manner.

In the example shown in FIGS. 46A and 46B, the adjunct 6224 is secured to the tissue-facing surface of the jaw using multiple attachment features 6228. However, in some embodiments, a single continuous attachment feature can be used to secure an adjunct to a jaw of an end effector. Such embodiments can be used, for example, if limited interconnection between the adjunct and the attachment feature is desired. In other words, the attachment feature can be coupled to the adjunct in fewer locations as compared to implementations in which two or more attachment features are used.

Figure 47A:
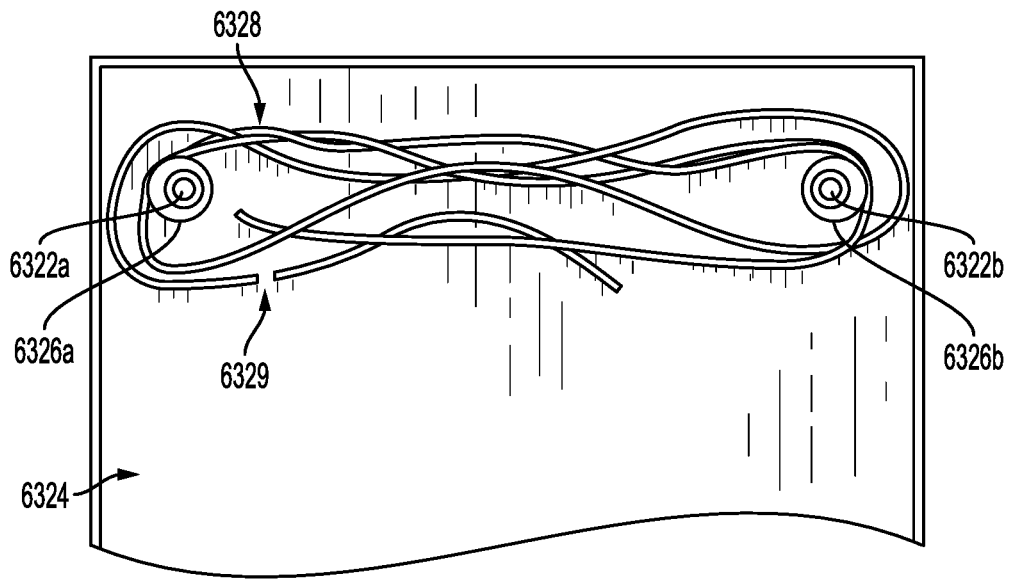
FIG. 47A is another perspective view an adjunct that has contractible attachment features disposed on a jaw of an end effector before the adjunct is coupled to the jaw.
Figure 47B:
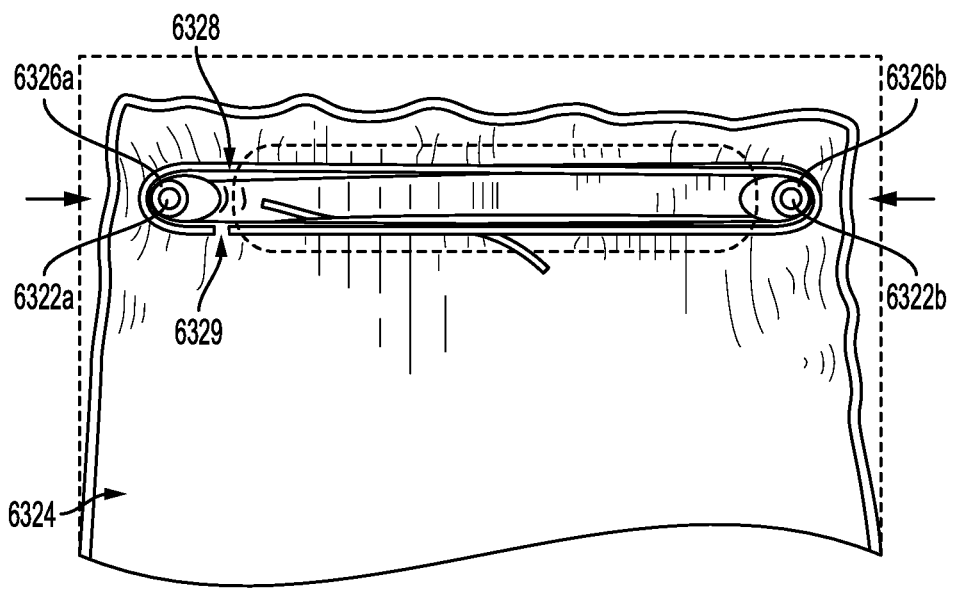
FIG. 47B is a perspective view of the adjunct of FIG. 48A, illustrating the adjunct coupled to the jaw by application of heat.

FIGS. 47A and 47B illustrate an embodiment in which a continuous attachment feature 6328 is used to couple an adjunct material or adjunct 6324 to a jaw (not shown), such as a jaw having an anvil (e.g., anvil 6104 in FIG. 45) or a jaw having a cartridge. In this example, the attachment feature 6328 is a relatively long continuous feature disposed over a portion of the adjunct 6324 as shown in FIG. 47A.

As shown, the adjunct 6324 is disposed over the jaw such that retaining members 6322a, 6322b formed on the jaw are mated with through openings 6326a, 6326b in the adjunct 6324. As also shown, the attachment feature 6328 can form one or more loops that encompass the retaining members 6322a, 6322b. As shown by way of example, the attachment feature 6328 can be coupled to the adjunct 6324 at a point 6329, though it should be appreciated that the attachment feature 6328 can be coupled to the adjunct 6324 at any number of points at any locations of the adjunct 6324. The attachment feature 6328 can be woven into, knitted through, stitched through, or otherwise coupled to the adjunct 6324. In addition, in some embodiments, one or more portions of the attachment feature 6328 can be coupled one another, e.g., using an adhesive. Additionally or alternatively, some of the portions can be tied, twisted, bonded together, etc.

In the example illustrated, as shown in FIG. 47B, when heat is applied to a region 6330 encompassing a portion of the attachment feature 6328, one or more portions of the attachment feature 6328 contract. As the contraction occurs, the attachment feature 6328 is brought closer towards the retaining members 6322a, 6322b such that the material of the attachment feature 6328 engages more tightly around the retaining members 6322a, 6322b, thereby releasably retaining the adjunct 6324 over the jaw. In other words, the attachment feature 6328 is held in tension around the retaining members 6322a, 6322b. When the staples are fired and a cutting element (e.g., a knife) is activated, the attachment feature 6328 is cut to thus allow the adjunct 6324 to separate from the jaw.

In this way, FIGS. 46A, 46B, 47A, and 47B illustrate that the adjuncts 6224, 6324 can be securely coupled to a jaw in a manner than allows manipulating the jaw as desired during a surgical procedure. A risk of the adjunct slipping off or otherwise being unintentionally and prematurely separated from the jaw is reduced or eliminated.

In the examples of FIGS. 46A, 46B, 47A, and 47B, the attachment features can be formed from any suitable materials. For example, they can be in the form of one or more PDO strands. A density of the PDO strands can vary throughout the attachment features and thus throughout the adjunct to which the feature(s) are attached. In this way, the degree of contraction of the attachment feature(s) varies in different parts of the adjunct. In some cases, elongate PDO strands can be woven throughout the entire adjunct such that more uniform adjunct contraction can be achieved. The PDO strands can also be wrapped around the retaining members to ensure that they effectively engage the retaining members when heat is applied and contraction occurs. As another example, the attachment features can be separate from the adjunct. In such cases, upon heating, the attachment features contract, and become secured in tension between the retaining members, thereby holding the adjunct in place, but the contraction of the attachment features may not have an impact on the configuration of the adjunct. Alternatively, as discussed above, the attachment features can be attached to the adjunct at certain attachment points, which can be based on the desired configuration of the adjunct and the amount of contraction.

Figure 48A:
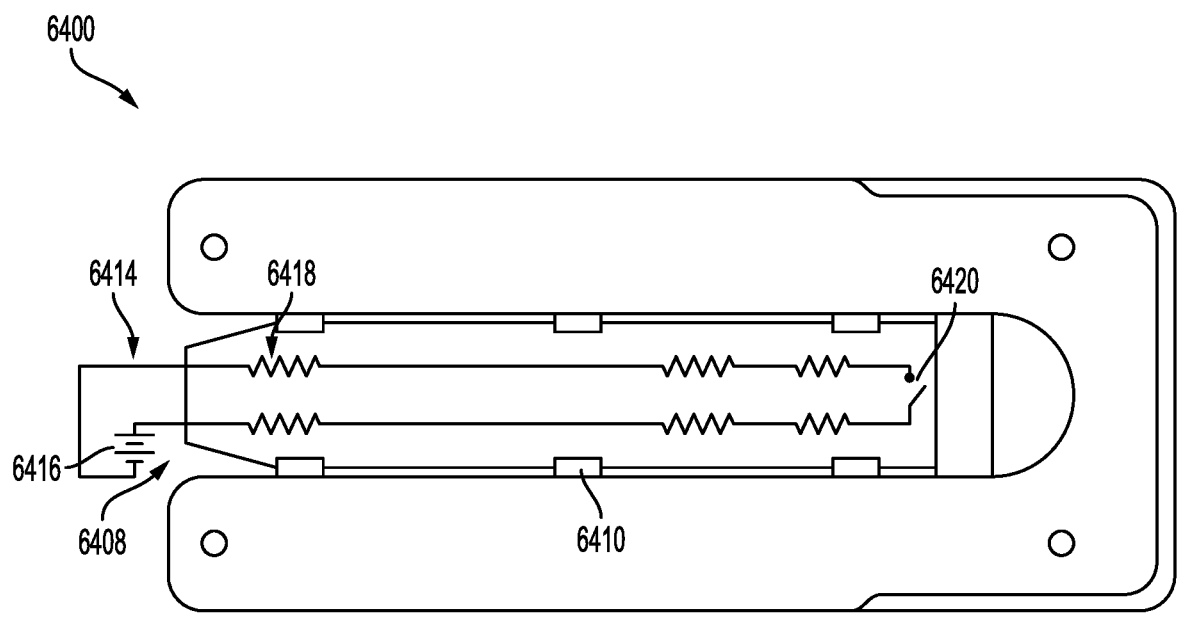
FIG. 48A is a top view of one embodiment of a loader.
Figure 48B:
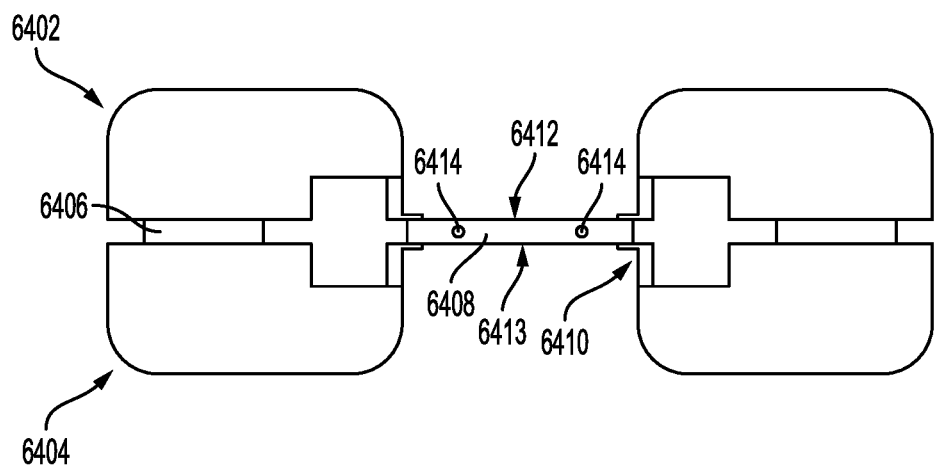
FIG. 48B is a cross-sectional view of the loader of FIG. 49A.

In the described embodiments, one or more attachment features can be used to releasably engage an adjunct with a jaw of an end effector using heat. The heat can be applied in a variety of ways. For example, in some embodiments, heat can be applied using a loader that is configured to apply the adjunct to the jaw. FIGS. 48A and 48B illustrate an example of a loader 6400 configured to apply an adjunct to a tissue-facing surface of a jaw. FIG. 48A shows a top view of the loader 6400, whereas FIG. 48B shows a cross-sectional view of the loader 6400.

As in the illustrated example, the loader 6400 in the form of a generally rectangular frame-like holder configured to releasably couple one or more adjuncts to one or both jaws of the end effector (not shown). In the illustrated example, the loader 6400 is in the form of a first (e.g., top) and second (e.g., bottom) generally rectangular housings 6402, 6404 coupled to one another e.g., via a coupling 6406, as shown in FIG. 48B. In this example, the loader 6400 can be used to apply a single adjunct to a jaw. It should be appreciated however, that, in some embodiments, a loader like the loader 6400 or a similar loader, can be used to apply a respective adjunct to each jaw of an end effector.

The loader 6400 includes at least one heating component 6408 configured to be activated to apply heat to attachment features, as described below. The heating component 6408 can have various configurations. For example, as shown in FIGS. 48A and 48B, the heating component 6408 includes a resistive heating element 6414 in the form of a wire. The heating element 6414 is connected to a power source 6416. In the illustrated example, the heating element 6414 includes higher resistance portions 6418 along its length. The locations of the higher resistance portions 6418 can correspond to regions on an adjunct to which heat is desired to be applied, e.g. region 6230 (FIG. 46B) or region 6330 (FIG. 47B). Thus, power can be applied to the heating element 6414 to cause localized heating near the higher resistance portions 6418. In some embodiments the heating element can include a switch 6420 that closes the circuit and allows current to flow through the heating element. The switch 6420 can be operated using a suitable trigger on the loader 6400 (e.g., a button), though the heating element 6414 can be activated in other suitable ways. The heat generated by the higher resistance portions 6418 causes the attachment features that are engaged with the adjunct to contract to effectively couple the adjunct with retaining members of the jaw, thereby releasably retaining the adjunct over the tissue-facing surface of the jaw.

The heating component 6408 can be of any suitable type. For example, the heating component 6408 can be made of a rigid material, e.g., ceramic, that is coated with an elastic or compliant material. In some embodiments, the heating component 6408 can be in the form of a resistive wire embedded into silicone, e.g., such that the silicone is cured around the resistive wire. The resistive wire is configured to effect the heating, whereas the silicone allows for some degree of compliance when clamping a stapler onto the loader. As shown in FIG. 48B, the heating component 6408 can be coupled to the housings 6402, 6404 via connecting features 6410, e.g., brackets.

The loader 6400 and heating component 6408 can generally be configured such that an adjunct (not shown) can be placed on a surface, e.g., an upward facing surface 6412 of the heating component as shown in FIG. 48B, and the jaws of the end effector can clamp over the heating component and adjunct. Although not illustrated, the loader 6400 and/or heating component 6408 can include retaining features that can releasably secure adjuncts to surfaces 6412 and 6413 such that the adjuncts can be secured to both jaws of an end effector simultaneously. For example, the heating component 6408 can have small posts or hooks that can grip the adjuncts to releasably secure them to surfaces 6412, 6413. In one embodiment, the heating component 6408 is disposable and it is coupled to adjuncts secured to the surfaces 6412, 6413. In such an embodiment, the loader 6400 is configured to receive a heating component 6408 with adjuncts attached thereto. The surgeon can load the heating component 6408 with the adjuncts into the loader 6400, and attach the adjuncts to jaws of an end effector.

Furthermore, in some embodiments, the heating component 6408 (or a heating component having another configuration) can be in the form of two heating components disposed in the removable loader such that each of the heating components is configured to apply heat to a different adjunct that can be associated therewith (e.g., via the loader or manually). In such implementations, with reference to FIG. 48B, for example, first and second adjuncts are placed on the surfaces 6412, 6413, respectively, and heat can be applied to the adjuncts using respective heating components associated with the surfaces 6412, 6413.

Regardless of the specific way in which the heating component 6408 is associated with the loader 6400, the loader 6400 can be used to both deliver the adjunct to the jaw (such that the adjunct is transferred from the loader to the jaw) and to apply heat to the adjunct. In use, the loader can be placed between the jaws of the end effector that are in an open configuration. The jaws can then be clamped over the loader 6400 to thereby clamp over the heating component 6408 and the adjunct such that the adjunct is transferred onto the jaw and retaining members on the jaw enter through openings on the adjunct, as illustrated, e.g., in FIGS. 46A and 47A. At least one attachment feature can be engaged with the adjunct, e.g., as shown for attachment features 6228, 6328 and adjuncts 6224, 6324 in FIGS. 46A and 47A, respectively. The heating element 6414 can be activated in a suitable manner such that heat applied therefrom to the at least one attachment feature can cause the attachment feature to contract, which causes the adjunct material to couple with the first and second retaining members.

In some embodiments, the act of clamping the jaws onto the heating component closes the switch 6420, thereby allowing current to flow through the heating element. Once the adjunct is secured to the jaw as desired, the jaws can be opened and removed from the heating component which allows the switch 6420 to open, thereby stopping the flow of current within the heating element 6414.

In other implementations, an adjunct may not be associated with a loader, such as the loader 6400, and the loader can be used only to apply heat to the adjunct (and thus to at least one attachment features). In such implementations, an adjunct is placed onto a tissue-facing surface of a jaw, and attachment features engaged with or disposed over the adjunct is looped around jaw's retaining members as desired to loosely secure the adjunct to the end effector. The end effector is then be clamped onto the loader with the heating component 6408 of the loader 6400, and the heating element 6414 is powered, thereby causing localized heating near the high resistance portions 6418 of the heating element 6414. The heat from those portions 6418 causes the attachment features that are engaged with the adjunct to contract to effectively couple the adjunct with the retaining members, thereby releasably retaining the adjunct over the tissue-facing surface of the jaw.

It should be appreciated that the loader 6400 is shown by way of example only. In some embodiments, a loader can use a chemical reaction to supply heat to the attachment features. For example, the loader can generally be similar to loader 6400, but rather than using a heating component that includes a resistive heating element, the loader can use a heating component including one or more fluid or crystalline structures. By way of example, the heating element can include a number of fluid or crystalline structures that can release heat when they come in contact with each other. In some implementations clamping jaws of an end effector onto the heating component can cause internal pockets containing fluid or crystalline structures to crack, thereby allowing their internal substances to combine. When the substances combine, the mixture undergoes an exothermal chemical reaction that releases heat. The heating component can be configured such that the chemical heating elements are in the desired locations, and wherein cracking the heating elements only breaks an internal barrier and does not cause the substances to spill from the heating component.

Furthermore, in some embodiments, heat can be applied to an adjunct with at least one attachment feature pre-loaded thereon using a device different from a loader. For example, the adjunct can be disposed on a jaw of an end effector and heat can be applied thereto using an infrared heater, UV heater, heat gun, or any other device configured to provide heat. In some cases, the heating can be done by placing the end effector with the adjunct disposed thereon in a suitable oven, heated chamber, or other enclosure configured to apply heat. The separate heating devices can be used in embodiments in which the adjunct is pre-applied to the end effector's jaws during manufacture of the end effector. The loader, such as the loader 6400, or a similar applicator (e.g., a small heating chamber) can be used in embodiments in which the adjunct is configured to be applied in the operating room by the surgeon or other person during or before a surgical procedure.

Regardless of the way in which heat is applied to the adjunct, a temperature of the heat and a duration of its application is selected so as to cause at least one attachment feature to contract and thus cause the adjunct to be attached to the jaw. For example, the heat can have a temperature of from about 6100 to about 130 degrees Celsius and it can be applied for, for example, from about 20 seconds to about 3 minutes to cause the attachment feature to transition into the contracted configuration. It should be appreciated, however, that a temperature in other ranges can be applied for any suitable time period.

Figure 49A:
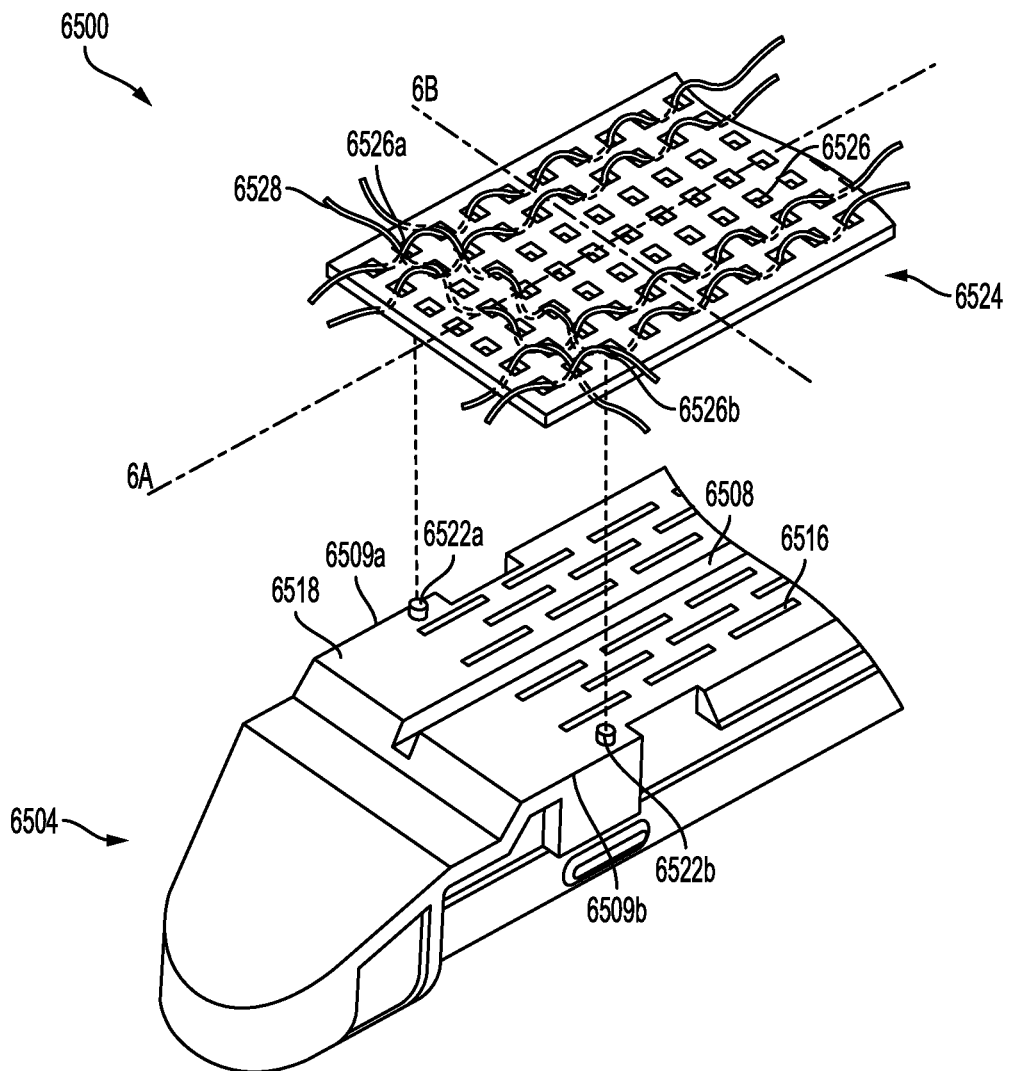
FIG. 49A is a perspective view of a jaw and an adjunct configured to be releasably coupled to the jaw.
Figure 49B:
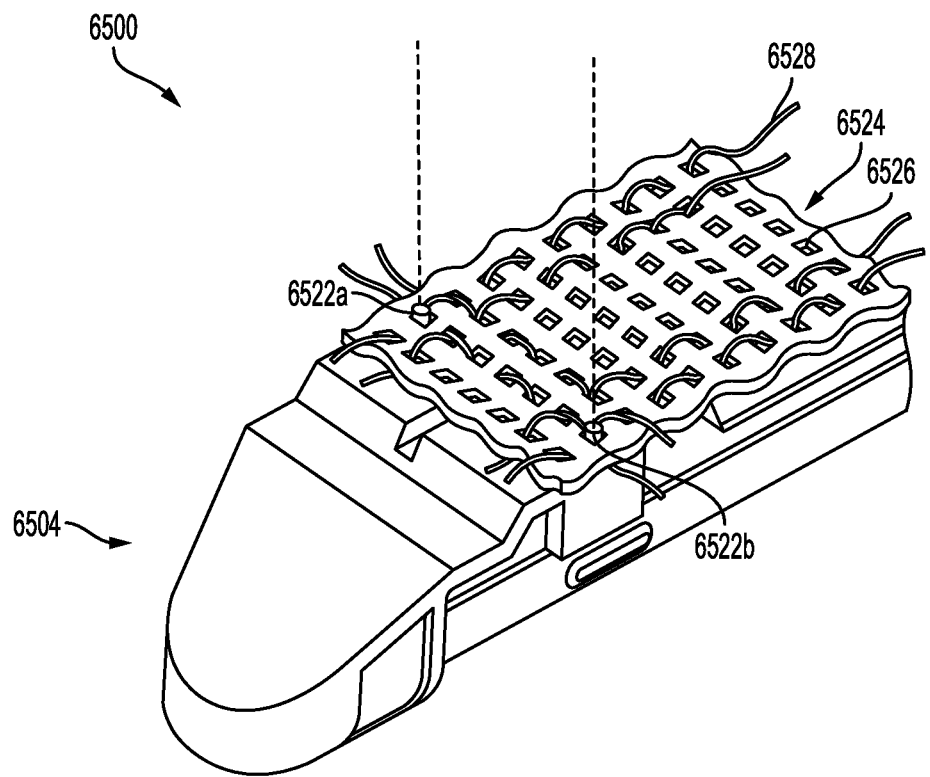
FIG. 49B is a perspective view of the jaw of FIG. 50A, illustrating the adjunct releasably coupled to the jaw.

In some applications, an adjunct can be formed such that a plurality of contractible attachment features are interwoven into the adjunct along a longitudinal axis of the adjunct and along an axis that is substantially perpendicular to the longitudinal axis of the adjunct. FIGS. 49A and 49B illustrate an example of such an adjunct. In particular, FIGS. 49A and 49B illustrate a portion of an end effector 6500 that is configured to have an adjunct 6524 coupled to a tissue-facing 6518 surface of a jaw, wherein the adjunct 6524 has contractible attachment features 6528 interwoven with the adjunct 6524 along a longitudinal axis 6A and along a lateral axis 6B that is substantially perpendicular to the longitudinal axis 6A.

The end effector 6500 can generally include components similar to those described with regard to end effector 6100 (FIG. 45). Thus, similar to the end effector 6100, the end effector 6500 can include an upper jaw (not shown) having an anvil and a lower jaw having a cartridge body 6504. The lower jaw includes the staple cartridge 6504 that has a plurality of staple-holding cavities 6516 configured to seat staples therein, the staple-holding cavities 6504 opening on a tissue-facing surface 6518 of the cartridge 6504. The staple cavities can form a certain pattern on the tissue-facing surface 6518 of the cartridge 6504 which corresponds to a pattern of staple-forming cavities formed in the anvil. The cartridge 6504 includes first and second retaining members 6522*a*, 6522*b*, located adjacent to opposed edges of the tissue-facing surface 6518, and a knife channel 6508 extending between distal and proximal ends of the cartridge 6504.

The retaining members 6522*a*, 6522*b* disposed on the tissue-facing surface 6518 of the cartridge 6504 are configured to releasably couple an adjunct material 6524 to the cartridge 6504. The first retaining member 6522*a* is disposed at one side of the tissue-facing surface 6518 in proximity to one edge 6509*a* of the tissue-facing surface 6518, and the second retaining member 6522*b* is disposed at another, opposed side of the tissue-facing surface 6518 in proximity to another, opposed edge 6509*b* thereof. In this way, the first and second retaining members 6522*a*, 6522*b* are disposed at opposed sides of the knife channel 6508.

The retaining members 6522*a*, 6522*b* can have a variety of different configurations. In the example illustrated, they are in the form of generally cylindrical posts extending from the tissue-facing surface 6518. However, the retaining members 6522*a*, 6522*b* can have other shapes, as the described implementations are not limited in this respect. For example, the retaining members 6522*a*, 6522*b* can be curved, have an hour glass shape, have a bulbous or widened end region, have notches, be angled toward the edges of the tissue-facing surface, have roughness features, etc. The retaining members can be configured in any manner suitable for assisting in retaining the adjunct on the jaw. Also, although two retaining members 6522*a*, 6522*b* are shown in FIG. 49A, the tissue-facing surface 6518 can have any other number of retaining members (e.g., one or greater than two) configured to couple an adjunct thereto. Furthermore, the retaining members can be formed at various locations on the tissue-facing surface 6518 of the cartridge 6504. For example, in some embodiments, two or more retaining members can be formed along each edge 6509*a*, 6509*b* of the tissue-facing surface 6518. The retaining members can be formed at any suitable distance from one another that allows securely retaining the adjunct material on the jaw's tissue-facing surface. In addition, although in the illustrated implementations the retaining members protrude above the surface of the tissue-facing surface, in some embodiments, the retaining members can be in the form of recesses or other features disposed at least partially below the tissue-facing surface of the jaw. This can be done in implementations in which a reload includes reverse drivers.

As shown in FIG. 49A, in the example illustrated, each of the retaining members 6522*a*, 6522*b* is formed outside of the area of the tissue-facing surface 6518 having the staple cavities 6516. However, in some implementations, one or more of the retaining members can be formed within the area having the staple cavities 6516.

The adjunct material 6524 is configured to releasably couple with the cartridge 6504 using a plurality attachment features 6528 configured to be transitioned from an original, non-contracted configuration to a contracted configuration under application of heat, as discussed in more detail below. The adjunct material 6524 couples with the cartridge 6504 in a secure manner, which helps ensure that the adjunct 6524 remains coupled to the cartridge 6504 while the end effector 6500 is manipulated as desired using a surgical procedure. The adjunct 6524 is held in engagement with the cartridge 6504 until an action, such as an activation of the end effector 6500 to release staples from its cartridge and/or an activation of a cutting element, is taken that causes the separation of the adjunct 6524 from the cartridge 6504.

To accommodate a contraction of the at least one attachment feature 6528 that occurs as a result of heating, the adjunct material 6524 can be configured such that it assumes an appropriate shape and size once heating has occurred so as to couple the adjunct material 6524 to the cartridge 6504. For example, the adjunct material 6524 can be sized such that it extends beyond the perimeter of the tissue-facing surface 6518 of the cartridge 6504 prior to heating, and adopts the appropriate size once heating has occurred.

The first and second retaining members 6522a, 6522b are configured to mate with respective mating features of the adjunct material 6524. In particular, in the described implementation, the adjunct material 6524 includes a plurality of through openings 6526, wherein at least first and second openings 6526a, 6526b of the openings 6526 are configured to be mated with the retaining members 6522a, 6522b. It should be appreciated that, depending on the number of the retaining members, more than two of the openings 6526 can mate with respective retaining members.

The openings 6526 in the adjunct 6524 can have any suitable size and shape, including different sizes and shapes. In this example, the openings 6526 are generally square, though it should be appreciated that the openings 6526 can have any other suitable shapes. In the illustrated example, the attachment features 6528 can be woven through the openings 6526 as shown in FIGS. 49A and 49B. Also, the openings 6526 can also be positioned and dimensioned to control the configuration of the adjunct and internal stress imposed upon the adjunct when heat is applied and the attachment features contract. The openings can be formed in the adjunct such that specific openings (e.g., openings 6526a, 6526b) are configured to receive corresponding retaining members. Alternatively, in some cases, when the adjunct is disposed over the jaw, the openings in the adjunct can "find" retaining members to mate with, and it may therefore not be necessary to make openings that specifically correspond to positions of the retaining members.

The contractible attachment features 6528 can be in the form of one or more strands of a shrinkable polymer, which can be coupled to the adjunct material 6524 at one or more locations. The adjunct 6524 can have any suitable number of attachment features interwoven into the adjunct 6524 such that at least one attachment feature is disposed along the longitudinal axis 6A and at least one attachment feature is disposed along the lateral axis 6B. In the example of FIG. 49A, fours strands of shrinkable polymer are disposed along the longitudinal axis 6A of the adjunct 6524 (two along each of the long sides) and two strands of shrinkable polymer are disposed along the lateral axis 6B of the adjunct 6524 (closer to the distal end of the jaw 6504). However, it should be appreciated that the attachment features 6528 can be in the form of any suitable number of strands that can be coupled to the adjunct 6524 in any desired manner. For example, in one embodiment, one or more of the stands can be coupled to the adjunct 6524 so as to be diagonally disposed with respect to the adjunct 6524. The strands can be coupled to the adjunct to be able to contract in a way so as to transition one or more portions of adjunct to a desirable shape and size. For example, the strands must be able to cause some of the openings in the adjunct to constrictably engage with the retaining members. In some cases, the same strand can be interwoven into the adjunct along the longitudinal axis 6A as well as the lateral axis 6B.

The adjunct material 6524 and the at least one contractible attachment feature 6528 can be made from a variety of materials. For example, in at least some embodiments, the adjunct 6524 can be made from VICRYL® (polyglactin 910) material, whereas the contractible attachment feature 6128 can be in the form of one or more PDO strands. Any other materials can be used additionally or alternatively.

In the described implementations, the retaining members 6522a, 6522b couple the adjunct 6524 to the cartridge 6504 by mating with two corresponding openings 6526a, 6526b. When heat is applied, the attachment features transition from a non-contracted configuration to a contracted configuration and thereby causing the at least the openings 6526a, 6526b to constrict around the retaining members 6522a, 6522b, as shown schematically in FIG. 49B. Thus, in the contracted configuration, the attachment features 6528 are coupled to the retaining members 6522a, 6522b or cause the adjunct 6524 to couple to the retaining members 6522a, 6522b. In this way, the adjunct material 6524 is retained in a secure and releasable engagement with the retaining members 6522a, 6522b and thus with the cartridge 6504, as illustrated in FIG. 49B. Heat can be applied to the adjunct 6524 with the attachment feature 6528 using a variety of techniques, as discussed above. For example, loader 6400 (FIGS. 48A and 48B), or any other device configured to provide heat can be used.

In the examples described above, an adjunct can be attached to a cartridge and/or anvil during manufacturing, or by a surgeon before or during a surgical procedure. The adjunct can be secured to the end effector using one or more shrinkable attachment features that can change their configuration under application of heat. In other embodiments, however, the adjunct can be releasably coupled to the jaw using other approaches that do not require application of heat.

Thus, in some embodiments, at least one first portion of an adjunct material or adjunct is configured to be reversibly stretched by an application of force. When the force is removed, the first portion transitions from a stretched configuration to a contracted configuration, thereby causing the adjunct material to engage a jaw of an end effector. The jaw can have one or more retaining features configured to mate with corresponding features of the adjunct. For example, first and second retaining features formed on the jaw can mate with mating features (e.g., openings) of the adjunct. Thus, the at least partially stretchable adjunct material (or portion(s) thereof) can be stretched and then allowed to contract, which causes the adjunct's mating features to engage the jaw's retaining features. In some embodiments, the adjunct can have one or more portions that are substantially non-stretchable.

Figure 50:
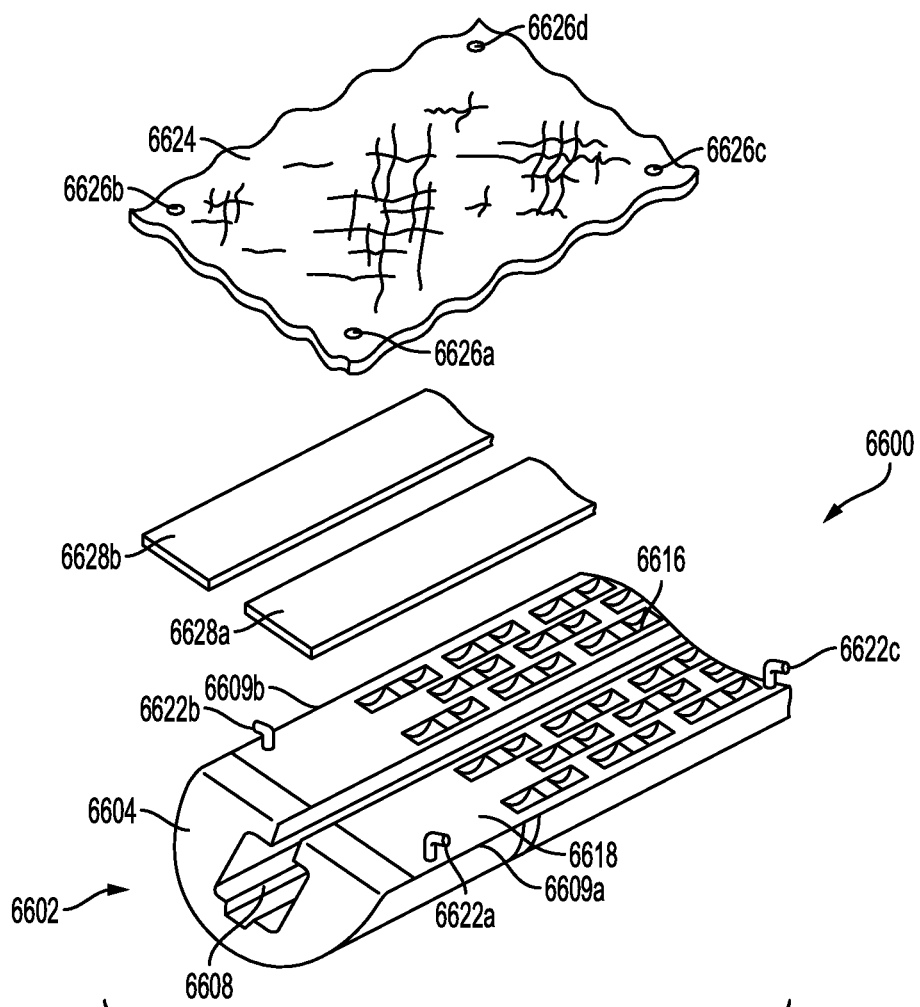
FIG. 50 is an exploded view of a jaw of an end effector and at least partially stretchable adjunct material configured to be releasably coupled to the jaw.

FIG. 50 illustrates an exploded view of an example of a jaw 6602 of an end effector 6600 of a surgical instrument that has an adjunct material releasably secured thereto using an approach that does not depend on application of heat. The end effector 6600 can generally include components similar to those described with regard to FIGS. 1-4, and can also include features and/or components that enable adjuncts to be releasably attached thereto. Thus, similar to surgical staplers 10 (FIG. 1) and 50 (FIG. 4), the end effector 6600 includes an upper jaw having an anvil and an lower jaw having a cartridge body (not shown), with only the upper jaw 6602 being shown in FIG. 50. The lower jaw can generally include a staple cartridge that has a plurality of staple-holding cavities configured to seat staples therein, the staple-holding cavities opening on a tissue-facing surface of the cartridge.

As shown in FIG. 11, the upper jaw 6602 having an anvil 6604 has an adjunct material 6624 releasably retained on a tissue-facing surface 6618 thereof, as discussed in more detail below. The anvil 6604 has staple-forming cavities 6616 formed on the tissue-facing surface 6618. As also shown, the tissue-facing surface 6618 has a knife channel 6608 configured to receive a cutting element (e.g., a knife).

As shown in FIG. 50, the tissue-facing surface 6618 of the anvil 6604 has at least first and second retaining members, e.g., retaining members 6622a, 6622b, and can additionally include one or more retaining members, as illustrated by retaining member 6622c. The retaining members are configured to couple the adjunct material 6624 to the anvil 6604. In the example illustrated, the retaining members can engage with openings formed in the adjunct material 6624, such as openings 6626a-6626d, as discussed below.

As shown in FIG. 50, the retaining members 6622a, 6622c are disposed one side of the tissue-facing surface 6618 in proximity to one edge 6609a of the tissue-facing surface 6618, and retaining member 6622b is disposed at another, opposed side of the tissue-facing surface 6618 in proximity to another, opposed edge 6609b thereof. It should be appreciated that the tissue-facing surface 6618 can have a fourth retaining member opposed to the retaining member 6622c, which is not shown because of the partial view of the jaw 6604 in FIG. 50. The retaining members 6622a, 6622b are disposed at opposed sides of the knife channel 6608.

The retaining members can have a variety of different configurations. In the example illustrated, they are in the form of curved posts, or hooks, that extend from the tissue-facing surface 6618 outward toward respective the edges 6609a, 6609b. For example, the retaining member 6622a is curved towards the edge 6609a, and the retaining member 6622b is curved towards the edge 6609b. However, the retaining members can have other shapes, as the described implementations are not limited in this respect. For example, the retaining members can be at least partially straight, have an hour glass shape, have a bulbous or widened end region, have one or more notches, be angled toward the edges of the tissue-facing surface, have roughness features, etc. The retaining members can be configured in any suitable manner suitable for assisting in retaining the adjunct on the jaw. Also, although three retaining members 6622a, 6622b and 6622c are shown in FIG. 50, the tissue-facing surface 6618 can have any other number of retaining members (e.g., one, two, or greater than three) configured to couple an adjunct thereto. Furthermore, the retaining members can be formed at various locations on the tissue-facing surface 6618 of the anvil 6604. For example, in some embodiments, two or more retaining members can be formed along each edge 6609a, 6609b of the tissue-facing surface 6618. The retaining members can be formed at any suitable distance from one another that allows securely retaining the adjunct material on the jaw's tissue-facing surface. In addition, the retaining members can be disposed symmetrically with respect to the knife channel 6608 or other features of the tissue-facing surface 6618, or they can be formed at various other ways on the surface 6618.

The retaining members 6622a, 6622b, 6622c (and any retaining members which are not shown in FIG. 50) are configured to mate with respective mating features of the adjunct material 6624. In particular, as mentioned above, the adjunct material 6624 includes through openings 6626a, 6626b, 6626c configured to receive the retaining members 6622a, 6622b, 6622c, respectively. The fourth opening 6626d is configured to engage a fourth retaining member, which is not shown in FIG. 50. The through openings 6626a-6626d in the adjunct 6624 are sized to receive therein the respective retaining members. In this example, the openings are generally round, though it should be appreciated that the openings can have any other suitable shapes.

In the embodiment shown in FIG. 50, the adjunct material 6624 is at least partially stretchable. For example, the adjunct 6624 is formed such that substantially its entire area is at least partially stretchable. The adjunct 6624 can be formed from any suitable material, for example, one or more suitable absorbable polymers. In embodiments in which the adjunct material is made from non-brittle polymers, deformations of the adjunct can be achieved through geometric changes (e.g., by reducing the adjunct's thickness until it becomes stretchy under a load, etc.). Additionally or alternatively, the adjunct material can be made at least partially stretchable by having one or more various features—for example, the adjunct can be in the form of a knitted sheet that has elasticity due to its geometry. The adjunct can be implemented as described, for example, in U.S. patent application Ser. No. 14/926,194, entitled "Extensible Buttress Assembly for Surgical Stapler," and filed on Oct. 29, 2015, which is hereby incorporated by reference herein in its entirety.

In some embodiments, as in the example illustrated, the adjunct material 6624 includes at least one second, substantially non-stretchable portion. The one or more substantially non-stretchable portions can have a variety of configurations (including different configurations among the portions) and they can be disposed in any suitable manner in relation to substantially stretchable portions of the adjunct. FIG. 50 illustrates that the adjunct material 6624 includes first and second non-stretchable portions 6628a, 6628b which can be associated with areas of the adjunct material 6624 that are disposed over the staple-forming cavities 6616 when the adjunct 6624 is placed over the jaw 6602. Thus, one or more areas of the adjunct 6624 configured to be penetrated by the staples can be reinforced by being made substantially non-stretchable. In the illustrated implementation, the portions 6628a, 6628b are coupled to the adjunct material 6624 such that the portions 6628a, 6628b are configured to be disposed between the tissue-facing surface 6618 and the adjunct 6624, and thus seat over the tissue-facing surface 6618.

In some embodiments, it can be beneficial to attach the non-stretchable portions 6628a, 6628b to the adjunct 6624 such that portions of the adjunct 6624 disposed over the staple-forming cavities 6616 are prevented from being stretched. In particular, if portions of the adjunct 6624 that are disposed over staple-cavities 6616 are stretched, then, when the adjunct 6624 is stapled to tissue and released from the jaw 6602, the adjunct 6624 can damage tissue by pulling on the staples as it releases tension in areas where staples are formed. In this way, the non-stretchable portions can stabilize the staples and help protecting tissue being stapled.

Figure 51:
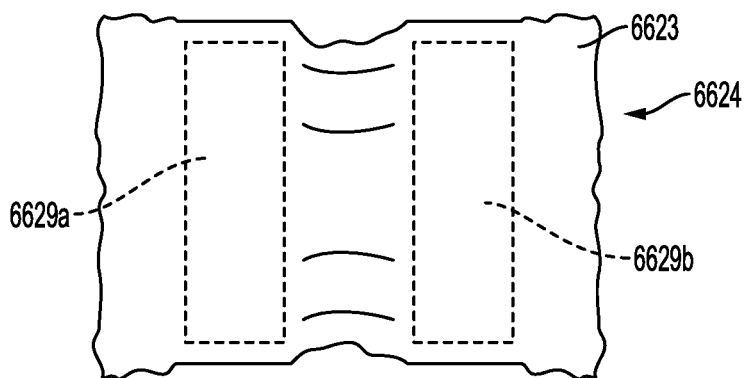
FIG. 51 is a schematic view of the adjunct material of FIG. 51, illustrating areas of the adjunct material configured to have non-stretchable portions.

The non-stretchable portions 6628a, 6628b can be formed in any suitable manner. For example, the portions 6628a, 6628b can be separate portions coupled to the adjunct 6624. In at least one embodiment, the portions 6628a, 6628b are formed from PDO and coupled to (e.g., laminated onto), the stretchable adjunct 6624. As an example, the portions 6628a, 6628b can be in the form of sheet laminates that are heat-pressed or otherwise attached onto the adjunct 6624 to create the portions that are resistant to stretching. However, the portions 6628a, 6628b can be coupled to the adjunct 6624 in various other ways, as the described techniques are not limited in any specific way in which one or more portions of at least partially stretchable adjunct are made substantially non-stretchable. FIG. 51 shows by way of example the adjunct 6624 having a first, at least partially stretchable portion 6623. As also schematically shown in FIG. 51, first and second areas 6629a, 6629b of the portion 6623 of the adjunct 6624 (which is, in this example, the entire adjunct) are configured to have portions 6628a, 6628b in the form of sheet laminates coupled thereto.

It should be appreciated that the two separate non-stretchable portions 6628a, 6628b are shown in FIG. 50 by way of example only. In some embodiments, one or more than two substantially non-stretchable portions can be associated with the adjunct material, and such portions can be disposed in various ways with respect to the stretchable portion(s) of the adjunct.

Furthermore, in at least one embodiment, the second portion can be in the form of a substantially non-stretchable second adjunct material that is coupled to the adjunct material and has any suitable size (e.g., it can have a smaller area than the "first" stretchable adjunct material). The second adjunct material is configured to reinforce and/or treat a treatment site in a patient, whereas the first stretchable adjunct material is configured to engage the first and second adjunct materials with the retaining members formed on the jaw. In some embodiments, the second adjunct can include drugs or other treating agents intended to be delivered to the treatment site. The non-stretchable portion(s) in the form of the second adjunct material can be coupled to the first adjunct material such that the second adjunct material is disposed on the tissue-facing surface of the jaw, similar to the non-stretchable portions 6628a, 6628b in FIG. 50. However, in some implementations, the second adjunct material can be disposed over the first adjunct material such that the stretchable adjunct material is disposed directly on the jaw.

It should further be appreciated that at least one substantially non-stretchable portion of the adjunct can be formed in other various ways. For example, the non-stretchable portion(s) can be part of the adjunct material. In particular, it can be in the form of at least one second portion having at least one property that is different from at least one property of other portions of the adjunct material. As an example, one or more portions of the adjunct (e.g., portions to be disposed over staple-forming or staple-holding cavities) can be more tightly woven, knitted, braded, or otherwise made non-stretchable or less stretchable than the remainder of the adjunct.

In use, the adjunct material 6624 is configured to be releasably coupled with the anvil 6604 by reversibly stretching at least a first portion of the adjunct (e.g., the at least partially stretchable portion) using an application of force such that, when the force is removed, the first portion transitions from a stretched configuration to a contracted configuration, thereby causing the adjunct material to be engaged with the retaining members. The adjunct material 6624 couples with the anvil 6604 in a secure manner, which helps ensure that the adjunct 6624 remains coupled to the anvil 6604 while the end effector 6100 is manipulated as desired using a surgical procedure. The adjunct 6624 is held in engagement with the anvil 6604 until an action, such as an activation of the end effector 6600 to release staples from its cartridge and/or an activation of a cutting element, is taken that causes the separation of the adjunct 6624 from the anvil 6604.

Figure 52A:
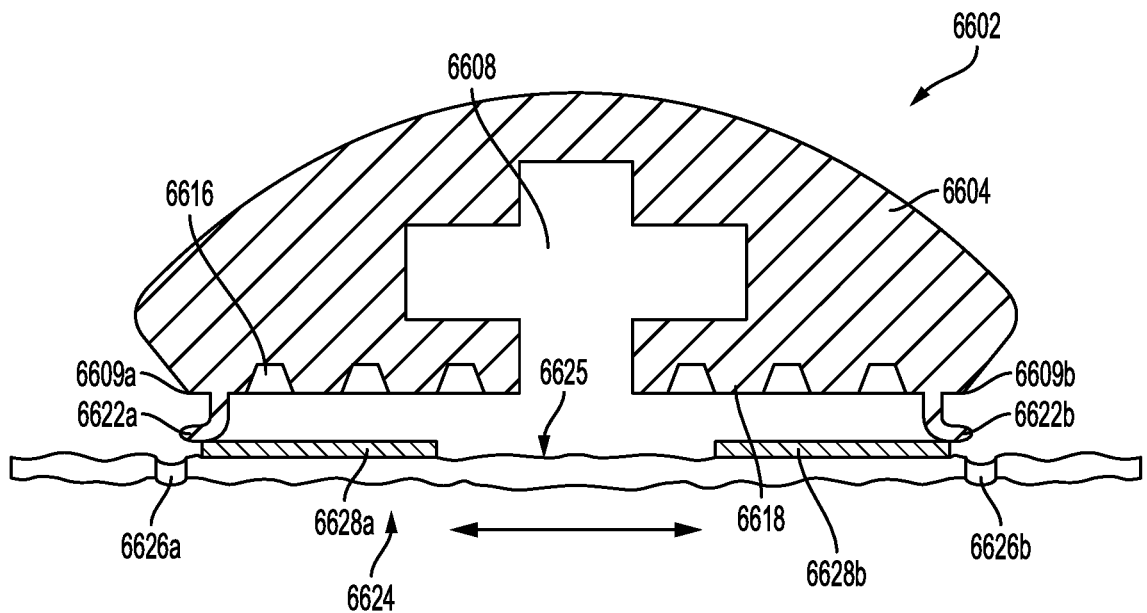
FIG. 52A is a cross-sectional view of a jaw of an end effector and at least partially stretchable adjunct material to be releasably coupled to the jaw.
Figure 52B:
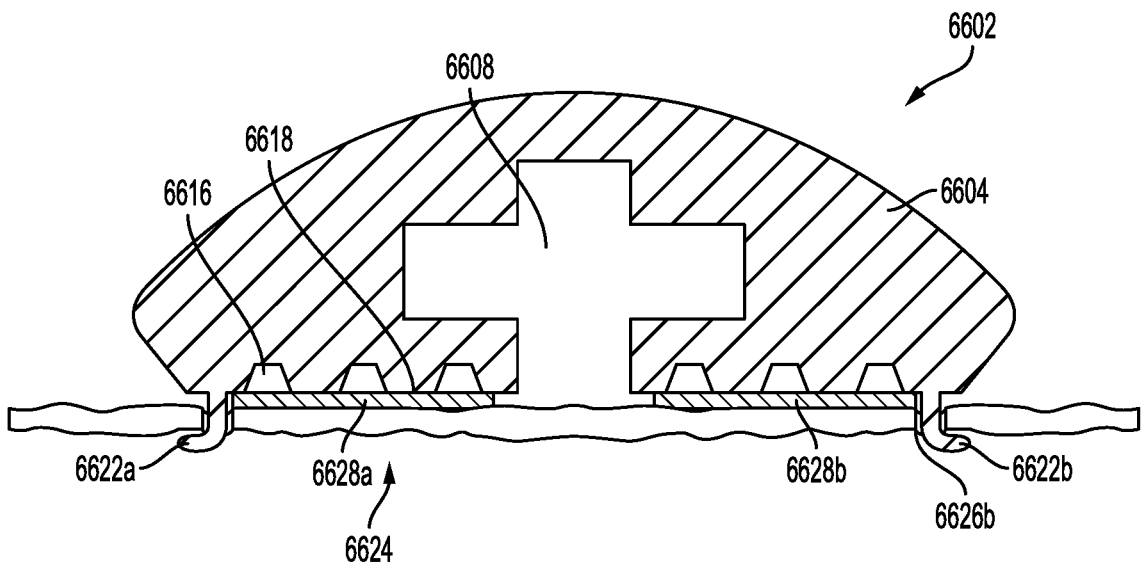
FIG. 52B is a cross-sectional view of the jaw of FIG. 53A, illustrating the adjunct material releasably coupled to the jaw.

FIGS. 52A and 52B illustrate an example of a method of coupling the adjunct material 6624 with the jaw 6602. FIG. 52A shows the jaw 6602 and the adjunct 6624 prior to the adjunct 6624 being coupled to the jaw 6602. As shown schematically in FIG. 52A, the adjunct 6624 is being stretched such that the openings 6626a, 6626b in the adjunct 6624 extend beyond the retaining members 6622a, 6622b formed on the jaw 6602.

The adjunct material 6624 has at least one portion configured to be reversibly stretched using application of a force. FIG. 52A shows a cross-section view of the upper jaw 6602 wherein the adjunct 6624 is stretched prior to being coupled to the upper jaw 6602, adjacent the tissue-facing surface 6618. As illustrated by the double-ended arrow, the adjunct 6624 is stretched laterally across the tissue-facing surface 6608 of the upper jaw 6602. In this example, non-stretchable portions 6628a, 6628b are attached to the adjunct 6624 between the adjunct 6624 and the tissue-facing surface 6618 of the upper jaw 6602 such that the areas of the adjunct 6624 having the portions 6628a, 6628b coupled thereto substantially do not stretch. In FIG. 52A, the portions of the adjunct 6624 that do not have the portions 6628a, 6628b coupled thereto, e.g., portion 6625 and other remaining adjunct's portions, are shown stretched such that the openings 6626a, 6626b extend beyond the retaining members 6622a, 6622b.

The at least one portion of the adjunct material 6624, such as the portion 6625, can be stretched using application of a force, as discussed in more detail below. When the force is removed, the stretched portion transitions from a stretched configuration to a contracted configuration, which causes the adjunct material 6624 to be engaged with the first and second retaining members 6622a, 6622b. Thus, FIG. 52B shows the upper jaw 6602 with the adjunct coupled to the tissue-facing surface 6618 thereof via the retaining members 6622a, 6622b. In particular, the retaining members 6622a, 6622b are received in openings 6626a, 6626b such that the adjunct is retained on the jaw. The adjunct material 6624 is thus held in tension by the retaining members 6626a, 6626b engaged with the openings 6626a, 6626b such that a possibility of the adjunct material 6624 prematurely slipping off the jaw is decreased or eliminated. During a surgical procedure, after the jaw 6602 with the adjunct material 6624 coupled thereto is manipulated and positioned as desired, the firing of staples and/or a cutting element releases the tension such that the adjunct material 6624 slips off the retaining members 6626a, 6626b and becomes separated from the jaw 6602.

Figure 53A:
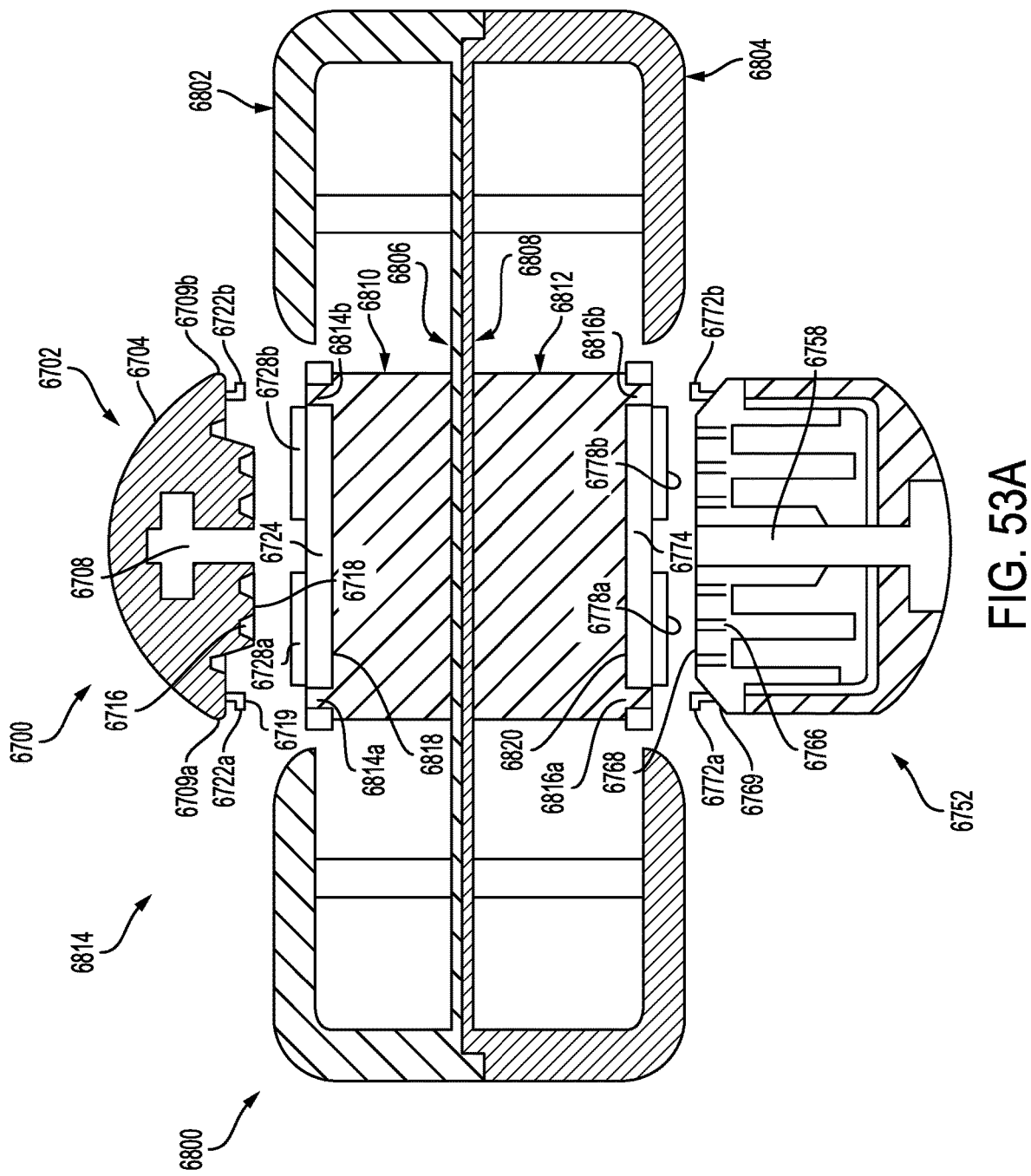
FIG. 53A is a cross-sectional view of jaws of an end effector and a loader prior to adjuncts being releasably coupled to the jaws.
Figure 53B:
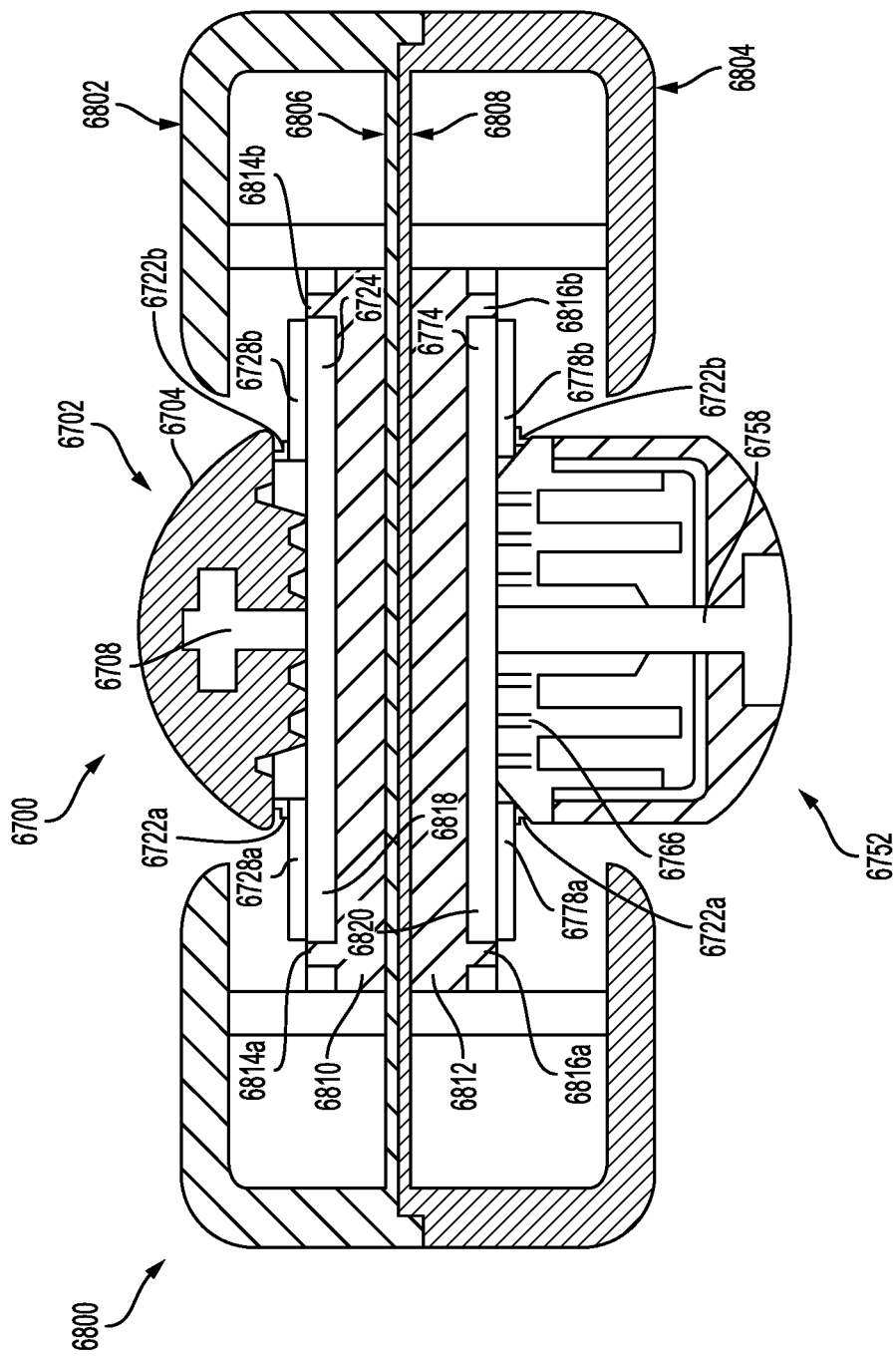
FIG. 53B is a cross-sectional view of the jaws and the loader of FIG. 54A, illustrating the jaws and the loader while the adjuncts are being transferred from the loader to the jaws.
Figure 53C:
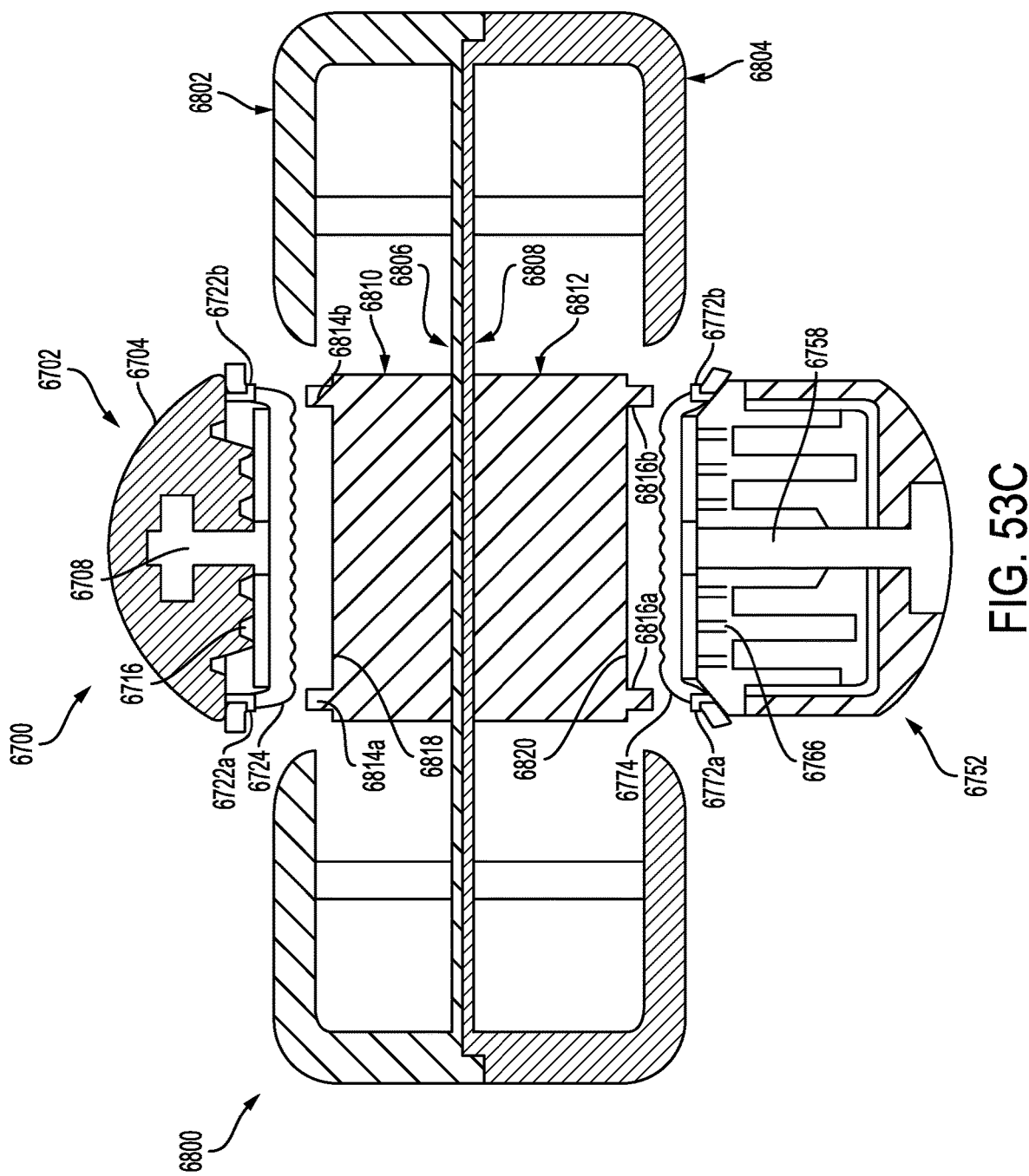
FIG. 53C is a cross-sectional view of the jaws and the loader of FIG. 54A, illustrating the jaws and the loader after the adjuncts have been transferred from the loader to the jaws and are releasably coupled to the jaws.

At least partially stretchable adjunct can be attached to one or both jaws of an end effector in a number of various ways. For example, in some embodiments, one or more adjuncts can be attached to jaws of an end effector using a removable loader member configured to releasably retain an adjunct material thereon until the adjunct material is applied to at least one jaw. FIGS. 53A-53C illustrate an example of an end effector 6700 that can be used with a member or loader 6700, to attach one or more adjunct materials or adjuncts to the end effector 6800.

The end effector 6700 can generally include components similar to those described with regard to end effector 6600, and can also include features and/or components that facilitate attaching one or more adjuncts thereto using a loader, e.g., loader 6800, to attach adjuncts. Thus, the end effector 6700 includes a first (upper in FIGS. 53A-53C) jaw 6702 having an anvil 6704 and a second (lower in FIGS. 53A-53C) jaw 6752 having a cartridge body. In this example, the loader 6800 is configured to apply first and second adjuncts 6724, 6774 to the first and second jaws 6702, 6752, respectively.

FIG. 53A shows a cross-sectional view of the end effector 6700, wherein the jaws 6702, 6752 of the end effector 6700 are disposed over the loader 6800 prior to the adjuncts 6724, 6774 being coupled to the jaws 6702, 6752. As shown in FIG. 53A, in this example, the anvil 6704 includes a multi-level (e.g., a two-plane or two-level) tissue-facing surface formed of surfaces 6718, 6719, wherein the surface 6718 extends in a plane closer to the cartridge 6752 and the surfaces 6719 are stepped out surfaces disposed in a plane that is further away from the cartridge 6752. At least portions of the tissue-facing surfaces 6718, 6719, have staple-forming cavities 6716 formed thereon. However, in some embodiments, the stepped surfaces 6719 may not have staple-forming cavities. The tissue-facing surface 6718 has a knife channel 6708 configured to receive a cutting element (e.g., a knife). It should be appreciated that the anvil 6704 is shown to have the two-level tissue-facing surface by way of example only, as the anvil 6704 can have a tissue-facing surface formed in substantially one planes, or, in some implementations, in more than two planes.

As shown in FIG. 53A, the tissue-facing surfaces 6719 of the anvil 6704 have at least first and second retaining members 6722a, 6722b formed thereon. The tissue-facing surfaces 6719 can additionally include other retaining members, similar to those discussed above with regard to end effector 6600. For example, each of distal and proximal ends of the tissue-facing surfaces 6719 can have two retaining members. However, other number and positions of the retaining members can be implemented additionally or alternatively. The retaining members are configured to couple the adjunct material 6724 to the anvil 6704. In the example illustrated, the retaining members can engage with openings formed in the adjunct material, as discussed below.

The cartridge 6752 has a plurality of staple-holding cavities 6766 configured to seat staples therein, the staple-holding cavities 6766 opening on tissue-facing surface 6768 of the cartridge 6752. The staple cavities can form a certain pattern on the tissue-facing surfaces 6768, which corresponds to a pattern of the staple-forming cavities 6716 formed in the anvil 6704. The cartridge includes first and second retaining members 6772a, 6772b, located on angled surfaces 6769 that are adjacent to the tissue-facing surface 6768. The retaining members 6772a, 6772b disposed on the angled surfaces 6769 are configured to releasably couple the adjunct material 6774 to the cartridge jaw 6752. As also shown, the tissue-facing surface 6768 has a knife channel 6758 configured to receive a cutting element (e.g., a knife). It should be appreciated that the cartridge 6752 is shown to have the angled surfaces 6769 by way of example only, as the cartridge 6752 may not have such surfaces in other implementations, or it may have other suitable configurations.

The loader 6800 can have any suitable configuration. In the example illustrated, the loader 6800 can be in the form of a generally rectangular frame-like holder configured to releasably couple one or more adjuncts to one or both jaws of the end effector. As shown in FIGS. 53A-53C, the loader 6800 can be in the form of a first (e.g., top) and second (e.g., bottom) generally rectangular housings 6802 and 6804 coupled to one another along interface A. Jaw-facing surfaces 6806, 6808, of the loader 6800 can have compressible (e.g., elastic, or pliable), members or bodies 6810, 6812, attached thereon. The compressible bodies 6810, 6812 can be made of, e.g., silicone, or any other compressible and at least partially resilient material suitable for being compressed. The elastic members 6810, 6812 can include gripping members 6814a, 6814b, 6816a, 6816b, that extend from jaw-facing surfaces 6818, 6820, respectively.

As illustrated in FIG. 53A, the adjuncts 6724, 6774, can be coupled to the elastic members 6810, 6812 of the loader 6800, which can be done during assembly of the loader 6800, or at any other time. The adjuncts 6724, 6774 can be substantially similar to adjunct 6624 (FIGS. 52A and 52B), and they can include openings, which can be mated with gripping members 6814a, 6814b, and 6816a, 6816b, to releasably secure the adjuncts to the elastic members 6810, 6812. Similar to the adjunct 6624, adjuncts 6724, 6774 each include first and second non-stretchable portions 6728a, 6728b, 6778a, 6778b.

To apply the adjuncts 6724, 6774 to the jaws 6702, 6752, the jaws 6702, 6752 can be clamped over the loader 6800 having the elastic members 6810, 6812 coupled to the adjuncts 6724, 6774, as illustrated in FIG. 53B. The clamping action causes the jaws 6702, 6752 to apply a force to the elastic members 6810, 6812 which, as a result, compress and stretch laterally, thereby causing the adjunct to also stretch, as shown in FIG. 53B. As also shown, the elastic members 6810, 6812 are configured to move from their original, non-compressed configuration to a compressed configuration such that they stretch in a substantially uniform manner, such that one or more portions of the adjuncts 6724, 6774 can also be stretched in a substantially evenly manner. In the illustrated example, the tissue-facing surfaces 6718, 6768 are configured to engage the adjunct prior to the retaining members 6722a, 6722b, 6772a, 6772b, which can allow the adjunct to expand without getting caught on the retaining members 6722a, 6722b, 6772a, 6772b.

When the jaws 6702, 6752 are opened and the clamping force applied by the jaws 6702, 6752 is removed, as shown in FIG. 53C, the adjuncts 6724, 6774 are released from the engagement with the elastic members 6810, 6812, which at least partially return to their original, non-compressed configuration, as also shown. This causes the adjuncts 6724, 6774 to at least partially contract. When sufficient contraction has occurred, the adjuncts 6724, 6774 are separated from the loader 6800. For example, the openings in the adjuncts 6724, 6774 can mate with the retaining members 6722a, 6722b, 6772a, 6772b that thus displace the gripping members 6814a, 6814b, 6816a, 6816b previously engaged with the openings. Additionally or alternatively, in some embodiments, the retaining members 6722a, 6722b, 6772a, 6772b formed on the jaws 6702, 6752 can engage portions of the adjuncts 6724, 6774 other than the openings. For example, one or more portions of the adjuncts can be stretched (as shown in FIG. 53B), then at least partially contracted and engaged with the retaining members 6722a, 6722b, 6772a, 6772b.

Regardless of the specific way in which the retaining members 6722a, 6722b, 6772a, 6772b can mate with the adjuncts 6724, 6774, the adjuncts 6724, 6754 are released from the gripping members 6814a, 6814b and become coupled to the jaws 6702, 6752, as illustrated in FIG. 53C. The adjuncts 6724, 6754 can be held over the jaws 6702, 6752 in at least partially stretched configuration. In this example, the substantially non-stretchable portions 6728a, 6728b, 6778a, 6778b of the adjuncts 6724, 6754 can be disposed over the jaws so as to be penetrated by the staples when the staples are ejected. The loader 6800 can then be removed. In use, after the end effector 6700 is manipulated as desired during a surgical procedure, the firing of the staples and/or a cutting element causes the adjuncts 6724, 6754 to separate from the jaws.

It should be appreciated that, although in FIGS. 53A-53C the loader 6800 is configured to deliver the adjuncts 6724, 6774 to both of the jaws 6702, 6752, in some embodiments the loader 6800 can be used to apply one of the adjuncts to one of the jaws. It should also be appreciated that the loader 6800 is shown by way of example only, as at least partially stretchable adjunct can be applied to one or both jaws of an end effector using a loader having any other suitable configuration.

In the embodiments described above, an adjunct material can be releasably coupled to a jaw of an end effector during manufacturing of the end effector or during a surgical procedure. Furthermore, the embodiments can have different variations. For example, a jaw of an end effector having a cartridge can seat a removable and replaceable cartridge, or the entire jaw with a cartridge can be removable and replaceable. A jaw can also be part of a disposable loading unit configured to be coupled distally to a shaft of a surgical instrument. As another example, although the systems and methods for releasably retaining an adjunct material over a jaw of an end effector are described in connection with linear staplers of various configurations, it should be appreciated that the described techniques can be implemented in connection with circular surgical staplers, e.g., circular surgical stapler 80 as illustrated in FIG. 5.

Suction Attachment of an Adjunct to a Surgical Instrument

In general, when using an adjunct in conjunction with a surgical stapler, the adjunct can be removably attached to the end effector. The adjunct will preferably remain secured to the end effector while the end effector is positioned at a treatment site, and is removed from the end effector when staples are deployed at the treatment site to provide the benefits discussed above. However, it has been observed that adjuncts can prematurely detach from the end effector prior to staple deployment. Detachment of the adjunct from the end effector can occur in various forms, depending on the manner in which the end effector is used. For example, detachment can include vertical lift off of the adjunct from the end effector, lateral sliding of the adjunct with respect to the end effector, and/or curling of the edges of the adjunct from the surface of the end effector. The adjunct can also slide sideways when an end effector is used to clamp and twist tissue.

FIGS. 54-58 illustrate various exemplary devices and methods for attaching an adjunct to a surgical instrument. In general, an adjunct can include a plurality of suction members configured to attach the adjunct to an end effector jaw of surgical instrument by a suction force/partial vacuum, which in certain aspects can be generated when the adjunct is compressed against the end effector jaw. The suction members can be further configured to release the suction/partial vacuum, decoupling the adjunct from the end effector jaw at a treatment site. Embodiments of the adjuncts are discussed below in conjunction with the stapler 10, where the suction members couple the adjunct to a tissue contacting surface 33 of the upper jaw 34 of an end effector 30. However, a person skilled in the art will appreciate that embodiments of the suction members can be employed with any surgical instrument without limit. Furthermore, embodiments of the suction members can be employed to couple adjuncts with the tissue contacting surface 33 of the upper jaw 34, a tissue contacting surface of the lower jaw 32, and combinations thereof.

Figure 54:
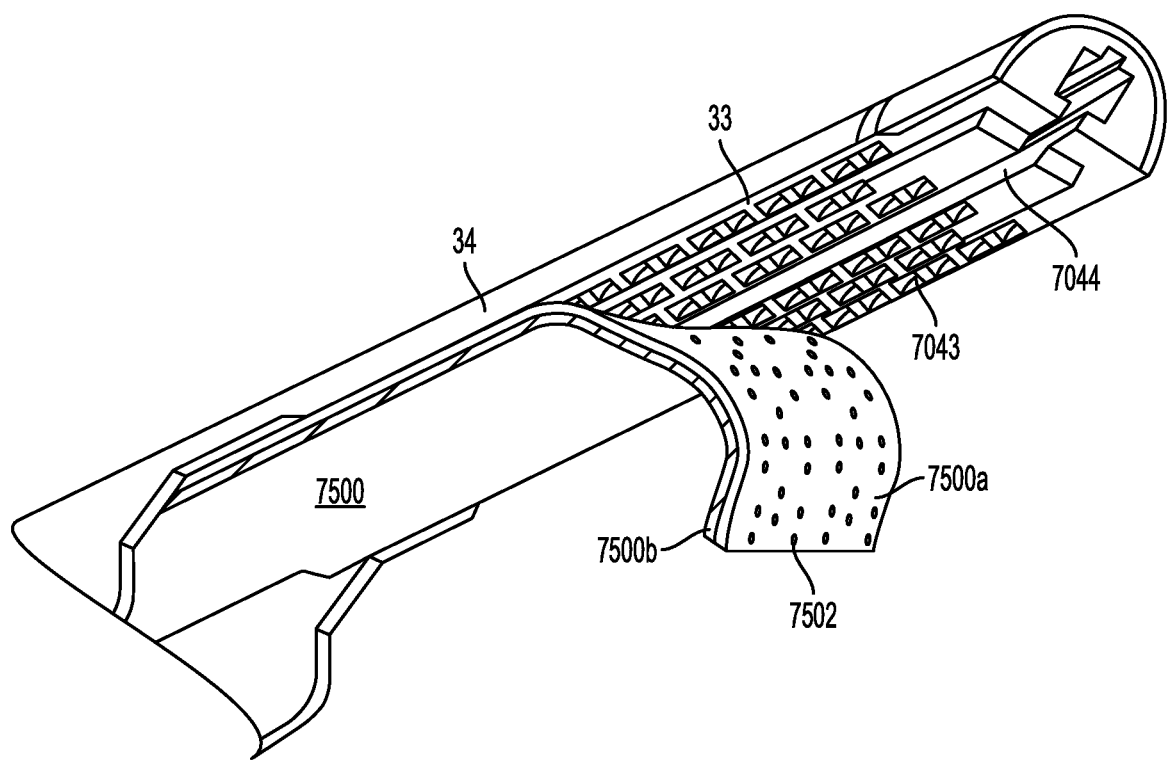
FIG. 54 is a perspective view of one embodiment of an adjunct coupled to an end effector jaw by suction.
Figure 55A:
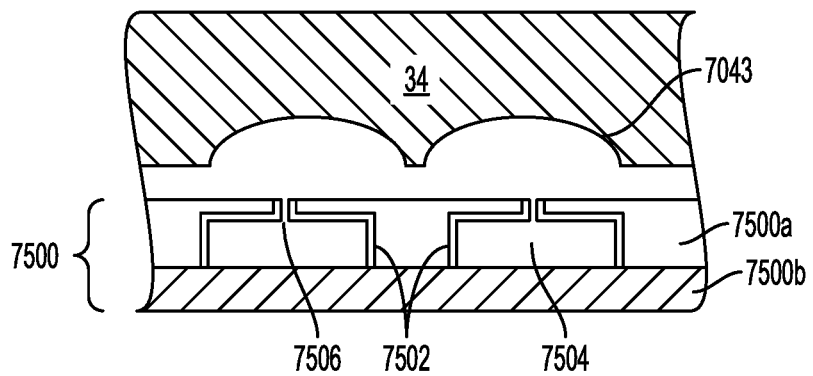
FIG. 55A is a cross-sectional view of the end effector jaw and adjunct of FIG. 54 showing the adjunct prior to contact with a tissue contacting surface of the jaw.
Figure 55B:
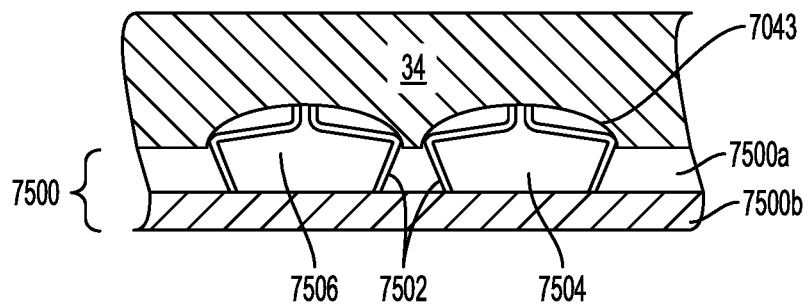
FIG. 55B is a cross-sectional view of the end effector jaw and adjunct of FIG. 55A showing the adjunct attached to the tissue contacting surface of the jaw by suction.
Figure 55C:
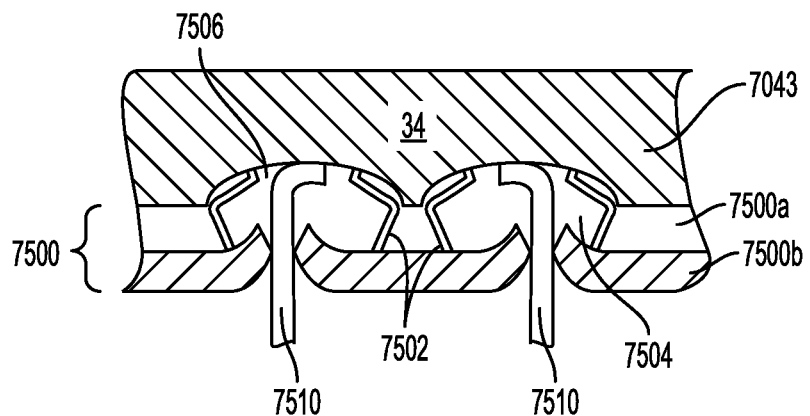
FIG. 55C is a cross-sectional view of the end effector jaw and adjunct of FIG. 55A showing the adjunct punctured by staples.

FIGS. 54-55C illustrate an embodiment of an adjunct 7500 that includes a plurality of suction members 7502 disposed upon the tissue contacting surface 33 (e.g., an anvil surface) of the upper jaw 34 of stapling device 10. As described in detail below, each of the suction members 7502 can be formed within the adjunct 7500 and can be configured to couple the adjunct 7500 to the upper jaw 34. For example, the suction members 7502 can provide a suction force/partial vacuum between the adjunct 7500 and the tissue contacting surface 33 that is sufficient to inhibit lateral sliding and vertical removal of the adjunct 7500 with respect to the tissue contacting surface 33 prior to placement at a treatment site.

In the embodiment shown in FIGS. 54-55C, the adjunct 7500 can be formed as a flexible laminate, including a first adjunct layer 7500*a* and a second adjunct layer 7500*b*. The first and second adjunct layers 7500*a*, 7500*b* can be coupled together along a common interface. In an exemplary embodiment, the first adjunct layer 7500*a* includes the plurality of suction members 7502 and the second adjunct layer 7500*b* is substantially solid, non-permeable, and void-free. The plurality of suction members 7502 include a plurality of air pockets or voids 7504 formed beneath the surface of the first adjunct layer 7500*a* and respective openings 7506 formed in an outer surface of the first adjunct layer 7500*a*. While the first and second adjunct layers 7500*a*, 7500*b* are illustrated as single layers, a person skilled in the art will appreciate that either or both of the first and second adjunct layers can be formed from two or more discrete layers fused together.

The plurality of suction members 7502 can be formed in a variety of ways. In one embodiment, the voids 7504 can be formed by cutting pockets having a selected shape through an inner surface and into a bulk of the first adjunct layer 7500*a*, separated from the outer surface by a selected distance. In another embodiment, the first adjunct layer can be cast from a melt using a mold that defines the pockets and, optionally, the openings 7506 therein. In either scenario, respective openings 7506 can be further formed through each of the pockets to the outer surface of the first adjunct 7500*a*. A diameter of each opening 7506 can be less than its corresponding pocket. Once the pockets and openings 7506 are formed, the first adjunct layer 7500*a* can be placed on the second adjunct layer 7500*b* and coupled thereto to close the pockets on all sides except for the openings 7506, forming the voids 7504. For example, the first and second adjunct layers 7500*a*, 7500*b* can be fused together along a common interface including the inner surface of the first adjunct layer 7500*a* by one or more of application of heat, adhesives, activation of the first and/or second adjunct layers 7500*a*, 7500*b* by a solvent, and any other mechanism for lamination of the first and second adjunct layers 7500*a*, 7500*b*. A person skilled in the art will appreciate that, while FIGS. 54 and 55A-55C illustrate the plurality of voids 7504 as having rectilinear shapes, they can adopt any desired shape.

A suction force/partial vacuum can be generated between the suction members 7502 and the tissue contacting surface 33 as follows. As illustrated in FIG. 55A, the adjunct 7500 can be oriented with the outer surface of the first adjunct layer 7500*a* opposite the tissue contacting surface 33 of the upper jaw 34. Subsequently, the adjunct 7500 can be positioned on the upper jaw 34, with the first adjunct layer 7500*a* contacting the tissue contacting surface 33, and the second adjunct layer 7500*b* can be compressed against the tissue contacting surface 33, as illustrated in FIG. 55B. This compression can establish a partial vacuum within the plurality of voids 7504 by elastically deforming the plurality of voids 7504 and expelling air from the plurality of voids 7504 to the environment via the plurality of openings 7506. Since the pressure of the surrounding atmosphere is greater than the pressure within the plurality of voids 7504, the atmosphere presses the plurality of voids 7504 against the tissue contacting surface 33, establishing the suction force/partial vacuum that secures the adjunct 7500 to the upper jaw 34. A person skilled in the art will appreciate that, while the adjunct 7500 is illustrated as a laminate in FIGS. 54-55C, alternative embodiments of the adjunct can be formed as a single layer that includes the plurality of suction members 7502.

The adjunct 7500 can be formed from one or more materials configured to allow flexure of the adjunct 7500 and deformation (e.g., elastic deformation) of the adjunct 7500 under compression. For example, the first and second adjunct layers 7500a, 7500b can each be independently selected from materials possessing a stiffness that provides a desired degree of elastic deformation under flexure and/or compression. Examples of suitable materials can include, but are not limited to, synthetic materials and biologic materials. Synthetic materials can include biodegradable polymers such as polydioxanone (PDS), Monocryl® (poliglecaprone 25, a copolymer of glycolide and ε-caprolactone; Ethicon, Inc.), polyhydroxy acids (e.g., poly-lactides, polyglycolides, polyhydroxybutyrates, polyhydroxy-valeriates), copolymers of lactide and trimethylene carbonate, copolymers of glycolide, lactide and trimethylene carbonate, polycaprolactones, polydioxanones, synthetic or natural oligo- and polyamino acids, polyphosphazenes, polyanhydrides, polyorthoesters, polyphosphates, polyphosphonates, polyalcohols, polysaccharides, and polyethers. Biologic materials can include, but are not limited to, naturally-occurring materials (e.g., collagens, gelatin), naturally-derived materials (e.g., bioabsorbable gel films cross-linked with omega-3 fatty acids), and oxygenized regenerated cellulose (ORC). In certain embodiments, a thickness of each of the first and second adjunct layers 7500a, 7500b can be independently selected from the range of about 8 μm to about 25 μm. The arrangement of the suction members 7502 within the adjunct 7500 can be configured to facilitate deformation of the adjunct 7500 under compression. For example, as further illustrated in FIG. 55B, at least a portion of the suction members 7502 can be formed in a pattern that substantially matches a pattern of staple-receiving cavities 7043 formed in the tissue contacting surface and aligned with the staple-receiving cavities 7043 when positioned on the upper jaw 34. The suction members 7502 aligned in this manner can be more easily compressed against the upper jaw 34, as compared to suction members 7502 that are not aligned because they are not supported by the upper jaw 34 (e.g., the tissue contacting surface 33 is recessed from the first adjunct layer 7500a by the staple-receiving cavities 7043). One skilled in the art will appreciate alternative embodiments of the suction members 7502 can alternatively or additionally be patterned for alignment with the pockets 41 of the tissue contacting surface of the lower jaw 32.

The adjunct 7500 can also be applied to the tissue contacting surface 33 using an applicator (not shown) that facilitates compression of the adjunct 7500. The applicator can include raised areas having a similar shape and/or distribution pattern as the staple-receiving cavities 7043. When a raised area of the applicator is aligned with a given suction member 7502 and staple-receiving cavity 7043, the raised area can extend within the staple-receiving cavity 7043 and compress the suction member 7502 by a greater degree than a planar applicator. One skilled in the art will appreciate alternative embodiments of the applicator can be patterned for alignment with the pockets 41 of the tissue contacting surface of the lower jaw 32.

The suction members 7502 can also be configured in a variety of ways to adjust the suction force/partial vacuum. In one example, the suction force/partial vacuum of a given suction member 7502 can be raised or lowered by increasing or decreasing the volume of the plurality of voids 7504, assuming a constant pressure difference between the atmosphere and the plurality of voids 7504. In another example, the total suction force exerted on the adjunct 7500 by the plurality of suction members 7502 can be raised or lowered by increasing or decreasing the number of suction members 7502 within the adjunct 7500, assuming each suction member 7502 is the same volume. Furthermore, by varying the location of suction members 7502 within the adjunct 7500, the suction force/partial vacuum can be locally increased or decreased at selected areas of the adjunct 7500.

The suction members 7502 can be further configured to release the adjunct 7500 from the tissue contacting surface 33 after penetration of staples through the adjunct 7500, allowing the adjunct 7500 to be retained at a tissue treatment site when the end effector 30 is retracted from the tissue. In one embodiment, the suction force/partial vacuum exerted by the plurality of suction members 7502 can be tailored, as discussed above, so that the force with which the adjunct 7500 is attached to the tissue by the staples is greater than the suction force. Thus, after the staples are deployed through the adjunct 7500 and the tissue, the adjunct 7500 can be released from the tissue contacting surface 33. In another embodiment, illustrated in FIGS. 55B-55C, at least a portion of the suction members 7502 can be aligned with respective staple-receiving cavities 7043. In an exemplary embodiment (FIG. 55C), staples 7510 fired through the adjunct 7500 and into the staple-receiving cavities 7043 can pierce the plurality of voids 7504 to break the suction/partial vacuum.

Embodiments of the adjunct 7500 can optionally include one or more features configured to work in combination with suction members 7502 to inhibit sliding of the adjunct 7500 when positioned on the tissue contacting surface 33. For example, the adjunct 7500 can include one or more protruding features (not shown) that extend outward from the surface of the first adjunct layer 7500a. These features can be dimensioned for receipt within one or more recessed areas formed within the tissue contacting surface 33. As shown in FIG. 54, one embodiment of the recessed areas can include a slot 7044 formed in the upper jaw 34 that is configured to receive the knife blade 36 or other cutting element during advancement between the jaws 32, 34. When the adjunct 7500 is positioned on the tissue contacting surface 33 one or more protruding features can extend within the slot 7044 and maintain the lateral position of the adjunct 7500 when experiencing shear stresses. The suction members 7502 can be distanced from the location of the protruding features to avoid interference with compression of the suction members 7502.

Figure 56A:
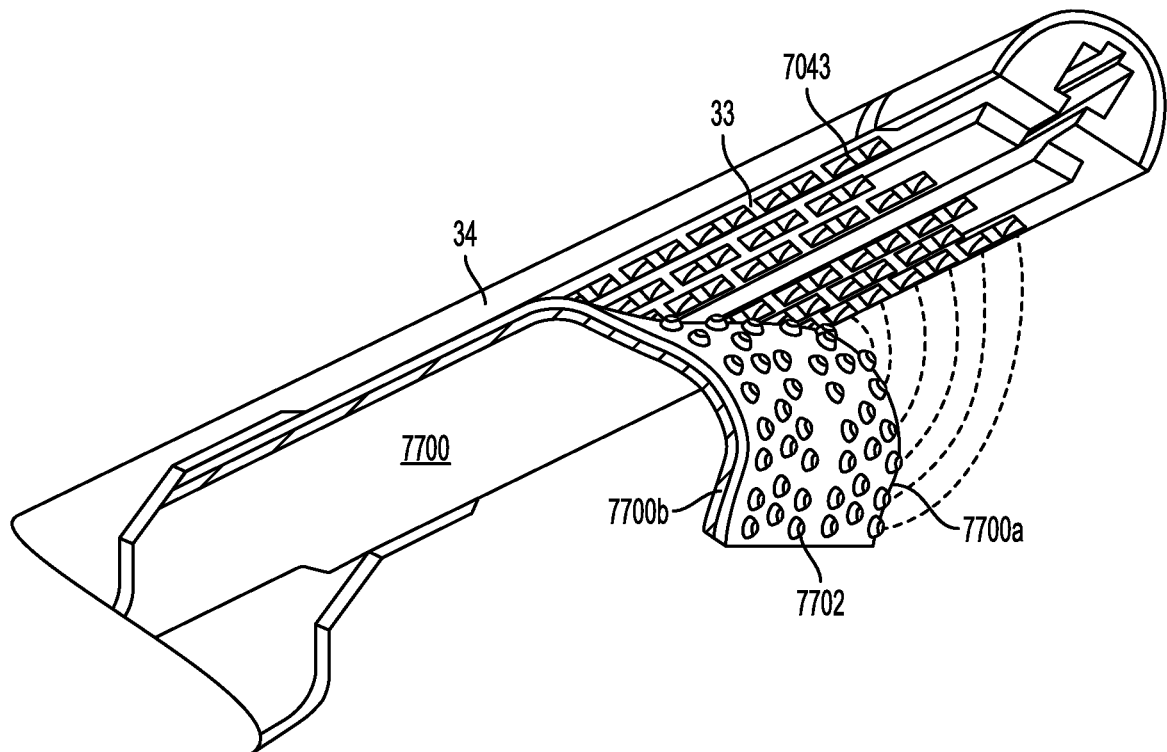
FIG. 56A is a perspective view of another embodiment of an adjunct coupled to an end effector jaw by suction.
Figure 56B:
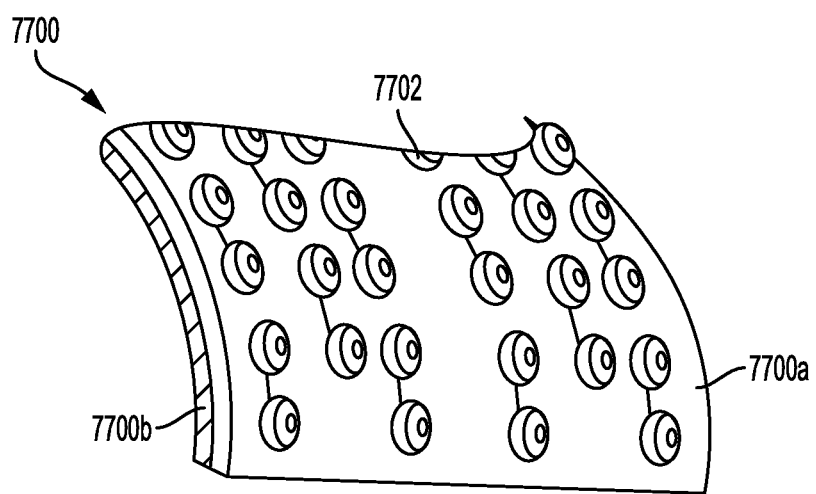
FIG. 56B is a perspective disassembled view of a portion of the adjunct of FIG. 56A.

Another embodiment of an adjunct 7700 is illustrated in FIGS. 56A-57C. The adjunct can generally be configured and used similar to the adjunct 7500, attaching to the tissue contacting surface 33 via suction force/partial vacuum and releasing from the tissue contacting surface 33 when staples are deployed. As shown in FIGS. 56A-56B, the adjunct 7700 includes coupled first and second adjunct layers 7700a, 7700b and a plurality of suction members 7702. In this implementation, the suction members 7702 can be formed as hollow protrusions extending outward from a surface of the first adjunct layer 7700a, opposite the second adjunct layer 7700b. The protrusions can define a plurality of air pockets 7704 in fluid communication with respective openings 7706 extending through each protrusion. While the first and second adjunct layers 7700a, 7700b are illustrated as single layers, a person skilled in the art will appreciate that either or both of the first and second adjunct layers can be formed from two or more discrete layers fused together.

Figure 57A:
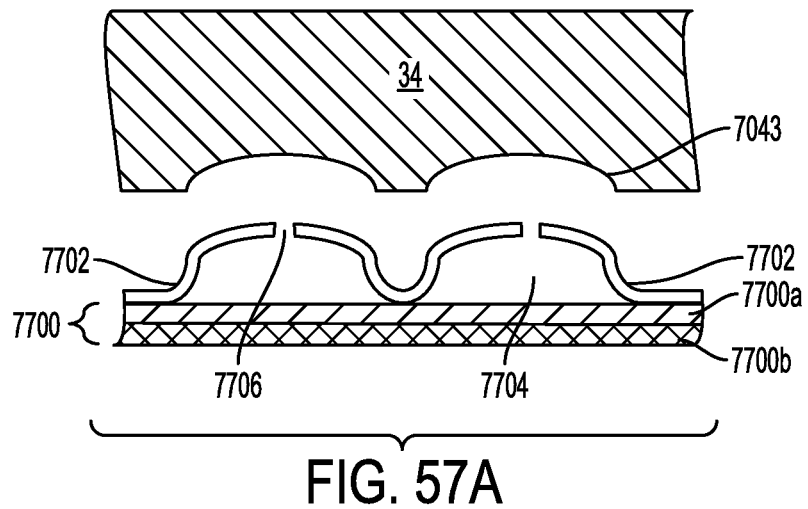
FIG. 57A is a cross-sectional view of the end effector jaw of FIG. 56A showing the adjunct prior to contact with a tissue contacting surface of the jaw.
Figure 57B:
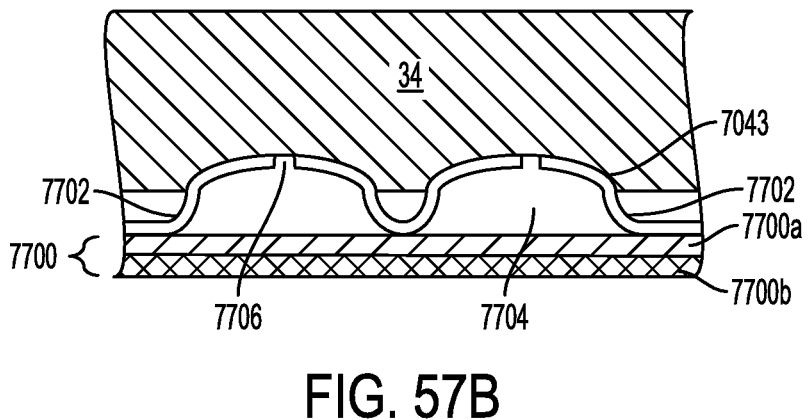
FIG. 57B is a cross-sectional view of the end effector jaw and adjunct of FIG. 57A showing the adjunct attached to the tissue contacting surface of the jaw by suction.
Figure 57C:
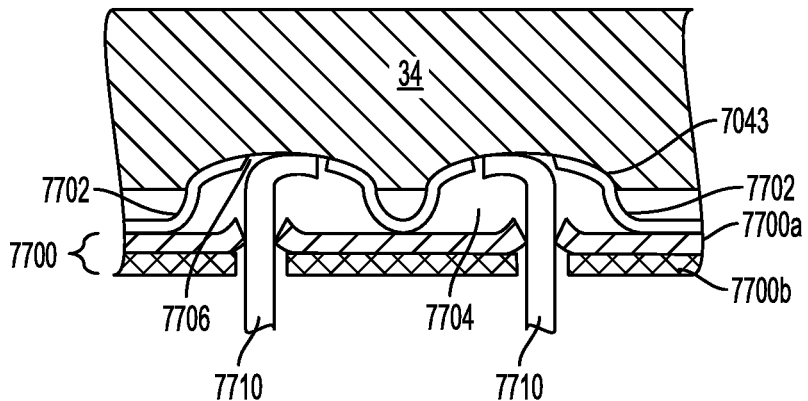
FIG. 57C is a cross-sectional view of the end effector jaw and adjunct of FIG. 57A showing the adjunct punctured by staples.
Figure 58:
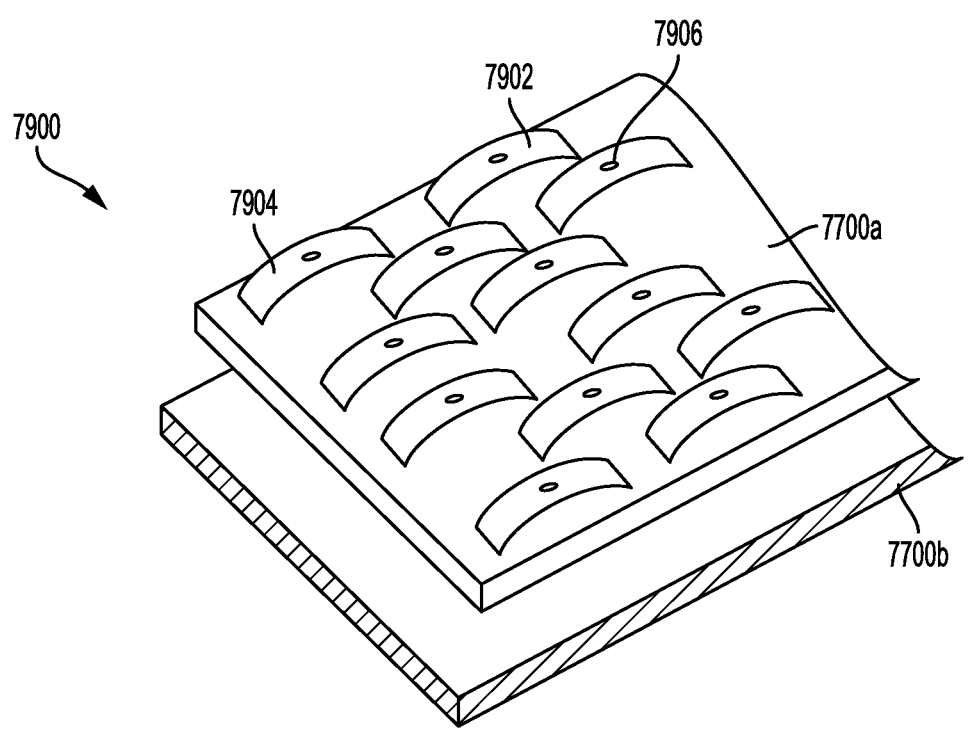
FIG. 58 is a perspective disassembled view of a portion of an adjunct according to another embodiment.

As shown in FIGS. 57A-57C, the adjunct 7700 can be positioned on the tissue contacting surface (FIG. 57A) and suction members 7702 can be compressed to expel air from the air pockets 7704 to the environment via the openings 7706, forming a suction force/partial vacuum therein (FIG. 57B). The air pockets 7704 can further release the suction resulting from the partial vacuum when the staples are fired through the adjunct 7700. In an exemplary embodiment, the suction force/partial vacuum can be released by piercing the air pockets 7704 with staples 7710, as shown in FIG. 57C. Alternatively or additionally, the force of the suction/partial vacuum provided by the plurality of suction members 7702 can be overcome by the strength of attachment of the staples 7710 to tissue (not shown) when the end effector 30 is removed from the tissue. A person skilled in the art will appreciate that, while FIGS. 56A-57C illustrate the plurality of suction members 7702 as having generally circular shapes, the suction members 7702 can adopt any desired shape. For example, FIG. 58 illustrates an embodiment of an adjunct 7900 that includes a plurality of suction members 7902 with air pockets 7904 formed therein and having openings 7906. As shown, the suction members 7902 have a shape that conforms to the shape of the staple-receiving cavities 7043.

The plurality of suction members 7702, 7902 can be formed in a variety of ways. In one embodiment, protrusions can be formed by casting the first adjunct layer 7700a from a melt using a mold that defines voids having a selected shape therein. Subsequently, respective openings 7706, 7906 can be formed through each of the voids to the outer surface of the first adjunct 7700a. A diameter of each opening 7706, 7906 can be less than a width of its corresponding void. After the voids and openings 7706, 7906 are formed, the first adjunct layer 7700a can be placed on the second adjunct layer 7700b and coupled thereto to close the voids on all sides except for the openings 7706, 7906, forming the air pockets 7704, 7904. For example, the first and second adjunct layers 7700a, 7700b can be fused together along a common interface including the inner surface of the first adjunct layer 7700a by one or more of application of heat, adhesives, activation of the first and/or second adjunct layers 7500a, 7500b by a solvent, and any other mechanism for lamination of the first and second adjunct layers 7700a, 7700b.

The plurality of suction members 7702, 7902 can also be configured to inhibit lateral sliding of the adjuncts 7700, 7900 when positioned on the upper jaw 34. In one embodiment, at least a portion of the suction members 7702, 7902 can possess a shape dimensioned for receipt within the plurality of staple-receiving cavities 7043. For example, the shape of the suction members 7902 can be configured to mate with the plurality of staple-receiving cavities 7043. In these implementations, when the suction members 7702, 7902 are received within the staple-receiving cavities 7043 and the adjunct 7700 is subjected to in-plane forces (e.g., shear forces), the lateral sides of the staple-receiving cavities 7043 can constrain the lateral motion of the suction members 7702, 7902, thereby inhibiting lateral motion of the adjuncts 7700, 7900.

In an embodiment, any of the adjuncts 7500, 7700, 7900 can also be configured to perform a healing function when positioned on tissue. Such healing functions can include, but are not limited to, delivering a medicant, reinforcing tissue, promoting tissue ingrowth or adhesions, deter adhesions, and the like.

Adjunct Material with Mating Features

In some implementations, an adjunct or adjunct material can be configured to be releasably retained on a jaw of an end effector for a surgical instrument using different types of features. Specifically, an adjunct material is provided that includes features for releasably attaching the adjunct material to the end effector and features for preventing stretching and/or displacement of the adjunct material as it is transferred to a treatment site in a patient.

The features for attaching the adjunct material to the end effector can be referred to as "retaining" features that are formed on the adjunct such that it can mate with respective features formed on the jaw (an anvil or a cartridge), to releasably retain the adjunct on the jaw. The adjunct is releasably retained on the jaw such that the adjunct remains attached to the jaw until the adjunct is applied to a treatment site. The adjunct additionally includes features that can be referred to as "non-retaining" features that are configured to mate with respective features on the jaw on which the adjunct is mounted such that the adjunct is able to move at least in a plane parallel to the tissue-facing surface. Such "non-retaining" features allow avoiding stretching, sliding off, and/or displacement of the adjunct material from its proper position at a treatment site to which the adjunct material is delivered when the staples are deployed. The adjunct is configured to be positioned on a jaw such that it is aligned with the staple pattern such that the staples, when ejected, penetrate the adjunct at desired locations.

When an end effector is deployed and tissue is clamped between the jaws such that the jaws apply force thereto, squeeze the tissue, and cause it to be penetrated by the deployed staples, the tissue is deformed. For example, portions of the tissue may flow out under the load and can form enlarged areas, which can cause the adjunct to be stretched and displaced from its intended position at the treatment site. This misalignment and displacement of the adjunct can negatively affect the proper reinforcement and/or treatment of the tissue at the surgical site with the adjunct material. Accordingly, the described techniques provide an adjunct material that includes features that prevent the undesirable stretching and/or displacement of the adjunct material. Such features of the adjunct can mate with complementary features formed on a jaw of an end effector on which the adjunct material is mounted.

In general, in the described implementations, a jaw of the end effector includes a plurality of male features formed on a tissue-facing surface of the jaw. The adjunct material can have a plurality of female features, with each female feature being able to encompass a corresponding one of the male features in a clearance fit such that the adjunct material is able to move with respect to the jaw on which it is mounted at least in a first plane parallel to the tissue-facing surface of the jaw. In this way, these "non-retaining" female and male features limit movement of the adjunct laterally and longitudinally (i.e. in the x and y directions), while not limiting movement of the adjunct in a vertical direction (i.e. in the z direction), which causes the adjunct to remain properly positioned during staple deployment at a treatment site.

The adjunct material also has at least one attachment feature configured to releasably retain the adjunct material on the at least one jaw. Such "retaining" features releasably retain the adjunct with respect to a tissue-facing surface of the jaw until the adjunct is caused to be transferred to the treatment site. Thus, the retaining features can be used to retain the adjunct on the jaw in a substantially non-movable manner. As the staples are deployed by being ejected from an end effector's cartridge, the staples cause the adjunct material to be separated from the jaw to become attached to the tissue with the staples.

Figure 59:
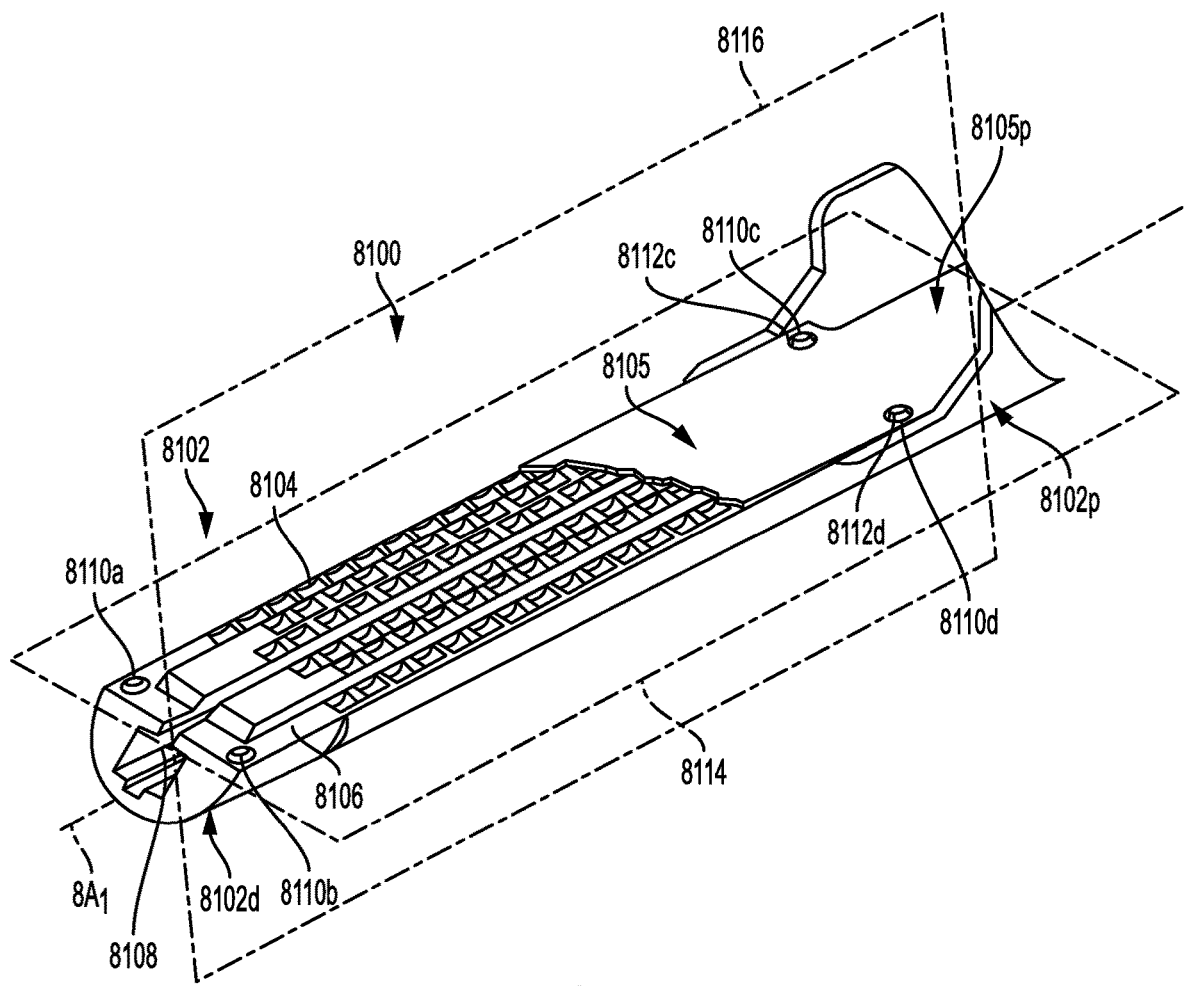
FIG. 59 is a perspective, partial cut-away view of a jaw of an end effector having an adjunct material releasably mounted thereon in accordance with the described techniques.

FIG. 59 illustrates an example of a portion of the end effector 8100 having first and second opposed jaws configured to clamp tissue therebetween, in accordance with the described techniques. The end effector 8100 can be used with any suitable surgical instrument, for example, a linear surgical stapler (e.g., stapler 10 in FIG. 1, stapler 50 in FIG. 4, or any other surgical stapler) which can be suitable for use with at least one adjunct. The end effector 8100, only a portion of which (an upper jaw or anvil 8102) is shown in FIG. 59, can be coupled to a distal end of a shaft of the surgical stapler (not shown). As shown in FIG. 59, the anvil 8102 has a plurality of staple-forming pockets or cavities 8104 formed on a tissue-facing surface 8106 of the anvil 8102. The staple-forming cavities 8104 form a certain pattern on the surface of the anvil 8102 which corresponds to a pattern of staple-holding cavities in the cartridge of the end effector 8100 (not shown in FIG. 59). The anvil 8102 includes an anvil knife channel 8108 extending between distal and proximal ends 8102d, 8102p of the anvil 8102. The anvil knife channel 8108 is configured to receive a cutting element (e.g., a knife) as the cutting element moves distally through a cartridge knife slot in the staple cartridge.

The end effector 8100 includes an adjunct material 8105 mounted thereon, a portion of which is shown in FIG. 59 for illustration purposes only. In the example illustrated, the generally rectangular adjunct material 8105 includes both retaining and non-retaining features for mating with the anvil of the end effector, as discussed below. It should be appreciated that the anvil 8102 is shown by way of example, as the adjunct material can also be mounted on a cartridge using the described techniques. Further, in some embodiments, both anvil and cartridge of an end effector have respective adjunct materials releasably mated thereto using both retaining and non-retaining features in accordance with the described techniques.

As shown in FIG. 59, the anvil 8102 includes non-retaining features in the form of male features, such as, in this example, four posts or projections 8110a, 8110b, 8110c, 8110d formed on the tissue-facing surface 8106 of the anvil 8102. As also shown in FIG. 59, the adjunct material 8105 also has non-retaining features such as female features in the form of openings configured to encompass corresponding male features in a clearance fit. Because the adjunct material 8105 is shown only partially in FIG. 59, two openings 8112c, 8112d in the adjunct material 8105 formed at a proximal end 8105p are shown. It should be appreciated, however, that, though not shown, the adjunct material 8105 also includes two other openings at a distal end thereof that correspond to the projections 8110a, 8110b formed on the tissue-facing surface 8106 of the anvil 8102 at the anvil's distal end 8102d.

Figure 60:
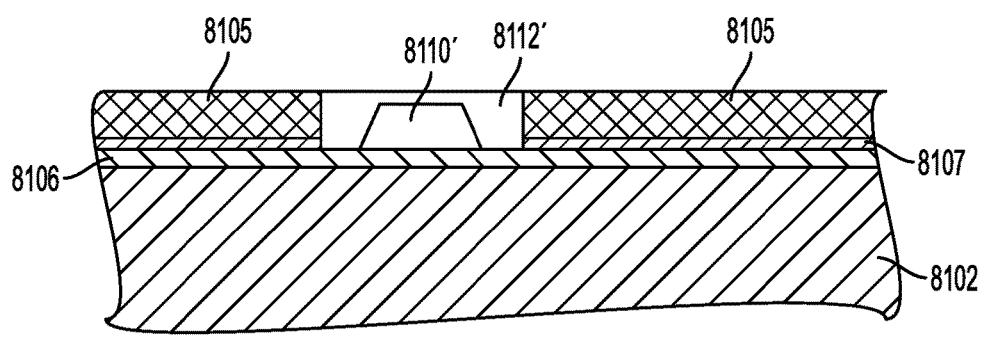
FIG. 60 is a cross-sectional view of a portion of the jaw of FIG. 59 with the adjunct material.

The adjunct material 8105 also has one or more retaining features that releasably retain the adjunct material 8105 on the jaw 8102. In the illustrated example, such features are in the form of a layer 8107 of an adhesive material disposed on the jaw-facing surface of the adjunct material 8105, as shown in FIG. 60. The adhesive material layer 8107 can be formed on the entirety of the adjunct material 8105 or it can be disposed on one or more portions of the adjunct material 8105. The adhesive material layer 8107 can be formed from any suitable material. For example, the adhesive material can be polydioxanone (PDO), a low molecular weight polyethylene glycol (PEG) or any other material (or a combination of materials) that can be used to attach the adjunct to the jaw. In some embodiments, the adhesive material can be a bioabsorbable and/or biodegradable pressure sensitive adhesive.

The female features of the adjunct material 8105 and the male features formed on the anvil 8102 can have many different configurations and the female and male features can mate in a variety of different ways. In this example, the female features of the adjunct material 8105 in the form of openings are configured to encompass the male features in the form of projections formed on the anvil 8102 in a clearance fit such that the adjunct material 8105 is able to move with respect to the anvil 8102 at least in a first plane 8114 parallel to the tissue-facing surface 8106 of the anvil 8102, which is schematically shown in FIG. 59. It should be appreciated, however, that the movement of the adjunct material 8105 in the first plane 8114 is restricted to the extent that corresponds to a degree of the clearance fit between the female and male features.

As shown in FIG. 60 illustrating a portion of the end effector 8100, the projection 8110', representing the projections 8110a, 8110b, 8110c, 8110d formed on the tissue-facing surface 8106 of the anvil 8102, is tapered in a direction that is perpendicular to a longitudinal axis 8A1 of the jaw 8102. As further shown in FIG. 60 illustrating a portion of the end effector 8100, an opening 8112' in the adjunct material 8105 (e.g., any of the openings 8112, 8112d, or other openings) is oversized with respect to a corresponding projection 8110' (e.g., any of the anvil's projections 8110a, 8110b, 8110c, 8110d) formed on the anvil 8102. As a result, the opening 8112' encompasses the projection 8110' in a clearance fit such that the adjunct material 8105 is able to move with respect to the anvil 8102 at least in the first plane 8114 shown in FIG. 59. When the opening 8112' is generally round in shape, as in the illustrated example, its diameter is larger than a largest dimension of the projection 8110' in the plane parallel to a plane of the tissue-contacting surface of the jaw.

The configuration and size of the female feature in the form of the opening 8112' is such that the male feature in the form of the projection 8110' encompassed by opening 8112' is not effective to retain the adjunct material 8105 in a second plane 8116 that is perpendicular to the first plane 8114. Thus, the projection 8110' is encompassed by the opening 8112' such that, if the jaw 8102 with the adjunct 8105 mounted thereon were to be turned upside down, and if the projection 8110' and the opening 8112' were the only features used to position the adjunct 8105 over the jaw (which is not the case), the adjunct 8105 would slide off the jaw 8102 with little or no force. It should be appreciated that the planes 8114, 8116 are referred to as "first" and "second" for purposes of description only, and not to indicate any particular order.

As mentioned above, the adjunct material 8105 and the female features formed thereon can have various configurations. In the example illustrated, the openings (e.g., the openings 8112c, 8112d shown in FIG. 59) in the adjunct material 8105 are generally circular in shape and they have a diameter that allows them to encompass the projections (e.g., the projections 8112c, 8112d) formed on the jaw 8102 in a clearance fit. However, it should be appreciated that the adjunct material 8105 can have openings having other shapes, which can be different from circular (e.g., oval, rectangular, square, or irregular shapes). Also, the adjunct material can include openings having the same size, or openings of different sizes and/or shapes can be formed in the adjunct material.

The male features, such as the projections 8110*a*, 8110*b*, 8110*c*, 8110*d* formed on the tissue-facing surface 8106 of the anvil 8102, can be formed at any suitable locations on the anvil 8102. The projections can be formed within an area of the tissue-facing surface 8106 occupied by the staple-forming pockets 8104, or the projections can be formed outside of this area. Thus, in the example of FIG. 59, the projections 8110*a*, 8110*b* formed at the distal end 8102*d* of the anvil 8102 are offset distally from the staple-forming pockets 8104. The projections 8110*c*, 8110*d* formed at the proximal end 8102*p* of the anvil 8102 can be formed within the anvil's area having the staple-forming pockets 8104. However, in some embodiments, the projections 8110*c*, 8110*d* can be formed on the area of the anvil 8102 outside of the area having the staple-forming pockets 8104.

In some implementations, as mentioned above, the projections on the tissue-facing surface of a jaw of the anvil can be formed within the area of the anvil having the staple-forming pockets such that the projections are formed between the staple-forming pockets. The adjunct material used in conjunction with the anvil having such projections can have corresponding female features disposed at locations of the adjunct material such that the female features can encompass the male features in a clearance fit. Furthermore, a cartridge of an end effector can have male features formed within the cartridge's area having the staple pockets (e.g., between the pockets), of the male features can be formed outside of the area having the staple pockets.

A jaw of an end effector can have any suitable number of male features configured to mate with corresponding adjunct's female features using the described techniques— in a non-retaining manner. The four projections 8110*a*, 8110*b*, 8110*c*, 8110*d* formed on the tissue-facing surface 8106 of the anvil 8102 are shown in FIG. 59 by way of example only. Thus, one, two, three, or more than four projections configured to mate with corresponding female features formed on the adjunct. In embodiments in which one projection is used, it can be in the form of an elongate, narrow feature, such as a rib or a slot. Alternatively, if the adjunct is configured to be constrained proximally by the end effector (e.g., between the tissue stops of the anvil), a single distal attachment point may be sufficient to apply the adjunct to the jaw. Furthermore, in some embodiments, at least one of the female features can be configured such that a single female feature encompasses more than one male feature. For example, one opening formed in the adjunct material can encompass in a clearance fit two or more male features formed on an anvil or on a cartridge.

The non-retaining male and female features (i.e., the features configured to mate such that an adjunct can move with respect to the jaw on which it is mounted at least in the first plane parallel to the tissue-facing surface, and such that the adjunct is not retained in the second plane that is perpendicular to the first plane) can have various configurations. Thus, the projections and openings are shown in FIGS. 59 and 60 by way of example only.

It should be appreciated that retaining attachment features (i.e., features configured to retain the adjunct with respect to the jaw on which it is mounted such that the adjunct cannot move in the first and second planes and can only be separated from the jaw when the staples are ejected) can also have various configurations. As discussed above, in the example shown in FIGS. 59 and 60, the attachment feature is the adhesive layer 8107 formed on the jaw-facing surface of the adjunct. Other attachment feature(s) can be used additionally or alternatively, as the described techniques are not limited to any specific attachment features configured to releasably retain the adjunct on the jaw. For example, the jaw can have one or more projections or other male features that can serve as the attachment features configured to mate with respective female features formed on the adjunct material. In some implementations, the attachment male features formed on the adjunct can be configured to mate with complementary female features formed on the jaw. Furthermore, different types of features (e.g., both female and male or combination(s) thereof) can be formed on the adjunct, which can mate with corresponding features of the jaw. The described techniques are also not limited with respect to a number of the attachment features and to specific locations of the attachment features on the jaw and on the adjunct material.

FIG. 61 illustrates another example of a distal portion of an end effector having features in accordance with the described techniques. The end effector can be used with any suitable surgical instrument. For example, it can be used with a linear surgical stapler, such as stapler 10 in FIG. 1, stapler 50 in FIG. 4, or any other surgical stapler. In this example, a jaw in the form of the cartridge 8202 of the end effector having staple pockets 8204 formed on a tissue-contacting surface 8206 thereof is shown. The staple pockets 8204 form several rows along a longitudinal axis 8A2 of the cartridge 8202. The cartridge 8202 can be a removable and replaceable cartridge. In some embodiments, the cartridge 8202 can be part of a replaceable and disposable loading unit configured to couple distally to a shaft (not shown) of the end effector.

As shown in FIG. 61, the tissue-contacting surface 8206 of the cartridge 8202 has male features in the form of multiple projections 8210 formed along a long side of the cartridge 8202. In this example, the projections 8210 form two rows on opposite sides of the area of the tissue-contacting surface 8206 having the staple pockets 8204, with the rows extending parallel to the longitudinal axis 8A2 of the cartridge 8202. Any suitable number of projections can be formed at a suitable distance from one another. The projections 8210 can be in the form of posts having a rounded and/or tapered head. It should be appreciated, however, that the projections 8210 can have any suitable configurations.

As also shown in FIG. 61, the cartridge 8202 can retain thereon an adjunct material 8205 having female features configured to mate with the jaw's male features in the form of the projections 8210 such that each female feature can encompass a corresponding one of the male features in a clearance fit. In this way, the adjunct material 8205 is able to move with respect to the jaw 8202 at least in a first plane 8214 parallel to the tissue-facing surface 8206 of the jaw 8202.

In the example of FIG. 61, the adjunct 8205 is formed from at least partially stretchable or expandable material formed of fibers such that at least some portions of the adjuncts are relatively loose. For example, the adjunct can be a fiber-based lattice which can be a woven fabric, knitted fabric or non-woven fabric. The adjunct can have multiple regions that can be formed from the same type of lattice or from different types of lattices that can together form the adjunct in a number of different ways. For example, the fibers can be woven, braided, knitted, or otherwise interconnected so as to form a regular or irregular structure. The fibers can be interconnected such that the resulting adjunct is relatively loose.

The expandable material can be, e.g., in the form of a mesh material having fibers forming regular or irregular patterns, or a combination of regular or irregular patterns. The adjunct 8205 has a plurality of female features in the form of expandable openings 8212 formed between fibers of the expandable material. The openings 8212 can be pre-formed in the adjunct material 8205 such that they are formed at predetermined locations. For example, the openings 8212 can be formed in two rows along opposite long sides of the adjunct material 8205, as shown in FIG. 61. In some embodiments, the expandable openings can exist in the adjunct material 8205 due to the nature of the fabric from which the adjunct material is formed. As mentioned above, the entire adjunct material or one or more portions thereof can be relatively loosely interconnected, and such loosely interconnected portions can have openings therein. In such embodiments, the male features formed on the jaw can "find" openings in the adjunct to mate with when the adjunct is placed over the jaw.

Regardless of the specific way in which the female features are formed in the adjunct material, the adjunct material can mate with the male features formed on the jaw because the expandable material stretches (e.g., its fibers separate) and thus enlarges in places where the male features are inserted at least through the mesh. FIGS. 62A, 62B, and 62C illustrate an example of openings 8212' in an adjunct material 8205' that can encompass posts or projections 8210' formed on a jaw, such as the cartridge 8202 or other jaw (which can be an anvil).

As shown in FIG. 62A, openings 8212' in an adjunct material 8205', three of which are labeled as openings 8217*a*, 8217*b*, 8217*c*, can be present in the expandable material forming the adjunct material 8205' due to the way in which the fibers of the adjunct material are interwoven. The openings 8217*a*, 8217*b*, 8217*c* exist between the interwoven fibers of the adjunct material 8205' and each can be expanded, enlarged, or deformed when it receives a respective projection therein. FIG. 62B illustrates by way of example of three projections 8219*a*, 8219*b*, 8219*c* of the multiple projections that can be formed on the jaw, such as the cartridge 8202 in FIG. 61 or other jaw.

When the adjunct material 8205' is laid over the jaw, the projections 8219*a*, 8219*b*, 8219*c* are received within the openings 8217*a*, 8217*b*, 8217*c* such that the material forming the adjunct material 8205' stretches over the projections 8219*a*, 8219*b*, 8219*c* in direction indicated by arrows 8220*a*, 8220*b*, as shown in FIG. 62C. The property of the material is such that it is stretched and/or deformed so that the adjunct material 8205' is able to move with respect to the jaw at least in a first plane parallel to the tissue-facing surface of the jaw and so that the adjunct material is not retained in a second plane that is perpendicular to the first plane.

In addition to female features described above, the adjunct material 8205 in FIG. 61 and the adjunct material 8205' shown in FIGS. 62A and 62C also have at least one attachment feature configured to releasably retain the adjunct material on the jaw. The at least one attachment feature can be an adhesive material layer formed over at least a portion of the adjunct material, or any other type of feature(s), such as a male or female feature, or a combination thereof. The at least one attachment feature can be configured to mate with the end effector's jaw on which the adjunct is mounted, in a way corresponding to a type of the attachment feature. For example, when the attachment feature is the adhesive material layer, such adhesive material layer attaches to the jaw due to its adhesive nature. When the attachment feature is one or more openings or projections, they are configured to mate with corresponding projections or openings formed on the jaw.

Regardless of the specific type, number, and location of attachment feature(s) formed on the adjunct material, they are formed to retain the adjunct material on the jaw in three dimensions, such that the adjunct can be separated from the jaw when the staples are ejected from the cartridge. The adjunct's non-retaining features (e.g., various female features described herein), which do not retain the adjunct with respect to the jaw in the plane perpendicular to a plane parallel to the jaw's tissue-contacting surface, are used to prevent stretching of the adjunct material and/or displacement (e.g., slipping or sliding off) of the adjunct from the jaws of the end effector. Thus, unlike the non-retaining adjunct's features that are only used to properly position the adjunct, the attachment features serve to releasably retain the adjunct on the jaw.

Figure 63:
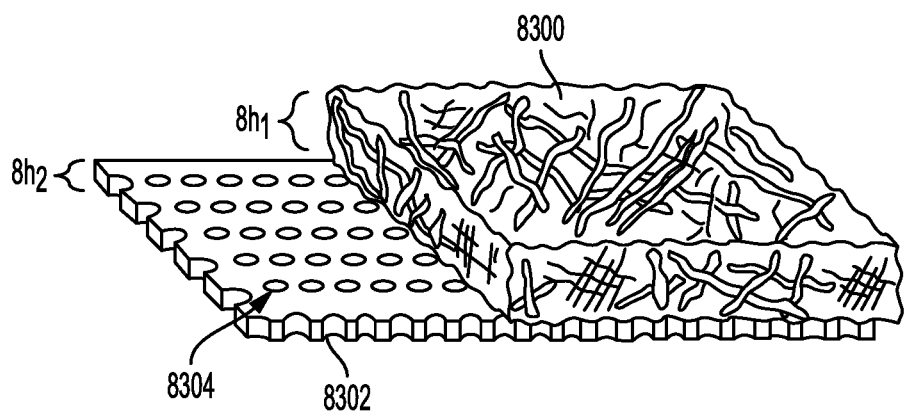
FIG. 63 is a perspective, partial cut-away view of an adjunct material having a backing layer in accordance with the described techniques.
Figure 64:
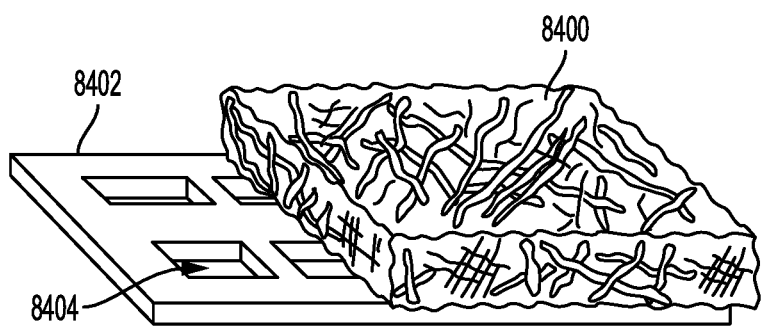
FIG. 64 is a perspective, partial cut-away view of another adjunct material having a backing layer in accordance with the described techniques.

In some embodiments, an adjunct material is formed from fibers and it comprises a backing layer non-removably attached thereto on a side of the adjunct material facing the jaw. The fibers can be a mesh, nonwoven fibers, or any other type(s) of fibers. The backing layer can have female features formed thereon for mating with respective male features formed on the jaw on which the adjunct material is mounted. FIGS. 63 and 64 illustrate example of such adjunct material, with the jaw not shown.

FIG. 63 illustrates an example of an adjunct material 8300 in the form of a generally rectangular fiber layer. The adjunct material 8300 has a backing layer 8302 non-removably attached thereto on a side of the adjunct material facing the jaw of an end effector. As shown in FIG. 63, the backing layer 8302 has a plurality of female features in the form of openings 8304 formed thereon. The openings 8304 can mate with corresponding male features of the jaw (e.g., a cartridge or anvil). In this example, the openings 8304 are configured to mate with the male features such that not every opening mates with the jaw. Thus, a pattern and/or number of male features formed on the jaw may be different from a pattern and/or number of female features formed on the adjunct material. For example, the jaw can have fewer male features (e.g., projections such as projections 8110 (FIG. 59), projections 8210 (FIG. 61), or any other male features) than the number of openings. In this way, for example, only some of the openings 8304 (which are oversized with respect to the male features) may surround respective male features. Thus, there is no requirement that specific openings surround specific male features. The adjunct material 8300 with multiple openings formed therein can thus be easily positioned over the jaw and the male features "find" openings that can surround the male features. The number of the male features can be selected such that it is sufficient to prevent displacement of the adjunct material from the end effector's jaw(s), in accordance with the described techniques.

The openings 8304 can have any suitable configuration. For example, while generally circular openings 8304 are shown in FIG. 63, the openings can be oval, rectangular, square, or they have can other regular or irregular shapes. Any suitable number of openings can be formed in any suitable pattern(s).

The backing layer 8302 can be formed from any suitable biodegradable and/or bioabsorbable material, such as, for example, polydioxanone (PDO) or any other suitable polymeric material(s). The material can be selected such that it biodegrades and/or bioabsorbs faster than the adjunct material 8320. As shown in FIG. 63, the backing layer 8302 has a thickness that is smaller than that of the adjunct material 8320. For example, in some embodiments, the height or thickness 8h1 of the adjunct material 8320 can be from about 0.004 inches to about 0.020 inches, whereas the height or thickness 8h2 of the backing layer 8302 can be from about 0.0002 inches to about 0.0012 inches. However, in some embodiments, the thickness 8h1 of the adjunct material can be greater—e.g., from about 0.01 inches to about 0.150 inches. The thickness 8h1 of the adjunct material, as well as the thickness 8h2 of the backing layer, can vary within other suitable ranges.

FIG. 64 illustrates another example of an adjunct material 8400 in the form of a generally rectangular fiber layer. The adjunct material 8400 has a backing layer 8402 non-removably attached thereto on a side of the adjunct material 8400 facing a jaw of an end effector (not shown). As shown in FIG. 64, the backing layer 8402 has a plurality of female features in the form of openings 8404 formed thereon. The openings 8404 can mate with corresponding male features of the jaw (e.g., a cartridge or anvil). The openings 8404 can be configured to mate with the male features such that one opening can surround two or more male features. Thus, as illustrated in FIG. 64, the backing layer 8402 has several (e.g., two, three, or greater than there) openings formed therein each of which can surround more than one male feature (e.g., projections, posts, etc.) formed on the jaw. For example, one opening (or "window") 8404 can surround a group of jaw's male features. Also, in some embodiments, only some of the openings 8404 will surround two or more male features.

Furthermore, in some embodiments, the backing layer can have one opening. For example, it can be a relatively large opening such that the backing layer can be in the shape of a frame that is coupled to the adjunct material along a perimeter of the adjunct. The frame-shaped backing layer can couple with a jaw via male features disposed on the jaw in a certain manner. For example, four or more male features (e.g., posts) can be disposed at opposed sides at the distal and proximal ends of the jaw and the frame-shaped backing layer, with the adjunct coupled thereto, can be retained on the jaw via such features received within the opening in the backing layer.

The openings 8404 can have any suitable configuration and size. For example, as shown in FIG. 64, the openings 8404 can be rectangular. However, they can alternatively be square, round, oval, etc. Also, the adjunct material can have openings of different sizes and/or shapes. The backing layer 8402 can be formed from one or more materials similar to the backing layer 8302 in FIG. 63.

Furthermore, although not shown separately in FIGS. 63 and 64, each of the adjunct materials 8300 and 8400 also includes one or more attachment features configured to releasable retain the adjunct material on the jaw. The attachment feature(s) can be in the form of an adhesive material layer, female, male, or other type of features that are used to retain the adjunct material on the jaw in all three dimensions. Furthermore, in some embodiments, the material from which the backing layer (e.g., backing layer 8302 in FIG. 63 or backing layer 8402 in FIG. 64) is formed can be an adhesive material serving as an attachment layer. The adhesive material can be any suitable polymer, such as polydioxanone (PDO), a low molecular weight polyethylene glycol (PEG) or any other material (or a combination of materials) that can be used to attach the adjunct to the jaw.

In some embodiments, the adhesive material can be a bioabsorbable and/or biodegradable pressure sensitive adhesive.

In the example of FIGS. 63 and 64, the backing layer non-removably attached to the adjunct material on jaw-facing surface thereof is formed substantially over entire surface of the adjunct material. In some embodiments, the backing layer can be in the form of discrete portions. In this way, while some portions of the adjunct material can be prevented from being stretched, other portions can be stretched once the adjunct material is applied to tissue at a treatment site. The adjunct material can thus move with the tissue at which it is implanted when the tissue moves, while remaining being coupled to the tissue. This may be desirable when tissue such as, for example, lung is being treated, which needs to be able to expand and contract to perform its function. Allowing the implanted adjunct material to stretch to some degree allows the tissue to heal appropriately.

Figure 65:
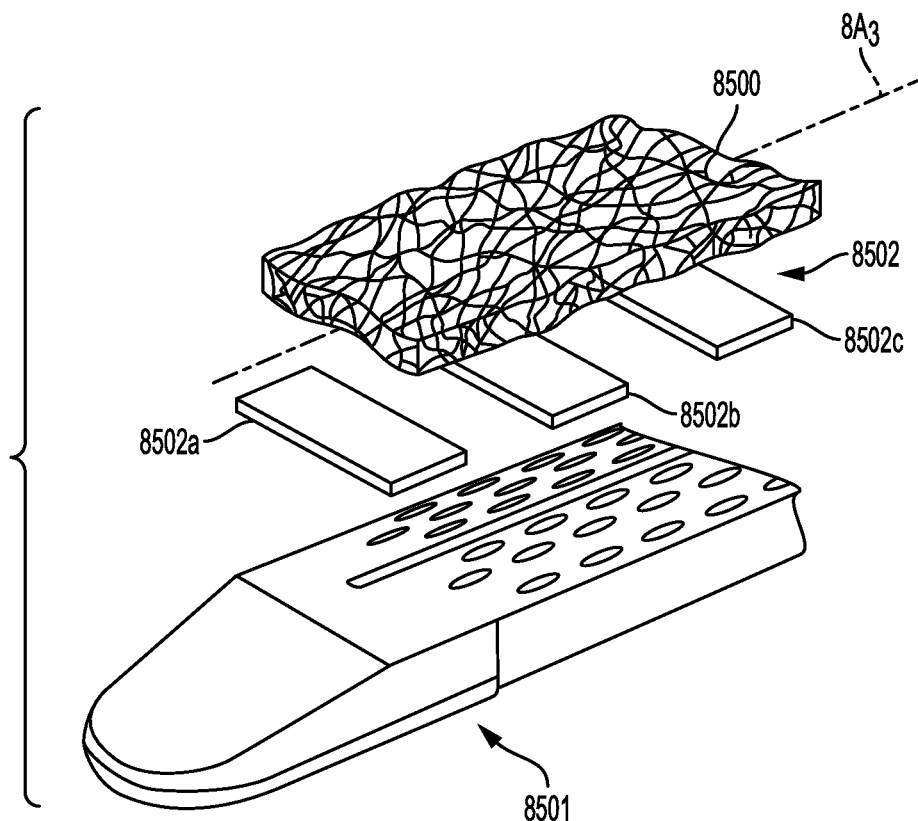
FIG. 65 is a perspective, partially exploded view of a distal portion of a jaw of an end effector and an adjunct material configured to be releasably mounted on the jaw in accordance with the described techniques.
Figure 66:
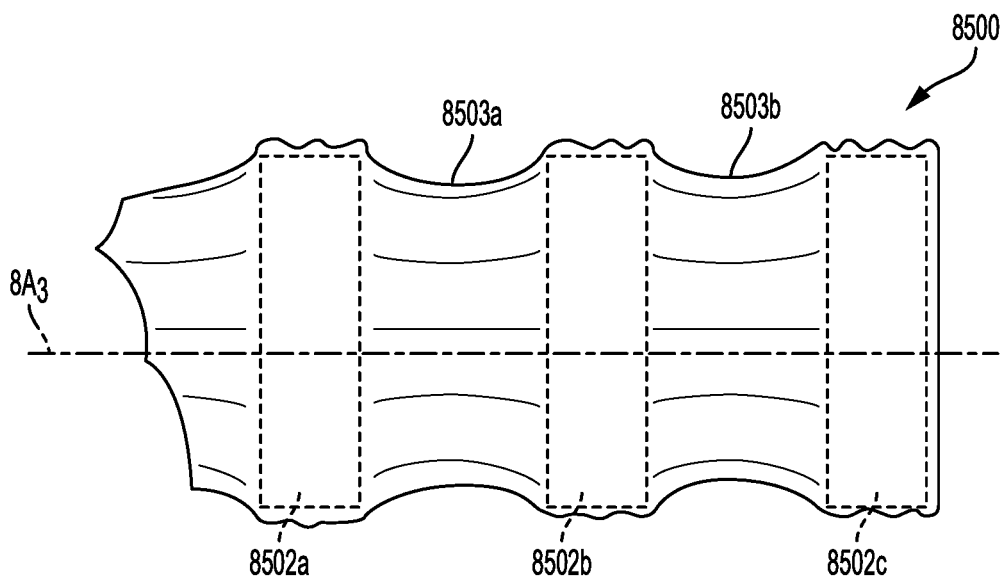
FIG. 66 is a bottom view of the adjunct material of FIG. 65, illustrating the adjunct material when it is retained at a treatment site in a patient.

FIGS. 65 and 66 illustrate an example of an adjunct material 8500 to be disposed over a jaw 8501 which is, in this example, a cartridge. The adjunct material 8500 can however be disposed over an anvil as well. As shown in FIG. 65, the adjunct material 8500 has discrete portion or panels 8502, 8502b, 8502c forming a backing side or layer 8502. As shown, the panels 8502, 8502b, 8502c non-removably attached to the adjunct material 8500 are disposed perpendicular to a longitudinal axis 8A3 of the adjunct material 8500. It should be appreciated that three panels 8502, 8502b, 8502c are shown by way of example only, as two or greater than three panels can span the adjunct material 8500 along a short side thereof.

The adjunct material 8500 can be formed from any suitable material described herein, which can be a mesh or a non-woven material. The backing layer 8502 can also be formed from any suitable material, such as a biodegradable and/or bioabsorbable material, e.g., polydioxanone (PDO) or any other suitable polymeric material(s). The material can be selected such that it biodegrades and/or bioabsorbs faster than the adjunct material 8500. The backing layer 8502 has a thickness that is smaller than that of the adjunct material 8500. For example, in some embodiments, the height or thickness of the adjunct material 8500 can be from about 0.004 inches to about 0.020 inches, whereas the height or thickness of the backing layer 8502 can be from about 0.0002 inches to about 0.0012 inches.

As shown in FIG. 66, illustrating by way of example a back side of the adjunct material 8500 with the panels 8502, 8502b, 8502c when the adjunct material 8500 is retained at the treatment side (the staples and tissue are not shown), the panels 8502, 8502b, 8502c prevent stretching of the portions of the adjunct material 8500 to which the panels 8502, 8502b, 8502c are attached. As also shown, the portions of the adjunct material 8500 between the panels 8502, 8502b, 8502c, such as portions 8503a, 8503b in FIG. 64, can stretch along the longitudinal axis 8A3 of the adjunct material 8500 once implanted on tissue. Thus, while the panels 8502, 8502b, 8502c prevent undesirable excessive stretching and displacement of the adjunct material 8500 at the treatment site, the portions of the adjunct material 8500 between the panels allow the adjunct stretching where desired.

It should be appreciated that the number, size, and location of the panels configured to prevent stretching of portions of the adjunct material can be selected to create a desired pattern of areas at which the adjunct is coupled to the jaw (e.g., the areas coupled to the panels) and areas at which the adjunct is allowed to stretch once implanted. In some embodiments, adjunct(s) that are at least partially stretchable at some portions thereof can be used in conjunction with a staple line that can be flexible as described, for example, in the above-mentioned U.S. Pat. Pub. No. 2016/0089142 entitled "Method for Creating a Flexible Staple Line," and filed on Sep. 26, 2014, which is hereby incorporated by reference herein in its entirety. Such implementations can be used for treatment of tissue which contracts and expands, such as lung. Furthermore, in some embodiments, the panels, such as the panels 8502, 8502*b*, 8502*c*, can be aligned with some staples and not others along the longitudinal length of the jaw. Also, when the adjuncts with the backing layer panels are disposed on both jaws of an end effector, the panels formed on the opposed adjuncts can have a pattern (e.g., a complementary pattern) such that a staple, once ejected, passes only through one of the backing layers. The panels and spacing between panels can be selected such that the panels form irregular and non-uniform patterns, and adhesive is applied to the panels.

As in other examples illustrating the described techniques, the adjunct material 8500 also includes one or more attachment features which can be in the form of an adhesive material layer formed at the jaw-facing surface of the panels 8502, 8502*b*, 8502*c*. Other attachment features can be formed additionally or alternatively. Furthermore, in some embodiments, the material from which the panels 8502, 8502*b*, 8502*c* are formed can be an adhesive material serving as an attachment layer. The adhesive material can be any suitable polymer, such as polydioxanone (PDO), a low molecular weight polyethylene glycol (PEG) or any other material (or a combination of materials) that can be used to attach the adjunct to the jaw. In some embodiments, the adhesive material can be a bioabsorbable and/or biodegradable pressure sensitive adhesive.

It should be appreciated that the adjunct materials described herein can be used with various types of end effectors that can be used in linear or circular stapler instruments. For example, it can be used in a linear surgical stapler, such as stapler 10 in FIG. 1 or stapler 50 in FIG. 4, or in a circular surgical, such as stapler 80 in FIG. 5, or in any other surgical stapler instrument. Thus, although generally rectangular adjuncts are shown in FIGS. 59, 61, 63, 64, 65, and 66, the adjuncts can be created such that they have a generally circular shape and such that their retaining and non-retaining features are configured for mating with an end effector of a circular stapler instrument. Also, as mentioned above, the adjunct can have or can be associated with various types "retaining" and "non-retaining" features.

Furthermore, the adjunct materials described herein can include one or more medicants which can be releasably incorporated into or associated with adjuncts in many different ways. Also, the adjunct materials can have various other features in addition to the features described herein.
Systems for Release of Adjunct in a Surgical Stapling Device Implantable adjuncts can be releasably attached to a jaw of an end effector of a surgical stapling device. The coupling can be done in various ways, for example, adhesives and/or adhesive features can be used to couple the adjunct to a surface of the jaw. This can allow manipulating the end effector with the adjunct during a surgical procedure, while the adjunct is prevented from being prematurely separated from the surface of the jaw before the adjunct is stapled to a tissue. After the adjunct has been stapled to the tissue, the adjunct can be detached from the jaw by a force exerted by the tissue (e.g., shearing force, pull, etc.). Attaching systems (e.g., those using polydioxanone adhesives) that attach the adjunct to the surface of the jaw in a secure (strong) manner can be advantageous as they ensure that the adjunct does not slip or slide off the jaw's surface prior to the stapling to the tissue. A strong attachment however can make the adjunct removal process challenging. This challenge can be obviated by including an adjunct removal mechanism or assembly in a jaw of the surgical stapling device that is configured to separate the adjunct from the jaw.

Accordingly, an adjunct removal mechanism can be configured to detach the adjunct from the surface of the jaw of the surgical stapler device after the adjunct has been stapled to the tissue. This can be done for example, by using a motion of a firing bar (in the surgical stapling device) from a fired position at the distal end of the end effector to an unfired position at the proximal end of the end effector. The firing bar can couple to the adjunct removal mechanism at the distal end, and return back to the proximal end (i.e., unfired position) with the adjunct removal mechanism. The adjunct removal mechanism can include an adjunct removal feature that separates the adjunct from the jaw of the surgical stapler device as the adjunct removal mechanism moves from the distal to the proximal end.

Figure 67A:
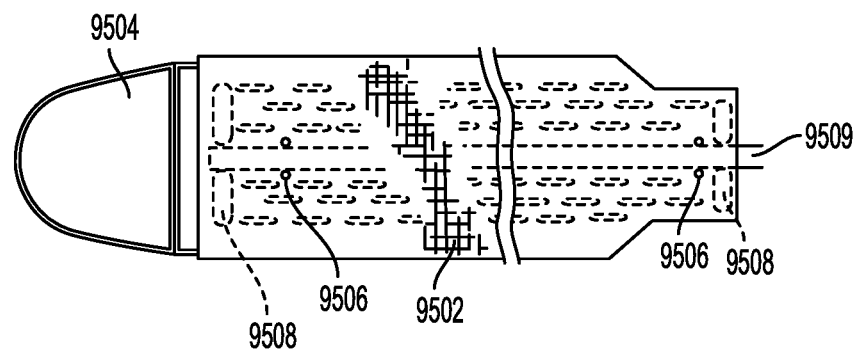
FIG. 67A illustrates an example of an adjunct releasably retained to a tissue facing surface of a surgical stapler device.

FIG. 67A illustrates an example of an adjunct 9502 releasably retained to a tissue facing surface of a lower jaw 9504 of an end effector of a surgical stapler device. One or more portions of the adjunct 9502 can be attached to the lower jaw 9504 by an adhesive 9508. The adhesive 9508 can be disposed at any suitable pattern—for example, it can be distributed between the adjunct 9502 and lower jaw 9504 at distal and proximal ends of the adjunct 9502, as shown in FIG. 67A. The adhesive can be, for example, a pressure sensitive adhesive (PSA). Additionally or alternately, a second adhesive, for example, cyanoacrylate (CA), can attach the adjunct 9502 to the tissue facing surface of the lower jaw 9504. For example, as shown in FIG. 67A, one or more portions of the adjunct 9502 can be coupled to the jaw 9504 via attachment portions or points 9506 formed from the second adhesive. It should be appreciated, however, that the first and second adhesives can be the same material (e.g., a PSA, CA, etc.), or a combination of suitable materials. The adjunct 9502 can be attached to the lower jaw 9504 by various mechanisms, for example, as described in U.S. patent application Ser. No. 15/436,183 entitled "Hybrid Mechanism for Attachment of an Adjunct to a Surgical Instrument" filed on even date herewith, the entire content of which is incorporated herein by reference.

As shown in FIG. 67A, the lower jaw 9504 includes a knife channel 9509 that extends longitudinally along the length of the lower jaw 9504. The attachment points 9506 of the second adhesive (or any other adhesive) can be distributed, for example, along and/or around the knife channel 9509. It should be appreciated however that four attachment points 9506 are shown by way of example only, as any suitable number of attachment points can be formed at any desired pattern(s). Further, in some embodiments, the attachment points, which can be configured to be broken by a suitable release mechanism, can be formed at areas at which the adjunct was heated and pressed onto the jaw and allowed to cool and thus conform to the geometry of the jaw. In this way, one or more portions of the adjunct mechanically "grip" the jaw (in some cases, in certain textured or roughened portions of the jaw).

Figure 67B:
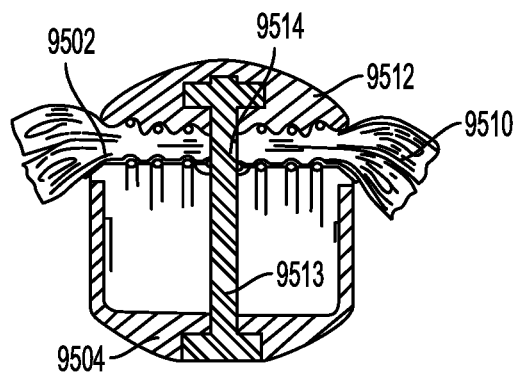
FIG. 67B illustrates a cross-sectional view of a tissue clamped between an upper jaw and a lower jaw of the surgical stapler device.

FIG. 67B illustrates the surgical stapler device clamping on a tissue 9510. The tissue 9510 is clamped between an upper jaw 9512 and the lower jaw 9504 of the stapler. The adjunct 9502 lies between the tissue 9510, and the tissue facing surface of the lower jaw 9504. Due to the adjunct 9502, portions of the tissue facing surface do not come in direct contact with the tissue 9510. A distal end 9513 of a firing bar 9518 (e.g., an I-Beam, an E-Beam, or otherwise configured end) extends vertically with respect to the tissue facing surface. The distal end 9513 includes flanges 9514 configured to scrape the adjunct 9502 from the tissue-facing surface of the lower jaw 9504. For example, the flange 9514 can cause adhesive 9506 to crack and thereby release portions of the adjunct 9502 when the firing bar 9518 moves from the proximal to the distal end or vice-versa. The flanges 9514 are shown as having slanted surfaces by way of example, and they can have other configurations.

Figure 67C:
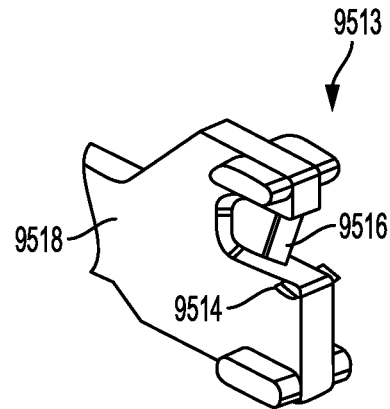
FIG. 67C illustrates a perspective view of an embodiment of a distal end of a firing bar of the surgical stapler device.

FIG. 67C illustrates a perspective view of an embodiment of the distal end 9513 of the firing bar 9518. The distal end 9513 includes a knife 9516 and the flange 9514. As the distal end 9513 travels from a proximal end to a distal end of the stapler, the knife 9516 cut the tissue 9510.

FIGS. 67A-67C illustrate that a knife of a firing bar assembly can be used to separate an adjunct from a jaw which has the adjunct releasably coupled thereto. In some embodiments, assemblies having other configurations can be used to separate an adjunct from a jaw of an end effector in conjunction with movement of the firing bar.

Figure 68A:
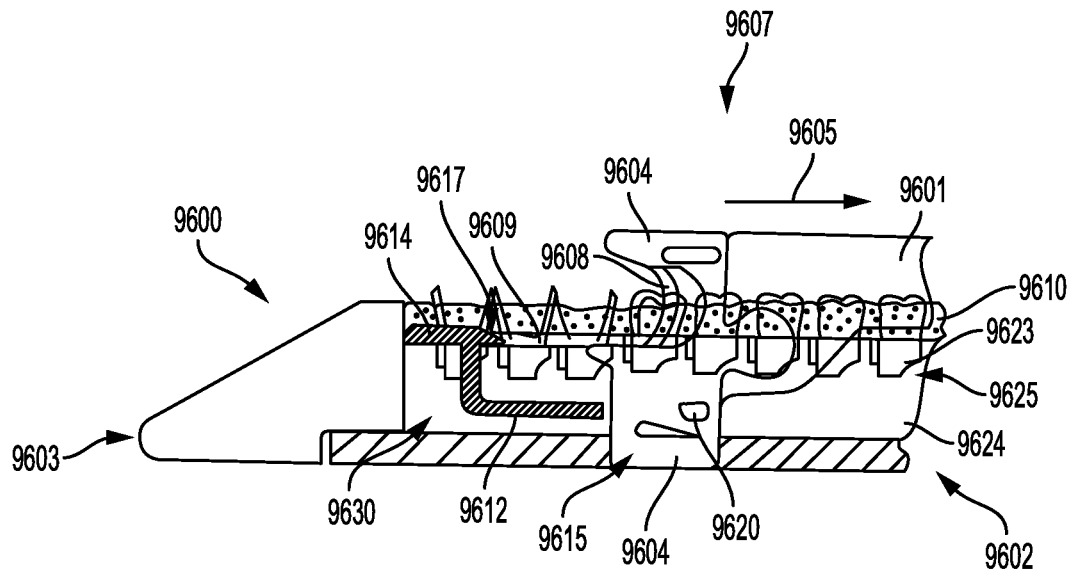
FIG. 68A is a side view of an embodiment of a jaw of an end effector, illustrating the jaw in a pre-fired configuration.
Figure 68B:
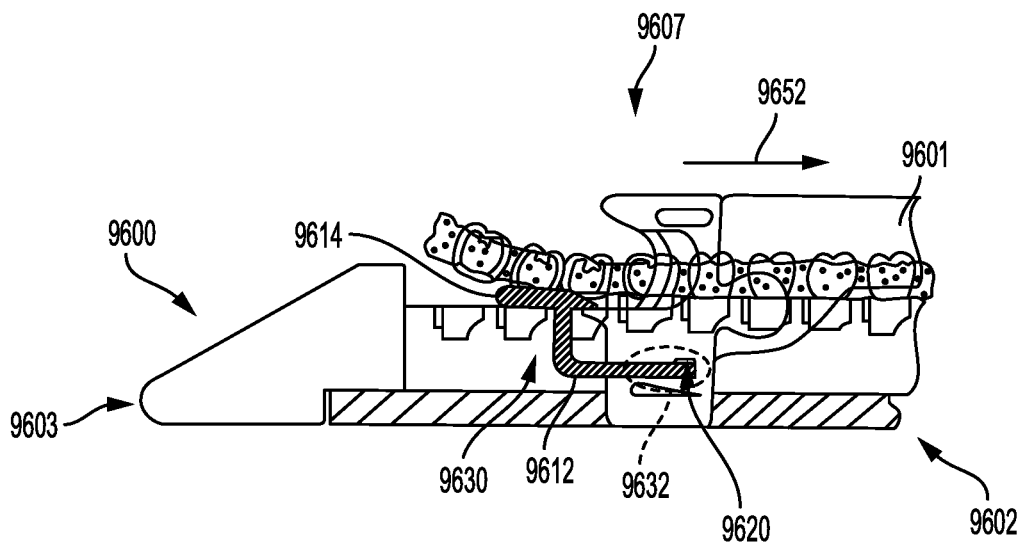
FIG. 68B is a side view of the jaw of FIG. 68A, illustrating the jaw in a fired configuration.

FIGS. 68A and 68B illustrate an example of a jaw 9600 of an end effector 9607. The end effector 9607 can be coupled to a distal end of a shaft of a surgical stapling device (not shown). The end effector 9607 can be used in any suitable surgical instrument, for example, a linear surgical stapler (e.g., stapler 10 in FIG. 1, stapler 50 in FIG. 4, or any other surgical stapler, including a circular stapler, such as stapler 80 in FIG. 5) which can be suitable for use with at least one adjunct.

The end effector 9607, shown partially in FIGS. 68A and 68B, has a first jaw having a cartridge with a plurality of staple cavities configured to seat staples therein, the staple cavities opening on a tissue-facing surface of the cartridge. For example, the end effector 9607 includes the jaw 9600 in the form of cartridge having a plurality of staple cavities 9625 configured to seat staples 9623 therein. The staple cavities 9623 open on a tissue-facing surface 9609 of the cartridge 9600. Although not shown in FIGS. 68A and 68B, the end effector 9607 also includes a second jaw opposing the first jaw in the form of the cartridge 9600 and having an anvil with a plurality of staple forming cavities formed on a tissue-facing surface thereof. The first and second jaws are configured to clamp tissue therebetween.

The end effector 9607 also includes an implantable adjunct material releasably retained on at least one of the first and second jaws. In particular, in this example, the jaw 9600 has an adjunct material or adjunct 9610 releasably retained on the tissue facing surface 9609 thereof. Although the jaw 9600 is also referred to herein as a cartridge, it should be appreciated that the jaw 9600 can have a staple channel configured to support a staple cartridge, which can be removably and replaceably seated within the staple channel. In some embodiments, the cartridge 9600 can be part of a disposable loading unit coupled distally to a shaft of a surgical instrument. The cartridge 9600 can be part of a cartridge reload assembly that is pre-assembled with an adjunct material. In such embodiments, a suitable adjunct loader can be used to attach an adjunct material to an anvil.

As shown in FIGS. 68A and 68B, the cartridge 9600 includes a firing bar 9601 configured to move longitudinally between a proximal end 9602 and a distal end 9603 of the cartridge 9600. The firing bar 9601 moves within a knife channel 9624 formed in the cartridge 9600 that extends longitudinally along the cartridge 9600 and guides the motion of the firing bar 9601 between the proximal and distal ends 9602, 9603. The knife channel 9624 can extend through a cartridge in the lower jaw. In the illustrated example, the firing bar 9601 is configured to move between an unfired position at the proximal end 9602 of the end effector 9607 and a fired position at the distal end 9603 of the end effector 9607.

The firing bar 9601 can have a variety of configurations. For example, in the illustrated embodiment, the firing bar 9601 includes at least one of a knife 9608 and a staple driving assembly 9615 configured to cause the staples 9625 to fire from the staple cavities 9623 against the staple forming cavities in the anvil (not shown). The distal end of the firing bar 9601 includes a distal guide 9604. It should be appreciated that the firing bar 9601 can have any other components additionally or alternatively.

In use, when tissue is clamped between the jaw 9600 with the adjunct 9610 and the anvil of the end effector 9607, as the firing bar 9601 moves from the unfired position to the fired position, the knife 9608 cuts through the adjunct 9610. During this motion, the guide 9604 can engage a wedge sled (not shown) that pushes the staples 9625 held in the staple cavity 9623 upwards towards an upper jaw (not shown) of the stapling device. In the process, the staples 9625 can pass through the adjunct 9610 and the tissue into the anvil of the upper jaw that faces the tissue. When the first and the second jaws clamp on the tissue, the staple forming cavities of the anvil guide the staples and cause the tissue and the adjunct 9610 to be stapled together.

The adjunct 9610 can be releasably retained on the tissue-facing surface 9609 of the cartridge 9600. The adjunct 9610 can be coupled to the tissue facing surface 9609 in various manners. For example, one or more adhesives (e.g., polydioxanone (PDS), CA, etc.) can be applied between the adjunct 9610 and the tissue-facing surface 9609 to releasably retain the adjunct 9610 on the cartridge 9600. In some embodiments, a backing layer made, e.g., of a PDS film, can be used to couple the adjunct 9610 to the jaw 9600. The backing layer can include one or more attachment points or portions (e.g., similar to the portions 9506, 9508 in FIG. 67A) that can be formed from an adhesive configured to be transitioned to an adhering state under application of heat. In other words, the adhesive can be at least partially melted (using, e.g., a loader configured to apply heat), in which state it can be used to couple the adjunct 9610 directly or via the PDS film to the jaw. When the attachment adhesive cools, it couples the adjunct 9610 (e.g., at one or more portions) to the jaw 9600 securely. Additionally or alternatively, various other features (e.g., additional polymer layer(s), attachment features, etc.) can be used to releasably couple the adjunct 9610 to the jaw 9600.

Regardless of the manner in which the adjunct 9610 is coupled to the cartridge 9600, the adjunct 9610 is coupled to the cartridge 9600 releasably, such that it is separated from the cartridge 9600 to remain with the tissue after the tissue stapling and/or cutting is completed during a surgical procedure. In some embodiments, the adjunct 9610 can be releasably coupled to the jaw 9600 in a secure manner, such that the end effector can be manipulated as desired, without the risk of the adjunct 9610 sliding or slipping off the jaw 9600. At the same time, such secure attachment can require certain actions to separate the adjunct 9610 from the cartridge 9600.

Accordingly, in the illustrated embodiments, the end effector 9607 includes an adjunct removal assembly 9630 configured to separate the adjunct 9610 from the cartridge 9600. The adjunct removal assembly 9630 is configured to couple to and move with the firing bar 9601 to separate the adjunct material 9610 from the end effector 9607 as the firing bar 9601 having the adjunct removal assembly 9630 coupled thereto is returned from the fired position to the unfired position, as discussed in more detail below. For example, as the adjunct removal assembly 9630 is moved proximally with the firing bar after the assembly is engaged by the firing bar, the adjunct removal assembly 9630 can break or crack attachment points (formed, e.g., by a hot-melt adhesive) between the adjunct 9610 and the cartridge 9600. In this way, the adjunct 9610 is separated from the cartridge.

As shown in FIGS. 68A and 68B, the adjunct removal assembly 9630 is disposed at the distal end 9603 of the cartridge 9600. The adjunct removal assembly 9630 is operably associated with the cartridge 9600. As shown in FIG. 68A, it can be disposed at the distal end 9603 of the end effector 9607 in a configuration in which the assembly 9630 is not coupled to the firing bar 9601 when the surgical stapling device is in a pre-fired configuration. The adjunct removal assembly 9630 can reside in the cartridge 9600 and it can move longitudinally along the knife channel 9624. In use, as the firing bar 9601 moves from the unfired position at the proximal end 9603 of the end effector 9607 to the fired position at the distal end 9602 of the end effector 9607, as shown by an arrow 9605 in FIG. 68A, the adjunct removal assembly 9630 couples to firing bar 9601 as discussed in more detail below. This movement results in the knife 9608 cutting tissue disposed between the jaw 9600 and the anvil (not shown). When the firing bar 9601 moves proximally from the fired position to the unfired position, as shown by an arrow 9652 in FIG. 68B, the adjunct removal assembly 9630 coupled thereto moves with the firing bar 9601.

The adjunct removal assembly 9630 can have a variety of configurations. In the example illustrated, the assembly 9630 includes an adjunct removal feature 9614 and a mating feature 9612. The adjunct removal feature 9614, which can have various configurations, is configured to separate the adjunct 9610 coupled to the jaw 9600 from the jaw. The mating feature 9612 is configured to mate with a respective mating feature 9620 included in the firing bar 9601 when the firing bar 9601 is actuated to achieve the firing position.

As shown in FIG. 68A, in a pre-fired configuration of the end effector 9607, the adjunct removal feature 9614 is configured to be placed between the tissue-facing surface 9609 and the adjunct 9610. As also shown, a leading edge 9617 of the adjunct removal feature 9614 is disposed between the tissue-facing surface 9609 and the adjunct 9610. When the firing bar 9601 has moved to the fired position and couples in this position to the adjunct removal assembly 9630, and then moves proximally to return to the per-fired configuration, the adjunct removal feature 9614 slides between the adjunct 9610 and the tissue facing surface 9609 thereby separating the adjunct 9610 from the jaw 9600, as shown in FIG. 68B. The leading edge 9617 of the adjunct removal feature 9614 facilitates separation of the adjunct 9610 from the jaw 9600. FIG. 68B shows the assembly 9630 coupled to the firing bar 9601 being pulled by the firing bar 9601 towards the proximal end 9602 of the end effector 9607. As the adjunct removal feature 9614 slides, it causes the adjunct 9610 to separate from the tissue facing surface 9609 of the jaw 9600.

The mating feature 9612 of the assembly 9630 is configured to mate with the mating feature 9620 of the firing bar 9601. The mating features 9612, 9620 can be complementary to one another. For example, the mating feature 9612 of the assembly 9630 can be in the form of one or more protrusions, whereas the mating feature 9620 of the firing bar 9601 can be in the form of one or more openings or cavities configured to mate with the protrusion(s). The protrusions configured to mate with the cavity in the firing bar can include, e.g., a pair of bars disposed such that the firing bar sits between the bars when the adjunct removal assembly 9630 is coupled to and moves with the firing bar. In particular, the bars can have a gap between them, as shown, for example, in FIG. 69 (pair of bars 9714a, 9714b). In use, the distal end of the firing bar 9601 can slide into the gap between the pair of bars of the mating feature 9612. FIG. 68B illustrates schematically (a circle 9632) the mating feature 9612 of the assembly 9630 coupled to the mating feature 9620 of the firing bar 9601. For example, the bars are snapped into the mating feature 9620 (e.g., a cavity), which can be assisted by mating elements or features that can be formed on the bars.

An example of a surgical method in accordance with the described techniques includes actuating the firing bar 9601 so as to move it from an unfired position at the proximal end of the end effector to the fired position in the distal end of the end effector. The adjunct removal assembly 9630 is engaged with the firing bar 9601 when the firing bar 9601 is in the fired position, and the firing bar 9601 is actuated to return it from the fired position to the unfired position such that, as the firing bar 9601 is actuated to return to the unfired position, the adjunct removal assembly 9630 is moved with the fired bar 9601 and thereby causes the adjunct material 9610 releasably retained on the jaw 9600 to be separated from that jaw.

It should be appreciated that the adjunct removal assembly 9630 is shown in FIGS. 68A and 68B to be operatively coupled to the cartridge 9600 by way of example only. Thus, in some implementations, an adjunct can be attached to a tissue-facing surface of a jaw of the surgical stapling device having an anvil. In such implementations, the adjunct removal assembly can be configured to be operatively coupled to the anvil such that it can slide longitudinally with a firing bar to separate the adjunct from a tissue-facing surface of the anvil. It should be appreciated that the adjunct may not be entirely removed from the jaw until the jaws are unclamped. Thus, the adjunct can be associated with the jaw (e.g., held against the jaw, albeit not coupled to the jaw) until the jaws are unclamped. Once the jaws are separated, the adjunct can be fully separated therefrom.

Figure 69:
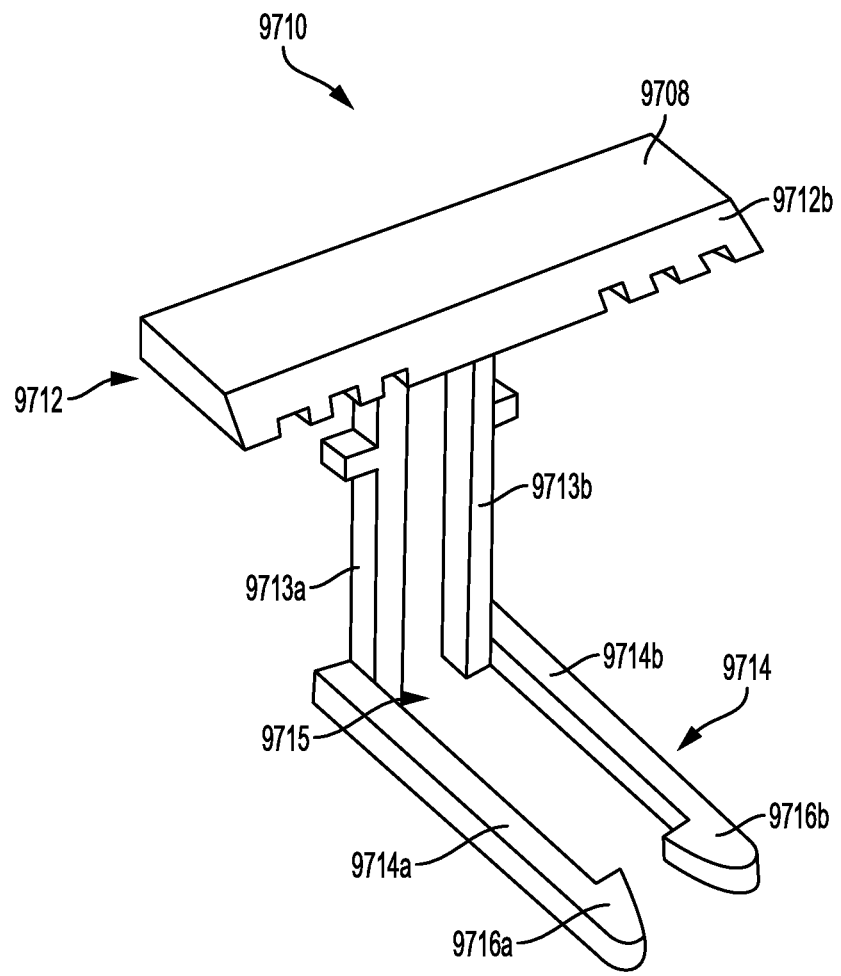
FIG. 69 illustrates a perspective view of an example of an adjunct removal system.

An adjunct removal assembly used to separate an adjunct material from a jaw of an end effector in accordance with the described techniques can have a variety of configurations. FIG. 69 illustrates an example of a portion of an adjunct removal system or assembly 9710. The adjunct removal assembly 9710 can be similar, for example, to adjunct removal assembly 9630 in FIGS. 68A and 68B. The adjunct removal assembly 9710 includes a stripper plate 9712, a mating feature 9714, and a pair of posts 9713a, 9713b coupling the stripper plate 9712 to the mating feature 9714. The stripper plate 9712 serves as an adjunct removal feature, and it can have various configurations. In this example, it is generally rectangular, includes an adjunct-facing surface 9708 and a leading surface 9712b disposed at an angle with respect to the surface 9708 and having a sharp leading edge that can facilitate the removal of the adjunct from the tissue facing surface of the cartridge. The adjunct-facing surface 9708 is configured to have an adjunct disposed thereon.

As shown in FIG. 69, the stripper plate 9712 is coupled to the pair of elongate posts 9713a, 9713b that can be attached to a mid-portion or approximately mid-portion of a side of the stripper plate 9712 that is opposed to the adjunct-facing surface 9708. The mating feature 9714 also includes a pair of bars 9714a, 9714b extending from the ends of the posts

9713*a*, 9713*b*, respectively, that are opposed to the ends of the posts coupled to the stripper plate 9712. As shown in FIG. 69, the bars 9714*a*, 9714*b* extend from the posts 9713*a*, 9713*b* such that the bars 9714*a*, 9714*b* form a gap 9715 therebetween. As shown in FIG. 69, the posts 9713*a*, 9713*b* also include a gap therebetween, and the gap 9715 can extend between the posts 9713*a* and 9713*b*. The bars 9714*a* and 9714*b* include mating features 9716*a*, 9716*b*, respectively (e.g., in the form of hooks facing one another), which can slide into a cavity in the distal end of the firing bar (not shown). As the distal end of the firing bar slides between the mating feature 9714 (into the gap 9715), it can push the bars 9714*a*, 9714*b* in an outward lateral direction. This can generate stress in the inward lateral direction that can cause the hook features 9716*a*, 16*b* to snap inwards into the cavity in the distal end of the firing bar. The mating feature 9714 can also guide the adjunct removal assembly 9710 through the knife channel as the adjunct removal system slides longitudinally with the firing bar.

Figure 70:
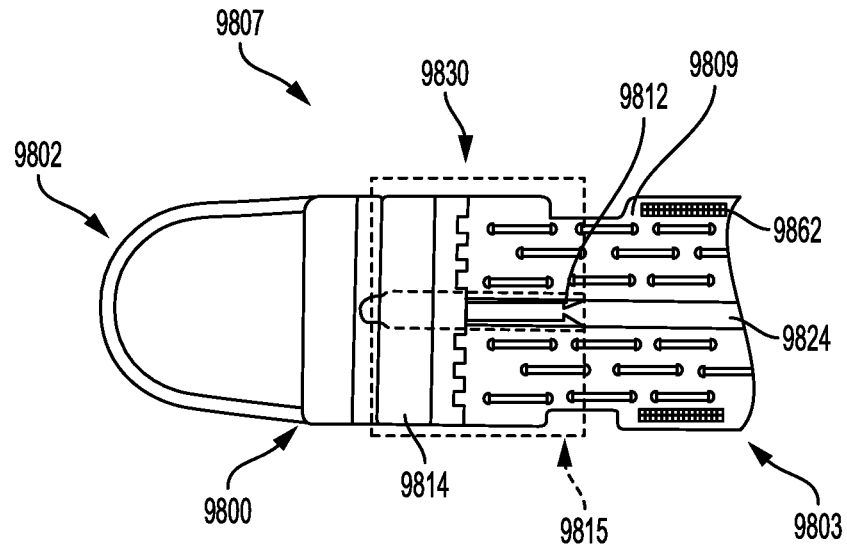
FIG. 70 illustrates a top-down view of a jaw of an end effector.

FIG. 70 illustrates a top view of an example of a jaw 9800 of an end effector 9807 that can be coupled to a suitable surgical stapler device (not shown). The jaw 9800 is in the form of a cartridge and it can have an adjunct (not shown) removably coupled thereto. The jaw 9700 can be similar to jaw 9600 in FIGS. 68A and 68B and is therefore not described in detail. The end effector 9807 includes an adjunct removal assembly 9830, shown schematically within a dashed area 9815, that can be similar to adjunct removal assembly 9830 shown in FIGS. 68A and 68B. Thus, as shown in FIG. 70, the adjunct removal assembly 9830 includes an adjunct removal feature 9814 and a mating feature 9812 configured to mate with a corresponding mating feature of a firing bar (not shown) when the firing bar is actuated to achieve a firing position.

The adjunct removal feature 9814 is shown disposed along a tissue-facing surface 9809 of the cartridge 9800. The mating feature 9812 of the of the adjunct removal assembly 9830 can guide the assembly 9830 along a knife channel 9824 when the adjunct removal assembly 9830 is coupled to and moved with the firing bar from a distal end 9802 to a proximal end 9803 of the end effector 9807. As shown by way of example only, the tissue-facing surface 9809 of the jaw 9800 can include features (e.g., rough surfaces 9862) that can facilitate attachment of the adjunct (not shown) to the jaw 9800. For example, the rough surfaces 9862 can provide traction to the adjunct and can thus allow an adhesive layer (which can have various features) between the adjunct and the surface 9809 to form a stronger bond.

Figure 71:
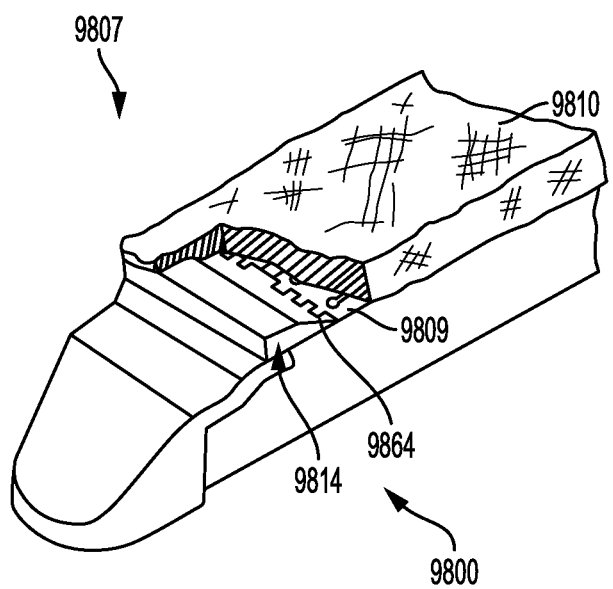
FIG. 71 illustrates a perspective, partially cut-away view of the jaw of the end effector of FIG. 70.

FIG. 71 illustrates the cartridge 9800 with an adjunct 9810 removably retained thereon. The adjunct removal assembly 9830 is shown partially and FIG. 71 illustrates a relative orientation of adjunct 9810 and the adjunct removal feature 9814 of the adjunct removal assembly 9830. In particular, in a pre-fired configuration of the end effector 9807, the adjunct removal feature 9814 is disposed between the jaw 9800 and the adjunct 9810. As illustrated, the adjunct removal feature 9814 has a sharp leading edge 9864 that can scrape the adjunct 9810 from the tissue facing surface 9809 of the cartridge 9800. As discussed above, in a fired configuration, the adjunct removal assembly couples to and moves with a firing bar (not shown) to separate the adjunct material from the cartridge 9800 as the firing bar having the adjunct removal assembly coupled thereto is returned from the fired position to the unfired position.

It should be appreciated that an adjunct material can be releasably coupled to at least one jaw of an end effector using various techniques. For example, as mentioned above, the adjunct material can be coupled to the jaw using an adhesive configured to transition from a non-adhering state to an adhering state under application of heat. Non-limiting examples of the systems that can be used to releasably couple the adjunct material to a jaw of an end effector are described in a U.S. patent application Ser. No. 15/436,328 entitled "Systems for Coupling Adjuncts to an End Effector" and filed on even date therewith, the content of which is incorporated by reference herein in its entirety.

It should also be appreciated that an adjunct removal assembly operatively coupled to an end effector can have a variety of configurations. For example, in some embodiments, the adjunct removal assembly can include a cutting element, such as a suture, string, or wire, that is "picked up" by a firing bar (e.g., by a knife) as the firing bar returns to an unfired position. As adjunct removal assembly is moved proximally with the returning firing bar, the cutting element separates the adjunct from the jaw.

Hybrid Mechanism for Attachment of an Adjunct to a Surgical Instrument

In general, when using an adjunct in conjunction with a surgical stapler, the adjunct can be removably attached to the end effector. The adjunct will preferably remain secured to the end effector while the end effector is positioned at a treatment site, and is removed from the end effector when staples are deployed at the treatment site to provide the benefits discussed above.

It has been observed that adjuncts can prematurely detach from the end effector prior to staple deployment. Detachment of the adjunct from the end effector can occur in various forms, depending on the manner in which the end effector is used. For example, detachment can include vertical lift off of the adjunct from the end effector, lateral sliding of the adjunct with respect to the end effector, and/or curling of the edges of the adjunct from the surface of the end effector. The adjunct could also slide sideways when an end effector is used to clamp and twist tissue.

Various exemplary devices, systems, and methods for attaching an adjunct to a surgical instrument are described herein. In general, a hybrid attachment mechanism is employed to attach an adjunct to an end effector jaw of a surgical stapler. In some embodiments, the hybrid attachment mechanism includes at least two attachment mechanisms, where each mechanism is configured to inhibit at least one form of adjunct detachment from the end effector jaw. For example, a first attachment mechanism can be configured to inhibit vertical removal of the adjunct from the jaw. A second attachment mechanism can be configured to inhibit sliding of the adjunct with respect to the jaw. A third attachment mechanism can be configured to inhibit curling of the adjunct upon itself. Each of the first, second, and third attachment mechanisms can operate in concert with the others, allowing the hybrid attachment mechanism to simultaneously inhibit multiple forms of adjunct detachment. The hybrid attachment mechanism can be further configured to decouple from the end effector jaw, permitting deployment of the adjunct at a treatment site.

Embodiments of the hybrid attachment mechanism are discussed below in conjunction with the stapler 10, where an adjunct is coupled to a tissue contacting surface 33 of the upper jaw 34 of an end effector 30. However, it may be understood that embodiments of the hybrid attachment mechanism can be employed with any surgical instrument without limit. Furthermore, embodiments of the hybrid attachment mechanism can be employed to couple adjuncts with the tissue contacting surface 33 of the upper jaw 34, a tissue contacting surface of the lower jaw 32, and combinations thereof.

Figure 72:
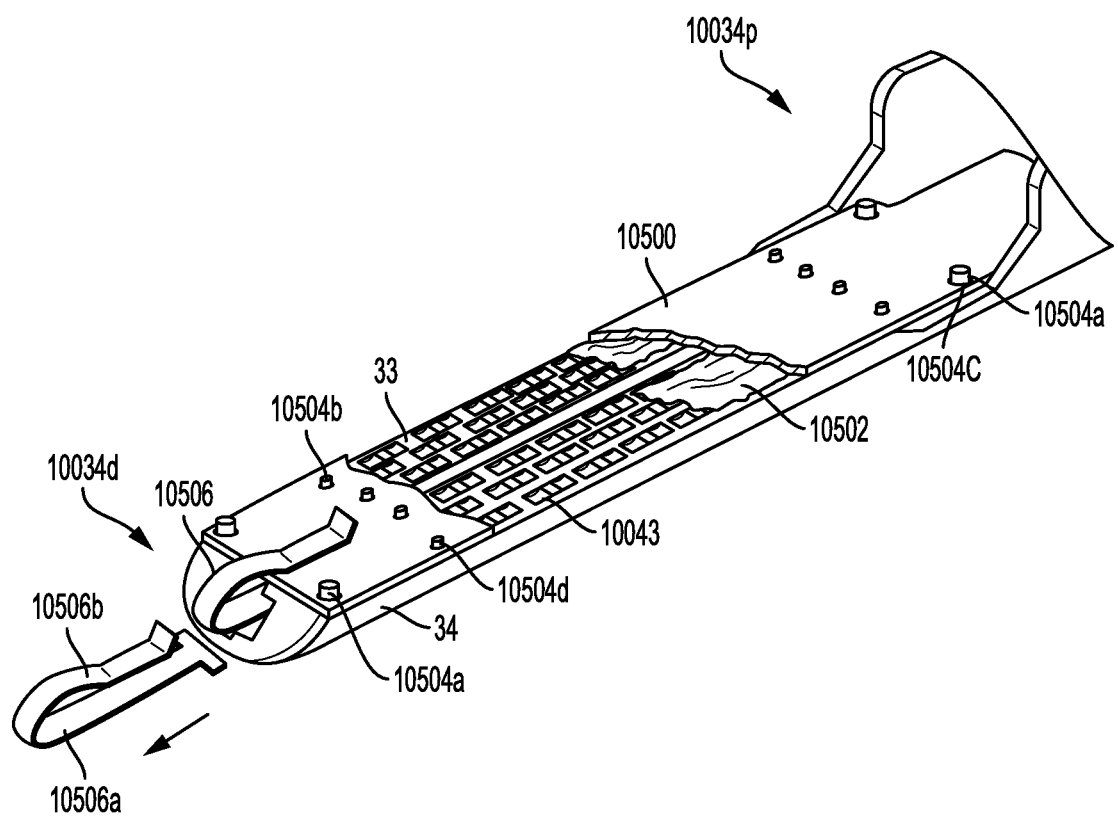
FIG. 72 is a perspective view of one embodiment of an adjunct coupled to an end effector jaw by a hybrid attachment mechanism.
Figure 73:
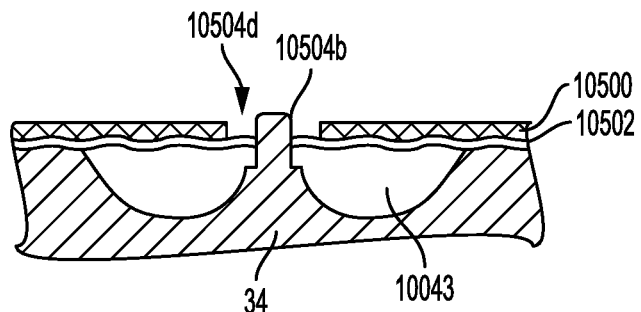
FIG. 73 is a cross-sectional view of the end effector jaw of FIG. 1, showing a portion of the adjunct of FIG. 72 coupled thereto.
Figure 74:
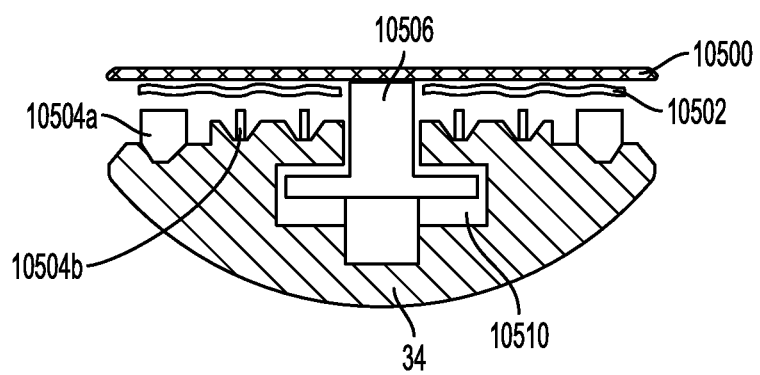
FIG. 74 is another cross-sectional view of the end effector jaw of FIG. 1, showing a portion of the adjunct of FIG. 72 coupled thereto.

FIGS. 72-74 show an adjunct 10500 disposed upon a tissue contacting surface 33 (an anvil surface) of an upper jaw 34 including staple forming pockets 10043 and a hybrid attachment mechanism configured to couple the adjunct 10500 to the tissue contacting surface 33. The hybrid attachment mechanism includes a first attachment mechanism 10502, a second attachment mechanism 10504, and a third attachment mechanism 10506.

In one embodiment, the first attachment mechanism 10502 can be configured to maintain the adjunct 10500 on the tissue contacting surface 33. For example, the first attachment mechanism 10502 can be configured to inhibit out-of-plane deformation of the adjunct 10500 and prevent vertical removal of the adjunct 10500 from the tissue contacting surface 33. In a specific embodiment, the first attachment mechanism can be an adhesive 10502 (e.g., a biocompatible adhesive) that adheres the adjunct 10500 to the tissue contacting surface 33. As illustrated in FIGS. 72-74, the adhesive 10502 is disposed between the tissue contacting surface 33 and the adjunct 10500. Adhesives can include, but are not limited to, pressure sensitive adhesives (PSAs), heat activated adhesives, heat softened adhesives, ultraviolet (UV) cured adhesives, cyanoacrylate-based adhesives, moisture-softened adhesives, and hydrogel-based adhesives.

Mechanical properties of the adhesive 10502 can be selected within ranges suitable to ensure that out-of-plane deformation of the adjunct 10500 is inhibited during placement of the surgical stapling device 10 at a treatment site and that the adjunct 10500 is released from the tissue contacting surface 33 when secured to tissue by one or more staples. Examples of suitable mechanical properties can include, but are not limited to, adhesion strength (peak load) and load-displacement response. These mechanical properties can be measured by one or more mechanical tests including, but not limited to, tension, compression, peel (90°, 180°, T), release force, loop tack, shear, and flexure performed at service temperatures (e.g., within the range between about room temperature and body temperature).

While the first attachment mechanism 10502 can act to inhibit out-of-plane deformation, it may fail to prevent in-plane deformation. For example, the adhesive 10502 can stretch longitudinally in response to applied in-plane tensile stresses, such as when sliding on tissue or when the knife (e.g., knife 36) is fired. As a result, at least a portion of the applied in-plane tensile stress can be felt by the adjunct 10500 and can cause longitudinal elongation of the adjunct 10500.

Accordingly, in another embodiment, the second attachment mechanism 10504 can be configured to inhibit in-plane (e.g., lateral and/or longitudinal) sliding or deformation of the adjunct 10500 along the tissue contacting surface 33. In one embodiment, the second attachment mechanism 10504 can include at least one post 10504a formed on one of the adjunct 10500 and the tissue contacting surface 33 and a corresponding bore 10504b formed on the other one of the adjunct 10500 and the tissue contacting surface 33 that is configured to receive its corresponding post 10504a. For example, the bore 10504b can have a diameter less than, greater than, or approximately equal to that of the post 10504a (FIG. 73). By combining the first attachment mechanism 10502 and the second attachment mechanism 10504, improved resistance to in-plane sliding or deformation is provided by the hybrid attachment mechanism.

In order to tailor the degree of resistance to in-plane sliding or deformation, the number of posts 10504a, the size of the posts 10504a, and their relative position with respect to the tissue contacting surface 33 can be varied. For example, as illustrated in the embodiment of FIGS. 72-74, multiple posts 10504a, 10504b are formed on the tissue contacting surface 33 and multiple respective bores 10504c, 10504d are formed on the adjunct 10500. The posts 10504a have a relatively larger diameter than the posts 10504b and are positioned adjacent to the proximal end 10034p and distal end 10034d of the jaw 34. As further illustrated in the embodiment of FIG. 72, the number of posts 10504b can be greater than the number of posts 10504a. In this configuration, the posts 10504a can act to inhibit sliding of the corners of the adjunct 10500, while the posts 10504b can act to inhibit stretching of the adjunct 10500 along its length.

Under certain circumstances, ability of the first attachment mechanism 10502 or the second attachment mechanism alone to prevent the adjunct 10500 from curling upon itself can be impaired in service. For example, in the context of the first attachment mechanism 10502, mechanical stresses experienced by the adjunct 10500 or the jaw 34 can overcome the adhesion strength of the adhesive. Alternatively, in the context of the second attachment mechanism 10504, mechanical stresses experienced by the adjunct 10500 or the jaw 34 can damage the posts 10504a. In either case, the ability of the first attachment mechanism 10502 or the second attachment mechanism 10504 to prevent the adjunct 10500 from curling upon itself can be overcome. Furthermore, it is observed that curling of the adjunct 10500 tends to occur most frequently at the distal end 10034p of the jaw 34 because the distal end 10034p of the jaw can frequently experience elevated stresses due to contact with tissue during use of the end effector 30.

Thus, in another embodiment, the third attachment mechanism 10506 can be configured to inhibit in-plane movement or deformation of the adjunct 10500 near a distal end of the jaw 34. Assuming the adjunct 10500 possesses an in-plane area that is approximately the same as the area of the tissue contacting surface 33, the third attachment mechanism 10506 can be configured to inhibit in-plane movement or deformation of a distal end of the adjunct 10500 proximate to the tissue contacting surface 33. For example, the third attachment mechanism 10506 can be configured to apply a compressive force to a distal-most end of the adjunct 10500 when secured to a distal-most end of the jaw 34.

As illustrated in the embodiment of FIGS. 72 and 74, in one embodiment, the third attachment mechanism 10506 can be a clip that reversibly couples to the jaw 34 to selectively permit or inhibit separation of the distal end of the adjunct 10500 from the distal-most end of the tissue contacting surface 33. The illustrated clip includes a base 10506a connected to an arm 10506b. The illustrated clip is formed in a "U" or hook shape, with the arm 10506b overlying the base 10506a. A socket 10510 can be formed in the distal-most end of the jaw 34 and extends longitudinally inward therefrom and is dimensioned to receive the base 10506a. When the illustrated clip is coupled to the jaw 34, the arm 10506b extends over the adjunct 10500 and can exert the compressive force upon distal-most end of the adjunct 10500. This compressive force prevents the distal end of the adjunct 10500 from separating from the distal-most end of the tissue contacting surface 33. By varying the separation of the base 10506a and the arm 10506b, and/or an elastic modulus of the clip, the compressive force can be varied. Alternatively, when the base 10506a of the clip is removed from the socket 10510, the arm 10506b of the clip does not extend over the adjunct 10500 and does not exert the compressive force upon distal-most end of the adjunct 10500, allowing separation of the distal-most end of the adjunct 10500 from the tissue contacting surface 33.

The third attachment mechanism 10506 can be configured to decouple from the jaw 34 upon ejection of a staple by the firing system. For example, as illustrated in FIGS. 72 and 74, the base 10506a can be aligned with a path of the knife blade 36. When the firing system is activated, the staples are ejected from the staple cartridge 40 and the knife blade 36 is advanced through the jaw 34. The advancement of the knife blade 36 can be sufficient to push the base 10506a out of the socket 10510, decoupling the third attachment mechanism 10506 from the jaw 34.

The third attachment mechanism 10506 can be further configured to operate in combination with the second attachment mechanism 10504. For example, as illustrated in the embodiment of FIG. 72, at least one post 10504a is formed proximal to the portion of the adjunct 10500 over which the arm 10506b extends and applies the compressive force. That is, when the clip is coupled to the jaw 34, the arm 10506b does not overlie any of the posts 10504a. Thus, the posts 10504a do not interfere with application of the compressive force to the adjunct 10500 by the arm 10506b. Furthermore, in addition to preventing curling of the adjunct 10500 at the distal-most end of the adjunct 10500, the compressive force exerted by the arm 10506b upon the adjunct 10500 can also act to inhibit in-plane sliding or deformation (longitudinally or laterally) of the distal end of the adjunct 10500.

Figure 75:
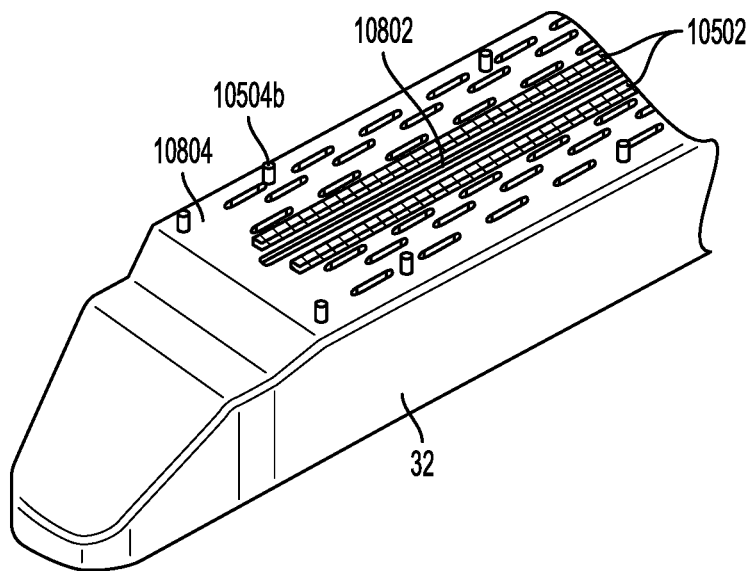
FIG. 75 is a perspective view of another embodiment of an adjunct coupled to an end effector jaw of FIG. 1.
Figure 76:
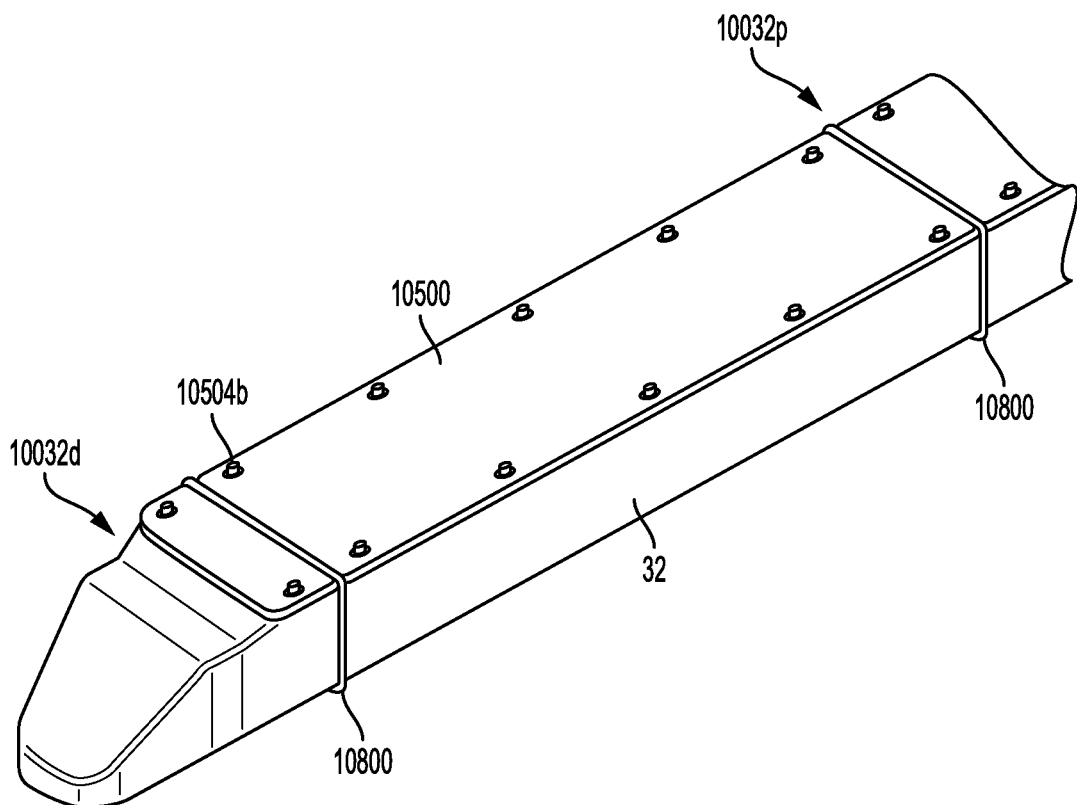
FIG. 76 is another perspective view of another embodiment of an adjunct coupled to an end effector jaw of FIG. 1.

FIGS. 75 and 76 illustrate another embodiment of a hybrid attachment mechanism configured for use with the stapler 10 and coupling the adjunct 10500 to a tissue contacting surface of the jaw 32. However, it may be understood that embodiments of the hybrid attachment mechanism can be employed with any surgical instrument without limit. Furthermore, embodiments of the hybrid attachment mechanism can be employed to couple adjuncts with the tissue contacting surface 33 of the upper jaw 34, a tissue contacting surface of the jaw 32, and combinations thereof.

The hybrid attachment mechanism can include the first attachment mechanism 10502, the second attachment mechanism 10504, and a fourth attachment mechanism 10800. As illustrated in FIG. 75, the first attachment mechanism 10502 is provided in the form of longitudinal strips adjacent to a slot 10802 that receives the knife 36 and the second attachment mechanism 10504 is provided in the form of the posts 10504a and/or 10504b are arranged along the length of the jaw 32, adjacent the lateral sides.

FIG. 76 illustrates the fourth attachment mechanism 10800 in combination with the adjunct 10500. The fourth attachment mechanism 10800 includes sutures that encircle a periphery of the jaw 32. For example, two sutures are positioned adjacent to a proximal end 10032p and a distal end 10032d of the jaw 32. However, any number of sutures can be provided and their location can be varied, as necessary. The sutures are configured to exert a compressive force upon the adjunct 10500, inhibiting longitudinal and/or lateral sliding of the adjunct 10500 with respect to the jaw 32, as well as vertical separation of the adjunct 10500 with respect to the jaw 32. Thus, by combining the first attachment mechanism 10502, the second attachment mechanism 10504, and the fourth attachment mechanism 10800, the hybrid attachment mechanism can provide improved resistance to out-of-plane deformation, maintaining the adjunct 10500 is on the tissue contacting surface 10804, as well as improving resistance to in-plane sliding or deformation.

In further embodiments, the fourth attachment mechanism 10800 can be configured to decouple from the jaw 32 to permit the adjunct 10500 to separate from the jaw 32. For example, the sutures extend laterally across the width of the jaw 32, intersecting the slot 10802. When the firing system is activated, staples are ejected from the staple cartridge 40 and the knife blade 36 is advanced through the jaw 32 within the slot 10802. The advancement of the knife blade 36 cuts the sutures, decoupling the third attachment mechanism 10506 from the jaw 34.

It may be understood that, while embodiments of the hybrid attachment mechanism discussed above include the first attachment mechanism 10502, the second attachment mechanism 10504, and the third attachment mechanism 10506, alternative embodiments of the hybrid attachment mechanism can include any two of the first attachment mechanism 10502, the second attachment mechanism 10504, the third attachment mechanism 10506, and the fourth attachment mechanism 10800. For example, the hybrid attachment mechanism can include the first attachment mechanism 10502 and the second attachment mechanism 10504, without the third attachment mechanism 10506. Alternatively, the hybrid attachment mechanism can include the first attachment mechanism 10502 and the third attachment mechanism 10506, without the second attachment mechanism 10504. Additionally, the hybrid attachment mechanism can include the second attachment mechanism 10504 and the third attachment mechanism 10506, without the first attachment mechanism 10502. Alternatively, the hybrid attachment mechanism can include the first attachment mechanism 10502 and the fourth attachment mechanism 10800.

Systems for Coupling Adjuncts to an End Effector

Adjunct materials can be applied to one or both jaws of an end effector of a surgical instrument in various ways. For example, an adjunct material can be manually positioned on a jaw. It is desired to releasably couple an adjunct to a jaw such that the adjunct does not slip off the jaw prior to application of the adjunct to tissue when staples are fired. However, some approaches may not result in a secure enough attachment of the adjunct to a jaw. This compromises the ability of a surgeon to manipulate the surgical instrument with the adjunct as desired during the surgical procedure.

Accordingly, in some embodiments, systems and methods are provided for applying an adjunct material to a jaw of an end effector to be releasably retained thereon. The adjunct material can be coupled to the jaw using an adhesive that can be applied to the adjunct and/or the jaw in a controlled manner. In some implementations, the adjunct material can be coupled to the jaw via an intermediate polymer layer.

In some embodiments, an adjunct loading member of a loading system can be used that is configured to releasably hold at least one adjunct material. The adjunct material is configured to be transferred from the adjunct loading member to a jaw of first and second jaws of an end effector. A supporting member of a suitable configuration is configured to releasably retain the adjunct material that can be associated with the supporting member in various ways. For example, the adjunct material can be disposed on the supporting member. Additionally or alternatively, the supporting member can be in the form of retaining feature(s) releasably holding the adjunct material in the adjunct loading member. The adjunct loading member also includes an adhesive depot having an adhesive configured to transition from a non-flowable state to a flowable state upon the application of heat when the adjunct material is released from the adjunct loading member and transferred to the jaw. Once the adhesive in the flowable state is cooled, it adheres to the jaw and is thus used to retain the adjunct material on the jaw.

The adjunct material is configured to be released from the adjunct loading member under application of a load. The adjunct is transferred to the jaw and is caused to adhere to the jaw using the adhesive disposed in the adhesive depot when the adhesive is in the flowable state. Heat can be applied to the adhesive prior to or at least partially at the time when the adjunct is being released from the adjunct loading member to the jaw. The load can be applied by the jaws of the end effector when the adjunct loading member is clamped therebetween. Alternatively, the load can be applied to the adjunct loading member manually or in other ways. The application of at least one of load and heat causes the adhesive from the adhesive depot to be used to retain the adjunct material on the jaw of the end effector.

Figure 77:
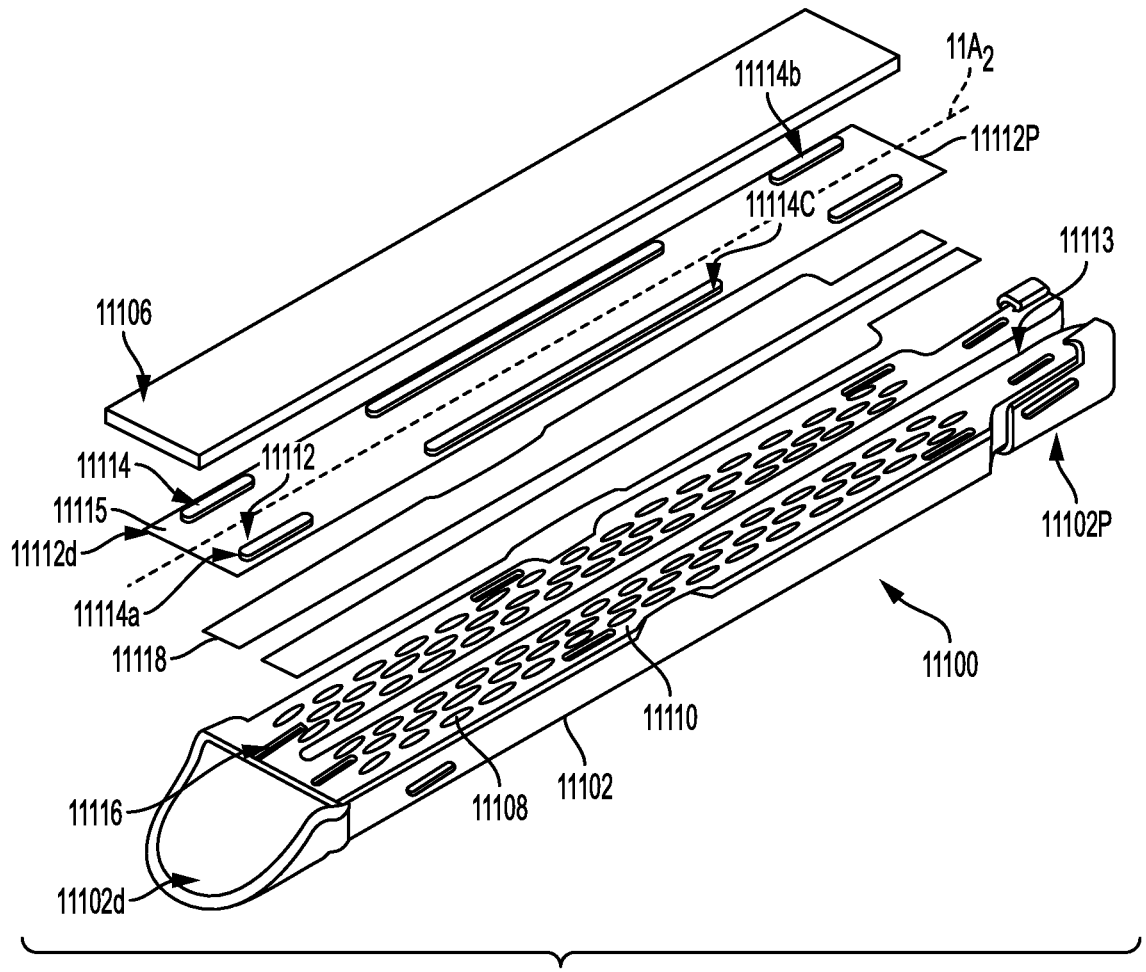
FIG. 77 is perspective, exploded view of a jaw of an end effector and an adjunct material configured to be coupled to the jaw via a polymer layer.

FIG. 77 illustrates an example of a portion an end effector 11100 configured to releasably retain an adjunct material on one or both of its first and second opposed jaws configured to clamp tissue therebetween, in accordance with the described techniques. The end effector 11100, partially illustrated in FIG. 77, has a first jaw having a cartridge body or cartridge 11102 and a second jaw having an anvil (not shown), with the first and second jaws being configured to clamp tissue therebetween. The cartridge body 11102 is configured to releasably retain thereon an implantable adjunct material 11106. The end effector 11100 can be coupled to a distal end of a shaft of the surgical instrument (not shown). The end effector 11100 can be used in any suitable surgical instrument, for example, a linear surgical stapler (e.g., stapler 10 in FIG. 1, stapler 50 in FIG. 4, or any other surgical stapler, including a circular stapler, such as stapler 80 in FIG. 5) which can be suitable for use with at least one adjunct.

As shown in FIG. 77, the cartridge body 11102 has a plurality of staple or staple-holding cavities 11108 configured to seat staples therein, the staple-holding cavities 11108 opening on a tissue-facing surface 11110 of the cartridge 11102. The staple cavities 11108 form a certain pattern on the surface of the cartridge 11102 which corresponds to a pattern of staple-forming cavities formed in the anvil (not shown). The cartridge 11102 includes a cutting element or knife channel 11113 extending between distal and proximal ends 11102d, 11102p of the cartridge 11102. The knife channel 11113 is configured to receive a cutting element (e.g., a knife) as it moves distally therethrough. As shown in FIG. 77, the staple cavities 11108 can form three rows on both sides of the cutting element channel 11113, though it should be appreciated that the staple cavities 11108 can form any other patterns on the tissue-facing surface 11110.

The cartridge body 11102 can be in the form of a staple channel configured to support a staple cartridge, which can be removably and replaceably seated within the staple channel. Furthermore, in some embodiments, the cartridge 11102 can be part of a disposable loading unit coupled distally to a shaft of a surgical instrument.

In this example, the end effector 11100 is configured to releasably retain thereon the implantable adjunct material (or "adjunct") 11106. In the illustrated implementation, the adjunct material 11106 releasably retained on the cartridge 11102 is discussed, though it should be appreciated that the anvil can also have an adjunct material releasably retained thereon. The adjunct material 11106 can be applied to the cartridge 11102 using a loading member of a loading system, such as an adjunct loading member 11200 shown in FIG. 79 and discussed in detail below.

Figure 78:
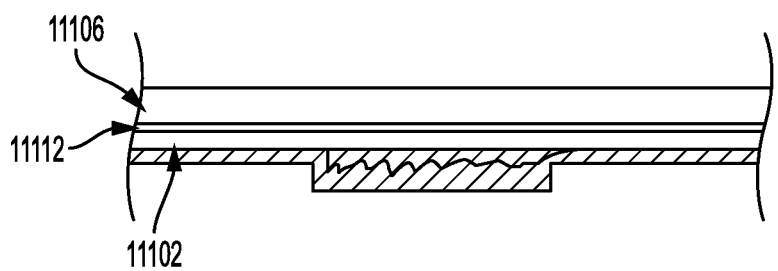
FIG. 78 is a cross-sectional view of a portion of the adjunct material of FIG. 78 coupled to the jaw of the end effector via the polymer layer.

Regardless of the configuration of the loading member, the adjunct material 11106 is configured to be transferred from the loading member to the cartridge 11102 using an adhesive depot having an adhesive configured to transition from a non-flowable state to a flowable state upon the application of heat when the adjunct material is released from the adjunct loading member and transferred to the jaw to retain the adjunct material on the jaw. The adhesive depot can have a variety of configurations and it can be configured to allow the adhesive to be released therefrom in a variety of ways. In this example, as shown in FIG. 77, the adhesive depot is in the form of protrusions formed on a polymer attachment layer or polymer layer 11112 disposed on a jaw-facing surface of the adjunct material 11106, as also shown schematically in FIG. 78. In particular, the polymer layer 11112, shown in FIG. 77 with its jaw-facing surface 11115 facing up for the illustration purposes only, has a plurality of protrusions 11114 including or formed from an adhesive. In FIG. 77, the polymer layer 11112 has two shorter protrusions (collectively referred to as 11114a, 11114b) at each of distal and proximal ends 11112d, 11112p thereof, respectively, and two longer protrusions 11114c disposed between the protrusions 11114a, 11114b. The pairs of protrusions 11114a, 11114b, 11114c are formed along a longitudinal axis 11A2 of the polymer layer 11112, and symmetrically with respect to a centerline of the polymer layer 11112.

As shown in FIG. 77, the tissue-facing surface 11110 of the cartridge 11102 can include attachment features 11116 configured to engage the protrusions 11114. In particular, the adhesive included in the protrusions 11114 or from which the protrusions 11114 are formed can be disposed on the attachment features 11116. The attachment features 11116 can have various configurations. For example, they can be formed as recesses in the cartridge 11102. Additionally or alternatively, the attachment features 11116 can include a roughness pattern, which can be formed in any suitable manner. The roughness pattern can have any suitable texture. For example, in one embodiment, the attachment features 11116 can be formed by making grooves having a pattern of multiple "Xs" (or other shapes or features) on the surface of the jaw. In this example, the cartridge 11102 is shown to have six attachment features formed at the distal and proximal ends 11102d, 11102p thereof, symmetrically with respect to the channel 11113. It should be appreciated however that a cartridge of an end effector can include any other number of the attachment features (e.g., less then eight or greater than eight).

The protrusions 11114 formed on the polymer layer 11112 and the attachment features 11116 formed on (or in) the cartridge 11102 can have various shapes, including different shapes. For example, they can be generally elongate and rectangular, as shown in FIG. 77. Additionally or alternatively, they can be square, semi-circular (e.g., having a semi-circular or oval shape as viewed from the top), and/or they can have any other suitable regular or irregular shapes.

In some embodiments, at least one protrusion can be formed at a location on the polymer layer corresponding to a location of an attachment feature formed on the jaw. Thus, as shown in FIG. 77, the six protrusions 11114 are formed on the polymer layer 11112 at locations that correspond to the locations of the six attachment features 11116. The length and width of the protrusions 11114 can be different from those of the attachment features 11116. In addition, in some cases, one protrusion can be disposed over more than one attachment feature, and vise versa. Thus, the protrusions formed on the polymer layer and the attachment features formed on the jaw can form various patterns and can correspond to one another in various manners.

Regardless of the specific number, size, and locations of adhesive protrusions formed on the polymer layer 11112, the polymer layer 11112 is used to attach the adjunct material 11106 to the cartridge 11102. The surface of the polymer layer 11112 that is opposed to the surface 11115 on which the protrusions 11114 are formed can be coupled to the adjunct material 11106 in various ways. For example, at least a portion of the polymer layer 11112 can be formed from a pressure-sensitive adhesive such that the adjunct material 11106 can be coupled with the polymer layer 11112 that is, in turn, coupled with the jaw.

In some embodiments, as shown in FIG. 77, the end effector 11100 can include an additional polymer layer 11118 shown in the form of two portions. The additional polymer layer 11118 can be disposed between the adjunct material 11106 and the polymer layer 11112 or between the polymer layer 11112 and the cartridge 11102. The additional polymer layer 11118 can be formed from an adhesive configured to transition from a non-flowable state to a flowable state upon the application of heat. Thus, when the additional polymer layer 11118 is configured to be disposed between the polymer layer 11112 and the cartridge 11102, it is effectively additionally used to couple the adjunct material 11106 to the jaw 11102. It should be appreciated however that the additional polymer layer 11118 is optional and may not be present.

The adjunct material 11106 can be formed from any suitable material or a combination of materials, which are discussed above. In some embodiments, the adjunct material 11106 can have a thickness of from about 0.006 inches to about 0.008 inches. In some embodiments, the adjunct material 11106 can have a thickness of from about 0.004 inches to about 0.0160 inches. The polymer layer can have a thickness of from about 0.002 inches to about 0.025 inches, and projections 11116d, 11116p can have a height or thickness of from about 0.005 inches to about 0.025 inches.

Figure 79:
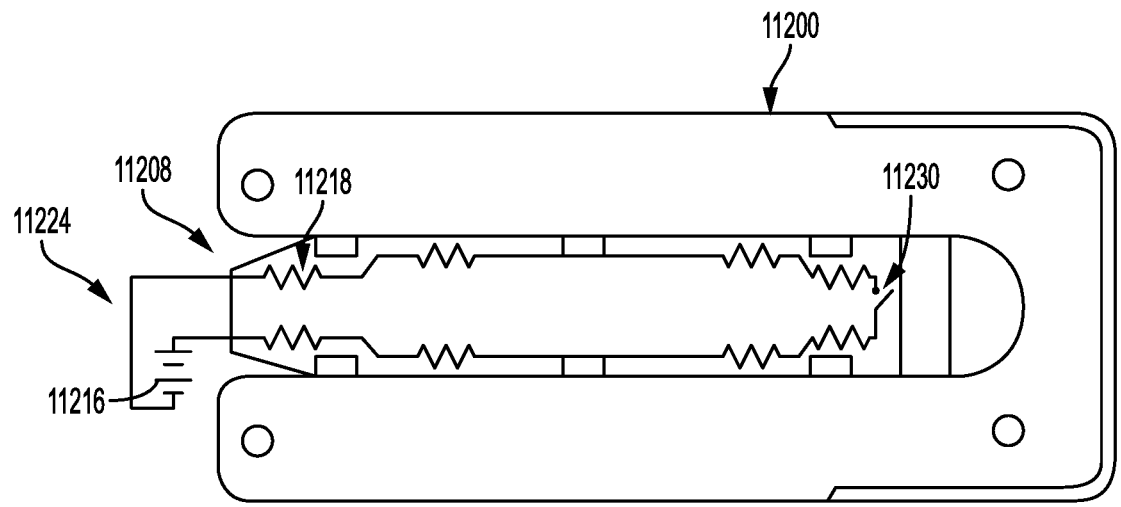
FIG. 79 is a top view of an adjunct loading member.
Figure 80:
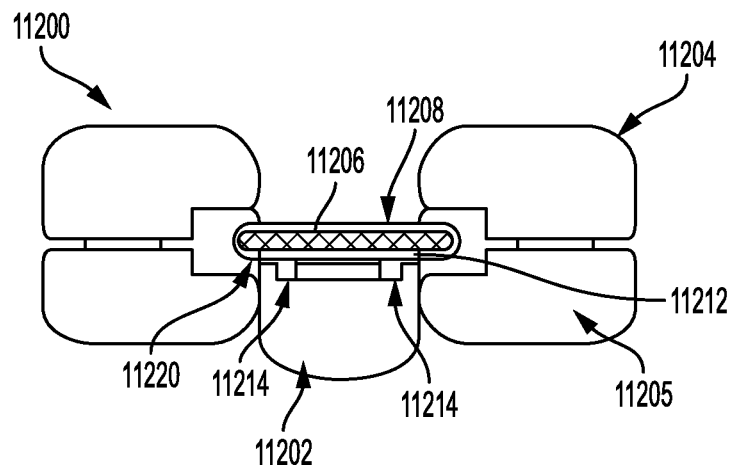
FIG. 80 is a cross-sectional view of the adjunct loading member of FIG. 79.

As mentioned above, in the described embodiments, the adjunct material is configured to be transferred from an adjunct loading member to a jaw of an end effector. FIGS. 79 and 80 show an example of an adjunct loading member 11200 of a loading system that is configured to release the adjunct material to retain the adjunct material in the jaw, using at least one of heat and load (force). FIG. 79 shows a top view of the adjunct loading member 11200, whereas FIG. 80 shows a cross-sectional view of the adjunct loading member 11200 when it is disposed on a jaw 11202 of an end effector.

As in the illustrated example, the adjunct loading member 11200 can be the form of a generally rectangular frame-like holder configured to releasably couple one or more adjuncts to one or both jaws of the end effector (not shown in FIGS. 79 and 80). In the illustrated example, the adjunct loading member 11200 is in the form of a first (e.g., top) and second (e.g., bottom) generally rectangular housings 11204, 11205 coupled to one another e.g., via a coupling member. In this example, the adjunct loading member 11200 can be used to apply a single adjunct to a jaw. It should be appreciated however, that, in some embodiments, a loader like the adjunct loading member 11200 or a similar loader, can be used to apply a respective adjunct to each jaw of an end effector.

As shown in FIG. 79, the adjunct loading member 11200 includes at least one heating component 11208 configured to be activated to apply heat to an adhesive depot having an adhesive configured to transition from a non-flowable state to adhering flowable state upon the application of heat. In this example, as shown in FIG. 80, the adjunct loading member 11200 can retain thereon an adjunct material 11206 and a polymer layer 11212 having protrusions 11214. The adjunct material 11206 and the polymer layer 11212 can be similar, for example, to the adjunct material 11106 and the polymer layer 11112, though any suitable number of the protrusions 11214 can be formed on the polymer layer 11212.

As shown in FIG. 79, the adjunct material 11206 can be releasably retained on a supporting member 11220 that can be configured in any suitable manner so as to retain the adjunct material 11206. The supporting member 11220 that can have or can be in the form of, for example, retaining features (not shown) configured to releasably hold the adjunct material 11206. The adjunct material 11206 can be disposed in any suitable way with respect to the supporting member. For example, in some embodiments, the supporting member 11220 can be in the form of features formed on one or more sides of the adjunct material 11206. In this way, when load is applied to the adjunct loading member 11200, the supporting member 11220 is caused to release the adjunct material 11206 therefrom, thus causing the adjunct material to be transferred to a jaw of an end effector. FIG. 80 illustrates by way of example a jaw of an end effector in the form of a cartridge 11202 that has the adjunct loading member 11200 associated wherewith. The cartridge 11202 is shown in FIG. 80 to have the adjunct material 11206 transferred thereto and coupled thereto using the polymer layer 11212. It should be appreciated that, although not shown in FIG. 80, in use, the load is applied to the adjunct loading member 11200 by a first jaw having an anvil and the second jaw having cartridge 11202 that are clamped together with the adjunct loading member 11200 disposed therebetween.

In the described embodiments, the adjunct material 11206 is transferred from the adjunct loading member 11200 to the cartridge 11202 under application of load and the adjunct material 11206 is caused to be retained on the cartridge 11202 using an adhesive that is caused to transition to a flowable state under application of heat. Thus, in use, the adjunct loading member 11200 releasably holding the adjunct material 11206 is positioned between the jaws of the end effector (only the cartridge 11202 of the end effector is shown in FIG. 80). To transfer the adjunct material 11206 from the adjunct loading member 11200 to the jaw 11202, the first and second jaws are approximated to thereby apply load to the adjunct loading member 11202, which causes the adjunct material 11206 to be released from the adjunct loading member 11200. The adjunct loading member 11200 can be configured such that it exposes the side of the polymer layer 11212 (having the adjunct 11206 coupled thereto) having the protrusions 11214. The application of load can cause the supporting member 11220 and, in some implementations, other portions or features of the adjunct loading member 11200 to crack, break, deform (e.g., bend, flex, etc.) or otherwise change their configuration to thereby release the adjunct 11206 from the adjunct loading member 11200. In some embodiments, the housings 11204, 11205 of the adjunct loading member 11200 can be configured to deform or break to release the adjunct 11206 from the adjunct loading member 11200 when the adjunct loading member 11200 is clamped between the jaws 11200 (and not shown) of the end effector such that the load is applied thereto. As such, the adjunct 11206 can be "squeezed out" of the adjunct loading member 11200. The adjunct loading member 11200 can be disposable such that it can be discarded after the adjunct 11206 (and the polymer layer 11212 coupled thereto) is transferred to the jaw.

Heat is applied to at least a portion of an adhesive depot such as the protrusions 11214 of the polymer layer 11212 having an adhesive and disposed in the adjunct loading member 11200 in association with the adjunct material 11206, which causes the adhesive to transition from a non-flowable state to adhering flowable state when the adjunct material 11206 is released from the adjunct loading member 11200 and transferred to the jaw 11202. For example, under the application of heat, the adhesive from which the protrusions 11214 are formed can transition from a substantially non-liquid state (in which it is in the non-flowable state) to at least partially liquid state (in which the adhesive is in the flowable state). In the at least partially liquid state, the protrusions 11214 can become less viscous such that their material can flow and interconnect or adhere with the surface of the cartridge 11202. The cartridge 11202 can have attachment features (e.g., similar to the attachment features 11116 in FIG. 77) that can have the protrusions 11214 in the flowable state disposed thereon such that the protrusions 11214 on the polymer layer 11212 adhere to the surface of the cartridge 11202. Because the polymer layer 11212 is coupled to the adjunct material 11206, adhering the polymer layer's protrusions 11214 to the cartridge 11202 causes the adjunct material 11206 to be releasably retained on the jaw 11202. When the material from which the protrusions 11214 are formed is cooled and thus transitions to the flowable state, the protrusions 11214 remain attached to the cartridge 11202.

In some embodiments, the adjunct loading member 11200 can be activated (e.g., using a button, switch, or other suitable trigger on the member 11200 or a remote trigger), to apply heat to the polymer layer 11212 before (or as) the load is applied to the adjunct loading member 11200. For example, the heating component 11208 can be activated before the adjunct loading member 11200 is positioned between the jaws of the end effector. The adjunct loading member 11200 can be configured to deliver to the polymer layer 11212 heat of a desired temperature (e.g., in a range of from about 105° C. to about 220° C.) for an appropriate duration of time (e.g., from about 5 seconds to about 60 seconds) such that the application of heat causes the protrusions 11214 of the polymer layer 11212 to transition from the non-flowable state to the flowable, deformable state. In some embodiments, an indicator configured to indicate that the adhesive has been sufficiently heated to the deformable state can be activated. This can be, for example, a light indicator, an audio indicator, etc.

Once the protrusions 11214 are in the flowable state, the adjunct loading member 11200 can be disposed between the approximated jaws that cause the protrusions 11214, and thus the adjunct 11206 coupled thereto, to attach to the jaw 11202. Furthermore, in some embodiments, heat can be applied once the adjunct loading member 11200 is disposed between the jaws but prior to the jaws applying the load to the adjunct loading member 11200. As another variation, the adjunct loading member 11200 can be activated to apply heat to at least a portion of the polymer layer 11212 and adjunct 11206 at least partially simultaneously with the load being applied to the adjunct loading member 11200.

Regardless of the specific timing of the application of load and heat to the adjunct 11206 and polymer layer 11212, the adhesive of the protrusions 11214 is caused to transition to the flowable state in which the protrusions 11214 attach to the jaw 11202 thus causing, after the heat is no longer applied, the polymer layer 11212 to be attached to the jaw. The application of at least one of the load and heat can also cause the adjunct 11206 to couple to the polymer layer 11212.

The heating component 11208 can have various configurations. For example, as shown in FIG. 79, the heating component 11208 includes a resistive heating element 11224 in the form of a wire, which is connected to a power source 11216. In the illustrated example, as shown, the heating element 11224 includes higher resistance portions 11218 along its length. The locations of the higher resistance portions 11218 can correspond to regions on the polymer layer to which heat is desired to be applied, e.g. regions having the protrusions 11114 (FIG. 77). Thus, power can be applied to the heating element 11224 to cause localized heating near the higher resistance portions 11218. In this way, the heat is applied selectively to the polymer layer and to the adjunct material coupled thereto.

In some embodiments the heating element 11224 can include a switch 11230 configured to close the circuit and to allow current to flow through the heating element. The switch 11230 can be operated using a suitable trigger associated with the adjunct loading member 11200 (e.g., a button or other switch on the loader 11200 activated by closure of the end effector or by the person loading the device or a remote control), though the heating element 11224 can be activated in other suitable ways. The heat generated by the higher resistance portions 11218 causes the adhesive portions of the polymer layer, such as the protrusions, to transition to the flowable state and thus couple the polymer layer and the adjunct coupled thereto to the jaw when the polymer layer and adjunct are transferred to the jaw.

The heating component 11208 can be of any suitable type. For example, the heating component 11208 can be made of a rigid material, e.g., ceramic, that is coated with an elastic or compliant material. In some embodiments, the heating component 11208 can be in the form of a resistive wire embedded into silicone, e.g., such that the silicone is cured around the resistive wire. The resistive wire is configured to effect the heating, whereas the silicone allows for some degree of compliance when clamping a stapler onto the loader. The heating component 11208 can be coupled to the housings 11204, 11205 in any suitable manner, e.g., via brackets.

As mentioned above, the adjunct loading member 11200 is generally be configured such that the adjunct 11206 is releasably retained in association therewith adjunct loading member 11200 using a supporting member 11220. The supporting member 11220 can be in the form of a surface and/or it can include retaining features that can releasably couple the adjunct 11206 and the polymer layer 11212 to the adjunct loading member 11200. The adjunct 11206 can be disposed on the heating component 11208, as shown schematically by way of example only in FIG. 80. In this way, once the heating component 11208 is activated, heat is applied to the adjunct 11206 and the polymer layer 11212 that faces the jaw 11202.

In some embodiments, an adjunct loading member, which can be similar to the adjunct loading member 11200 can be configured to releasably retain first and second adjuncts, each configured to be transferred to a respective one of first and second jaws of an end effector. The adjuncts can be secured to both jaws of the end effector simultaneously. A heating component can be configured to apply heat to polymer layer's protrusions or other adhesive depots associated with the adjuncts to retain the adjuncts on the respective jaws. Furthermore, in some embodiments, the heating component can be in the form of two heating components disposed in the removable loader such that each of the heating components is configured to apply heat to a different adjunct that can be associated therewith (e.g., via the loader or manually).

After the adjunct 11206 is coupled to the jaw 11202 and the heat is no longer applied thereto, the adhesive from which the protrusions 11214 are formed can at least partially return to the original state, although not to the original shape. This can occur because the heat source is removed (i.e. the adjunct loading member 11200 is removed, or the power to the heaters is switched off after a set time) and the adhesive is exposed to a room temperature. This can be done while the polymer layer 11212 remains at least partially associated with the adjunct loading member 11200. Also, the adjunct loading member 11200 can be part of a loading system including other components, and such loading system can be configured to cool the adhesive coupling the polymer layer 11212 to the jaw. For example, a cool air can be applied to the polymer layer 11212 coupled to the adjunct 11206. In some embodiments, the cooling can be done using a separate component.

In some embodiments, a trigger associated with the loader (e.g., a switch) is configured to be activated to turn on the heating components once the end effector is clamped onto the loader. This causes the resistors to be heated which thus cause the polymer layer to be heated. The compression or load from the end effector causes the adhesive to flow and conform to the features on the jaw. The power to the resistors can automatically cease after a preset time (either a timer in the circuit, or the circuit can self-destruct with time/heat, or the battery can expire, etc.). After the heat is no longer applied, the polymer adhesive will cool, e.g., due to the thermal mass of the jaws. The loader, or other suitable component, can be configured to, after a time sufficient for the adhesive to cool and thus transition to an adhered state has passed, provide an indication indicating that the process of adhering the adhesive (and thus coupling the adjunct to the jaw) has been completed. The indication can be provided in any suitable way—for example, it can be a visual (e.g., light) indicator, audio indicator, any combination of a visual/audio indicator, etc.

Regardless of the manner in which the adhesive coupling the polymer layer 11212 to the jaw 11202 is cooled, the adhesive at least partially hardens or solidifies. The adjunct 11206 is coupled to the jaw 11202 via the polymer layer 11212 with the protrusions 11214 in a releasable manner and can thus be separated from the jaw 11202. For example, when staples are fired from the jaw 11202, the bond between the adhesive and the jaw 11202 can break or crack.

The polymer layer 11212 and the protrusions 11214 formed thereon can be made from any suitable material or a combination of materials. Also, they can be bioabsorbable and/or biodegradable. The protrusions 11214 can be formed from a material having a lower melting point than a melting point of a material from which the polymer layer 11212 is made. For example, if the material from which the protrusions 11214 are made is PDO, its melting point can be less than about 105° C. However, materials with a melting point that is less than about 180° C. can be used additionally or alternatively. When heat is applied to the polymer layer 11212 (e.g., selectively, such that portion(s) of the protrusions are exposed to heat), the adhesive of the protrusions 11214 can be transitioned to a flowable state, whereas the state of an adhesive from which the polymer layer 11212 is made does not change.

In some embodiments, an adhesive depot having an adhesive configured to transition from a non-flowable state to a flowable state upon the application of heat is in the form of a plurality of reservoirs. The plurality of reservoirs can be formed in a supporting layer of an adjunct loading member and each can releasably hold the adhesive.

Figure 81A:
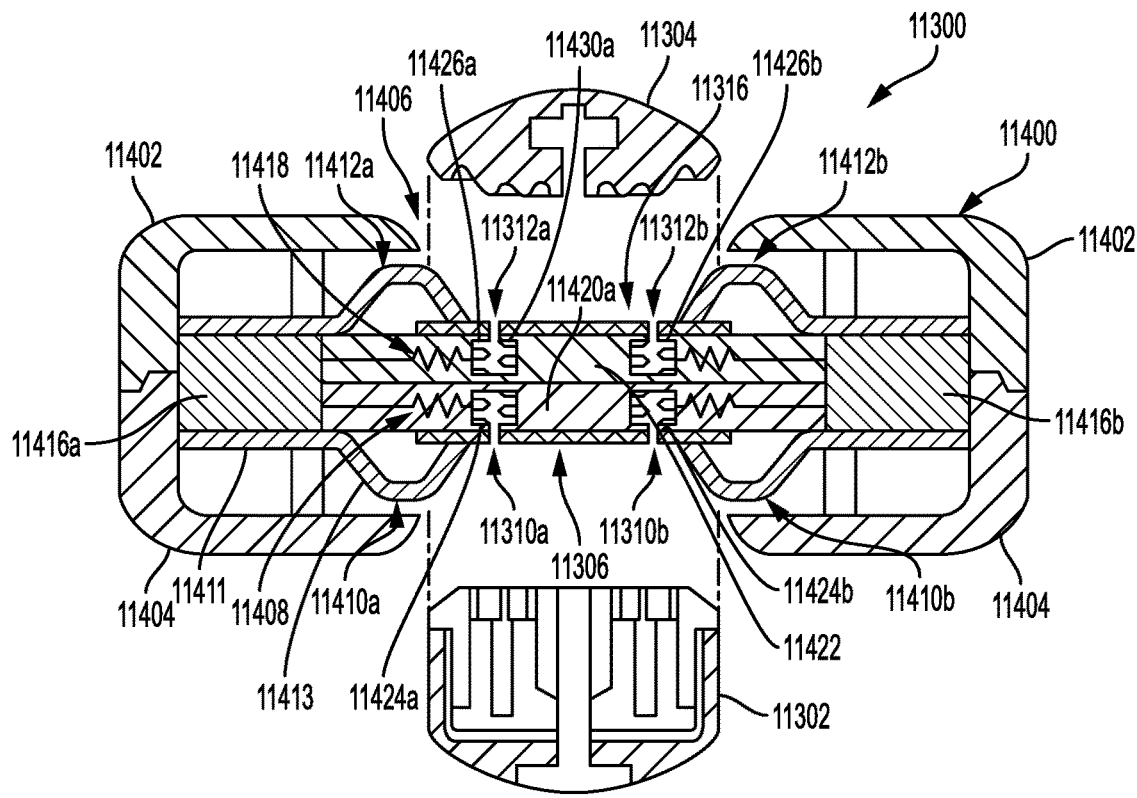
FIG. 81A is a cross-sectional view of an adjunct loading member configured to apply an adjunct material to first and second jaws of an end effector.
Figure 81B:
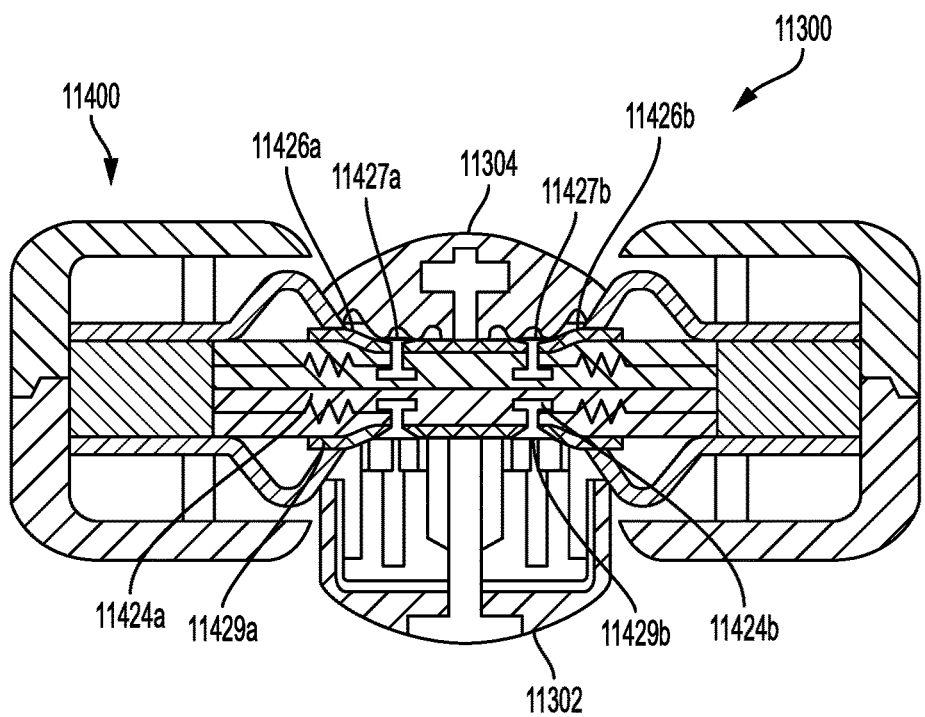
FIG. 81B is a cross-sectional view of the adjunct loading member of FIG. 81A, illustrating the adjunct material applied to the first and second jaws of the end effector.

FIGS. 81A and 81B illustrate an embodiment of an adjunct loading member 11400 releasably holding first and second adjunct materials 11306, 11316 on first and second supporting members 11420, 11422, respectively. The adjunct loading member 11400 is used to transfer the first and second adjunct materials 11306, 11316 to first and second jaws 11302, 11304 of an end effector 11300, as discussed below. In this example, the first jaw 11302 has a cartridge (which can be removably and replaceably seated in the jaw or which can be part of a reloadable unit including the first jaw 11302 or both the first and second jaws 11302, 11304), and the second jaw 11304 has an anvil.

In the illustrated embodiment, the adjunct loading member 11400 is in the form of a generally rectangular member having first and second generally rectangular housings 11402, 11404 coupled to one another. As shown, the adjunct loading member 11400 includes an adjunct holding member 11406 extending between the housings 11402, 11404 and including various components. In particular, the adjunct holding member 11406 includes body members 11416*a*, 11416*b* shown in the left and right sides of the adjunct loading member 11400, respectively, brackets 11410*a*, 11412*a* at one side of the adjunct loading member 11400 (left in FIGS. 81A and 81B), brackets 11410*b*, 11412*b* at another side of the adjunct loading member 11400 (right in FIGS. 81A and 81B), and the first and second supporting members 11420, 11422 extending between the body members 11416*a*, 11416*b*.

The supporting members 11420, 11422 are disposed in the adjunct loading member 11400 such that their mid-portions having the first and second adjunct materials 11306, 11316 releasably retained thereon are not encompassed by the housings 11402, 11404. The brackets 11410*a*, 11410*b* extend over the body members 11416*a*, 11416*b* at one side thereof (bottom in FIGS. 81A and 81B) and retain the first adjunct 11306 over the supporting member 11420. In a similar manner, the brackets 11412*a*, 11412*b* extend over the body members 11416*a*, 11416*b* at another, opposed side thereof (top in FIGS. 81A and 81B) and retain the second adjunct 11316 over the supporting member 11422.

As shown, each of the brackets has a straight portion (e.g., a portion 11411 of the bracket 11410*a*) extending along and over one of the body members 11416*a*, 11416*b*, and a trapezoid-shaped deformable portion (e.g., a portion 11413 of the bracket 11410*a*) extending from the straight portion towards a center of the adjunct loading member 11400. One end of each of the trapezoid-shaped deformable portion of the brackets 11410*a*, 11410*b*, and 11412*a*, 11412*a* is disposed over the first and second adjunct materials 11306, 11316, respectively. It should be appreciated that the brackets are shown to have the trapezoid-shaped deformable portion by way of example only, as the brackets can have any other configuration.

In the illustrated embodiments, the adhesive depots are in the form of reservoirs formed in the supporting members. Thus, as shown in FIG. 81A, the supporting member 11420 has reservoirs 11424*a*, 11424*b*, and the supporting member 11422 has reservoirs 11426*a*, 11426*b*. Each of the reservoirs

11424*a*, 11424*b*, 11426*a*, 11426*b* releasably holds an adhesive and includes an opening through which the adhesive can be released from that reservoir. For example, in FIG. 10, the reservoir 11426*a* is shown to have an opening 11430*a*, and other reservoirs have similar openings. As also shown, each of the adjunct materials 11306, 11316 includes a plurality of openings each having a reservoir with adhesive associated therewith. In particular, the adjunct material 11306 has openings 11310*a*, 11310*b* disposed adjacent to the openings in the reservoirs 11424*a*, 11424*b*. Similarly, the adjunct material 11316 has openings 11312*a*, 11312*b* disposed adjacent to the openings in the reservoirs 11426*a*, 11426*b*. It should be appreciated, however, that in some embodiments, the reservoirs can be configured differently—e.g., they may not have openings, but can have a breakable, meltable, or otherwise removable enclosure that allows to retain the adhesive in the reservoirs and that can be removed when it is desired to release the adhesive. Additionally or alternatively, openings configured to allow an adhesive to flow from the reservoir can be formed in the supporting member.

The openings, such as the openings 11310*a*, 11310*b* in the adjunct material 11306 and the openings 11312*a*, 11312*b* in the adjunct material 11316, are formed at locations in the adjuncts at which it is desired to form attachment portions or points (made of an adhesive) that couple the adjuncts to the jaw. The opening locations in each of the adjuncts can be selected so as to facilitate attachment of the adjunct to the jaw and to also facilitate release of the adjunct from the jaw. It should be appreciated that the adjuncts 11306, 11316, which are shown in FIGS. 81A and 81B in cross-section, can include more than two openings. Multiple openings can be formed so as to attach the adjunct to the jaw using an adhesive at more than two locations. For example, four, six, eight, or more openings can be formed in each of the adjuncts. Also, although, as in the example in FIGS. 81A and 81B, the openings can be formed in pairs (e.g., they can be disposed symmetrically along a centerline of the adjunct), an odd number (e.g., three, five, etc.) of openings can be formed, which corresponds to an odd number of attachment points to be formed when the adjunct is coupled to the jaw.

The adjunct loading member 11400 has first and second heating components 11408, 11418 extending through the supporting members 11420, 11422 that are configured to apply heat to the adhesive held in the reservoirs 11424*a*, 11424*b* and 11426*a*, 11426*b*, respectively, to cause the adhesive to transition from a non-flowable state to a flowable state. In some implementations, a single heating component can be used. Also, the first and second heating components 11408, 11418 can be parts of the same heating component. The openings 11310*a*, 11310*b*, 11312*a*, 11312*b* are configured to receive the adhesive transitioning to the flowable state when the adhesive material is released from a respective one of the reservoirs and through the opening to a jaw-facing surface of the respective adjunct material to thereby retain that adjunct material on the jaw.

In use, the adjunct loading member 11400 having the adjunct materials 11306, 11316 releasably retained thereon is disposed between the first and second jaws 11302, 11304 of the end effector 11300, as shown in FIG. 81A that illustrates the adjunct loading member 11400 before a load is applied thereto. The load is then applied to the adjunct loading member 11400 by the first and second jaws 11302, 11304 that clamp the adjunct loading member 11400 therebetween, as shown in FIG. 81B. Under the application of load exerted by the jaws, the adjunct loading member 11400 is at least partially deformed, which causes the adjunct materials 11306, 11316 to be transferred to the jaws 11306, 11316, respectively. For example, the brackets 11410*a*, 11410*b*, and the brackets 11412*a*, 11412*a* can be at least partially deformed. Also, the supporting members 11420, 11422, which can be formed from a silicone or other deformable and resilient material(s), are deformed under the load, as shown in FIG. 81B. When load is applied to the adjunct loading member 11400, the supporting members 11420, 11422 apply pressure to the adjunct materials 11306, 11316, which can be done in the manner that facilitates uniform application of the load to the adjunct materials. This helps apply the adjunct to the jaws in a uniform manner.

In the illustrated example, the adjunct loading member 11400 is configured so that the adjunct materials 11306, 11316 are transferred substantially simultaneously to the jaws 11306, 11316. It should be appreciated, however, that in some embodiments the adjunct loading member can be configured to transfer one adjunct to an end effector's jaw.

Before or at the time when the load is applied to the adjunct loading member 11400, the heating components 11408, 11418 are activated to cause heat to be applied to the reservoirs 11424*a*, 11424*b* and 11426*a*, 11426*b*, respectively, to cause the adhesive in the reservoirs to transition from the non-flowable state to the flowable state. The adhesive can be stored in the reservoirs 11424*a*, 11424*b*, 11426*a*, 11426*b* in a substantially non-liquid state, and, under the application of heat, the adhesive can become at least partially liquid such that it can be used to couple the adjunct materials to the jaws. As shown in FIG. 81B, when the load is applied, the adhesive is released from the reservoirs, through the openings in the adjuncts 11306, 11316, and onto the surface of the jaws 11302, 11304. In this way, the portions of adhesive 11427*a*, 11427*b* and 11429*a*, 11429*b* released from the reservoirs 11424*a*, 11424*b* and 11426*a*, 11426*b*, respectively, are used to retain the adjunct materials on the opposed jaws of the end effector 11300.

The reservoirs 11424*a*, 11424*b*, 11426*a*, 11426*b* can have any suitable configurations and they can be configured to release the adhesive stored therein in various ways. In the illustrated example, they are at least partially enclosed structures that store the adhesive. For example, they can be formed from a rigid plastic having a liquid adhesive (e.g., a pressure-sensitive adhesive) stored therein. As mentioned above, the reservoirs can have openings formed on the side thereof adjacent to the adjunct.

Furthermore, in some embodiments, the adjunct loading member 11400 can include a closure component that can be disposed so as to temporarily enclose one side of the reservoirs and thereby retain the adhesive therein. With reference to FIG. 81A, such a closure component can be disposed between each of the supporting layers and a respective adjunct material. The closure (or a cap) can be a removable component that is removed to allow the adhesive to flow from the reservoirs. As another variation, the closure component can be in a form of component that can be disposed in at least two different ways with respect to the reservoirs. In particular, the closure component can have openings that can align with the openings in the reservoirs. However, before the adhesive is released from the reservoirs, the closure component can be disposed such that the openings therein are not aligned with the openings in the reservoirs and the closure is thus blocking the openings in the reservoirs and prevents release of the adhesive therefrom. The closure component can be, for example, slidable such that it can be moved to configuration in which its openings are aligned with the openings in the reservoirs. In some embodiments, the closure component can be in the form of a membrane or other thin member configured to rupture when pressure applied thereto exceeds a threshold.

The adjunct loading member 11400 is configured such that it can be separated from the end effector 11300 after the adjuncts 11306, 11316 are transferred to the jaws 11302, 11304 and are retained on the jaws using the adhesive. The adhesive can solidify and thus securely retain each adjunct on the jaw. In some embodiments, as discussed above, the adhesive can be allowed to solidify at a room temperature. Additionally or alternatively, it can be actively cooled using, e.g., a forced cool air.

The adhesive releasably retained in the reservoirs can be any suitable material. For example, it can be a flowable material such as polydioxanone (PDO), a high molecular weight poly(ethylene glycol) (PEG), or any other material. As mentioned above, the adhesive can be a pressure-sensitive adhesive.

Although in the illustrated embodiments heat is applied to an adhesive using an adjunct loading member, it should be appreciated that the heat can be applied in other manners. For example, in some implementations, an end effector can be configured to apply heat to the adhesive which can be releasably held in any type of an adhesive depot (e.g., a polymer layer having adhesive features, reservoirs in an adjunct loading member, etc.). The end effector can include a wire or other component that can be heated and can thus apply heat to the adhesive which thereby softens and can retain an adjunct on a jaw. In some embodiments, a separate heating component can be applied, which is not part of an end effector.

At least one adjunct can be applied to one or both jaws of the end effector during assembly of the end effector. For example, a jaw having a cartridge or both of the end effector's jaws can be pre-loaded with an adjunct during the assembly. In some cases, the jaw with the cartridge can be pre-loaded with an adjunct during the assembly, whereas an adjunct can be applied to the jaw having an anvil (e.g., using any of the adjunct loading members described herein) by a surgeon before or during a surgical procedure. Alternatively, as in the embodiments illustrated in FIGS. 81A and 81B, adjuncts can be applied to both jaws of the end effector by a surgeon (this however can be done during assembly as well).

Figure 82:
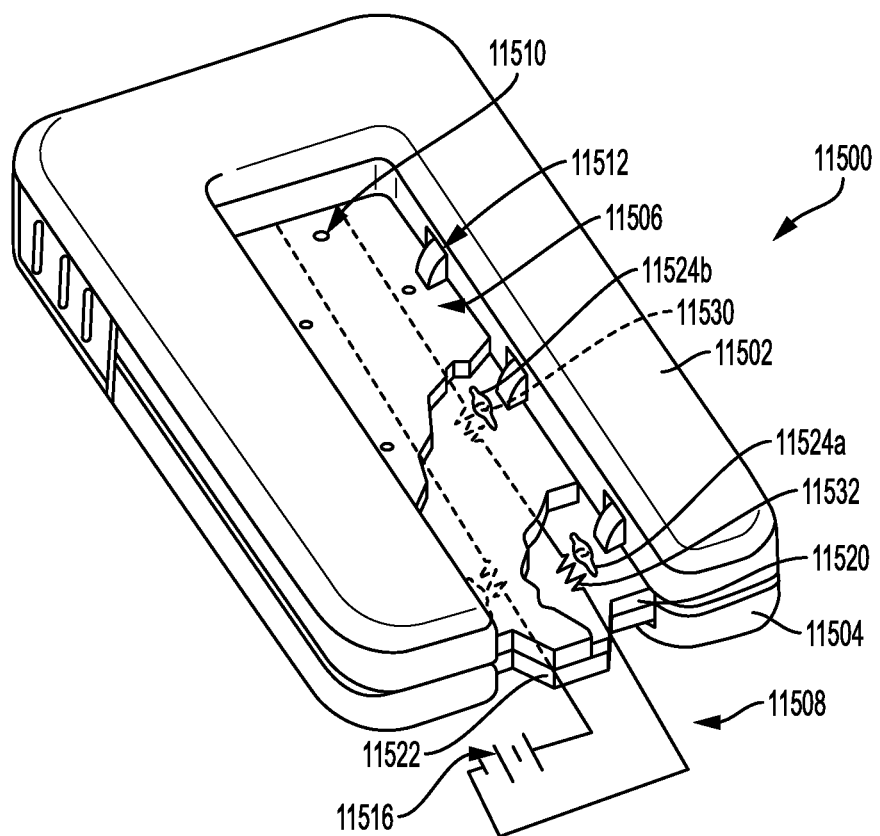
FIG. 82 is a perspective view of an adjunct loading member.

A configuration of an adjunct loading member can vary in different ways. FIG. 82 illustrates an example of an adjunct loading member 11500 which can be similar to adjunct loading member 11400 in FIGS. 81A and 81B. Thus, as shown in FIG. 82, the adjunct loading member 11500 includes housings 11502, 11504 coupled to one another. The adjunct loading member 11500 also includes supporting members 11520, 11522 disposed in the loading member 11500 such that the housing 11502, 11504 enclose the supporting members 11520, 11522 along their perimeters. One side of the supporting members 11520, 11522 is not enclosed, as shown.

The supporting members 11520, 11522 have reservoirs releasably holding an adhesive, with one of the reservoirs, a reservoir 11524a, shown formed in the supporting layer 11520. A top of another reservoir 11524b is also shown formed in the supporting member 11520. One or both of the reservoirs and supporting members in which the reservoirs are formed can have openings that allow the adhesive stored in the reservoirs to be released therefrom. Thus, the reservoir 11524b is shown to have an opening 11530 above it, which can be formed in either the reservoir 11524b itself or in the supporting member 11520. Also, as discussed above, a closure component can be used (not shown), and an opening can be formed in this component as well.

FIG. 82 shows that the adjunct loading member 11500 releasably retains therein an adjunct material 11506, which is shown partially for illustration purposes. The adjunct material 11506 includes openings 11510 that are configured to receive the adhesive transitioning to the flowable state when the adhesive is released from a respective one of the reservoirs and through the opening to a jaw-facing surface of the respective adjunct material to thereby retain that adjunct material on the jaw. The adjunct material 11506 is releasably retained on the supporting member 11520. It should be appreciated that, although it is obscured in FIG. 82, the loading member 11500 can include a second adjunct material releasably retained on the supporting member 11522.

The adjunct material 11306 is releasably retained in the adjunct loading member 11500 using retainer elements 11512, which can have any suitable configurations. Although the retainer elements 11512 on one side of the adjunct material 11306 are shown, it should be appreciated that they can also be formed on the opposed side of the adjunct material 11306, in which case they are obscured in FIG. 82. Also, the retainer elements 11512 can be configured such that they can be movable—e.g., when load is applied to the adjunct loading member 11500, the retainer elements can be caused to move towards the edges of the housings 11502, 11504, such that the retainer elements release the adjunct material 11306.

As shown in FIG. 82, a heating component 11508 coupled to a power source 11516 is disposed between the supporting members 11520, 11522. The heating component 11508, e.g., its higher resistance portions 11532 are used to apply heat to respective reservoirs to cause the adhesive stored in the reservoirs to transition from a non-flowable state to a flowable state.

Similar to the adjunct loading member 11400 in FIGS. 81A and 81B, the adjunct loading member 11500 is configured to have load applied thereto to cause it to release one or more adjunct materials therefrom which are transferred to jaw(s) of an end effector and are coupled to the jaw(s) using the adhesive.

In some embodiments, an adhesive depot can include an adhesive that is substantially liquid in a non-cured state and that is configured to be transitioned to an adhering, cured state in which it is at least partially non-liquid. This can involve curing the adhesive, which can be done using application of ultra violet (UV) light or infrared radiation. Additionally, load (or pressure) applied to the adhesive can facilitate curing the adhesive in some instances. In the cured, at least partially non-liquid state, the adhesive is used to couple an adjunct to a jaw of an end effector.

Figure 83A:
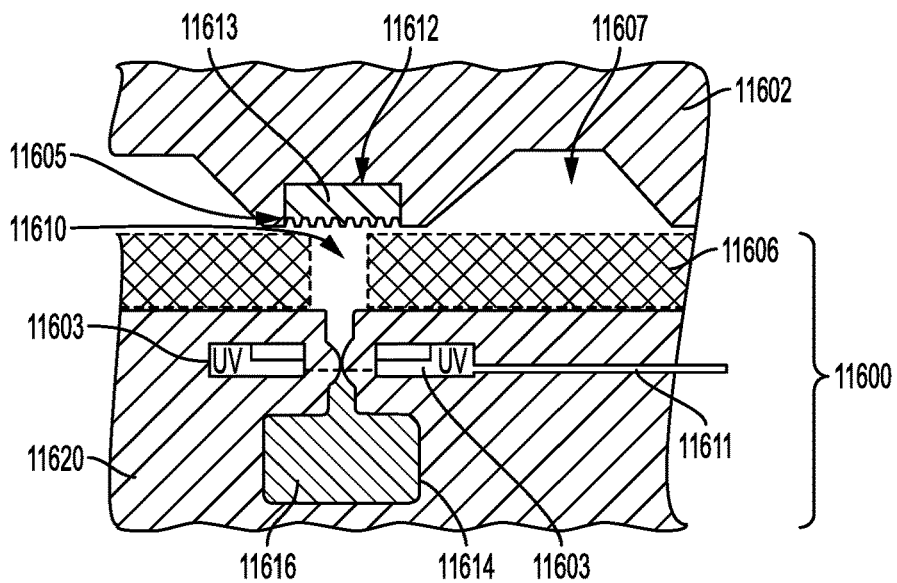
FIG. 83A is a cross-sectional view of a portion of an adjunct loading member configured to apply an adjunct material to a jaw of an end effector using a curable adhesive.
Figure 83B:
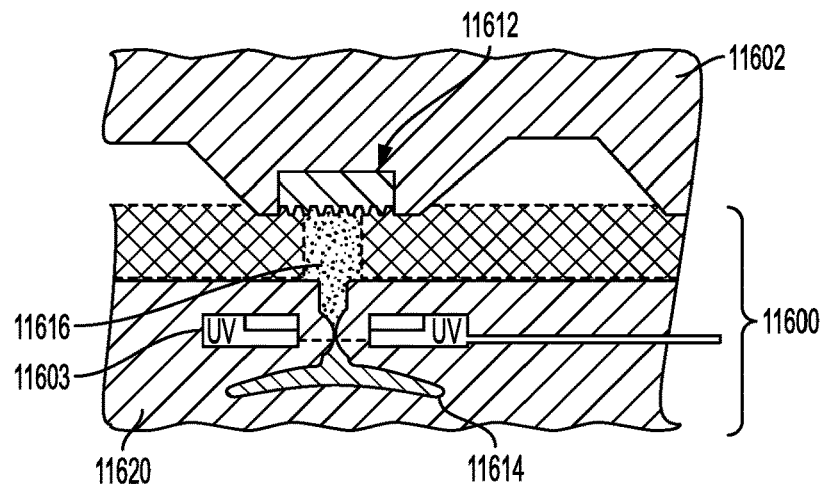
FIG. 83B is a cross-sectional view of the adjunct loading member of FIG. 83A, illustrating the adjunct loading member when load is applied thereto.
Figure 83C:
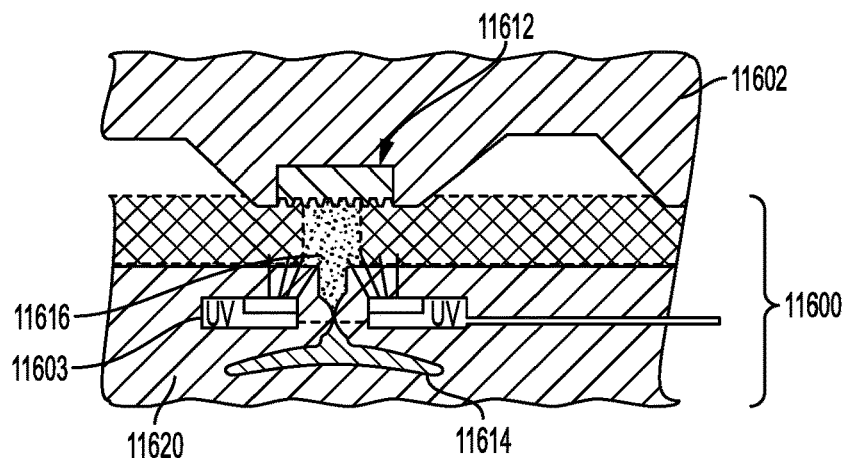
FIG. 83C is a cross-sectional view of the adjunct loading member of FIG. 83A, illustrating the adjunct loading member when load is applied thereto and the adhesive is being cured.

FIGS. 83A-83C illustrate an example of a portion of an adjunct loading member 11600 including a supporting member 11620 releasably retaining an adjunct material 11606. The supporting member 11620, which can be at least partially made from a silicone or other compressible material, includes one or more reservoirs holding an adhesive, one of which is shown as a reservoir 11614 storing an adhesive 11616. As shown in FIG. 83A, the reservoir 11614 is disposed adjacent to an opening 11610 in the adjunct material 11606. The reservoir 11614 can be an enclosed structure (e.g., formed from a suitable plastic) releasably holding the liquid adhesive 11616. The adhesive 11616 can be any suitable UV-curable adhesive, such as, for example, polyurethane, cyanoacrylate, or any other adhesive(s).

The adjunct material 11606 is configured to be transferred to a jaw 11602 of an end effector which is, in this example, a jaw having an anvil. The anvil 11602 can have a tissue-facing surface 11605 having staple-forming cavities or pockets 11607. Also, as shown in FIGS. 83A-83C, the tissue-facing surface 11605 has attachment portions, one of which is shown as an attachment portion 11612 that is configured to receive the adhesive released from the reservoir 11614. The attachment portions can be formed between the staple-forming pockets 11607, though they can be formed in other areas of the tissue-facing surface 11605. In some embodiments, as shown in this example, the attachment portion 11612 can include an attachment feature 11613 made from an elastomeric material (e.g., a pad) that is coupled to the tissue-facing surface 11605. This feature can be patterned (e.g., knurled or otherwise roughened), which facilitates adherence of the adhesive to this portion. Also, the elastomeric material allows the attachment feature 11613 to be deformed when the bond between the attachment portion 11612 on the surface 11605 and the adhesive coupled thereto (which retains an adjunct over the surface 11605) is broken, as discussed in more detail in the example shown in FIGS. 86A-86C below.

As shown, the adjunct loading member 11600 also includes UV light applicators 11603 configured to apply UV light to the adhesive as it is released from the adhesive reservoirs. The UV light applicators 11603 are coupled to a cable 11611 (e.g., a fiber optic cable) that couples the applicators to a UV light source. Also, in some embodiments, the UV light applicators 11603 can be associated with UV-emitting light emitting diodes (LEDs).

FIG. 83A illustrates the adjunct loading member 11600 before load is applied thereto. When the load so applied to the adjunct loading member 11600 (e.g., using the jaws of the end effector, manually, etc.), the reservoir 11614 is deformed, broken, or its configuration is otherwise changed such that the adhesive 11616 is transferred from the reservoir 11614, through the opening 11610 in the adjunct 11606, and onto the surface of the jaw 11302, as shown in FIG. 83B. The adhesive 11616 is transferred to the tissue-facing surface 11605 of the jaw 11302 so as to be disposed on the surface of the attachment portion 11612. As the adhesive 11616 is being released, the UV light applicators 11603 are activated to apply UV light to the adhesive 11616 to cause it to cure, as illustrated in FIG. 83C. In this way, the adhesive 11616 is deposited on the surface of the jaw in the adhering, non-cured state (or only partially cured) in which it is then cured and thus attaches the adjunct 11606 to the jaw 11602. The adjunct loading member 11600 can then be separated from the end effector.

It should be appreciated that the portion of the adjunct loading member 11600 is shown in FIGS. 83A-83C by way of example only. Also, the adjunct loading member 11600 can include multiple reservoirs with the adhesive, more than one openings can be formed in the adjunct, as well as other variations are possible.

Figure 84A:
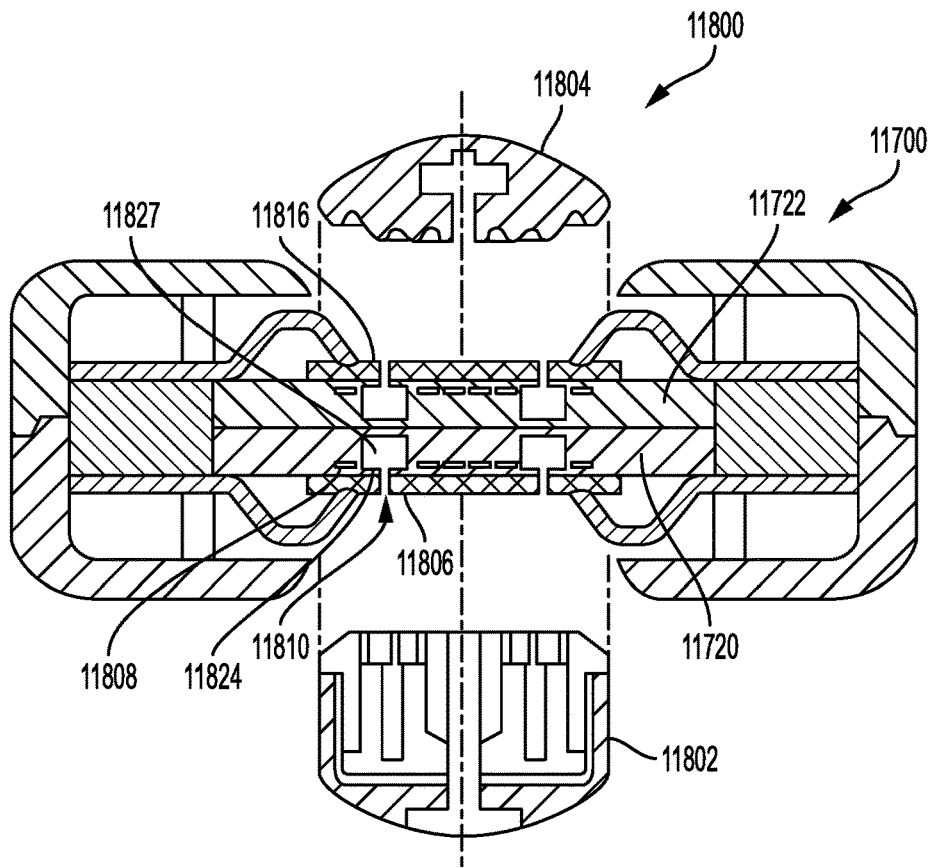
FIG. 84A is a cross-sectional view of a portion of an adjunct loading member configured to apply an adjunct material to first and second jaws of an end effector using a curable adhesive.
Figure 84B:
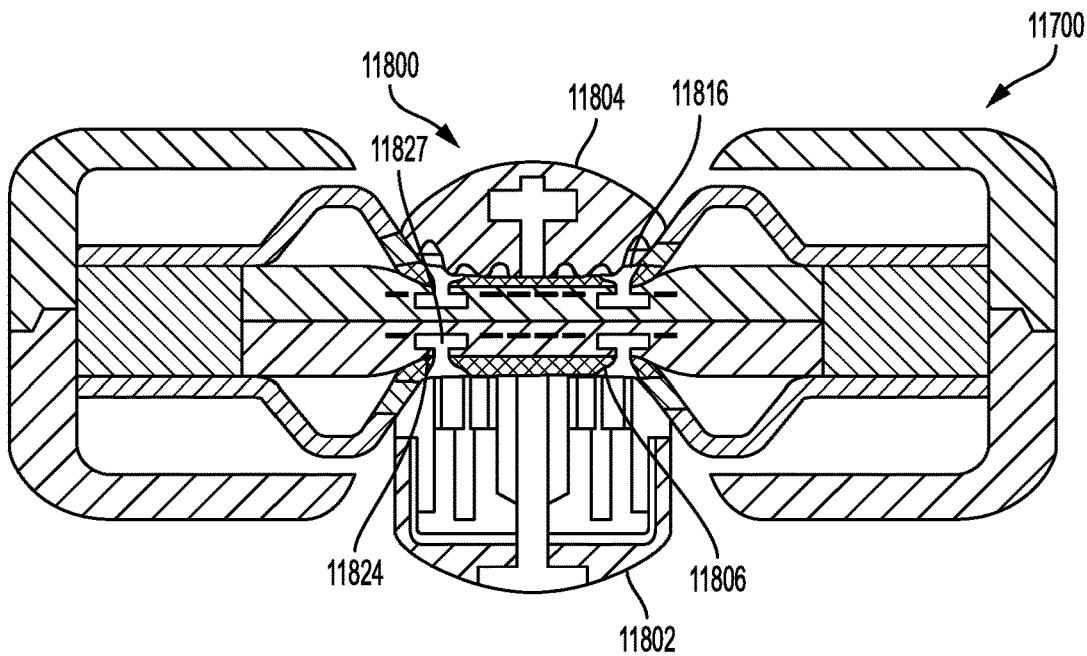
FIG. 84B is a cross-sectional view of the adjunct loading member of FIG. 84A, illustrating the adjunct loading member when load is applied thereto.

FIGS. 84A and 84B illustrate another example of an adjunct loading member 11700 configured to releasably hold first and second adjunct materials 11806, 11816 and to apply these adjunct materials to first and second jaws 11802, 11804 of an end effector 11800. Similar to adjunct loading member 11600 in FIGS. 83A-83C, a substantially liquid adhesive released from the adjunct loading member 11700 is configured to be cured using UV light, heat, or in other manner. As shown in FIGS. 84A and 84B, the adjunct loading member 11700 is similar to adjunct loading member 11400 shown in FIGS. 81A and 81B, and therefore a detailed description is not repeated. However, as mentioned above, the adjunct loading member 11700, releasably stores in reservoirs formed in first and second supporting members 11720, 11722 an adhesive that is cured upon it is release from the reservoirs such that it is used to retain the adjuncts on the jaw in its cured state.

Describing by way of example one of the reservoirs included in the adjunct loading member 11700, a reservoir 11824 in the supporting member 11720 is configured to provide an adhesive 11827 stored therein when load is applied to the adjunct loading member 11700 as shown in FIG. 84B. A UV light applicator 11808 or other (e.g., infrared radiation) applicator is configured to apply UV or other radiation to the adhesive 11827 as it is released from the reservoir 11824. In this way, the adhesive is used to retain the adjunct on the jaw as the adjunct is transferred to the jaw.

Figure 85:
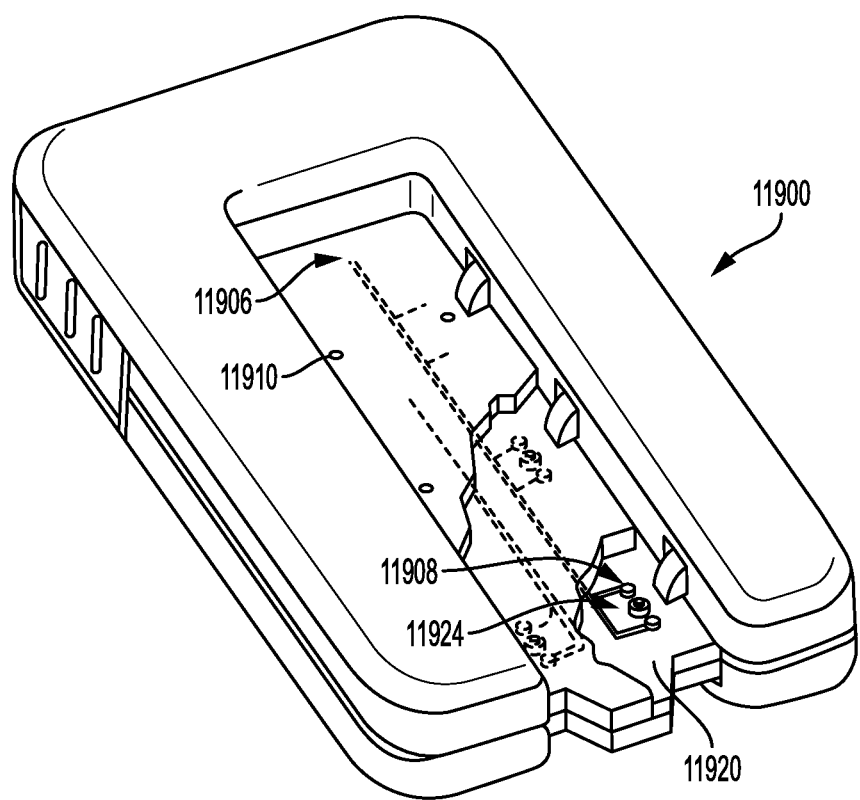
FIG. 85 is a perspective view of an adjunct loading member.

Any suitable component can be used to apply radiation to an adhesive to cause it to transition from a state in which it is not cured to an adhering state in which it is cured. FIG. 85 illustrates one embodiment of an adjunct loading member 11900 that can be used to apply radiation to an adjunct material 11906. The adjunct loading member 11900 can be generally similar to adjunct loading member 11500 in FIG. 82 and is therefore not described in detail. In this example, an adhesive stored in a reservoir, such as a reservoir 11924 formed in a supporting member 11920 is configured to be cured when it is released from the reservoir 11924 when load is applied to the adjunct loading member 11900 and the adhesive is cured using radiation emitted from a UV applicator 11908. Other types of radiation, however, can be used additionally or alternatively. Similar to the manner described above in connection with the adjunct loading member 11500 (FIG. 82), the adhesive can be released from the reservoir and caused to flow through an adjacent opening 11510 formed in the adjunct 11906. Although not shown in FIG. 85, the adjunct loading member 11900 can also have a second adjunct material releasably retained therein and configured to be transferred therefrom and attached to a second jaw of an end effector similar to the adjunct 11906.

Figure 86A:
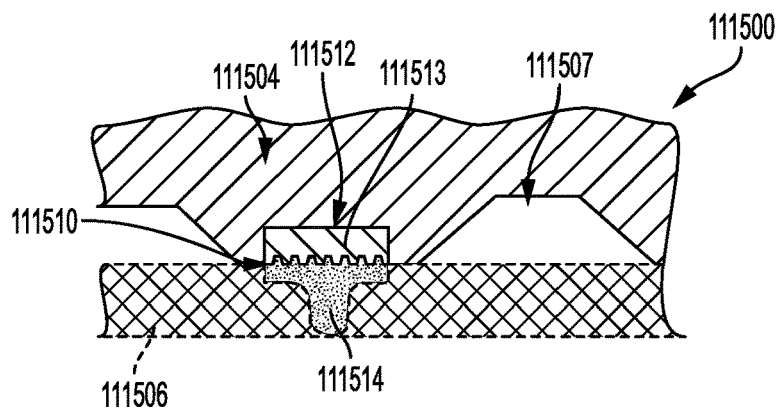
FIG. 86A is a cross-sectional view of a portion of an adjunct material releasably coupled to a first jaw of an end effector using an adhesive.

Regardless of the specific way in which an adjunct material is coupled to a jaw of an end effector, it is required to properly separate the adjunct material from the jaw when the adjunct is applied to tissue. It is desired to release the adjunct from the jaw in an efficient manner. This can be achieved, for example, by fracturing the adhesive that attaches the adjunct to the end effector. FIG. 86A illustrates an example of a portion of an adjunct material 111506 attached to the jaw 111504 of an end effector 111500 by an adhesive 111514, which can be cured in a desirable manner (e.g., using a UV light applied via a loader, or in other manners). The adhesive 111514 releasably attaches the adjunct material 111506 to the jaw 111504 by being at least partially disposed in an opening 111510 formed in the adjunct material 111506.

Similar to adhesive 11616 in FIGS. 83A-83C, the adhesive 111514 in FIG. 86A is coupled to the jaw 111504 at an attachment region or portion 111512 on the surface of the jaw 111504. Similar to attachment portion 11612 in FIGS. 83A-83C, the attachment portion 111512 can have a deformable attachment feature 111513 that is patterned to facilitate coupling the adhesive thereto. The attachment feature 111513 can be formed from an elastomeric material such that it can deform when a force is applied thereto.

Figure 86B:
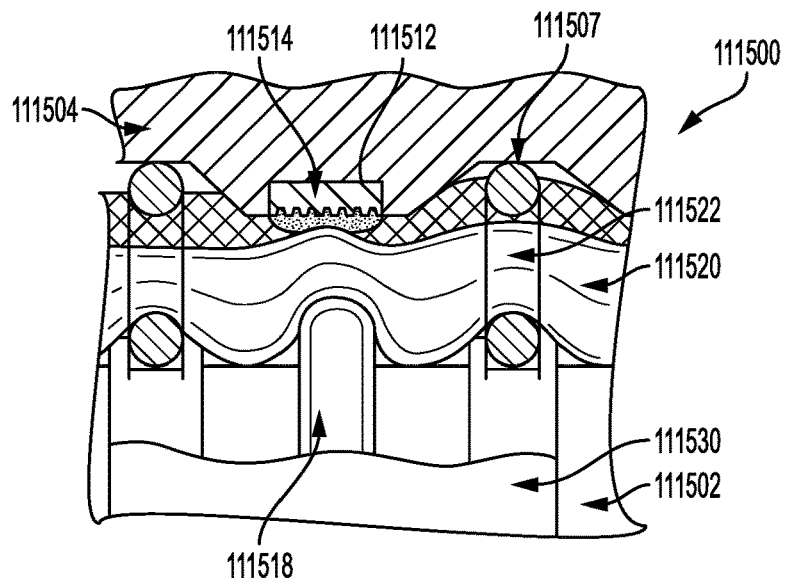
FIG. 86B is a cross-sectional view of the adjunct material of FIG. 86A, illustrating staples fired from a second jaw of the end effector and the end effector causing the adhesive to break.

The end effector 111500 can be configured to cause the adjunct material 111506 to separate from the jaw 111504 when staples are fired from a jaw 111502 having a cartridge that is shown schematically in FIG. 86B. For example, as shown, the jaws 111502, 111504 are approximated to clamp tissue 111520 therebetween and a stapler driver 111530 movably seated in the jaw 111502 causes staples 111522 to fire from staple holding cavities in the jaw 111502 so as to penetrate the tissue 111520 and the adjunct 111506. The staples 111522 are urged into corresponding staple-forming cavities or pockets 111507 formed on the surface of the jaw 111504 such that the staples 111522 are closed and attach the adjunct 111506 to the tissue 111520.

In the example illustrated, the stapler driver 111530 includes protruding members 111518 configured to push the cured adhesive 111514 towards the attachment portion 111512 and into the attachment feature 111513 (which can deform to some degree) when the staples 111522 are fired. This can cause the adhesive 111514 to break, fracture, deform, or otherwise change its configuration. In some instances the cured adhesive 111514 can be brittle and applying load thereto causes it to fracture, crack, or break.

Figure 86C:
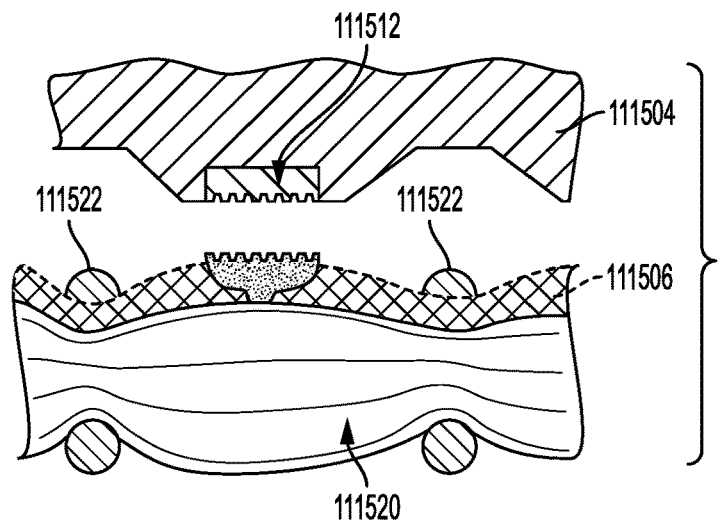
FIG. 86C is a cross-sectional view of the adjunct material of FIG. 86A, illustrating the adjunct material separated from the end effector.

It should be appreciated that only portions of the adjunct 111506 and the end effector 111500 are shown in FIGS. 86A-86C and that multiple attachment portions similar to the attachment portion 111512 (or having other configurations) can be formed on the jaw 111504 and are used to couple the adjunct 111506 to the jaw 111504 using the adhesive 111514. Accordingly, multiple corresponding protruding members on the stapler driver 111530 can cause the adhesive at the corresponding attachment portions to break. In this way, the adjunct 111502 can be decoupled from the attachment region 111512 and thereby be released from the jaw 111504. Thus, FIG. 86C illustrates the tissue 111520 and the adjunct 111506 stapled together by the staples 111522 and decoupled from the jaw 111504 and thus from the end effector 111500. A portion of the adhesive 111514, which can be a biodegradable and/or bioabsorbable material, can remain with the adjunct 111506, as shown.

It should be appreciated that the described adjunct materials and systems and methods used to apply the adjunct materials to at least one jaw of an end effector can have various configurations. For example, although, as discussed above, the adjunct materials can have openings formed therein that allow an adhesive from an adhesive despot to be applied to the surface of the adjunct, in some embodiments, the openings may not be formed. In such embodiments, the adhesive can be flowed from an adhesive depot (e.g., one or more reservoirs) through pores, spaces between fabric strands, or other structures in the adjunct material. For example, the adjunct material can be porous and the adhesive are flow therethrough to a surface of the jaw. The pores can be formed at any suitable ways, and, in some instances, they can be larger at predetermined locations through which the adhesive can flow easier.

Adjunct Loader for Surgical Staplers

Various adjunct loaders are provided for cleaning and affixing an adjunct to an end effector of a surgical stapling device. While the adjunct loaders are described in connection with end effectors of surgical staplers, the adjunct loaders can be used in connection with any type of surgical device. In an exemplary embodiment, an adjunct loader can be configured to clean at least one tissue-engaging surface of an end effector on a surgical stapler, and the adjunct loader can be configured to attach an adjunct to the tissue-engaging surface of the end effector. For example, an adjunct loader can have two slots, each configured to seat at least one jaw of the end effector therein. One slot can be configured to clean the end effector, and the other slot can be configured to attach the adjunct to the end effector. The adjunct loader can thus allow a user to rapidly clean and attach an adjunct to a surgical stapler for use during an operation, increasing the speed and convenience of using adjuncts with a surgical stapler.

Figure 87:
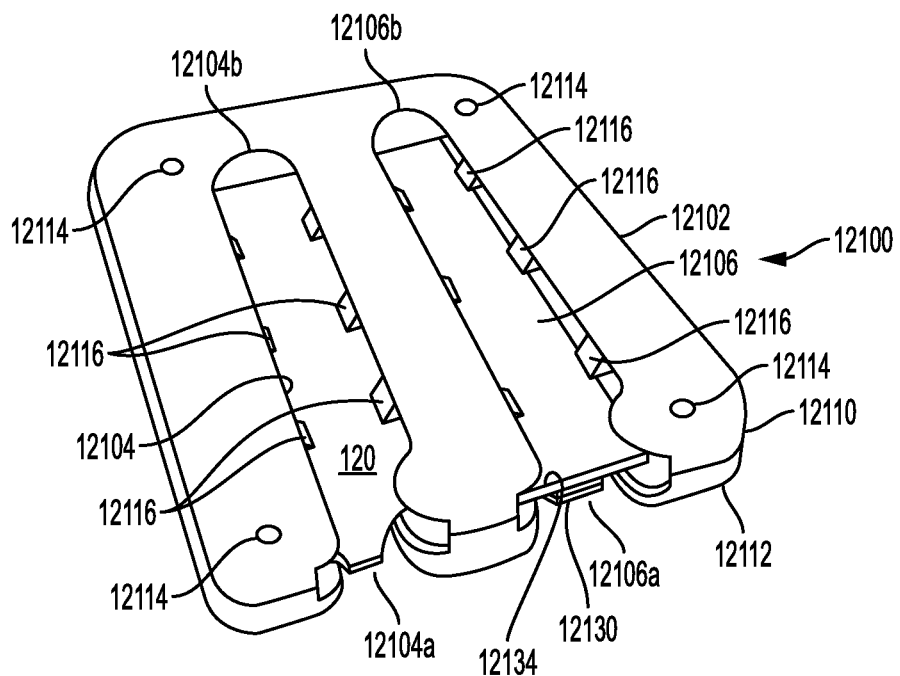
Figure 88:
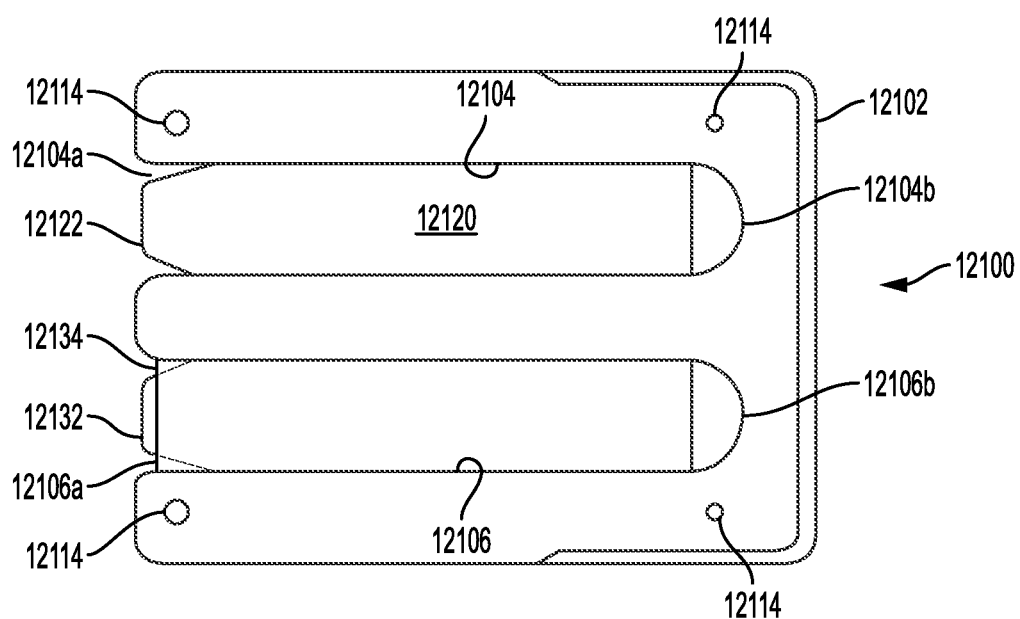
Figure 89:
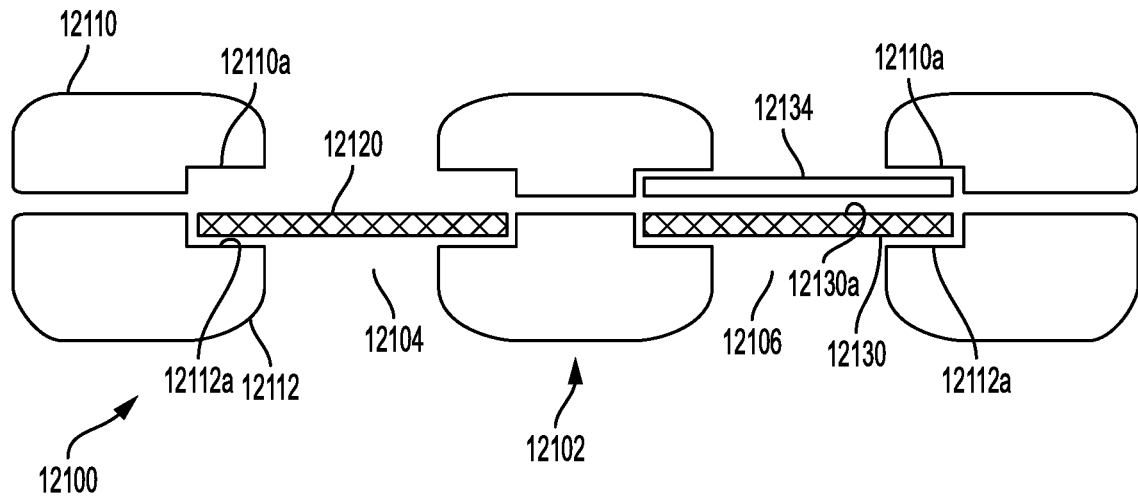

Cleaning the end effector and attaching the adjunct can be achieved through a variety of techniques. FIGS. 87-89 illustrate one embodiment of an adjunct loader 12100. The illustrated adjunct loader 12100 has a frame 12102, a cleaning slot 12104, and a loading slot 12106. The frame 12102 can have any shape, such as a rectangular housing with a top portion 12110 and a bottom portion 12112. The top portion 12110 and the bottom portion 12112 can snap or clip together using, for example, posts 12114 that extend from one of the top or bottom portions 12110, 12112 and snap into the other of the top or bottom portions 12110, 12112. In other embodiments, the two portions can be closed together in any number of ways, such as being glued, sealed, or formed as a single unit.

The frame 12102 can have the cleaning slot 12104 and the loading slot 12106 formed therein. The cleaning slot 12104 and the loading slot 12106 can be configured to receive at least a portion of an end effector on a surgical stapler. For example, the slots 12104, 12106 can take the form of longitudinal openings formed in the frame 12102 and can be sized and shaped to receive a linear end effector therein, such as the elongate jaws of the surgical staplers 10, 50. The slots 12104, 12106 can extend parallel to each other and can have open ends 12104a, 12106a on one side of the frame 12102 and closed ends 12104b, 12106b on an opposite side of the frame 12102. The closed ends 12104b, 12106b can have a semicircular shape, but a variety of different configurations are possible. The top portion 12110 and the bottom portion 12112 of the frame 12102 can have ledges 12110a, 12112a formed along the slots 12104, 12106 and configured to create a groove that extends along a perimeter of at least the longitudinal edges of the slots 12104, 12106 when the top portion 12110 and the bottom portion 12112 are snapped together, as illustrated in FIG. 89.

Each slot 12104, 12106 can be configured to retain a material therein, such as a cleaning material or an adjunct. In the illustrated embodiment, each of the top portion 12110 and the bottom portion 12112 of the frame 12102 can have a plurality of fingers 12116 that extend into the slots 12104, 12106. The fingers 12116 can have a variety of shapes, such as a wedge shape with a triangular cross-section as illustrated in FIG. 87, and can be configured to retain material between the top portion 12110 and the bottom portion 12112 within the slots 12104, 12106. In the cleaning slot 12104, the fingers 12116 can be fixed and configured to remain in place even under a pulling or tugging force. In the loading slot 12106, the fingers can be deflectable and/or spring biased to release material held therebetween under a pulling or tugging force. For example, the fingers 12116 in the loading slot 12106 can be configured to be retractable into the frame 12102 when jaws of an end effector clamp onto an adjunct therebetween. In some embodiments, the jaws can push the fingers 12116 into the frame 12102 when engaging the adjunct thereby disengaging the fingers from the adjunct and releasing the adjunct from the loader 12100.

The cleaning slot 12104 can have a cleaning pad 12120 that extends between the open end 12104a and the closed end 12104b of the cleaning slot 12104. The cleaning pad 12120 can have a variety of shapes, such as a rectangular shape. In an exemplary embodiment, the shape corresponds to the shape of an end effector to be cleaned, such as elongate jaws of a linear surgical stapler. The cleaning pad 12120 can have a tongue 12122 that extends from one end of the cleaning pad 12120 and into the open end 12104a of the cleaning slot 12104. The cleaning pad 12120 can extend the length between the two ends or can extend some distance less than entirely between the two ends, for example as illustrated in FIG. 88 in which the cleaning pad 12120 terminates before reaching the closed end 12104*b*. The cleaning pad 12120 can extend into the groove formed by the ledges 12110*a*, 12112*a* and can be held between the top portion 12110 and the bottom portion 12112 of the frame 12102 by the plurality of fingers 12116. In some embodiments, the fingers can be configured to hold an adjunct in the loading slot 12106 (discussed in more detail below) while the cleaning pad 12120 can be configured to be secured to the frame 12102 through various other techniques. For example, the cleaning pad 12120 can be configured to be secured with holes in the pad 12120 that extend over pins in the frame 12102. Other examples can include securing the cleaning pad 12120 by the pad 12120 being glued in place, welded in place, held in place by other posts from the housing 12102 that are formed into mushrooms with heated tooling, etc.

The cleaning pad 12120 can have a variety of configurations. For example, the cleaning pad 12120 can be made from an abrasive material with a cleaning solvent saturated therein and configured to remove a variety of substances, such as adhesive, tissue, and/or oily residue. The cleaning pad 12120 can be configured to remove any build-up and/or adhesive left on jaws (particularly an anvil) on an end effector left over from any previous firings with an adjunct. This cleaning can be beneficial to prevent any adhesive build up on the device, which can cause a variety of problems such as causing staples to be malformed, causing over-compression of tissue, etc. In various embodiments, a solution that aids in adhesion can also be added to the cleaning pad 12120. The cleaning pad 12120 can be configured to be engaged by opposed jaws on an end effector of a surgical stapler, and it can be configured to clean one side of the surgical stapler, such as the anvil side or to clean both sides as may be needed. In certain embodiments, the cleaning pad 12120 can have various configurations, such as different sides of the pad with a cleaning side and a neutral side, different layers of the pad with a cleaning layer and a neutral layer, a cover or film on one side to prevent cleaning, etc.

The loading slot 12106 can have an adjunct 12130, such as any of the buttresses, adjuncts, and/or medicants discussed above, Vicryl matrix, etc., disposed therein. The adjunct 12130 can have a variety of shapes, such as a rectangular shape. In an exemplary embodiment, the shape corresponds to the shape of an end effector to be cleaned, such as elongate jaws of a linear surgical stapler. The adjunct 12130 can have a tongue 12132 that extends from one end of the adjunct 12130 and into the open end 12106*a* of the loading slot 12106. The adjunct 12130 can extend entirely between the open end 12106*a* and the closed end 12106*b* of the loading slot 12106, or it can extend some distance less than entirely between the two ends, for example as illustrated in FIG. 88 in which the adjunct 12130 terminates before reaching the closed end 12106*b*. The adjunct 12130 can be held between the top portion 12110 and the bottom portion 12112 of the frame 12102 and can be held in place by the plurality of fingers 12116 in the groove formed by the ledges 12110*a*, 12112*a*. The adjunct 12130 can be configured to be released by the fingers 12116 upon application of a threshold force on the adjunct 12130 such that the adjunct 12130 will be free from the adjunct loader 12100. For example, the fingers 12116 can defect out of the slot as the adjunct 12130 is engaged by jaws of an end effector to thereby release the adjunct 12130.

The adjunct 12130 can have a variety of configurations, as discussed above, and can have a variety of attachment mechanisms thereon, such as an adhesive coated on a surface of the adjunct 12130. A variety of adhesives can be used, such as 50-50 PCL-PGA, other absorbable polymers such as mixes of poloxamers, natural substances such as bees wax, etc. The adhesive can be spread on one or both surfaces of the adjunct 12130. For example, the adjunct 12130 can have an adhesive spread on upper surface 12130*a* of the adjunct 12130 that is configured to contact a tissue-facing surface of a surgical stapler. A cover 12134 can be disposed in the loading slot 12106 with the adjunct 12130. The cover 12134 can have a variety of configurations, such as a rectangular-shaped thin sheet of material that extends between the open end 12106*a* and the closed end 12106*b* of the loading slot 12106 with the adjunct 12130. The cover 12134 can be held between the top portion 12110 and the bottom portion 12112 of the frame 12102 with the adjunct 12130 and can cover the adhesive surface 12130*a* of the adjunct 12130. The cover can be made from a variety of materials. For example, the cover can be a compliant but non-porous material, various plastics, etc. The cover 12134 can be configured to be manually removed, although a variety of different retraction options are possible. For example, the cover can be configured to automatically snap open upon use of the cleaning slot 12106, be rolled up inside the adjunct loader 12100 by, for instance, having a pressure-sensitive rolling mechanism in the adjunct loader 12100 that is configured to sense clamping on the cleaning pad 12120 and then trigger rolling or retraction of the cover from the adjunct 12130, etc.

In use, the jaws of a surgical stapler can first be clamped onto the cleaning pad 12120 in the cleaning slot 12104. With the end effector engaging the cleaning pad 12120, the jaws of the surgical stapler can be pulled out of the slot 12104. Because the surgical stapler is still clamped on the cleaning pad 12120 as it is retracted, the cleaning pad 12120 can scrub and clean the tissue facing surface of the anvil and/or the cartridge. In some embodiments, the cleaning pad 12120 can be used to clean just the anvil side of a surgical stapler without cleaning the cartridge side, by using the various approaches discussed above. As the surgical stapler is retracted out of the slot 12104, the fingers 12116 or other retention mechanisms can retain the cleaning pad 12120 in the cleaning slot 12104. A user can remove the cover 12134 from the loading slot 12106 or it can be automatically removed upon cleaning, exposing the adhesive side 12130*a* of the adjunct. The user can clamp the surgical stapler onto the adjunct 12130 in the loading slot 12106 with one of the anvil or the cartridge of the surgical stapler contacting the adhesive side 12130*a*. The adjunct 12130 will attach to the tissue facing surface adjacent the adhesive, and the jaws can be retracted from the slot 12106 after unclamping the jaws. Because the adjunct 12130 is attached to the surgical stapler, the adjunct will be released from the adjunct loader 12130 upon application of a threshold force, for example by having the fingers 12116 release the adjunct 12130 under application of force or by withdrawing the adjunct 12130 distally through the open end 12106*a* of the loading slot 12106. The adjunct 12130 is ready for delivery to tissue. Provided above is an embodiment of a single-step, two-stage adjunct loader. Two step loaders are also possible, in which a user clamps a surgical stapler onto a first loader that only cleans the surgical stapler before clamping the surgical stapler onto a second, separate loader with an adjunct that loads the adjunct onto the surgical stapler (similar to the loading process described above).

Figure 90:
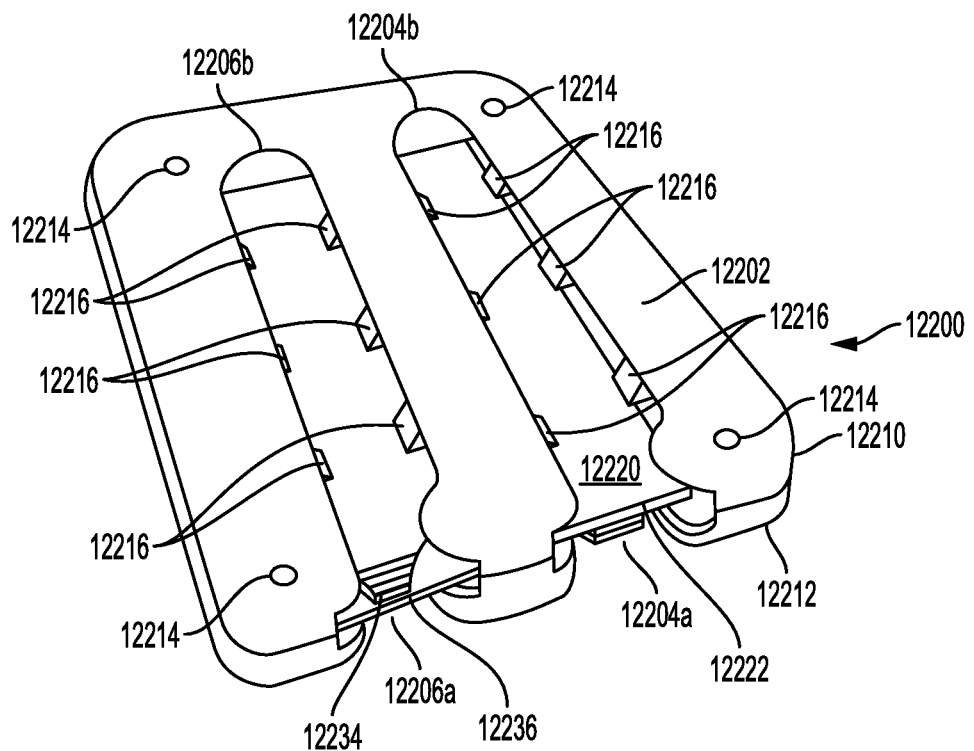
Figure 91:
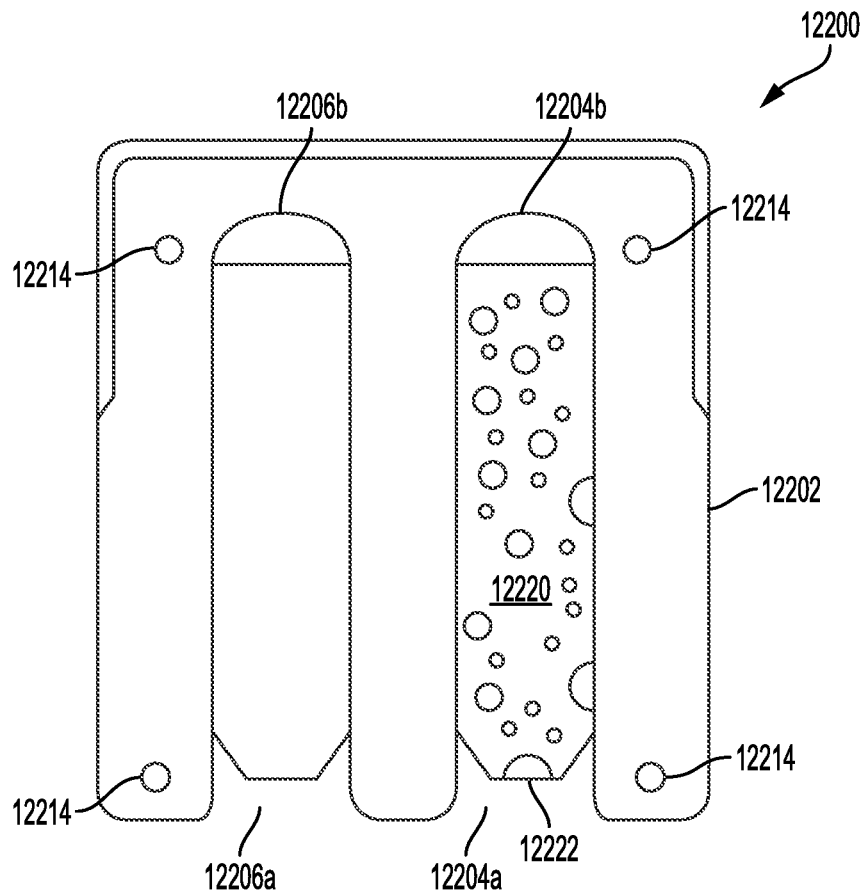
Figure 92:
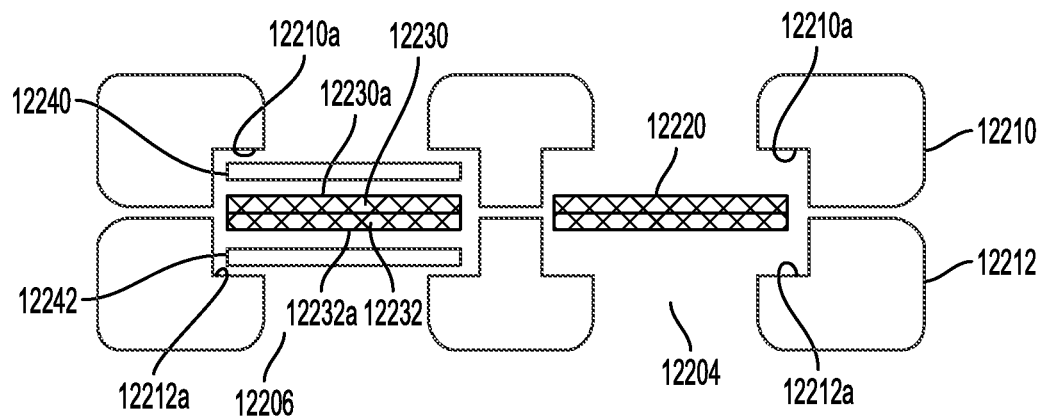

The adjunct loader 12100 illustrates an adjunct 12130 designed to be attached to only one side of a surgical stapler, but a variety of other configurations are possible. For example, FIGS. 90-92 illustrate an adjunct loader 12200 that is similar to the adjunct loader 12100 discussed above. The adjunct loader 12200 can have a frame 12202, a cleaning slot 12204, and a loading slot 12206. The frame 12202 can have an approximate M shape with a top portion 12210 and a bottom portion 12212. The top portion 12210 and the bottom portion 12212 can snap or clip together using, for example, posts 12214 that extend from one of the top or bottom portions 12210, 12212 and snap into the other of the top or bottom portions 12210, 12212. The frame 12202 can have the cleaning slot 12204 and the loading slot 12206 formed therein. The slots 12204, 12206 can take the form of longitudinal openings formed in the frame 12202 and can be sized and shaped to receive a linear end effector of a surgical stapler therein, such as the staplers 10, 50. The slots 12204, 12206 can extend parallel to each other and can have open ends 12204a, 12206a on one side of the frame 12202 and closed ends 12204b, 12206b on an opposite side of the frame 12202. The top portion 12210 and the bottom portion 12212 of the frame 12202 can have ledges 12210a, 12212a formed along the slots 12204, 12206 and configured to create a groove that extends along at least the longitudinal edges of the slots 12204, 12206 when the top portion 12210 and the bottom portion 12212 are snapped together. Each of the top portion 12210 and the bottom portion 12212 of the frame 12202 can have a plurality of fingers 12216 that extend into the slots 12204, 12206. The fingers 12216 can be configured to retain material between the top portion 12210 and the bottom portion 12212 within the slots 12204, 12206, as described above.

The cleaning slot 12204 can have a cleaning pad 12220, similar to cleaning pad 12120, that extends between the open end 12204a and the closed end 12204b of the cleaning slot 12204. The cleaning pad 12220 can have a rectangular shape and a tongue 12222 that extends from one end of the cleaning pad 12220 and into the open end 12204a of the cleaning slot 12204. The cleaning pad 12220 can be held between the top portion 12210 and the bottom portion 12212 of the frame 12202 by the plurality of fingers 12216 and/or other means described above and the groove formed by the ledges 12210a, 12212a. The cleaning pad 12220 can be made from an abrasive material with a cleaning solvent saturated therein and configured to remove adhesive from previous firings, tissue, oily residue, etc. The cleaning pad 12220 can be configured to have an end effector of a surgical stapler closed thereon and can be configured to clean both sides of the surgical stapler.

The loading slot 12206 can have a first and second adjunct 12230, 12232 similar to the adjunct 12130 discussed above. The first adjunct 12230 can be placed on top of the second adjunct 12232 in the loading slot 12206. The adjuncts 12230, 12232 can have rectangular shapes, and each adjunct 12230, 12232 can have a tongue 12234, 12236 that extends from one end of the adjunct 12230, 12232 adjacent the open end 12206a of the loading slot 12206. The adjuncts 12230, 12232 can extend between the open end 12206a and the closed end 12206b of the loading slot 12206. The adjuncts 12230, 12232 can be held between the top portion 12210 and the bottom portion 12212 of the frame 12202 by the plurality of fingers 12216 and the groove formed by the ledges 12210a, 12212a. In other embodiments, the adjunct can be configured to be secured to the loading slot in a variety of different ways. For example, these could include less adhesive or less-aggressive adhesive than on the device-contacting side of the adjunct, breakaway features that pull through holes in the adjunct, etc. The adjuncts 12230, 12232 can be configured to be released by the fingers 12216 upon application of a threshold force such that the adjuncts 12230, 12232 will be free from the adjunct loader 12200. The adjuncts 12230, 12232 can have a variety of configurations, as discussed above, and can have a variety of attachment mechanisms thereon, such as an adhesive. The adhesive can be spread on an outward-facing surface 12230a, 12232a of each of the adjuncts 12230, 12232 so that each of the surfaces 12230a, 12232a are configured to attach to a tissue-facing surface of a surgical stapler. For example, the surface 12230a of the first adjunct 12230 can be configured to adhere to an anvil of a surgical stapler, while the surface 12232a of the second adjunct 12232 can be configured to adhere to a cartridge of the same surgical stapler. A first cover 12240 can be disposed in the loading slot 12206 in contact with the first adjunct 12230. The first cover 12240 can be held between the top portion 12210 and the bottom portion 12212 of the frame 12202 and can cover the adhesive surface 12230a of the first adjunct 12230. A second cover 12242 can be disposed in the loading slot 12206 in contact with the second adjunct 12232. The second cover 12242 can be held between the top portion 12210 and the bottom portion 12212 of the frame 12202 and can cover the adhesive surface 12232a of the second adjunct 12232. The covers 12240, 12242 can be made from a variety of materials, such as compliant but non-porous materials, various plastics, etc. The covers 12240, 12242 can be configured to be manually removed, although a variety of different retraction options are possible, as discussed above.

In use, an end effector of a surgical stapler can first be clamped onto the cleaning pad 12220 in the cleaning slot 12204. While the jaws are clamped, the surgical stapler can be pulled away from the adjunct loader 12200. The cleaning pad 12220 can scrub and clean the tissue-facing surface of each jaw as it is removed. As the surgical stapler is pulled away from the adjunct loader 12200, the fingers 12216 will retain the cleaning pad 12220 in the cleaning slot 12204. A user can remove the first and second covers 12240, 12242 from the loading slot 12206, or they can retract automatically, exposing the adhesive sides 12230a, 12232a of the first and second adjuncts 12230, 12232. The user can clamp the surgical stapler onto the adjuncts 12230, 12232 such that the anvil of the surgical stapler closes on the adhesive side 12230a of the first adjunct 12230, and the cartridge of the surgical stapler closes on the adhesive side 12232a of the second adjunct 12230. Clamping can cause the fingers 12216 to deflect, such as retracting into the frame 12202. The first and second adjuncts 12230, 12232 will attach to the jaws, and the surgical stapler can be unclamped and pulled away from the adjunct loader 12200. This motion will cause the adjuncts 12230, 12232 to be pulled away as well, and the adjuncts 12230, 12232 can then be deployed in an operation.

Figure 93:
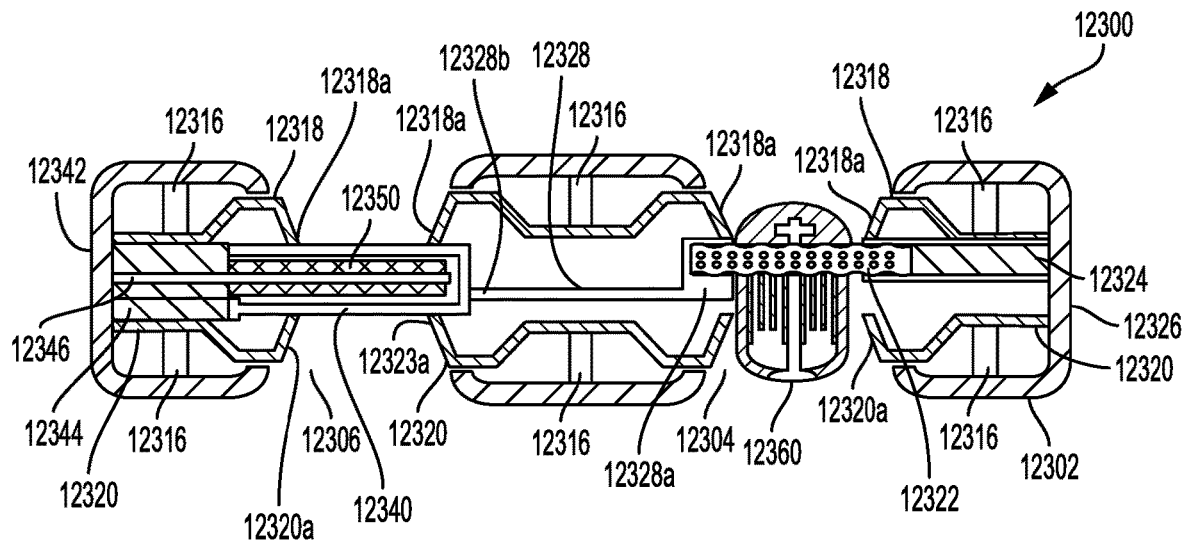
Figure 94:
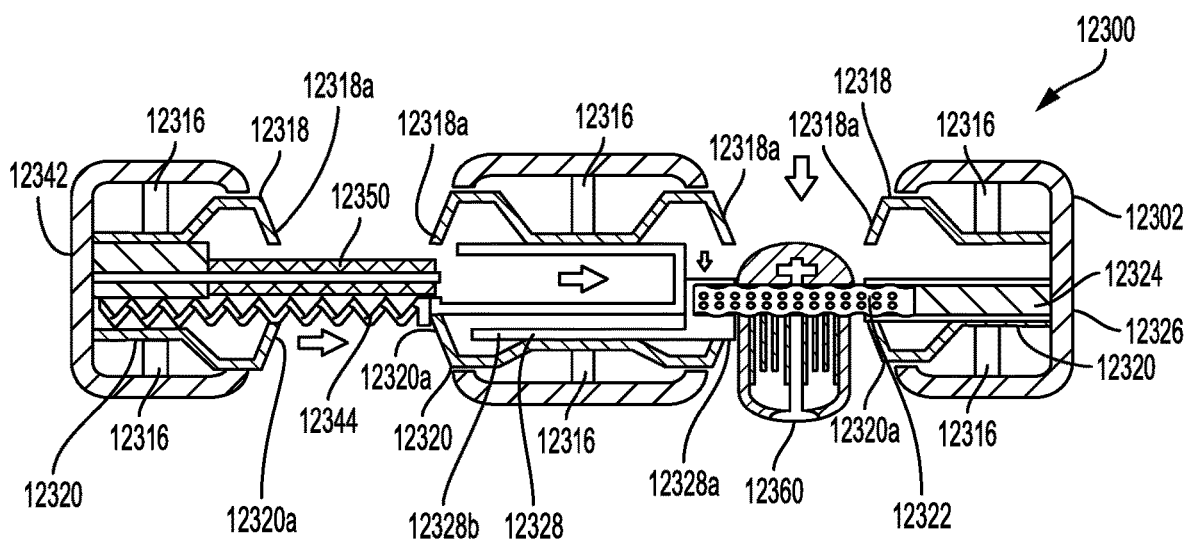

While the covers can be manually removed, covers in other embodiments can be automatically retracted upon clamping of a surgical stapler on the cleaning pad. For example, FIGS. 93-94 illustrate an adjunct loader 12300 similar to the adjunct loader 12200. The adjunct loader 12300 can have a frame 12302, a cleaning slot 12304, and a loading slot 12306. The frame 12302 can have an approximate M shape and can have internal support structures. For example, posts 12316 can extend inward from the frame 12302 to provide support to an upper internal framework 12318 and a lower internal framework 12320. The upper and lower internal framework 12318, 12320 can extend throughout an interior of the frame 12302 and be configured to provide support to material disposed within the slots 12304, 12306 and to facilitate receipt of the end effector. For example, the upper and lower internal framework 12318, 12320 can have angled ends 12318a, 12320a that extend at an angle into the slots 12304, 12306 to guide the jaws into the slots 12304, 12306. The slots 12304, 12306 can take the form of longitudinal openings formed in the frame 12302 and can be sized and shaped to receive a linear end effector of a surgical stapler therein, such as the staplers 10, 50. The slots 12304, 12306 can extend parallel to each other and can have open ends on one side of the frame 12302 and closed ends on an opposite side of the frame 12302.

The cleaning slot 12304 can have a cleaning pad 12322, similar to cleaning pad 12220, that extends between the open end 12304a and the closed end 12304b of the cleaning slot 12304. A cleaning support structure 12324 can be disposed in one of the outer legs of the M shaped frame 12302, extending between an external wall 12326 of the frame 12302 and the cleaning pad 12322, and it can be configured to hold a longitudinal edge of the cleaning pad 12322 in the cleaning slot 12304. On an opposite side of the cleaning pad 12322 and disposed within the inner leg of the M shaped frame 12302 is a movable lever 12328 that has an approximately L shaped cross-sectional shape. A first end 12328a holds a longitudinal edge of the cleaning pad 12322 opposite to the cleaning support structure 12324. The movable lever 12328 extends through an interior of the frame 12302 toward the loading slot 12306. A second end 12328b of the movable lever 12328 can be disposed in contact with an adjunct cover 12330. The cleaning support structure 12324 and the movable lever 12328 are configured to move up and down together within the frame 12302 and to be initially in contact with the angled ends 12318a that extend at an angle into the cleaning slot 12304.

The loading slot 12306 can have an adjunct 12350 similar to the adjunct 12230 that extends between the open end 12306a and the closed end 12306b of the loading slot 12306. A rectangular-shaped adjunct support 12346 can be disposed in one of the outer legs of the M shaped frame 12302 on the opposite side to the cleaning support structure 12324, extending from an external wall 12342 of the frame 12302 and into the loading slot 12306, and it can be configured to hold the adjunct 12350 in the loading slot 12306. A spring 12344 can be disposed between the external wall 12342 and the adjunct cover 12330 and inside the outer leg of the M shaped frame 12302 with the adjunct support 12346.

The cleaning pad 12322 can have a rectangular shape and a tongue that extends from one end of the cleaning pad 12322 adjacent the open end 12304a of the cleaning slot 12304. The cleaning pad 12322 can be held between the upper and lower internal framework 12318, 12320 and can be held in the cleaning slot 12304 initially against the angled ends 12318a. In one embodiment, the cleaning pad 12322 can be made from an abrasive material with a cleaning solvent saturated therein and configured to remove tissue and oily residue. The cleaning pad 12322 can be configured to have an end effector of a surgical stapler clamped thereon and it can be configured to clean one or both sides of the surgical stapler.

The adjunct 12350 can have first and second portions 12350a, 12350b similar to the adjuncts 12230, 12232. The first portion 12350a can be placed on top of the adjunct support 12346, and the second portion 12350b can be placed on bottom of the adjunct support 12346. The first and second portions 12350a, 12350b can have rectangular shapes, and each portion 12350a, 12350b can have a tongue that extends adjacent the open end 12306a of the loading slot 12306. The first and second portions 12350a, 12350b of the adjunct 12350 can extend between the open end 12306a and the closed end 12306b of the loading slot 12306. The adjunct 12350 can be held between the upper and lower internal framework 12318, 12320. The adjunct 12350 can have a variety of configurations, as discussed above, and can have a variety of attachment mechanisms thereon, such as an adhesive. The adhesive can be spread on an outward-facing surface of each of the first and second portions 12350a, 12350b so that each of the surfaces is configured to attach to a tissue-facing surface of a surgical stapler.

In this embodiment, the cross-sectional shape of the cover 12340 is U shaped with upper and lower horizontal sidewalls and a shorter vertical sidewall extending therebetween. The cover 12340 can be disposed in the loading slot 12306 such that it surrounds the adjunct 12350. Each of the upper and lower sidewalls of the U shaped cover 12340 can initially extend over the first and second portions 12350a, 12350b of the adjunct 12350 and can be configured to cover and protect the adjunct 12350 until use. The vertical sidewall of the U shaped cover 12340 can be disposed within the interior of the inner leg of the M shaped frame 12302 and can contact the second end 12328b of the lever arm 12328. Ends of the upper and lower sidewalls of the cover 12340 opposite the vertical sidewall can extend into the outer leg of the M shaped frame 12302 with the adjunct support 12346 and the spring 12344, and one of the ends of the upper and lower sidewalls of the cover 12340 can be disposed in contact with the spring 12344.

Initially, the cleaning pad 12322 can be held in an upper starting position in which the lever arm 12328 and the cleaning support structure 12324 support the cleaning pad 12322 and both contact the angled ends 12318a of the upper interior framework 12318. The second end 12328b of the lever arm 12328 can extend through the interior of the frame 12302 to the loading slot 12306 and can contact the cover 12340. The arm 12328 can act on the cover 12340 to force the cover toward the spring 12344, keeping the spring 12344 compressed between the cover 12340 and the outer wall 12342 and keeping the cover 12340 over the adjunct 12350. When a surgical stapler, such as the stapler 12360, clamps onto the cleaning pad 12322, the movement causes the cleaning pad 12322 to move downward. With movement of the cleaning pad 12322, the cleaning support structure 12324 and the lever arm 12328 both move downward as well. As they move downward, the second end 12328b of the lever arm 12328 moves out of contact with the cover 12340. As soon as the lever arm 12328 is no longer in contact with the cover 12340, the spring 12344 decompresses and forces the cover 12340 to move toward the cleaning slot 12304 and out of the loading slot 12306. The cover 12340 will come to rest in the inner leg of the M shaped frame 12302 with the lever arm 12328, leaving the adjunct 12350 uncovered, as shown in FIG. 94. The spring 12344 can be located at only a single point along the frame 12302, so the spring 12344 will not block access of a surgical stapler to either side of the adjunct 12350. In some embodiments, the spring can be anchor in a center position and can be held in a stretched state by the lever. When released, the spring can be configured to retract and pull the covers to the center position. In such embodiments, there is thus no concern with the spring being too off-center to pull the covers or be in the way of the adjuncts. After a user finishes cleaning the end effector of the surgical stapler 12360, the surgical stapler 12360 can be clamped onto the adjunct 12350 so that the first and second portions 12350a, 12350b will each attach to opposite sides of the surgical stapler 12360, as described above.

Figure 95:
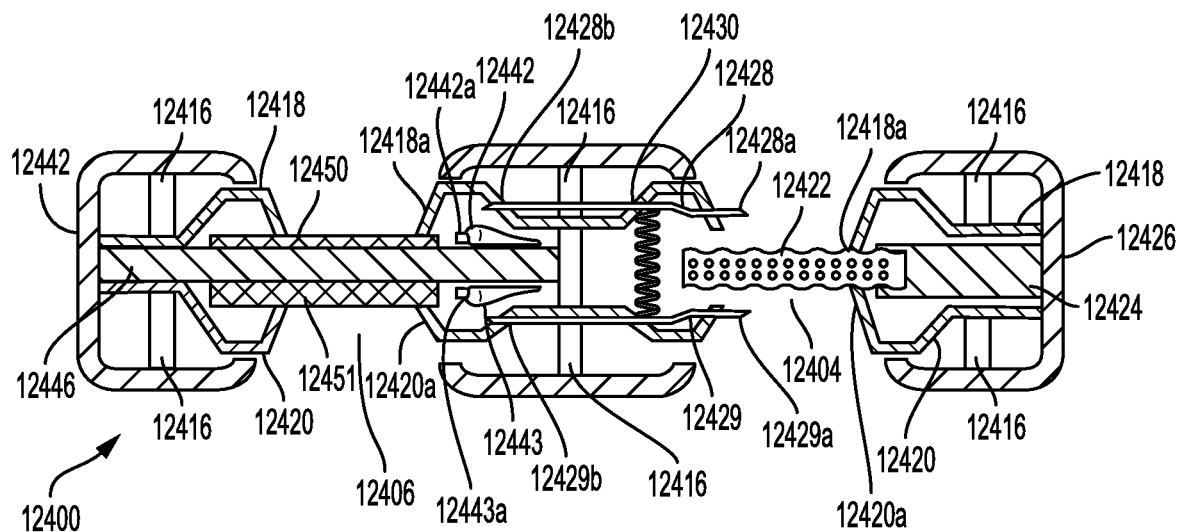
Figure 96:
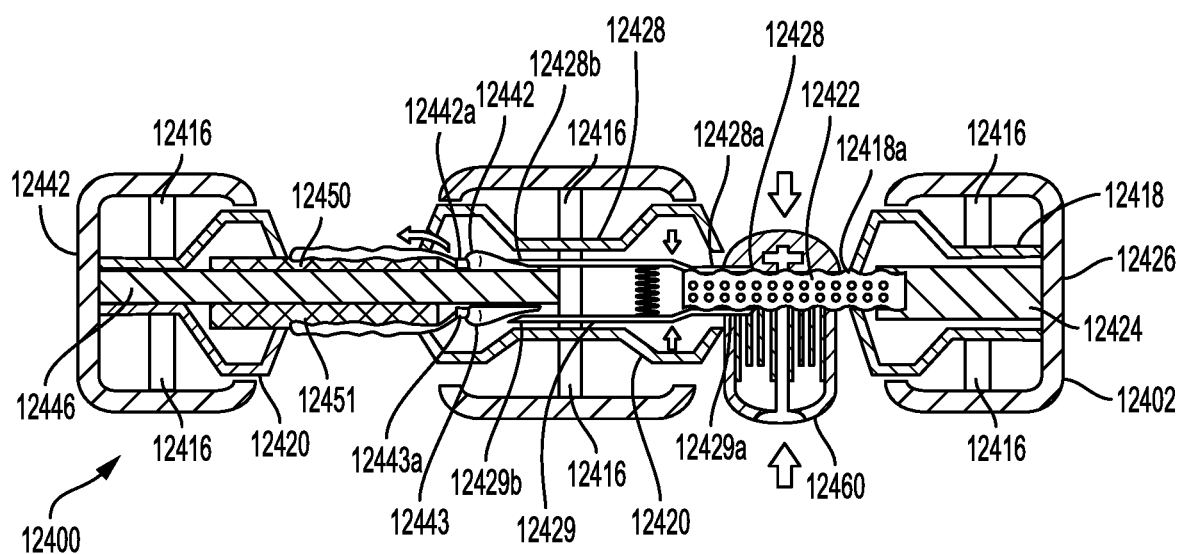

Some embodiments can lack covers while still protecting the adjunct from being disturbed before a user is ready to attach the adjunct to a stapler. For example, FIGS. 95-96 illustrate an adjunct loader 12400 similar to the adjunct loader 12300 but lacking a formal cover. The adjunct loader 12400 can have a frame 12402, a cleaning slot 12404, and a loading slot 12406. The frame 12402 can have an approximate M shape and can have internal support structures. For example, posts 12416 can extend inward from the frame 12402 to provide support to an upper internal framework 12418 and a lower internal framework 12420. The upper and lower internal framework 12418, 12420 can extend throughout an interior of the frame 12402 and can be configured to provide support to material disposed within the slots 12404, 12406. For example, the upper and lower internal framework 12418, 12420 can have angled ends 12418a, 12420a that extend at an angle into the slots 12404, 12406 for engaging adjunct or cleaning material, and for guiding jaws into the slots 12404, 12406. The cleaning slot 12404 and the loading slot 12406 can be formed in the frame 12402. The slots 12404, 12406 can take the form of longitudinal openings through the frame 12402 and can be sized and shaped to receive a linear end effector of the surgical stapler therein, such as the staplers 10, 50. The slots 12404, 12406 can extend parallel to each other and can have open ends on one side of the frame 12402 and closed ends on an opposite side of the frame 12402.

The cleaning slot 12404 can have a cleaning pad 12422, similar to cleaning pad 12322, that extends between the open end 12404a and the closed end 12404b of the cleaning slot 12404. A cleaning support structure 12424 is disposed in one of the outer legs of the M shaped frame 12402, extending between an external wall 12426 of the frame 12402 and the cleaning pad 12422, and it can be configured to hold a longitudinal edge of the cleaning pad 12422 in the cleaning slot 12404. Unlike cleaning support structure 12324, structure 12424 is immovable and is fixed in place. On an opposite side of the cleaning pad 12422 and disposed within the inner leg of the M shaped frame 12402 are upper and lower levers 12428, 12429. The levers 12428, 12429 each have a long, rectangular shape and an arm 12428a, 12428b that extends into the cleaning slot 12404. A spring 12430 is disposed between the levers 12428, 12429 and biases the levers 12428, 12429 away from each other such that the upper lever 12428 is configured to extend along the upper internal framework 12418 and the lower lever 12429 is configured to extend along the lower internal framework 12420 in an initial position. The levers 12428, 12429 extend through an interior of the frame 12402 toward the loading slot 12406. Second ends 12428b, 12429b of the upper and lower levers 12428, 12429 are disposed above and below, respectively, upper and lower applicators 12442, 12443 with nozzles 12442a, 12443a that face into the loading slot 12406. The upper and lower levers 12429, 12429 are configured to move up and down with application of force to the arms 12428a, 12429a that overcomes the spring force of spring 12430.

The loading slot 12406 can have upper and lower adjuncts 12450, 12451, similar to adjunct 12350, that extends between the open end 12406a and the closed end 12406b of the loading slot 12406. A rectangular-shaped adjunct support 12446 is disposed in one of the outer legs of the M shaped frame 12402 on the opposite side to the cleaning support structure 12424, extending from an external wall 12442 of the frame 12402 across the loading slot 12406 and terminating in the inner leg of the M shaped frame 12402, and it is configured to hold the adjuncts 12450, 12451 in the loading slot 12406.

The cleaning pad 12422 can have a rectangular shape and a tongue that extends from one end of the cleaning pad 12422 and adjacent the open end 12404a of the cleaning slot 12404. The cleaning pad 12422 can be held between the upper and lower internal framework 12418, 12420 and between the arms 12428a, 12429a of the upper and lower levers 12428, 12429. In one embodiment, the cleaning pad 12322 can be made from an abrasive material with a cleaning solvent saturated therein and configured to remove tissue and oily residue. The cleaning pad 12422 can be configured to have an end effector of a surgical stapler closed thereon and can be configured to clean one or both sides of the surgical stapler, such as the anvil side.

The upper adjunct 12450 can be placed on top of the adjunct support 12446, and the lower adjunct 12451 can be placed on bottom of the adjunct support 12446. The adjuncts 12450, 12451 can have rectangular shapes, and each one can have a tongue that extends adjacent the open end 12406a of the loading slot 12406. The adjuncts 12450, 12451 can extend between the open end 12406a and the closed end 12406b of the loading slot 12406. The adjuncts 12450, 12451 can be held between the upper and lower internal framework 12418, 12420. The adjuncts 12450, 12451 can have a variety of configurations, as discussed above, and can have a variety of attachment mechanisms. For example, the adjuncts 12450, 12451 can have no attachment mechanism thereon, and instead can be positioned adjacent to the upper and lower applicators 12442, 12443.

Initially, as shown in FIG. 95, the upper and lower arms 12428a, 12429a are expanded above and below the cleaning pad 12422. The second ends 12428b, 12429b can extend through the interior of the frame 12402 to the loading slot 12406 and are positioned above and below the upper and lower applicators 12442, 12443. The spring 12430 keeps the upper and lower levers 12429, 12429 in this expanded configuration. When a surgical stapler, such as the stapler 12460, clamps onto the cleaning pad 12422, the stapler 12460 clamps onto the arms 12428a, 12429a of the upper and lower levers 12428, 12429 and forces the arms 12428a, 12429a to move toward one another against resistance of the spring 12430. The compressing movement of the arms 12428a, 12429a cause the upper and lower levers 12428, 12429 to move toward one another, causing the ends 12428b, 12429b to also move toward one another. The ends 12428b, 12429b compress against the upper and lower applicators 12442, 12443, causing adhesive to squirt from the nozzles 12442a, 12443a that face into the loading slot 12406. An adhesive is thus applied to the outward facing surfaces of the adjuncts 12450, 12451. A person skilled in the art will appreciate that multiple applicators can be disposed along the entire length of each adjunct, as needed. After a user finishes cleaning the surgical stapler 12460, the surgical stapler 12460 can be clamped onto the upper and lower adjuncts 12450, 12451 with the newly applied adhesive so that the upper and lower adjuncts 12450, 12451 will each attach to opposite sides of the jaws of the surgical stapler 12460.

While the adhesive is applied in this embodiment, other application methods are possible. For example, in some embodiments a heat activated or softened adhesive can be applied to the adjunct. Clamping a surgical stapler onto a cleaning side of an adjunct loader can activate a heater within the loader that can heat and/or apply a heat activated or softened adhesive to the adjunct(s). For instance, the stapler can clamp onto the adjunct, causing the loading slot to sense the presence of the stapler and hold the end effector while heating PDS attachment points that affix adjuncts to one or both sides of the end effector. In such an embodiment, lights on the adjunct loader (such as green and red LEDs) can indicate when the adjunct(s) are attached and when the adjunct loader releases the end effector.

The adjunct loaders are not limited to horizontal configurations or manual cleaning and loading. For example, in some embodiments a box can be used with vertical slots. The first slot can have a cleaning system to clean the end effector, similar to the methods described above or incorporating a motor, solvents, scrub brushes, etc. Another slot could apply the adjunct, similar to the methods described above or by a motorized process. In other embodiments activation of the cleaning step could automatically trigger the loading step. In various embodiments, cleaning and loading can be disposed in separate housings.

End Effector with Adjunct Materials

An adjunct can be releasably retained on a jaw of an end effector for a surgical tool using various retaining or attachment features. In some implementations, the attachment feature can be disposed over the adjunct material and it can be releasably coupled to the jaw on which the adjunct is disposed. The adjunct material can be separated from the jaw in a suitable way. For example, the attachment feature retaining the adjunct on the jaw can be cut by a suitable cutting element (e.g., a knife) as the cutting element translates distally to cut tissue retained between the jaws. In some embodiments, when staples are ejected from staple-holding cavities of a cartridge, the staples cause the adjunct material to be separated from the jaw. For example, the force with which the staples are ejected can cause the adjunct material to be disengaged from the jaw. Additionally or alternatively, one or more portions of the attachment feature, or the entire attachment feature can be biodegradable and/or bioabsorbable, and the attachment feature or a portion thereof can therefore remain with the adjunct material when it is transferred to a treatment site in a patient.

In some implementations, an adjunct material is releasably retained on a jaw of an end effector using an attachment feature having a retaining filament. The retaining filament can have an intermediate portion and first and second ends disposed on opposed sides of the intermediate portion. Each of the first and second ends can have a respective end feature configured to mate with the jaw. To retain the adjunct material on the jaw, the attachment feature can be arranged such that at least a part of its intermediate portion is disposed over the adjunct material and such that the first and second ends are spaced apart. The first and second ends can be disposed on a side of the jaw opposed to the tissue-facing surface, and they can be spaced apart across a cutting element channel of the jaw. It should be appreciated that, the "first" and "second," as used herein in connection with the ends of the retaining filament or in connection with any other elements, features, or portions described herein, are used for the description purposed only, and not to indicate any particular order.

Figure 98:
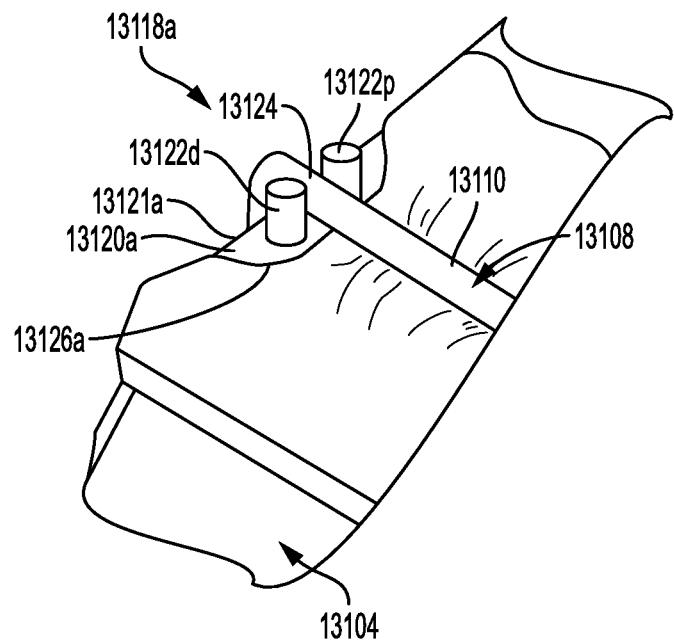

FIGS. 97-99 illustrate an implementation of an adjunct material 13100 releasably retained on a jaw of an end effector 13102 in accordance with the described techniques. The end effector 13102, shown only partially in FIG. 97, can be used with any suitable surgical instrument, for example, a linear surgical stapler (e.g., stapler 10 in FIG. 1, stapler 50 in FIG. 4, or any other surgical stapler) that is suitable for use with at least one adjunct. The end effector 13102 can be coupled to a distal end of a shaft of the surgical stapler (not shown). The jaw of the end effector 13102 is in the form of a cartridge body 13104 with a plurality of staple cavities configured to seat staples therein. The staple cavities, which are obscured by the adjunct material 13100 in FIG. 97, open on a tissue-facing surface 13106 of the cartridge body 13104. The cartridge body 13104 can be or can have a removable and replaceable cartridge retained therein, or, in some embodiments, the cartridge body 13104 can be part of a disposable loading unit removably coupled to an elongate shaft of a surgical instrument.

Although not shown in FIG. 97, the end effector 13102 also has an anvil opposing the cartridge body 13104, with a plurality of staple forming cavities formed on a tissue-facing surface thereof. It should be appreciated that the adjunct material 13100 is shown in FIG. 97 to be releasably retained on the jaw in the form of the cartridge body 13104 by way of example only, as an adjunct material can be retained in a similar manner on an anvil of an end effector as well.

As shown in FIG. 97, the adjunct material 13100 is retained on the cartridge body 13104 using an attachment feature in the form of an elongate retaining filament 13108. In this implementation, the retaining filament 13108 has an intermediate portion 13110 and first and second ends 13112a, 13112b disposed on opposed sides of the intermediate portion 13110, which are shown in FIG. 99. As shown in FIG. 97, the retaining filament 13108 is arranged on the cartridge body 13104 such that at least a part of the intermediate portion 13110 is disposed over the adjunct material 13100. The intermediate portion 13110 of the retaining filament 13108 also encompasses opposed sides walls of the cartridge body 13104, one of which, side wall 13105, is shown in FIG. 97.

In this implementation, the intermediate portion 13110 of the retaining filament 13108 extends over the side walls of the cartridge body 13104 such that the first and second ends 13112a, 13112b are spaced apart. In particular, the first and second ends 13112a, 13112b are disposed on a side 13116 (back side when the end effector's jaws are closed) of the cartridge body 13104 that is opposed to the tissue-facing surface 13106 thereof, as shown in FIG. 99. The first and second ends 13112a, 13112b can be spaced apart across a cutting element channel 13113 of the cartridge body 13104 extending longitudinally across a mid-portion of the cartridge body 13104.

At least a portion or the entirety of the retaining filament 13108 can be removably attached to the cartridge body 13104 in a variety of different ways. For example, in the illustrated embodiments, the retaining filament 13108 can be attached to the cartridge body 13104 using a hot-melt adhesive or any other suitable type of adhesive or glue material. The adhesive can be, for example, polydioxanone (PDO) that can function as an adhesive when heated. Additionally or alternatively, cyanoacrylates or UV curing adhesives can be used.

The retaining filament 13108 can be used to retain the adjunct material 13100 on the jaw 13104 using one or more suitable features that can be formed on the jaw and/or on the adjunct material. In the illustrated example, as shown in FIGS. 97 and 98, the cartridge body 13104 has retaining members 13118a, 13118b disposed at opposed sides 13120a, 13120b of the tissue-facing surface 13106 in proximity to the respective edges of the tissue-facing surface 13106. Each of the retaining members 13118a, 13118b can be in the form of a pair of adjacent posts, each of which is configured to engage at least a part of the intermediate portion 13110 of the retaining filament 13108. FIG. 98, showing the retaining member 13118a, illustrates a pair of adjacent posts 13122*d*, 13122*p* disposed on the side 13120*a* of the tissue-facing surface 13106 of the cartridge body 13104, in proximity to the edge 13121*a* of the tissue-facing surface 13106. The distance between the adjacent posts 13122*d*, 13122*p* is such that the posts 13122*d*, 13122*p* engage the part of the intermediate portion 13110, indicated in FIG. 98 as the part 13124 that extends between the posts 13122*d*, 13122*p*. The part 13124 of the retaining filament 13108 passing between the posts 13122*d*, 13122*p* can be engaged with the posts 13122*d*, 13122*p* via interference fit. As shown in FIG. 97, similar to the retaining member 13118*a* (FIG. 98), the retaining member 13118*b* formed on the opposite side 13120*b* of the tissue-facing surface 13106 can be in the form of a pair of adjacent posts.

In some embodiments, the posts in a pair of posts formed on the tissue-facing surface of the jaw can be spaced from one another such that they have a portion of the retaining filament (e.g., an intermediate portion) passing therethrough without being engaged between the posts. In this way, the posts ensure that the retaining filament is positioned as desired and prevent the retaining filament from sliding proximally or distally. Additionally or alternatively, the retaining filament can be retained over the jaw's surface using adhesive which can be used to couple one or more portions of the retaining filament to the jaw.

As shown in FIGS. 97 and 98, the posts 13122*d*, 13122*p* are disposed along the edge 13121*a* such that the post 13122*d* is more distal (e.g., closer to the distal end 13104*d* of the cartridge body 13104) than the adjacent post 13122*p*. Also, in the illustrated exemplary implementation, the posts 13122*d*, 13122*p* are offset by the same or substantially the same distance from the edge of the cartridge body 13104 such that the posts 13112*d*, 13112*p* are disposed along the same line parallel to a longitudinal axis 13A1 of the cartridge body 13104. It should be appreciated, however, that the posts 13122*d*, 13122*p* can be disposed on the tissue-facing surface 13106 in other ways. Moreover, more than two posts or other retaining elements can be formed on the tissue-facing surface 13106 for engaging the part of the intermediate portion 13110. Furthermore, in some embodiments, the retaining member can be in the form of a single element formed on the tissue-facing surface 13106, the single element having one or more prongs, arms, or other retaining elements configured to frictionally engage an attachment features therebetween. As another options, different types of retaining members can be formed on opposed sides of the tissue-facing surface of the jaw of an end effector.

The adjunct material 13100 releasably retained on the tissue-facing surface 13106 of the jaw 13104 can have a variety of different configurations. As shown in FIG. 97, the adjunct material 13100 is generally rectangular and it is sized such that its width is substantially the same as the width of the tissue-facing surface 13106. The length of the adjunct material 13100 can be greater than that of the tissue-facing surface 13106—as shown in FIG. 97, the adjunct 13100 extends distally beyond the tissue-facing surface 13106. This makes it possible to retain the adjunct 13100 using the retaining members 13118*a*, 13118*b* formed at close proximity to the distal end of the tissue-facing surface 13106.

The adjunct material 13100 can have features that facilitate its temporary engagement with the cartridge body 13104. Thus, as shown in FIGS. 97 and 98, the adjunct material 13100 has cut-outs 13126*a*, 13126*b* formed on opposite sides thereof such that the retaining members 13118*a*, 13118*b* are disposed within the cut-outs 13126*a*, 13126*b*, respectively.

In the illustrated implementation, the cartridge body 13104 can have, in addition to the retaining members 13118*a*, 13118*b*, other features that facilitate releasable attachment of the adjunct material 13100 to the cartridge body 13104. Thus, as shown in FIG. 99, the side 13116 of the cartridge body 13104 opposed to the tissue-facing surface 13106 has roughened portions 13130*a*, 13130*b* which the first and second ends 13112*a*, 13112*b* of the retaining filament 13108 engage frictionally. The first and second ends 13112*a*, 13112*b* can have end features in the form of flattened leaf portions or members 13114*a*, 13114*b* (or other types of end features) formed thereon that are configured to frictionally engage with the roughened portions 13130*a*, 13130*b*, respectively. FIG. 99 illustrates that the first and second ends 13112*a*, 13112*b* with the leaf members 13114*a*, 13114*b* are spaced apart across the cutting element channel 13113 of the cartridge body 13104.

The leaf portions can be formed in a variety of ways. For example, they can be pre-formed elements with a texture and/or surface features that allow them to engage the roughened portions. In some embodiments, however, the leaf portions can be formed by heat-pressing or otherwise processing end portions of the retaining filament to flatten them and thus form leaf-like ends. In such embodiments, the end portions of the retaining filament can be caused to deform and to be "pressed" onto the roughened portions. The heat pressing can be performed in a variety of ways, for example, by pressing the end portion of the retaining filament (which can be made from a thermoplastic material) into the roughened portions with a heated iron device so that the thermoplastic material is heated and cooled after mechanically "locking" into the roughened portions of the jaw.

The roughened portions 13130*a*, 13130*b* can be created in many different ways. In the illustrated implementation, they are formed by modifying a surface texture of a portion of the cartridge's side 13116. For example, the portions of the cartridge's side 13116 can be knurled or otherwise roughened to create the roughened portions 13130*a*, 13130*b* of a desired size at appropriate locations. FIG. 101 illustrates an example of a knurled or roughened portion 13140, which can be any of the roughened portions 13130*a*, 13130*b*. As shown in FIG. 101, the roughened portion 13140 has a regular pattern of small four-sided pyramids, though the regular pattern can be formed from elements of any other type(s). Also, the roughened portion 13140 can be an irregular rough portion configured to engage with a portion of an attachment feature, e.g., the first and second ends 13112*a*, 13112*b* with the leaf portions 13114*a*, 13114*b* or with otherwise shaped elements.

The roughened portions 13130*a*, 13130*b* can be created in any suitable manner. For example, they can be created by laser etching, chemically etching, heat altering (flame treated, heat pressed/stamped, etc.) or mechanically etching (grinding, sand blasting, $CO_2$ blasting, etc.) the surface of the jaw. In some implementations, the roughened portions 13130*a*, 13130*b* can be created by depositing certain materials (e.g., pressure-sensitive adhesives) over the surface of the cartridge body 13104, or by otherwise modifying the texture of a portion of the side 13116 of the cartridge body 13104.

Accordingly, in the example of FIGS. 97-99, a mid-portion of the intermediate portion 13110 of the retaining filament 13108 extends over the adjunct material 13100 and portions extending from both sides of the mid-portion encompass the opposed side walls of the cartridge body 13104 such that the spaced apart first and second ends 13112*a*, 13112*b* are disposed over the side 13116 opposed to the tissue-facing surface 13106. The adjunct material 13100 is releasably retained on the cartridge body 13104 using the pairs of the adjacent posts 13118*a*, 13118*b* and the roughened portions 13130*a*, 13130*b*.

The retaining filament 13108 can have any form and it can be made from any suitable materials. For example, it can be in the form of a suture, wire, cable, strap, or in any other form. It can be made from any suitable absorbable or non-absorbable polymers, examples of which include polyglactin, polyglycolic acid, catgut, polyglecaprone, polydioxanone, etc. Non-limiting examples of non-dissolvable suture materials include polypropylene, polyamide, polyester, silk, etc. In some embodiments, the retaining filament 13108 can be formed from at least partially resilient and/or pliable material such that it can be manipulated to conform to a shape of a body of a jaw which it partially encompasses.

The end features in the form of leaf members 13114*a*, 13114*b* formed on the first and second ends 13112*a*, 13112*b* of the retaining filament 13108, which can be formed integrally with the retaining filament 13108 or can be coupled to the retaining filament 13108 in a suitable manner, can also be formed from any suitable material(s), including the absorbable or non-absorbable polymers mentioned above. As mentioned above, each leaf member can be formed by pressing (e.g., heat-pressing) a portion of the retaining filament onto the jaw's surface. In some implementations, the leaf members 13114*a*, 13114*b*, or other members configured to engage the roughened portions 13130*a*, 13130*b*, can be made from a relatively rigid material. The leaf members 13114*a*, 13114*b* can have surface features (e.g., ridges, hooks, barbs, or any other protruding features) formed thereon that allow the leaf members 13114*a*, 13114*b* to frictionally and removably engage with the roughened portions 13130*a*, 13130*b*. Furthermore, in some embodiments, the leaf members 13114*a*, 13114*b* can be formed from at least partially magnetic material such that they can be magnetically retained on the roughened portions 13130*a*, 13130*b*. Also, in other embodiments, the leaf members 13114*a*, 13114*b* can be coupled to the roughened portions 13130*a*, 13130*b* using a polymer-based magnetic gels, or in other manner.

The roughened portions can be formed at any one or more portions of the jaw that can be engaged with a retaining filament. In the implementations described above, the roughened portions can be formed on a side that is opposite to a tissue-facing surface, such as an upper side of an anvil or a backside of a cartridge. In some implementations, additionally or alternatively, regardless of their configuration(s) and the way in which they are formed, one or more roughened portions can be formed on various others portions of a jaw of an end effector. For example, FIG. 100 shows an example of a jaw 13202 of an end effector having an adjunct material 13200 releasably retained thereon using an attachment feature. The attachment feature is in the form of a retaining filament 13201 engaged with roughened portions formed on opposed side walls of the jaw 13202. The engagement can be chemical (e.g., using an adhesive), frictional or other mechanical engagement, or any other type of engagement, including a combination of different ways. In some embodiments, a heat pressing approach can be used to allow mechanical interlocks of complementary matches of the surface geometry.

In this example, the jaw 13202 is in the form of a cartridge body which can be similar to the cartridge body 13104 in FIGS. 97-99. The adjunct material 13200, which can be similar to the adjunct material 13100 (FIGS. 97-99) is disposed on a tissue-facing surface 13206 of the jaw 13202. Similar to the adjunct material 13100, the adjunct material 13200 has cut-outs 13203*a*, 13203*b* formed in proximity to a distal end 13200*d* thereof on both long sides of the adjunct 13200.

As shown in FIG. 100, side walls of the cartridge body 13104 can be roughened, which can be done in a manner similar to a manner in which the roughened portions 13130*a*, 13130*b* are created on the cartridge body 13104. FIG. 100 illustrates that a portion of one of the side walls (13208) of the jaw 13202 is roughened to thus form a roughened portion 13210. A portion 13205 of the retaining filament 13201, encompassing the side wall of the jaw 13202, frictionally engages the roughened portion 13210 and thereby releasably retains the adjunct material 13200 on the jaw 13202. The opposite side of the jaw 13202, which is not shown in FIG. 100, can have similar roughened portion which the retaining filament 13201 encompassing that side wall frictionally engages. The jaw 13202 can also have one or more roughened portions on a side thereof that is opposed to its tissue-facing surface 13206, and such roughened portions can be similar to the roughened portions 13130*a*, 13130*b* of the jaw 13204 shown in FIG. 99. Also, although the jaw 13202 is shown without any other retaining features that can be used to temporarily engage the retaining filament 13201 with the jaw 13202, it should be appreciated that the jaw 13202 can have other retaining features. For example, the jaw 13202 can include retaining members similar to the retaining members 13118*a*, 13118*b* in the form of pairs of adjacent posts (FIGS. 97 and 98), roughened portions on the backside side of the jaw and/or any other retaining features.

FIG. 102 illustrates another implementation of retaining members formed on a jaw 13302 of an end effector having an adjunct material 13300 releasably retained thereon. In this example, a side 13304 (upper side) of the jaw 13302 that is opposite to a tissue-facing surface of the jaw 13302 is shown (e.g., the side 13116 of the jaw 13102 in FIG. 99). In FIG. 102, the jaw 13302 is in the form of an anvil. However, as a person skilled in the art will appreciate, an end effector's jaw having retaining members as described in connection with FIG. 102 can be a cartridge body.

The adjunct material 13300 is releasably retained on the jaw 13302 using an attachment feature in the form of a retaining filament 13301, portions of which are shown in FIG. 102. The retaining filament 13301 has an intermediate portion a part of which is disposed over the adjunct 13300 (not shown in FIG. 102) and other parts of which (e.g., 13303) encompass the jaw's side wall.

The retaining filament 13301 also has first and second ends 13305*a*, 13305*b* disposed on both sides of the intermediate portion adjacent to the parts of the retaining filament 13301 encompassing the side wall of the jaw 13302. In the example shown in FIG. 102, the first and second ends 13305*a*, 13305*b* are disposed on the upper side 13304 of the jaw 13302 and retained on that side via the respective retaining members. The retaining members are spindle-type retaining members 13306*a*, 13306*b* disposed on opposed sides of the surface of the jaw's side 13304 in proximity to the edges of the jaw 13302. Each of the spindle-type retaining members 13306*a*, 13306*b* is a generally cylindrical member having a relatively small diameter and height. For example, in at least one embodiment, the diameter of the retaining members 13306*a*, 13306*b* can be about 0.060 inches, and its height can be about 0.025 inches. Regardless of its size, each of the of the spindle-type retaining members

13306a, 13306b has a radial recess formed in the member's side wall around the entire circumference of the wall. Thus, FIG. 102 shows that the retaining members 13306a, 13306b have radial recesses 13308a, 13308b, respectively. The retaining members 13306a, 13306b also have respective holding notches or recesses 13310a, 13310b that are formed along each of the member's diameter on the top side of that member.

It should be appreciated that the spindle-type retaining members 13306a, 13306b are shown in FIG. 102 by way of example only, and that any other features can be used to couple the retaining filament to the jaw. For example, in some embodiments, the jaw (a cartridge or an anvil) can be configured to decrease in width so as to "grab" the filament. As another example, the jaw can have a groove with a cam feature, a post with an adjacent cam feature, or any other feature(s) configured to retain the retaining filament which can be a rope, wire, suture, thread, or any other element.

The radial recesses 13308a, 13308b and the holding recesses 13310a, 13310b are used to retain therein a portion of the at least one of the first and second ends 13305a, 13305b. In particular, as shown in FIG. 102, the retaining member 13306a has the first end 13305a of the retaining filament 13301 receiving within the radial recess 13308a such that the first end 13305a is wrapped around the retaining member 13306a. After the first end 13305a encircles the retaining member 13306a at least once, a portion of the first end 13305a is fittingly received through the top recess 13310a of the retaining member 13306a. In this way, the first end 13305a of the retaining filament 13301 engages with the retaining member 13306a.

The holding recesses 13310a, 13310b can have a configuration that facilitates retention of a portion of the retaining filament 13301. For example, the holding recess 13310b of the retaining member 13306b (shown in FIG. 102 free of the retaining filament for the illustration purposes only) has a first wider portion 13307 and a second, narrower portion 13309 extending from the first portion 13307. The holding recess 13310a of the retaining member 13306a is configured in a similar manner. In use, after a portion of the second end 13305b of the retaining filament 13301 is wrapped around the radial recess 13308b, the first portion 13307 receives therein another portion of the second end 13305b and this filament's portion is then received through the narrower portion 13309 of the holding recess 13310b so as to be fittingly retained therein. Thus, in use, the second end 13305b can be slightly stretched and passed through the holding recess 13310b so as to be retained within the recess. The first end 13305a is engaged with the holding recess 13310a in a similar manner and is shown in FIG. 102 as being wrapped around the radial recess 13308a and retained within the holding recess 13310a. In this way, both ends of the retaining filament 13301 are temporarily engaged with the jaw 13302.

As in the examples above, the retaining filament 13301 can be disengaged from the jaw 13302 when a knife or other cutting element traverses a cutting element channel 13313 and thereby cuts a portion of the retaining filament 13301 disposed over the adjunct material 13300. The rest of the retaining filament 13301 remains with the jaw 13302.

It should be appreciated that, regardless of the specific configurations of attachment features (e.g., retaining filaments or other features) described herein, jaw(s) of an end effector, the attachment features, and one or more adjunct materials are configured such that the jaw having one or more adjunct materials releasably retained thereon using one or more attachment features fits within a trocar. In some embodiments, one or more attachment features (e.g., posts or other features) can be formed at a bottom of one or more recesses formed in a jaw, such that the attachment features do not affect the overall size of the jaw. The adjunct material(s) are configured to be retained on the jaw in a manner that does not interfere with normal manipulations and operation of the jaw.

An adjunct material can be releasably retained on an end effector's jaw using various other types of attachment features in the form of a retaining filament. For example, in some implementations, an attachment feature has an intermediate portion and first and second ends with deformable elements. The deformable elements can be configured such that, when the attachment feature is disposed over an adjunct material placed on the jaw of an end effector, the deformable elements reversibly deform and change their configuration as they are received within openings or recesses in the jaw. When the deformable elements are engaged with the recesses in the jaw, they at least partially adopt their non-deformed configuration to thus retain the attachment feature in place.

FIGS. 103 and 104 illustrate an example of an adjunct material 13400 configured to be releasably retained on a jaw 13402 of an end effector using an attachment feature 13401. The attachment feature 13401 has an intermediate portion 13404 and first and second ends 13406a, 13406b. The intermediate portion 13404, in turn, includes a mid-portion 13408 and first and second arm portions 13410a, 13410b extending from opposite sides of the mid-portion 13408 and terminating at the first and second ends 13406a, 13406b. As shown in FIGS. 103 and 104, the first and second ends 13406a, 13406b have deformable elements 13412a, 13412b configured to be reversibly deform. In this example, the deformable elements 13412a, 13412b are in the form of t-shaped barb members. However, it should be appreciated that the deformable elements 13412a, 13412b can have any other suitable configurations. For example, they can be configured as Christmas tree-type, umbrella-like, or any other types of deformable elements configured to be used to retain an adjunct material on a jaw as discussed in more detail below.

The jaw 13402 can be configured in many different ways. In the example of FIGS. 103 and 104, the jaw 13402 is in the form of a cartridge body or cartridge having a plurality of staple cavities 13403 configured to seat staples therein, the staple cavities opening on a tissue-facing surface 13405 of the cartridge 13402. As shown in FIG. 103, the staple cavities 13403 form three rows on both sides of a cutting element channel 13407 extending through a mid-portion of the cartridge 13402 along a longitudinal axis 13A2 thereof. It should be appreciated, however, that any suitable number of the staple cavities 13403 can have any suitable pattern(s) on the tissue-facing surface 13405 of the jaw 13402, as the described embodiments are not limited in this respect.

The cartridge 13402 can have suitable features configured to retain an adjunct material thereon. As shown in FIGS. 103 and 104, the cartridge 13402 has a first pair of recesses 13414a, 13414b formed in the tissue-facing surface 13405 thereof. The recesses of the first pair of recesses 13414a, 13414b are spaced from opposed edges of the tissue-facing surface 13405 and are disposed on opposed sides of the cutting element channel 13407 extending centrally through the cartridge 13402 along the longitudinal axis 13A2 thereof. The first recesses 13414a, 13414b are formed on a distal portion 13405d of the tissue-facing surface 13405 that is free of the staple cavities, as shown in FIGS. 103 and 104. In some embodiments, however, the first recesses 13414a, 13414b can be formed within the area of the tissue-facing surface 13405 having the staple cavities formed thereon.

The first recesses 13414a, 13414b formed in the tissue-facing surface 13405 of the cartridge 13402 can have many different configurations. In this example, the first recesses 13414a, 13414b can have a generally oval cross-sectional shape and they can be sized to allow therewithin the first and second ends 13406a, 13406b with the deformable elements 13412a, 13412b. Although not shown in FIGS. 103 and 104, the inner walls of the first recesses 13414a, 13414b can have a configuration and size that allow the deformable elements 13412a, 13412b to be at least partially deform as they are received within the recesses 13414a, 13414b and to then return at least in part to their non-deformable configuration to thus be retained in the recesses 13414a, 13414b. Furthermore, in some implementations, the first recesses 13414a, 13414b can be formed through the entire thickness of the jaw 13402 such that the deformable elements 13412a, 13412b return at least in part to their non-deformable configuration on the side of the jaw 13402 that is opposed to the tissue-facing surface 13405 of the jaw 13402.

The adjunct material 13400 can have many different configurations. In the illustrated embodiment, the adjunct material 13400 is generally rectangular, with its width and length generally corresponding to the width and length of the tissue-facing surface 13405 of the cartridge 13402. In the illustrated example, the adjunct material 13400 has features configured to retain it on the cartridge 13402. In particular, the adjunct material 13400 has a second pair of through openings or recesses 13418a, 13418b formed therein. As shown schematically in FIGS. 103 and 104, the second recesses 13418a, 13418b are formed at locations in the adjunct material 13400 that correspond to the location of the first recesses 13414a, 13414b formed in the tissue-facing surface 13405 of the cartridge 13402. Each of the second recesses 13418a, 13418b can have a size that is similar to sizes of the first recesses 13414a, 13414b, or the size of each of the second recesses 13418a, 13418b can be slightly smaller than that of the first recesses 13414a, 13414b.

In use, when the adjunct material 13400 is disposed on the tissue-facing surface 13405 of the cartridge 13402, the adjunct's second recesses 13418a, 13418b align with the cartridge's first recesses 13414a, 13414b. In this way, the second recess 13418a is disposed above and communicates with the first recess 13414a, and the second recess 13418b is disposed above and communicates with the first recess 13414b. The retaining filament 13301 is manipulated to cause its first and second ends 13406a, 13406b to be pushed through the adjunct's second recesses 13418a, 13418b and then to be allowed within the second recesses 13418a, 13418b in the cartridge 13402. The mid-portion 13408 of the retaining filament 13301 is disposed over the adjunct 13400, as shown in FIG. 104. The first and second arm portions 13410a, 13410b extend through the thickness of the adjunct 13400 and can at least partially extend through the body of the cartridge 13402.

FIG. 103 shows the deformable elements 13412a, 13412b in their natural, non-deformed state. Thus, for example, in the non-deformed state or configuration of the element 13412b, its prongs 13413a, 13413b are perpendicular to a post 13415. The deformable elements 13412a, 13412b can be resiliently deformable such that, as they are passed through the second recesses 13418a, 13418b in the adjunct 13400, under the load applied thereto, they are caused to accept at least partially non-deformed state, e.g., the prongs 13413a, 13413b of the element 13412b come closer to its post 13415. In such at least partially unexpanded configuration, the elements 13412a, 13412b are then passed though the openings of the first recesses 13414a, 13414b in the jaw 13402, upon which the elements 13412a, 13412b return at least in part to their expanded configuration, to be retained within the first recesses 13414a, 13414b. Thus, in the example of the element 13412b, the prongs 13413a, 13413b move away from the post 13415 to form an acute angle with the post 13415 or to be disposed perpendicular thereto (if they fully return to the expanded configuration). In the implementations in which the first recesses 13414a, 13414b in the jaw 13402 are in the form of through openings, the deformable elements 13412a, 13412b can expand on the surface of the jaw opposite to the tissue-facing surface 13405 thereof. In this way, for example, the prongs 13413a, 13413b will be pressed against that surface of the jaw.

The adjunct material 13400 releasably retained on the cartridge 13402 can be separated from the cartridge 13402 in different ways. For example, a cutting element (e.g., a knife), as it translates through the cutting element channel 13407 formed centrally in the jaw 13402, can cut the retaining filament 13401 disposed, as shown in FIG. 104, above the channel 13407.

It should be appreciated that the cartridge 13102 can have other features for releasably retaining therein the adjunct material 13400. For example, in some embodiments, a proximal end 13405p of the tissue-facing surface 13405 can include retaining members similar to the first recesses 13414a, 13414b. In such embodiments, the adjunct material 13400 can also have openings similar to the second recesses 13418a, 13418b. Additionally or alternatively, other retaining features can be formed on the cartridge and/or on the adjunct.

In some embodiments, an end effector can have two separate adjunct materials releasably retained thereon. One ("first") of the separate adjunct materials can be configured to be disposed on one jaw of the end effector (e.g., a cartridge body), and another ("second") adjunct material can be configured to be disposed on another jaw of the end effector. The first and second adjunct materials have respective first and second mating features formed at proximal ends thereof. The end effector has an attachment feature formed at a proximal end thereof and configured to mate with at least one the first and second mating features of the first and second adjunct materials.

FIGS. 105 and 106 illustrate an implementation of an end effector 13500 having two separate adjunct materials releasably retained thereon. The end effector 13500 can have first and second jaws configured to clamp tissue therebetween, such as a jaw having a cartridge with a plurality of staple cavities configured to seat staples therein, and another, opposing jaw having an anvil with a plurality of staple forming cavities formed on a tissue-facing surface thereof. In this example, only a portion of the end effector 13500 in the form of a jaw having a cartridge body 13502 (also partially shown) is illustrated.

The end effector 13500 can be used with any suitable surgical instrument, for example, a linear surgical stapler (e.g., stapler 10 in FIG. 1, stapler 50 in FIG. 4, or any other surgical stapler) that is suitable for use with at least one adjunct material. The end effector 13500 can be coupled to a distal end of a shaft of the surgical stapler (not shown). The cartridge body 13502 has a plurality of staple cavities 13504 that are configured to seat staples therein and that open on a tissue-facing surface 13506 of the cartridge body 13502. The cartridge body 13502 can be in the form of a channel that removably and replaceably seats a cartridge therein, or the cartridge body 13502 with the staples can itself be a removable and replaceable unit. Also, in some embodiments, the cartridge body 13502 holding the staples can part of a disposable loading unit removably coupled to an elongate shaft of a surgical instrument.

As mentioned above, the end effector 13500 has first and second adjunct materials 13512, 13514 configured to be releasably coupled thereto. The end effector 13500 has an attachment feature configured to mate with the first and second adjunct materials 13512, 13514. Specifically, as shown in FIG. 105, the end effector 13500 has an attachment feature 13508 formed at a proximal end 13500p thereof. In this implementation, the attachment feature 13508 is coupled to a proximal end 13502 of the cartridge body 13502, though in other implementations of the present subject matter, the attachment feature 13508 can be coupled to an anvil or to element(s) of the end effector that are not part of the cartridge or the anvil.

Furthermore, in the described implementation, the attachment feature 13508 is in the form of a substantially cylindrical bar 13510 positioned above the tissue-contacting surface 13506 of the cartridge body 13502 and oriented so as to be transverse to a longitudinal axis 13A3 of the end effector 13500. The cylindrical bar 13510 is coupled to a support member 13511 so as to be positioned above the tissue-contacting surface 13506, as shown in FIG. 105. The cylindrical bar 13510 can be integrally and/or monolithically formed with the support member 13511, or it can be coupled to the support member 13511 in a suitable member.

The first adjunct material 13512 having proximal and distal ends 13512p, 13512d is configured to be releasably retained on one jaw of the end effector 13500, such as, in this example, the cartridge body 13502. The second adjunct material 13514 having proximal and distal ends 13514p, 13514d is configured to be releasably retained on another, opposed jaw of the end effector 13500, such as an anvil which is not shown. Each of the first and second adjunct materials 13512, 13514 has a respective mating feature at the proximal end 13512p, 13514p thereof for mating with the end effector's attachment feature 13508. In particular, as shown in FIG. 105, the first adjunct material 13512 has a first mating feature in the form of first open-ended loop features 13516a, 13516b. Each of the first open-ended loop features 13516a, 13516b includes an arm 13515a, 13515b and an open-ended loop 13517a, 13517b. As shown in FIG. 105, the open-ended loops 13517a, 13517b have their gaps or open ends on the top of the loops such that the open ends face away from the cartridge body 13502, in a direction substantially transverse to the longitudinal axis 13A3 of the end effector 13500 and towards the opposed jaw (not shown). As also shown in FIG. 105, the open-ended loop features 13516a, 13516b of the first adjunct material 13512 are formed on the proximal end 13512p such that they are spaced away from opposed edges 13513a, 13513b of the proximal end 13512p and are thus formed adjacent to one another and in proximity to a mid-portion of the proximal end 13512p.

The second adjunct material 13514 has a second mating feature in the form of second open-ended loop features 13518a, 13518b. Each of the second open-ended loop features 13518a, 13518b includes an arm 13521a, 13521b and an open-ended loop 13523a, 13523b. As shown in FIG. 105, the open-ended loops 13523a, 13523b have their gaps or open ends on the side of the loops such that the open ends face away from the cartridge body 13502, in a direction substantially parallel to the longitudinal axis 13A3 of the end effector 13500. The open-ended loop features 13518a, 13518b are formed on the proximal end 13514p of the second adjunct material 13514 such that they are adjacent to opposed edges 13519a, 13519b of the proximal end 13514p.

The configurations of the mating features of the first and second adjunct materials 13512, 13514 allow the mating features to mate with the attachment feature 13508 as shown in FIG. 106. The open-ended loops of the first and second open-ended loop features 13516a, 13516b, 13518a, 13518b have circumferences that are slightly undersized relative to cylindrical bar 13510 such that the open-ended loops can slightly deform to encompass the bar 13510. The first and second open-ended loop features 13516a, 13516b, 13518a, 13518b can be formed from at least partially resilient material such that the features can be snapped onto the bar 13510 through the gaps in the open-ended loops. The non-limiting examples of the materials include polymers such as, e.g., polydioxanone (PDO), poly(glycerol sebacate) (PGS)/poly(lactic acid) (PLA), poly(glycolic acid) (PGA)/polycaprolactone (PCL), trimethylene carbonate (TMC)/PGA, or any other suitable material or a combination of materials.

Further, the first and second open-ended loop features 13516a, 13516b, 13518a, 13518b are configured to engage the bar 13510 such that the first open-ended loop features 13516a, 13516b engage the bar 13510 at locations different from locations at which the second open-ended loop features 13518a, 13518b engage the bar 13510. In particular, as shown in FIG. 106, the first open-ended loop features 13516a, 13516b engage the bar 13510 at the locations on the bar 13510 between the locations at which the second open-ended loop features 13518a, 13518b engage the bar 13510. In this way, both the first and second open-ended loop features 13516a, 13516b, 13518a, 13518b movably engage the bar 13510 to thereby engage the separate first and second adjunct materials 13512, 13514 with the end effector 13500. In some embodiments, the open-ended loops can be segmented in such a way that the opposing sides are not directly opposite to one another. For example, the loops can be staggered.

In some implementations of the current subject matter, one or both of the first and second adjunct materials 13512, 13514 can have additional attachment features configured to releasably couple the adjunct materials 13512, 13514 with the respective opposed jaws of the end effector. For example, one or more portions of the second adjunct material 13514 configured to be disposed on the anvil can be releasably coupled to the anvil using an adhesive material. Other attachment features can be formed on the second adjunct material 13514 and/or on the anvil in addition to the second open-ended loop features 13518a, 13518b. Also, in some implementations, the first adjunct material 13512 can be coupled to the cartridge body 13502 using one or more additional attachment features.

FIG. 107 illustrates another embodiment of an end effector 13600 having first and second adjunct materials 13612, 13614 releasably coupled thereto via respective mating features. FIG. 107 shows only a portion of the end effector 13600, a cartridge body 13602, which is configured to releasably retain thereon the first adjunct material 13612. An opposed jaw, an anvil, which is not shown in FIG. 107, is configured to releasably retain thereon the second adjunct material 13614.

In this implementation, the cartridge body 13602 has the first adjunct material 13612 releasably coupled thereto. The first adjunct material 13612 has a size and shape complementary to a size and shape of a tissue-facing surface of the cartridge body 13602 (obscured by the adjunct material 13612), and the first adjunct material 13612 can be coupled to the cartridge body 13602 using adhesive material(s) or in other suitable ways.

In this embodiments, the first and second adjunct materials 13612, 13614 have respective mating features that are configured to couple (e.g., interlock) to one another to thereby couple the first and second adjunct materials 13612, 13614 to one another. Thus, the first adjunct material 13612 has a slot 13616 formed at a proximal end 13612p thereof. The second adjunct material 13614, which can have a size and shape complementary to a size and shape of a tissue-facing surface of the end effector's anvil (not shown), has a tab 13618 extending from a proximal end 13614p thereof and configured to be received within the slot 13616. FIG. 108 shows the tab 13618 of the second adjunct material 13614 mating with the slot 13616 of the first adjunct material 13612. The tab 13618 can have a length such that it engages with the slot 13616 to retain the second adjunct material 13614 in engagement with the first adjunct material 13612. Also, in use, the tab 13618, when engaged with the slot 13616, can operate as a tissue stop to prevent or reduce tissue from being displaced or leaked from the treatment site when the jaws of the end effector 13600 are grasping the tissue.

It should be appreciated that the slot 13616 in the first adjunct material 13612 and the tab 13618 in the second adjunct material 13614 are shown by way of example only, as the first and second adjunct materials 13612, 13614 can have any other mating features configured to couple with one another. In some embodiments, such mating features can be complementary to one another.

In some implementations, the first and second adjunct materials 13612, 13614 can be coupled to the respective jaws of the end effector 13600 using other additional features. For example, adhesive can be used to releasably couple the adjunct materials 13612, 13614 to the jaws. Any other attachment features can be used additionally or alternatively.

In some embodiments, attachment features can be formed on an adjunct material configured to be releasably disposed on a jaw of an end effector. These embodiments can be used in connection with end effectors having gripping features that extend from a shorter side of each staple pocket in a cartridge of the end effector. For example, the gripping features can be implemented in accordance with ECHELON™ Gripping Surface Technology such that each of the staple pockets has opposed extension features configured to provide a grip that holds tissue in place during firing.

FIGS. 109, 110A and 110B illustrate an embodiment of a cartridge 13700 of an end effector (not shown) having gripping extensions formed at staple pockets 13704 in a tissue-contacting surface 13702. As shown in FIGS. 109 and 110B, each staple pocket has extension features formed at opposite sides of the pocket along a longitudinal axis of the pocket. For example, a staple pocket 13706 has first and second extension features 13706a, 13706b formed at opposed sides of the pocket 13706 along a longitudinal axis thereof. Some or all of the other staple pockets can be configured in a similar manner. The extension features 13706a, 13706b of the staple pocket 13706 typically are formed integrally with the tissue-contacting surface 13702.

The extension features 13706a, 13706b of the staple pocket 13706 (as well as extension features of other staple pockets) can have any of a variety of configurations. For example, as shown in FIG. 110B, illustrating by way of example the staple pocket 13706 in cross-section, the extension features 13706a, 13706b can be in the form of slightly curved features that are also slightly inclined towards a mid-portion of the staple pocket 13706. It should be appreciated, however, that the extension features 13706a, 13706b can have any other configurations and that the described techniques are not limited to any particular type of extension features adjacent to staple pockets.

In the illustrated example, an adjunct material 13708 is configured to be releasably retained on the tissue-contacting surface 13702 of the cartridge 13700. The adjunct material 13708 can have a plurality of mating features for releasably mating with the cartridge 13700. In particular, in this implementation, the mating features are in the form of openings 13710 formed on the side 13712 of the adjunct material 13708 facing the tissue-contacting surface 13702. The openings 13710 are configured to mate with the extension features formed on the cartridge 13700. For example, openings 13710a, 13710b shown in FIG. 109 are configured to mate with the extension features 13706a, 13706b, respectively, such that the extension features 13706a, 13706b are received within the openings 13710a, 13710b. Thus, the openings 13710 can be configured to fit the extension features 13706a, 13706b therewithin, such that the size of the openings 13710 corresponds to the size of the extension features 13706a, 13706b. Also, the openings 13710 can be spaced from one another in accordance with a distance of the extension features 13706a, 13706b from one another, as discussed in more detail below.

The openings 13710 can be formed on the adjunct 13708 at predetermined locations such that each pair of openings (e.g., the openings 13710a, 13710b) is configured to be mated with corresponding extension features (e.g., the extension features 13706a, 13706b). The adjunct 13708 can have openings formed thereon that correspond to each of the staple pocket's extension features, or, in some embodiments, only some of the openings can mate with the extension features, and vice versa. In other words, the number of the openings may be different from the number of extension features.

The openings in the adjunct can be relatively small. For example, in at least one embodiment, they can have a diameter of about 0.010 inches, though the openings can have another diameter. In some implementations, the openings can be formed in the adjunct at certain distances from one another without taking into considerations specific pairs of extension features to mate with the pairs of openings. In such implementations, for example, when the adjunct is disposed over a cartridge and some force is applied thereto (e.g., the adjunct is pressed over a tissue-contacting surface of the cartridge), all or at least some of the openings will "find" extensions features to mate with, and vice versa. Thus, the adjunct can have multiple openings at a certain distance from one another (which can be smaller than a distance between the openings that are configured to mate with specific extension features) and at least some of these openings can mate with the extension features of the cartridge.

As mentioned above, in the example illustrated, the openings 13710 can be spaced from one another in accordance with a distance of the extension features 13706a, 13706b from one another. Furthermore, as in the example illustrated, the adjunct material 13708 can be made from at least partially stretchable material such that, when it is placed over the cartridge 13700 (which can be done with application of some force), one or more portions of the adjunct material 13708 can stretch. For example, the portions between at last some of the openings 13710 can stretch so that the openings at opposed sides of the portions are placed in positions for mating with respective extension features.

Thus, as illustrated in FIGS. 110A and 110B, before the adjunct 13708 is placed on the cartridge 13700, the openings 13710a, 13710b (as also shown in FIG. 109) are disposed at a distance 13d1 from one another. When the adjunct 13708 is caused into engagement with the cartridge 13700 when force is applied thereto (via a user's hand or using any removable applicator, frame, etc.), the adjunct 13708 is caused to stretch such that the openings 13710a, 13710b move further apart from one another, as shown by arrows 13714a, 13714b in FIG. 110B. In particular, the openings 13710a, 13710b become spaced apart at a distance 13d2 that is greater than the distance 13d1 (FIG. 110A), as shown in FIG. 110B. In this way, the openings 13710a, 13710b become disposed at the distance from one another that allows them to mate with the extension features 13706a, 13706b of the staple pocket 13706 having a staple 13707 ejectably disposed therein. When the adjunct 13708 is caused to engage the tissue-contacting surface 13702 of the cartridge 13700, portion(s) of the adjunct 13708, including the portion between the openings 13710a, 13710b can be displaced until one or both of the openings receives the corresponding extension feature therein. In other words, the adjunct 13708 can be stretched, until the openings 13710a, 13710b in the adjunct 13708 engage with the corresponding extension features 13706a, 13706b. Other openings in the adjunct engage the extension features in the cartridge in a similar manner, and the adjunct 13708 thus becomes releasably engaged with the cartridge 13700. In embodiments in which the number of openings in the adjunct is greater that the number of extension features, at least some of the openings can engage with the extension features in a similar manner.

End Effector Configured to Mate with Adjunct Materials

In some implementations, an adjunct material is configured to be releasably retained on a jaw of an end effector for a surgical instrument using complementary mating features formed on the jaw and on the adjunct. In particular, the adjunct material can have discrete or longitudinal projections formed thereon at least at distal and proximal ends of the adjunct material. The projections are configured to be received within the complementary recesses formed in a jaw of the end effector to thereby releasably mate the adjunct material with the jaw. In some embodiments, the end effector can include an attachment feature in the form of a polymer attachment layer that can be used to attach the adjunct material to the jaw.

Furthermore, the end effector includes a removable applicator member configured to apply force to the adjunct material to cause the adjunct material to be releasably retained on the jaw. The applicator member can be in the form of an applicator or retainer removably coupled to the end effector, or in the form of a frame-like applicator configured to releasably hold the adjunct material, or in other forms. Thus, in some implementations, in use, the applicator member is removably coupled to the end effector and used to apply force to the adjunct material (and in some embodiments to a polymer attachment layer) to cause the projections of the adjunct material (and in some embodiments projections formed on the polymer attachment layer) to be at least partially received within corresponding recesses formed in the jaw. In other implementations, a frame-like applicator member holding at least one adjunct material is clamped between the jaws of the end effector. In this way, force is applied to the applicator member, which causes the applicator member to release the at least one adjunct material and to transfer the at least one adjunct material to at least one respective jaw of the end effector. After use, the applicator member can be separated from the end effector.

The described techniques can also employ other ways and structures to releasably retain an adjunct material on at least one jaw of an end effector of a surgical instrument.

FIGS. 111-113B illustrate an example of an end effector 14100 configured to releasably retain an adjunct material on one or both of its first and second opposed jaws configured to clamp tissue therebetween, in accordance with the described techniques. The end effector 14100, partially illustrated in FIGS. 111 and 112, has a first jaw having a cartridge body 14102 and a second jaw having an anvil 14104. The cartridge body 14102 is configured to releasably retain thereon an implantable adjunct material 14106. The end effector 14100 can be coupled to a distal end of a shaft of the surgical instrument (not shown). The end effector 14100 can be used in any suitable surgical instrument, for example, a linear surgical stapler (e.g., stapler 10 in FIG. 1, stapler 50 in FIG. 4, or any other surgical stapler) which can be suitable for use with at least one adjunct.

As shown in FIG. 111, the cartridge body 14102 has a plurality of staple-holding cavities 14108 configured to seat staples therein, the staple-holding cavities 14108 opening on a tissue-facing surface 14110 of the cartridge 14102. The staple cavities 14108 form a certain pattern on the surface of the cartridge 14102 which corresponds to a pattern of staple-forming cavities (obscured in FIG. 111) formed in the anvil 14104. The cartridge body 14102, also referred to as a cartridge, includes a cutting element channel 14113 extending between distal and proximal ends 14102d, 14102p of the cartridge 14102. The knife channel 14113 is configured to receive a cutting element (e.g., a knife) as it moves distally therethrough. As shown in FIG. 111, the staple cavities 14108 can form three rows on both sides of the cutting element channel 14113, though it should be appreciated that the staple cavities 14108 can form any other patterns on the tissue-facing surface 14110.

The cartridge body 14102 can be in the form of a staple channel configured to support a staple cartridge, which can be removably and replaceably seated within the staple channel. Furthermore, in some embodiments, the cartridge 14102 can be part of a disposable loading unit coupled distally to a shaft of a surgical instrument.

The end effector 14100 has the implantable adjunct material (or "adjunct") releasably mounted on one or both of the cartridge 14102 and the anvil 14104. In the illustrated implementation, the adjunct material 14106 releasably retained on the cartridge 14102 is discussed, though it should be appreciated that the anvil 14104 can also have an adjunct material releasably retained thereon. As shown in FIGS. 111 and 112, the end effector also includes a loading member 14105 configured to apply force to the adjunct material 14106 to cause the adjunct material 14106 to be retained on the cartridge 14102, as discussed in more detail below. As also shown in FIGS. 111 and 112, and additionally illustrated in FIGS. 113A-113B, the end effector 14100 can further include a polymer attachment layer 14107 configured to be positioned between the cartridge 14102 and the adjunct material 14106, as also discussed in more detail below.

In the illustrated implementation, the cartridge 14102 can have at least one recess formed therein that opens on its tissue-facing surface 14110, with the at least one recess being configured to mate with a respective projection formed in the adjunct 14106. Thus, as shown in FIGS. 111 and 112, the cartridge 14102 has at least one first recess 14112*d* formed at the distal end 14102*d* thereof and at least one second recess 14112*p* formed at the proximal end 14102*p* thereof. In the example illustrated, some of the recesses are obscured by the adjunct 14106, and the at least one first recess 14112*d* is in the form of two recesses formed on opposite sides of the cutting element channel 14113. The at least one second recess 14112*p* is similarly in the form of two recesses formed on opposite sides of the cutting element channel 14113.

The recesses 14112*d*, 14112*p* formed in the cartridge 14102 can have a variety of different configurations. In the illustrated example, as shown in FIG. 111, each of the recesses is a discrete recess that has a generally circular top cross-section such that the recess is cylindrical. It should be appreciated, however, that the recesses in the end effector's jaw, such as the cartridge, can have other configurations. For example, the recesses can be square, rectangular, semicircular (e.g., having a semi-circular or oval shape as viewed from the top), and/or they can have any other suitable regular or irregular shapes. Regardless of their specific configuration(s), the recesses formed in the cartridge are configured to receive therein at least a portion of a respective projection formed on an adjunct material or another member, as discussed below.

As shown in FIG. 112, the adjunct material 14106 has projections that are complementary to the recesses 14112*d*, 14112*p* formed in the cartridge 14102 and that are configured to mate with the recesses 14112*d*, 14112*p* to retain the adjunct material 14106 on the cartridge 14102. In the illustrated embodiments, the adjunct material's projection(s) are disposed at least at proximal and distal ends of the adjunct material. In particular, as shown in FIG. 112, the adjunct material 14106 has at least one first projection 14116*d* formed at the distal end 14106*d* thereof and at least one second projection 14116*p* formed at the proximal end 14106*p* thereof. In the example illustrated, where some of the projections are obscured, the at least one first projection 14116*d* and the at least one second projection 14116*p* are each in the form of two respective projections.

The adjunct material 14106 can be formed from any suitable material or a combination of materials, which are discussed above. In some embodiments, the adjunct material 14106 can have a thickness from about 0.004 inches to about 0.160 inches. In some embodiments, the adjunct material 14106 can have a thickness from about 0.006 inches to about 0.008 inches. The projections 14116*d*, 14116*p* can have a height or thickness from about 0.005 to about 0.010 inches. In some embodiments, the projections, which can be formed from an elastomeric material, can have a height in a range from about 0.005 inches to about 0.015 inches, in a range from about 0.003 inches to about 0.006 inches, or a height that varies in other ranges. However, in some embodiments, the projections 14116*d*, 14116*p* can have a height or thickness up to about 0.180 inches or greater.

The locations of the first projections 14116*d* and the second projections 14116*p* formed on the adjunct material 14106 correspond to the locations of the first recesses 14112*d* and the second recesses 14112*p* formed on the cartridge 14102, respectively. However, in some embodiments, as discussed below, the first distal projections 14116*d* can be closer to one another than the first distal recesses 14112*d*, and similarly the second proximal projections 14116*p* can be closer to one another than the second proximal recesses 14112*d*. Furthermore, the configuration and size of the projections 14116*d*, 14116*p* corresponds to those of the recesses 14112*d*, 14112*p*. In this way, the projections 14116*d*, 14116*p* can be caused to be at least partially received within the recesses 14112*d*, 14112*p*, respectively.

For example, as shown in FIG. 111, the projections 14116*d*, 14116*p* configured to be at least partially received in the recesses 14112*d*, 14112*p* are complementary in shape to the recesses such that the projections 14116*d*, 14116*p* each have a generally circular top cross-section and are generally cylindrical. Furthermore, in the example of FIG. 111, the projections 14116*d*, 14116*p* are formed in the adjunct material 14106 such they have an open-end channel extending least partially therethrough that opens on a side 14121 of the adjunct material 14106 opposed to its side facing the cartridge 14102. For example, the projection 14116*d*, which can represent all of the projections formed on the adjunct material 14106, is shown to have a channel 14119 extending therethrough. The channel 14119 can be formed through the entire projection or through a portion thereof such that a recess can be formed on the side 14121. Moreover, in some implementations, the projections 14116*d*, 14116*p* formed in the adjunct material 14106 may not have a channel extending at least partially therethrough.

As mentioned above, in addition to the adjunct material 14106, the end effector 14100 of the illustrated implementation includes the polymer attachment layer 14107 used in conjunction with the adjunct material 14106. In particular, the polymer attachment layer 14107 is disposed between the cartridge 14102 and the adjunct material 14106, as shown in FIGS. 111 and 14112. The polymer attachment layer 14107, which can be made from a pressure-sensitive adhesive or other suitable material, is used as an attachment or retaining feature. For example, non-limiting examples of materials can include materials described in U.S. Pat. Pub. No. 2016/0278774 entitled "Method of Applying a Buttress to a Surgical Stapler," filed on Mar. 25, 2015, which is hereby incorporated by reference herein in its entirety. The polymer attachment layer 14107 is configured to hold the adjunct material 14106 in a releasable engagement with the cartridge 14102. Also, the polymer attachment layer 14107 can provide additional reinforcement to a treatment site. The polymer material 14107 can have a size that is the same or approximately the same to that of the adjunct material 14106 such the entire surface of the adjunct material 14106 is disposed on the polymer material 14107. The polymer layer may also serve as a reservoir for medicants such as antimicrobials, chemotherapeutic agents, etc. or be radiopaque for imaging purposes.

As shown in FIG. 112, the polymer attachment layer 14107 includes distal and proximal projections 14117*d*, 14117*p* facing the cartridge 14102. FIG. 112 also illustrates that the distal and proximal projections 14117*d*, 14117*p* are formed on the polymer material 14107 at locations corresponding to the locations of the adjunct's projections 14116*d*, 14116*p*, respectively. Thus, the distal projections 14117*d* can be spaced from the proximal projections 14117*p* along a longitudinal axis 14A1 of the polymer attachment layer 14107 by the same distance by which the distal projections 14116*d* are spaced from the proximal projections 14116*p*. The projections 14117*d*, 14117*p* can be configured similarly to the adjunct's projections 14116*d*, 14116*p*—for example, the projections 14117*d*, 14117*p* can each optionally have an open-end channel extending least partially therethrough (not shown).

Also, the distal and proximal projections 14117*d*, 14117*p* of the polymer attachment layer 14107 can have a length or diameter, as measured along the longitudinal axis 14A1, that is similar to that of a length or diameter of the distal and proximal projections 14116*d*, 14116*p* of the adjunct material 14106. In some embodiments, the polymer attachment layer 14107 can have a thickness from about 0.0005 inches to about 0.001 inches. The projections 14117d, 14117p can have a height or thickness from about 0.005 to about 0.010 inches. In some embodiments, the projections, which can be formed from an elastomeric material, can have a height in a range from about 0.005 inches to about 0.015 inches, in a range from about 0.003 inches to about 0.006 inches, or a height that varies in other ranges. However, in some embodiments, the projections 14116d, 14116p can have a height or thickness up to about 0.180 inches or greater.

The polymer attachment layer 14107 can be formed from any suitable material such as, for example, polydioxanone (PDO), PLA/PGA copolymers, or any other suitable polymeric material(s), including pressure sensitive adhesive(s). Thus, the adjunct material 14106 can be releasably engaged with the cartridge 14102 via the polymer attachment layer 14107. The polymer layer's projections 14117d, 14117p can be formed from the same material as the rest of the polymer attachment layer 14107. Also, in some embodiments, the distal and proximal projections 14117d, 14117p can be formed from a different material than the material forming the polymer attachment layer 14107. Because the material forming the polymer attachment layer 14107 is biodegradable and/or bioabsorbable, the polymer attachment layer 14107 can be implanted to a treatment site together with the adjunct 14106. It should be appreciated that, in some embodiments, the polymer attachment layer 14107 may not be present.

As mentioned above, the end effector 14100 can be removably coupled with the loading member 14105 having distal and proximal projections 14115d, 14115p and configured to apply force to the adjunct material 14106 to thereby cause the adjunct material 14106 to mate with the end effector 14100. In particular, the application of force by the loading member 14105 (and thus by the distal and proximal projections 14115d, 14115p thereof) to the adjunct material 14106 causes the adjunct material's projections 14116d, 14116p to be at least partially received in the recesses 14112d, 14112p of the cartridge 14102. Also, in embodiments such as in the example illustrated in which the polymer attachment layer 14107 is disposed between the adjunct material 14106 and the tissue-facing surface 14110 of the cartridge 14102, the application of force by the loading member 14105 to the adjunct material 14106 and thus to the polymer attachment layer 14107 causes the polymer layer's projections 14117d, 14117p to be at least partially received in the recesses 14112d, 14112p of the cartridge 14102. Furthermore, the adjunct material's projections 14116d, 14116p can be caused to be at least partially received within the polymer layer's projections 14117d, 14117p, respectively, as discussed below.

The distal and proximal projections 14115d, 14115p of the loading member 14105, each of which can be in the form of two respective projections, can be configured in a number of different ways. For example, the distal and proximal projections 14115d, 14115p can have a length (measured along a longitudinal axis 14A2 of the loading member 14105) that is similar to that of the adjunct material's projections 14116d, 14116p and the polymer layer's projections 14117d, 14117p. The distal and proximal projections 14115d, 14115p can have an open-end channel extending least partially therethrough and opening on a side of the loading member 14105 facing the anvil 14104, as shown in FIG. 111. However, in some implementations, one or more of the projections 14115d, 14115p may not include such channel.

Also, the distal and proximal projections 14115d, 14115p of the loading member 14105 can be spaced apart from one another along the longitudinal axis 14A2 by approximately the same distance as the adjunct material's projections 14116d, 14116p and the polymer layer's projections 14117d, 14117p. In some embodiments, however, the distal and proximal projections 14115d, 14115p of the loading member 14105 can be configured and/or formed on the loading member 14105 in a different way. Furthermore, in some implementations, the loading member 14105 may not include the distal and proximal projections 14115d, 14115p, or the loading member 14105 may include only one projection, or other number (e.g., more than two) projections of any suitable configurations.

The loading member 14105 can have a variety of different configurations. For example, the loading member 14105 can be in the form of an applicator or retainer that can be removably coupled to the end effector 14100. For example, in the illustrated implementation, as shown in FIGS. 111 and 112, the member 14105 is an elongate, generally rectangular component having a length and width generally corresponding to the length and width of the tissue-contacting surface of the cartridge 14102. The member 14105 also has a distal tongue portion 14120 in the form of a downward bent and a generally flat portion extending distally from the bend. The distal tongue portion 14120 can facilitate grip and can serve as a lever. In use, the surgeon can hold the distal tongue portion 14120 and apply force thereto in the direction towards the tissue-facing surface 14110 of the cartridge 14102 to thereby cause the member 14105 to apply load to the adjunct material 14106. The distal tongue portion 14120 can be grasped and moved (e.g., moved away from the cartridge body 14102) to remove the loading member 14105 from the end effector 14100.

Additionally or alternatively, the loading member 14105 can be "preloaded," or releasably coupled with, the adjunct material 14106 and the polymer attachment layer 14107 in a suitable manner. When force is applied to the adjunct material 14106, either by operating the loading member 14105, or when the loading member 14105 is clamped between the cartridge and anvil 14102, 14104, the adjunct material 14106, and the polymer attachment layer 14107 (if present) are transferred to the cartridge 14102. The loading member 14105 can then be removed from the end effector 14100.

The loading member 14105 can be coupled to the end effector 14100 in many different ways. In the illustrated example, the loading member 14105 is coupled to the proximal end 14102p of the cartridge 14102 using one or more suitable features. For example, the loading member 14105 can have at a proximal end 14105p thereof a tab 14118 (FIG. 112) configured to engage the proximal end 14102p of the cartridge body 14102. It should be appreciated, however, that any other suitable feature(s) can be used to removably couple the member 14105 to the cartridge body 14102. Furthermore, in some implementations, the loading member 14105 may not be coupled to the end effector 14100—e.g., as discussed above it can be clamped between the end effector's jaws to thereby cause the adjunct material 14106 (and the polymer attachment layer 14107, if present) to be transferred to the cartridge 14102.

In some embodiments, the adjunct material 14106 and the polymer attachment layer 14107 can be coupled to the loading member 14105 in a suitable manner before the adjunct material 14106 and the polymer attachment layer 14107 are delivered to the cartridge body 14102. Regardless of its configuration and the way in which it is used to cause the adjunct material to be releasably retained on a jaw of an end effector (e.g., the cartridge 14102), the loading member 14105 is configured to evenly apply force to the surface of the adjunct material 14106 such that the adjunct material 14106 becomes attached to the jaw.

In some embodiments, as mentioned above, projections of the adjunct material can be at least partially received within the projections the polymer layer. FIGS. 113A and 113B demonstrate such an example where first and second projections 14216a, 14216b of an adjunct material 14206 are at least partially received within first and second projections 14217a, 14217b of a polymer layer 14207. The adjunct material 14206 and the polymer layer 14207 can be similar, for example, to the adjunct material and polymer layer 14106, 14107 (FIGS. 111 and 112), respectively. It should be appreciated that. while FIGS. 111 and 112 illustrate the adjunct material's and polymer layer's distal and proximal projections, FIGS. 113A and 113C show, by way of example, only respective pairs of distal projections formed on the adjunct material 14206 and the polymer layer 14207. Thus, for example, the first and second projections 14216a, 14216b of the adjunct material 14206 can be similar to the at least one distal projection 14116d of the adjunct material 14106 in FIG. 112. It should be appreciated that the adjunct material 14206 and the polymer layer 14207 can also have respective proximal projections, similar, for example, to the at least one proximal projection 14116p and at least one proximal projection 14117p (FIG. 112), respectively.

As shown in FIG. 113A, the first and second projections 14216a, 14216b of the adjunct material 14206 extend from the top into the first and second projections 14217a, 14217b of the polymer layer 14207. The adjunct material 14206 and the polymer layer 14207 can be mated in this way in a number of different ways. For example, the adjunct material 14206 can be preloaded with the polymer layer 14207. Alternatively, the projections of the adjunct material 14206 can be mated with the projections of the polymer layer 14207 using the loading member or other component(s) configured to apply force to the adjunct material.

Regardless of the way in which the adjunct material 14206 is mated with the polymer layer 14207 so as to result in the structure as shown in FIG. 113A, such adjunct material/polymer layer structure can be caused (e.g., using the loading member 14105 or another suitable component) to be engaged with the jaw of an end effector. For example, FIG. 113B illustrates that force can be applied (shown by arrow 14210) to the adjunct material 14206 mated with the polymer layer 14207 to cause the first and second projections 14217a, 14217b of polymer layer 14207 (and thus the first and second projections 14216a, 14216b of the adjunct material 14206 mated therewith) to be engaged with corresponding first and second recesses 14212a, 14212b formed in a jaw 14202. The jaw 14202 can be a cartridge body (e.g., cartridge body 14102 in FIGS. 111 and 112). However, the jaw 14202 can also be an anvil, as the described techniques can be used to releasably retain an adjunct material on an anvil of the end effector as well.

A distance between the first and second recesses 14212a, 14212b formed in the jaw 14202 can be greater than a distance between the first and second projections 14217a, 14217b of polymer layer 14207 (and thus between the first and second projections 14216a, 14216b of the adjunct material 14206), prior to mating the polymer layer 14207 and the adjunct material 14206 with the jaw 14202. As a result of the force applied to the adjunct material 14206 mated with the polymer layer 14207, a distance between the first and second projections 14217a, 14217b (and thus between the first and second projections 14216a, 14216b) can increase, as shown in FIG. 113A by arrows 14211. In this way, as the force is applied to the adjunct material 14216 and its thickness thus decreases, the projections of the polymer layer 14207 and of the adjunct material 14206 "find" the first and second recesses 14212a, 14212b formed in the jaw 14202 to thereby releasably mate the adjunct material 14206 with the jaw 14202.

Projections formed on an adjunct material in accordance with the described embodiments can have various configurations. For example, in some embodiments, the projections can be longitudinal projections formed on opposed sides of the adjunct material. The longitudinal projections formed on the adjunct material can be configured to be mated with complementary features (e.g., recesses) formed on a jaw of an end effector.

FIGS. 114-116 illustrate an embodiment of an end effector 14300 having a cartridge 14302 and an anvil 14304, at least one of which can be configured to be releasably mated with an adjunct material having longitudinal projections. As shown in FIG. 114, the cartridge 14302 has a plurality of staple cavities 14308 configured to seat staples therein, the staple cavities formed on a tissue-facing surface 14310 of the cartridge 14302. The anvil 14304 of the end effector 14300, shown in FIG. 116, has a plurality of staple forming cavities (not shown) formed on a tissue-facing surface 14314 thereof.

In the illustrated implementation, the end effector 14300 can have an adjunct material releasably retained on one or both of the jaws 14302, 14304. Thus, as shown in FIG. 114, an adjunct material 14306 can be releasably mated with the cartridge 14302. The adjunct material 14306 has a first longitudinal projection 14316a formed on one side 14315a of the adjunct material 14306 and a second longitudinal projection 14316b formed on another, opposite side 14315b of the adjunct material 14306. As shown, the first and second longitudinal projections 14316a, 14316b extend between distal and proximal ends 14306d, 14306p of the adjunct material 14306.

The first and second longitudinal projections 14316a, 14316b of the adjunct material 14306 are configured to mate with respective first and second complementary recesses 14312a, 14312b formed in the tissue-facing surface 14310 of the cartridge 14302. As shown in FIG. 114, the first and second longitudinal recesses 14312a, 14312b extend along a longitudinal axis 14A3 of the cartridge 14302, are formed on opposed sides of a cutting element channel 14313, and are each adjacent to opposed sides 14311a, 14311b of the tissue-facing surface 14310.

The longitudinal projections 14316a, 14316b formed on the adjunct material 14306 can have a number of different configurations. For example, the first and second longitudinal projections 14316a, 14316b of the adjunct material 14306 have mating features 14318a, 14318b formed thereon that are configured to be at received within the corresponding recesses 14312a, 14312b. In this example, the mating features 14318a, 14318b are in the form of arrows facing towards the recesses 14312a, 14312b formed in the cartridge 14302.

The longitudinal projections 14316a, 14316b can be formed from at least partially flexible and/or deformable material such that, as the projections 14316a, 14316b are received within the corresponding recesses 14312a, 14312b, the projections 14316a, 14316b contract to fit into the recesses and, once in the recesses, expand to be fittingly received within the recesses. Thus, the arrow-shaped mating features 14318a, 14318b extending from the adjunct material's longitudinal projections 14316*a*, 14316*b* can have a width that is greater than that of the respective recesses 14312*a*, 14312*b*. When the mating features 14318*a*, 14318*b* are forced into the recesses 14312*a*, 14312*b*, they can first be caused to contract as they are forced into the recesses, where they then expand to be releasably retained therein. It should be appreciated that the arrow-shaped mating features 14318*a*, 14318*b* are shown by way of example only, and the mating features formed on the projections can have any suitable configuration. For example, the mating features can be C-shaped, J-shaped, or they can have any other configuration(s), including different configurations.

As shown in FIG. 116, an adjunct material 14320 configured to be releasably retained on the anvil 14304 can have first and second longitudinal projections 14322*a*, 14322*b*, which can be similar to the longitudinal projections 14316*a*, 14316*b* formed on the adjunct material 14306 configured to be releasably retained on the cartridge 14302. For example, similar to the cartridge 14302, the anvil 14304 can have longitudinal recesses formed therein that are configured to receive therein the longitudinal projections 14322*a*, 14322*b*.

One or both of the adjunct materials 14306, 14320 can be releasably retained on the jaws 14302, 14304, respectively, using an applicator member 14305 shown in FIG. 115. The applicator member 14305 can be in the form of a frame-like holder configured to releasably retain one or both of the adjunct materials 14306, 14320. In the illustrated example, the applicator member 14305 is in the form of first (e.g., bottom) and second (e.g., top) generally rectangular housings 14324, 14326 coupled to one another as shown in FIG. 115. As also shown in FIG. 115, the first and second housing 14324, 14326 can encompass edges of the long sides of the adjunct materials 14306, 14320 disposed within the applicator member 14305. In other words, the applicator member 14305 can be in the shape of a generally rectangular frame following an outer perimeter of at least two sides (e.g., long sides) of one or two adjunct materials. In particular, as shown in FIG. 115, the applicator member 14305 encompasses at least in part the portions of the adjunct materials 14306, 14320 having first and second longitudinal projections 14316*a*, 14316*b*, and 14322*a*, 14322*b*, respectively, extending therefrom. The rest of the surface area of the adjunct materials 14306, 14320 may be not encompassed by the applicator member 14305, as shown in FIG. 115. The adjunct material 14320 to be retained on the anvil is disposed over the adjunct material 14306 to be retained on the cartridge. It should be appreciated that the adjunct materials 14306, 14320 and the first and second housings 14324, 14326 of the applicator member 14305 encompassing them can be symmetrical. Thus, either of the adjunct materials 14306, 14320 can be applied to the anvil or the cartridge.

The applicator member 14305 can be formed from any suitable material (e.g., plastic), and its walls can be relatively thin and it can be disposable. In use, to transfer the adjunct materials 14306, 14320 to the cartridge and anvil 14302, 14304, respectively, the cartridge and anvil 14302, 14304 can be clamped over the applicator member 14305. In this way, force applied by the jaws 14302, 14304 causes the adjunct materials 14306, 14320 to separate from the applicator member 14305 and to be engaged with the jaws 14302, 14304. In particular, in this example, as force is applied to the applicator member 14305 by the jaws 14302, 14304 of the end effector 14300, the longitudinal projections 14316*a*, 14316*b* formed in the adjunct material 14306 mate with the recesses 14312*a*, 14312*b* in the cartridge 14302, and, similarly, the longitudinal projections 14322*a*, 14322*b* formed in the adjunct material 14320 mate with the complementary recesses (not shown) in the anvil 14304.

After the adjunct materials 14306, 14320 are transferred to the cartridge and anvil 14302, 14304, the cartridge and anvil 14302, 14304 can be opened and the applicator member 14305 can be separated from the end effector 14300. The end effector 14300 having its cartridge and anvil 14302, 14304 thus mated with the adjunct materials 14306, 14320, as shown in FIG. 116, can then be used as desired in a surgical procedure.

It should be appreciated that the applicator member 14305 is shown to releasably retain both of the adjunct materials 14306, 14320 by way of example only, as the applicator member 14305 or a similar component configured to releasably hold at least one adjunct material can be used to transfer an adjunct material only to an end effector's anvil or an end effector's cartridge.

In some embodiments, at least one projection formed on the adjunct material can be in the form of a plurality of discrete projections formed from an at least partially flowable or bendable material that has a changeable configuration. When a suitable applicator applies force to the adjunct material to cause each of the discrete projections to be at least partially received within a corresponding recess in a jaw of an end effector, the configuration of each of the discrete projections that is at least partially received within the corresponding recess changes to conform to a configuration of the corresponding recess. The discrete projections are configured to separate from the adjunct material and remain within the recesses in the jaw after the staples are formed against the staple forming cavities to apply the adjunct material to a tissue clamped between the end effector's jaws.

FIGS. 117-119 illustrate anther embodiment of an end effector 14400 having a cartridge 14402 and an anvil 14404, at least one of which can have an adjunct material releasably retained thereon that is has projections made from an at least partially flowable material. The projections can also be formed from at least partially bendable, free-flowing, or waxy materials. In other words, the material from which the projections are formed can be deformable in various ways. For example, they can be made from polymers/elastomers may deform or bend and still retain memory of their original shape.

In this example, as shown in FIG. 117, both the cartridge 14402 and the anvil 14404 can have respective adjunct materials 14406, 14420 to be releasably retained thereon. As shown in FIG. 117, the adjunct material 14406 releasably retained on a tissue-facing surface 14410 of the cartridge 14402 has a plurality of discrete projections 14416 configured to be releasably mated with recesses 14412 formed in the tissue-facing surface 14510. As shown in FIG. 117, the discrete projections 14416 are formed along a longitudinal axis 14A4 of the adjunct 14406. It should be appreciated that the projections 14416 and recesses 14412 do not need to be evenly spaced and, in some embodiments, they can be disposed at varied distances from one another. The locations and number of the projections 14416 and recesses 14412 can be selected based on a desired manner of attaching the adjunct material to the end effector's jaw. Accordingly, the seven evenly spaced projections 14416 are shown in FIG. 117 by way of example only, as suitable number of projections can be formed, and the projections can be formed asymmetrically and unevenly spaced with respect to one another.

The adjunct material 14420 releasably retained on a tissue-facing surface 14411 of the anvil 14402 also has a plurality of discrete projections 14421 configured to be releasably mated with recesses 14434 formed in the tissue-facing surface 14411. It should be appreciated that each of the discrete projections 14416, 14421 can be formed such that it spans the entirety of, or only a portion of, the width of the respective jaw. Also, in some implementations, each of the discrete projections 14416, 14421 can be in the form of two projections formed on opposed sides of the tissue-facing surface of the jaw, although only one of such projections is shown in FIG. 117.

In this example, the discrete projections 14416 formed on the adjunct material 14406 and the discrete projections 14421 formed on the adjunct material 14420 have a generally rectangular shape, as shown in FIG. 117 (where the projections of the anvil's adjunct material 14420 are shown partially separated from the anvil 14404). The discrete projections 14416, 14421 can be formed from an at least partially flowable material and can have a changeable configuration such that, when each of the discrete projections is at least partially received within a corresponding recess in the jaw, the configuration of each discrete projection changes to conform to a configuration of the corresponding recess. The at least partially flowable material can be any suitable material or a combination of materials. Examples of the materials can include a suitable polymeric material, elastomeric material (e.g., silicone), wax, and any other material(s). For example, collagen, gelatin hyaluronic acid, sodium alginate, or any other hydrogels can be used. Also, non-limiting examples of materials can include materials described in U.S. Pat. Pub. No. 2016/0278774 entitled "Method of Applying a Buttress to a Surgical Stapler," filed on Mar. 25, 2015, which is hereby incorporated by reference herein in its entirety.

In some embodiments, a more rigid polymer/elastomer can be used that can be perforated/slitted at the end, such that it frays outward into a T-slot pocket, rather than deforming in bulk, which would require a material with very low shear-resistance. In some embodiments, a material from which the adjunct is formed can be used to fill out the recess on its own. This may be possible with non-woven fabrics having fibers that areable to slide/shear relative to each other.

Accordingly, in the illustrated implementation, each of the generally rectangular projections 14421 formed on the adjunct material 14420 to be releasably retained on the anvil 14404, "flows" into, or conforms, to the configuration of each of the recesses 14434, as shown in FIG. 117. As also shown in FIG. 117, the projections 14416 of the adjunct 14406 (which can also be generally rectangular projections) "flow" into the T-shaped recesses 14412 formed in the cartridge 14402 to thus conform to the shape of the recesses 14412.

The adjunct materials 14406, 14420 can be transferred to the cartridge and anvil 14402, 14404 using an applicator member 14405 shown in FIG. 119, which can be similar to applicator member 14305 (FIG. 115). Thus, as shown in FIG. 119, the applicator member 14405 can be a frame-like holder having first and second portions 14424, 14426 releasably holding the adjunct materials 14406, 14420. To transfer the adjunct materials 14406, 14420 from the applicator member 14405 to the end effector 14400, the jaws 14402, 14404 can be clamped upon the applicator member 14405, which causes the adjunct materials 14406, 14420 to be mated with the cartridge and anvil 14402, 14404, respectively. In particular, as discussed above, the projections on the adjunct materials 14406, 14420 are received in the recesses 14412, 14434 in the cartridge and anvil 14402, 14404 so that the projections (which are formed from at least partially flowable material) change their configuration to fill in the recesses and thus adopt the shape of the recesses. Similar to the applicator member 14305 (FIG. 115), after the applicator member 14405 is used to transfer the adjunct materials 14406, 14420 to the end effector's jaws, the applicator member 14405 can be separated from the end effector 14400.

During a surgical procedure, as shown in FIG. 118, a tissue 14T is clamped between the cartridge 14402 and anvil 14404 of the end effector 14400 and staples 14409 are formed against the staple forming cavities of the anvil 14404. The ejection of the staples from the staple-holding cavities opening on the tissue-facing surface 14410 of the cartridge 14402 causes the adjunct materials 14406, 14420 to be released from engagement with the cartridge 14402 and anvil 14404 and to be applied to opposed sides of the tissue 14T, as also shown in FIG. 118. As further shown in FIG. 118, the discrete projections 14416, 14421 separate from the adjunct materials 14406, 14420 applied to the tissue 14T and remain within the recesses 14412, 14434, respectively. Such embodiments can be employed in implementations where, for example, the end effector 14400 is part of a disposable loading unit configured to be coupled distally to a surgical tool and that is configured to be disposed after use.

In some embodiments, an adjunct material configured to be releasably retained on a jaw of an end effector can be formed from at least partially expandable or stretchable material and/or in the form of a film. The jaw, such as an anvil or a cartridge, can have one or more recesses formed therein that are configured to receive portions of the adjunct material. An applicator member, such as, e.g., loading member 14305 in FIG. 115, applicator member 14405 in FIG. 119, or a member having any other configuration that has projections formed thereon, can be used to mate the adjunct material with the jaw. For example, when the applicator member is used to apply force to the adjunct material, the projections formed on the applicator member cause portions of the adjunct material to be releasably received within the one or more recesses formed in the jaw.

FIGS. 120-122 illustrate one example of an implementation of an adjunct material 14506 configured to be mated with a jaw 14500 of an end effector of a surgical instrument. In this example, the jaw 14500 is shown generally as a jaw that can be either a cartridge or an anvil. Regardless of its particular configuration, the jaw 14500 can have recesses 14503 formed in a tissue-facing surface 14510 thereof. It should be appreciated that the recesses 14503 can be formed at any locations within tissue-facing surface 14510. Also, the six recesses 14503 are shown in FIG. 120 for illustrating purposes only, as any suitable number of recesses 14503 (e.g., less than six or greater than six) can be formed on the jaw. Also, the recesses 14503 do not need to be evenly spaced and, in some embodiments, they can be disposed at varied distances from one another. The locations and number of the recesses 14503 can be selected based on a desired manner of attaching the adjunct material to the end effector's jaw.

For example, the recesses 14503 can be formed in the area of the tissue-facing surface 14510 occupied by staple-forming cavities (if the jaw 14500 is an anvil) or by staple-holding cavities or pockets (if the jaw 14500 is a cartridge). As another example, one or more of the recesses 14503 can be formed in area(s) of the tissue-facing surface 14510 that does not have the staple-forming cavities or the staple-holding pockets. For example, in one embodiment, one or more recesses can be formed at a distal end of the jaw 14500 outside of the area having the staple-forming cavities or the staple-holding pockets, and one or more recesses can be formed at a proximal end of the jaw 14500 outside of the area having the staple-forming cavities or the staple-holding pockets. Furthermore, in some implementations, one or more of the recesses 14503 can be the staple-forming cavities or the staple-holding pockets.

The recesses 14503 are shown by way of example only as having a generally circular cross-section. However, the recesses 14503 can have other suitable shapes, as the described embodiments are not limited in this respect. One or more of the recesses 14503 can have features that facilitate their ability to retain a portion of the adjunct material therein. For example, as shown in FIG. 121, the recess 14503 can have retaining features 14512a, 14512b that can be in the form of hooks, teeth, rings, barbs, or retaining elements having any other configuration. It should be appreciated that one or more of the retaining features can be formed, or the recesses 14503 can be free of any additional features.

Regardless of the way in which the recesses 14503 are formed in the jaw 14500, each recess (e.g., the recess 14503 shown in FIG. 121) is configured to receive therein a corresponding projection or post 14515 formed on an applicator member 14505. The applicator member 14505, having one or more posts (one of which is shown in FIGS. 121 and 122), can have any suitable configuration that enables force to be applied by the applicator member 14505 to the adjunct material 14506. As mentioned above, the adjunct material 14506 can be formed from an at least partially stretchable material. Thus, as shown in FIG. 122, when force is applied by or to the applicator member 14505 (as shown by arrow 14511), the applicator member 14505 is brought in proximity to the tissue-facing surface 14510 such that the post 14515 is at least partially received within the recess 14503. As a result, the post 14515 pushes a portion 14508 of the adjunct material 14506 into the recess 14503, as also shown in FIG. 122. In this example, the retaining features 14512a, 14512b extending from the inner walls of the recess 14503 facilitate retention of the portion 14508 of the adjunct material 14506 within the recess 14503.

Other recesses formed in the jaw 14500 can similarly receive at least partially therein posts formed on the applicator member 14505 that thus push portions of the adjunct material 14506 into the recesses. In this way, the adjunct material 14506 becomes releasably mated with the jaw 14500.

The number and locations of the posts, such as the post 14515, formed on the applicator member 14505 can correspond to those of the recesses 14503 in the jaw 14500. Thus, each of the recesses 14503 can receive therein a portion of the adjunct material pushed into the recess using a corresponding post. In other implementations, however, only some of the recesses can receive corresponding posts therein.

The post 14515, representing just one example of the multiple posts that can extend from the applicator member 14505, is shown as a generally cylindrical element by way of example only, as the post 14515 can have other configurations. For example, the post 14515 can be mushroom-shaped (e.g., shaped as a "reversed mushroom") or it can have a generally rectangular, square, or otherwise shaped cross-section. The size of the post 14515 can be selected such that it fits with clearance within the recess 14503 and pushes the portion 14508 of the adjunct material 14506 into the recess 14503 in a manner that allows retaining that portion 14508 in the recess 14503, as shown in FIG. 122. The portion 14508 can be retained in the recess 14503 using the retaining features 14512a, 14512b as shown in FIGS. 121 and 122, or any other type(s) of retaining features.

After the adjunct material 14506 is mated with the jaw 14500 using the applicator member 14505, the applicator member 14505 is removed, whereas the adjunct material portion 14508 remains in the recess 14503. When the adjunct material 14506 is separated from the jaw 14500 to be transferred to a tissue at a treatment site (e.g., when staples are ejected from the jaw's cartridge), the adjunct material portion 14508 is caused to exit the recess 14503.

In the illustrated example, the adjunct material 14506, which can be in the form or a film and/or at least partially stretchable member, can be generally rectangular or it can have other configurations. The size of the adjunct material 14506 can be such that, when its portions (e.g., the portion 14508 in FIGS. 121 and 122) are mated with the jaw 14500, the adjunct material 14506 still covers a desired area of the tissue-facing surface 14510 of the jaw 14500. In other words, the adjunct material 14506 can be oversized relative to a size of the tissue-facing surface 14510 of the jaw 14500. Also, even though some extra material becomes available after the adjunct material's portions are released from the recesses in the jaw, this does not affect the ability of the adjunct material 14506 to reinforce and/or treat a site in a patient's body.

In some embodiments, an adjunct material can be releasably retained on a jaw of an end effector using a material that can change its configuration when heat is applied thereto. FIGS. 123 and 124 illustrate an embodiment of an end effector 14600 having a cartridge body 14602 and an anvil 14604, which can have an adjunct material 14606 configured to be retained on at least one of the cartridge body and anvil 14602, 14604 using an attachment layer 14607. In particular, in the example illustrated, the attachment layer 14607 can be used to couple the adjunct material 14606 to the cartridge body 14602, as discussed in more detail below.

As shown in FIG. 123, a tissue-facing surface 14610 of the cartridge body 14602 can have recesses 14612a, 14612b disposed outside of the area of the cartridge body 14602 having staple-holding pockets 14608. The two recesses 14612a, 14612b formed at a distal end 14602d of the cartridge body 14602 are shown, and a proximal end 14602p of the cartridge body 14602 can have a similar pair of recesses. The recesses 14612a, 14612b are disposed at opposed sides of a cutting-element channel 14613 in the cartridge body 14602, though the recesses 14612a, 14612b can be disposed at other areas of the tissue-facing surface 14610 of the cartridge body 14602.

As shown in FIG. 123, the adjunct material 14606 can have retaining features 14616a, 14616b formed at a distal end 14606d thereof, and similar retaining features 14616c, 14616d formed at a proximal end 14606p thereof. In the illustrated implementation, the retaining features 14616a, 14616b, 14616c, 14616d are in the form of cupcake-like depressions in the adjunct material 14606 extending towards the cartridge body 14602 and opening on a side of the adjunct material 14606 opposite to its side facing the cartridge body 14602. It should be appreciated, however, that the retaining features 14616a, 14616b, 14616c, 14616d can have any other shapes, and that the number of the retaining features can be different from four (e.g., less than four or greater than four). Furthermore, as in the example illustrated, the retaining features 14616a, 14616b, 14616c, 14616d can be formed as closed depressions in the adjunct material 14606, or they can be open-ended features opening into the cartridge's recesses when the adjunct is mated therewith.

The distal retaining features 14616a, 14616b are configured to be received within the distal recesses 14612a, 14612b in the cartridge body 14602. In a similar manner, the proximal retaining features 14616c, 14616d of the adjunct material 14606 are configured to be received within the proximal recesses formed in the cartridge body 14602, which are obscured in FIG. 123.

The attachment layer 14607, which can be formed from a suitable heat meltable material, can be used to attach the adjunct material 14606 to the cartridge body 14602. For example, to releasably attach the adjunct material 14606 to the cartridge body 14602, the adjunct material 14606, which can have the attachment layer 14607 coupled thereto in a suitable manner, can be disposed on the tissue-facing surface 14610 of the cartridge body 14602. The attachment layer 14607 can be coupled to the adjunct material 14606 or it can be disposed over the adjunct material 14606 such that the adjunct material 14606 is located between the tissue-facing surface 14610 of the cartridge body 14602 and the attachment layer 14607. Regardless of the way in which the attachment layer 14607 is associated with the adjunct material 14606, the adjunct material 14606 is disposed over the cartridge body 14602 such that the retaining features 14616a, 14616b, 14616c, 14616d are received within the respective recesses formed in the cartridge body 14602. For example, the retaining features 14616a, 14616b are received within the recesses 14612a, 14612b.

A suitable device can then be used to apply heat to the attachment layer 14607 such that at least some of its portions melt and the attachment layer's material flows into the retaining features 14616a, 14616b, 14616c, 14616d in the adjunct material 14606 that, in turn, at least partially seat within respective recesses formed in the cartridge body 14602. In this way, the material of the attachment layer 14607 deposited within each of the retaining features 14616a, 14616b, 14616c, 14616d of the adjunct material 14606 mates the adjunct material 14606 with the cartridge body 14602. FIG. 124 illustrates by way of example a recess 14612' in the cartridge body 14602, which can be representative of any of the recesses (e.g., 14612a, 14612b or others) that can be formed in the cartridge body 14602. As shown in FIG. 124, the recess 14612' can seat therein a respective retaining feature 14616' (e.g., any of the retaining features 14616a, 14616b, 14616c, 14616d) that in turn, is lined with the material of the attachment layer 14607.

The attachment layer 14607 can be formed from any suitable bioabsorbable and/or biodegradable material. Non-limiting examples of the material include polydioxanone (PDO), lactide/glycolide copolymers, poly-L-lactide, poly-L-lactide-co-D,L-lactide, poly-L-lactide-co-glycolide, poly-4-hydroxybutrate, polycaprolactone, poly lactide-co-glycolide), Poly-L-lactide. Exemplary materials are also disclosed in U.S. patent application Ser. No. 14/871,195, entitled "Compressible Adjunct Assemblies with Attachment Layers" and Ser. No. 14/871,087, entitled "Implantable Adjunct Comprising Bonded Layers."

Heat of a suitable temperature such as, for example, between 80 C° and 120 C°, can be applied to the end effector 14600 in any of various ways. Though, other ranges can be used as well, including higher temperatures. For example, a suitable heater device (e.g., an infrared (IR) heater, ultraviolet (UV) heater, resistive heater, etc.) can be used.

In some implementations, the adjunct material 14606 and the attachment layer 14607 can be coupled to the jaw of the end effector 14600, such as the cartridge body 14602, using an applicator member (not shown) configured to apply the adjunct material 14606 with the attachment layer 14607 to an end effector's jaw. The applicator member can be similar, e.g., to the applicator member 14305 (FIG. 115), but can also be equipped with a heating element (e.g., a resistive wire element, UV element, IR element, etc.). Similar to the applicator member 14305, the heat-applying applicator member can releasably hold the adjunct material 14606 and the attachment layer 14607. Regardless of the specific way in which the applicator member is configured to generate heat, in use, the applicator member can be clamped between the jaws 14602, 14604 of the end effector 14600 and activated to generate heat to thus melt at least portions of the attachment layer 14607. After the attachment layer 14607 is received within the retaining features of the adjunct material 14606 (e.g., as shown in FIG. 124), the jaws 14602, 14604 can be open and the applicator member can be separated from the end effector 14600 while leaving the adjunct material 14606 and the attachment layer 14607 mated with the end effector 14600 (in this example, with the cartridge body 14602).

It should be appreciated that, additionally or alternatively, an adjunct material can be configured to be releasably mated with an anvil in a manner similar to that shown in FIGS. 123 and 124.

In the embodiments described herein, an adjunct material for use with an end effector of a surgical instrument is provided that has at least one projection configured to mate with a corresponding at least one recess formed in the end effector. However, in other embodiments, an adjunct material can be releasably retained on a jaw of an end effector using recesses formed in the adjunct material that are configured to mate with corresponding projections formed on the jaw.

FIGS. 125-127 illustrate an embodiment of an end effector 14700 having a cartridge 14702 and an anvil 14704, at least one of which can be configured to be releasably mated with an adjunct material having longitudinal channels or recesses. In this embodiment, the end effector 14700 has a cartridge 14702 and an anvil 14704 having any suitable configurations, at least one of which can be configured to be releasably mated with an adjunct material having longitudinal recesses. For example, as shown, the end effector 14700 can have adjunct materials releasably retained on both of the jaws 14702, 14704. Thus, as shown in FIG. 125, an adjunct material 14706 can be releasably mated with the cartridge 14702. The adjunct material 14706 has a first longitudinal recess 14717a formed on one side of the adjunct material 14706 and a second longitudinal recess 14717b formed on another, opposite side of the adjunct material 14706. As shown, the first and second longitudinal recesses 14717a, 14717 extend between distal and proximal ends 14706d, 14'706p of the adjunct material 14706.

The first and second longitudinal recesses 14717a, 14717b of the adjunct material 14706 are configured to mate with respective first and second complementary projections 14715a, 14715b formed on a tissue-facing surface 14710 of the cartridge 14702. The projections 14715a, 14715b can have mating features 14718a, 14718b formed thereon that are configured to mate with the corresponding recesses 14717a, 14717b in the adjunct material 14706. In this example, the mating features 14718a, 14718b are in the form of arrows facing towards the adjunct material 14706, as shown in FIGS. 125-127. It should be appreciated that the arrow-shaped mating features 14318a, 14318b are shown by way of example only, and the mating features formed on the projections can have any suitable configuration. For example, the mating features can be C-shaped, J-shaped, or they can have any other configuration(s), including different configurations.

The longitudinal recesses 14717a, 14717b formed in the adjunct material 14706 can have a number of different configurations. For example, the first and second longitudinal recesses 14717a, 14717b can have a shape that is complementary to that of the first and second projections 14715a, 14715b. In this way, as in the example illustrated, at least a portion of each of the first and second longitudinal recesses 14717a, 14717b can be arrow-shaped. However, the recesses 14717a, 14717b can have any other suitable configuration(s).

The longitudinal projections 14715a, 14715b can be formed from at least partially flexible and/or deformable material such that, as the projections 14715a, 14715b are received within the corresponding recesses 14717a, 14717b in the adjunct material 14706, the projections 14715a, 14715b are contracted to fit into the recesses and, once in the recesses, are then expanded to be fittingly received within the recesses.

As shown in FIG. 127, an adjunct material 14720 configured to be releasably retained on the anvil 14704 can also have first and second longitudinal recesses 14723a, 14723b, which can similar to the longitudinal recesses 14717a, 14717b formed on the adjunct material 14706 configured to be releasably retained on the cartridge 14702. For example, similar to the cartridge 14702, the anvil 14704 can have longitudinal projections formed therein that are configured to be received within the longitudinal recesses 14723a, 14723b. Similar to the example shown in FIGS. 114-116, one or both of the adjunct materials 14706, 14720 can be releasably retained on the jaws 14702, 14704, respectively, using an applicator member 14705 shown in FIG. 126. The applicator member 14705, which can releasably retain therein the adjunct materials 14706, 14720, can be similar to the applicator member 14305 (FIG. 115) and is therefore not described in detail herein.

It should be appreciated that the adjunct materials described herein can include one or more medicants which can be releasably incorporated into or associated with adjuncts in many different ways. Also, the adjunct materials can have various other features in addition to the features described herein.

Methods and Devices for Delivering and Securing Adjunct Materials to a Treatment Site FIG. 128A illustrates one embodiment for depositing a flowable adjunct precursor 15500 upon a surface of a tissue 15502 by an applicator 15504. As shown, the applicator 15504 is positioned adjacent to the tissue 15502 and activated to cause the adjunct precursor 15500 to flow from the applicator 15504 to the tissue 15502 for deposition at the treatment site. The viscosity of the adjunct precursor 15500 can be low enough to facilitate flow from the applicator 15504 to the tissue 15502 and high enough to inhibit substantial flow once deposited upon the tissue 15502. Additionally, the rheology of the adjunct precursor 15500 can be selected to provide a shear thinning effect. As an example, the adjunct precursor 15500 can exhibit a lower viscosity during application due the shear generated and exhibit a relatively higher viscosity once applied due to the near absence of shear.

The adjunct precursor 15500 can be applied to one or more surfaces of the tissue 15502. In one aspect, the adjunct precursor 15500 can be applied to opposed surfaces of the tissue 15502 at approximately the same location. In another aspect, not shown, the adjunct precursor 15500 can be applied to a first surface of the tissue 15502 and a solid adjunct, different from the adjunct precursor 15500, can be applied to a second surface of the tissue 15502 opposite the first surface of the tissue 15502.

Embodiments of the applicator 15504 can take various forms. As illustrated in FIG. 128A, in one embodiment, the applicator 15504 can include a tubular shaft in fluid communication with a reservoir (not shown) of the adjunct precursor 15500. Under the influence of pressure, the adjunct precursor 15500 is urged from a distal end of the applicator 15504 and onto the surface of the tissue 15502. A person skilled in the art will appreciate that the applicator can adopt other configurations suitable for deposition of the adjunct precursor 15500 upon the tissue 15502. As illustrated in FIG. 128B, in another embodiment, an applicator 15506 can include a brush that contains the adjunct precursor 15500 (e.g., within bristles 15508 of the brush).

The adjunct precursor 15500 can be configured to solidify after deposition upon the tissue 15502 to form a solid adjunct. Solidification of the adjunct precursor 15500 to form the solid adjunct can be accomplished using various techniques, such as moistening the adjunct precursor, heating or cooling the adjunct precursor, exposing the adjunct precursor to light energy, applying a hardener to the adjunct precursor, waiting a selected time duration after deposition, etc.

In one embodiment, the adjunct precursor 15500 can be a biologically compatible heterogeneous mixture including one or more solid components and one or more solvents. The solvent(s) can evaporate over time due to body heat from the tissue 15502 and/or externally supplied heat, forming the solid adjunct from the remaining solid components.

In an alternative embodiment, the adjunct precursor 15500 can be a biologically compatible chemical composition that solidifies (e.g., cures or hardens) after exposure to one or more of light energy (e.g., ultraviolet light), heat, or one or more co-reactants (e.g., catalysts, hardeners, etc.). Solidification of the chemical composition can take the form of cross-linking between components of the chemical composition or components of the chemical composition and co-reactants. Embodiments of the adjunct precursor 15500 that are configured to solidify after exposure to one or more co-reactants can receive the co-reactants in a variety of ways. In one aspect, the co-reactant can be mixed with the adjunct precursor 15500 at a selected time prior to deposition upon the tissue 15502 (e.g., immediately prior to deposition). In another aspect, the co-reactant can be applied to the adjunct precursor 15500 after deposition (e.g., by a dropper or sprayer). In a further aspect, the co-reactant can be transferred from the surface of an object to the adjunct precursor 15500 by contact. For example, as shown in FIG. 5C, a mesh 15510 including the co-reactant can be applied to the deposited adjunct precursor 15500 prior to solidification (e.g., over the adjunct precursor 15500 and/or embedded within the deposited adjunct precursor 15500). The co-reactant can be positioned on the surface of the mesh 15510 or contained within the mesh 15510 and released upon contact with the adjunct precursor 15500. Alternatively or additionally, at least a portion of the mesh 15510 can be formed from the co-reactant. In further embodiments, the co-reactant can be provided in any combination of the above. Beneficially, use of the mesh 15510 can provide further reinforcement to the solid precursor.

Following solidification of the adjunct precursor 15500 to form the solid adjunct 15512, one or more staples 15514 can be delivered through the solid adjunct 15512 and into the tissue 15502. As illustrated in FIGS. 128D-128E, the end effector 30 of the stapler 10 can grasp the tissue 15502 at the location of the solid adjunct 15512 using the jaws 32, 34 and the firing system can be actuated to eject one or more staples 15514 into the clamped tissue 15502. As discussed above, the knife blade 36 (see FIG. 3) or other cutting element can be associated with the firing system to cut the tissue 15502 during the stapling procedure, after tissue fixation has started.

FIGS. 129A-129B illustrate placement of another embodiment of an adjunct 15600 upon a surface of a tissue 15602 by an adjunct delivery device 15604. The adjunct delivery device 15604 can generally be configured and used similarly to the stapler 10 for grasping the tissue 15602, except that the staple cartridge and firing system are omitted. As an example, the adjunct delivery device 15604 can include an elongate shaft 15606 having a non-stapling end effector 15610 at a distal end 15606*d* with opposed first and second jaws 15612, 15614 configured to grasp the tissue 15602 therebetween. The adjunct delivery device 15604 can further include a handle assembly (not shown) connected to a proximal end of the shaft 15606 and configured to manipulate and operate the non-stapling end effector 15610 similar to the handle assembly 12.

The non-stapling end effector 15610 can be configured to secure the adjunct 15600 thereon for placement of the adjunct 15600 at a treatment site of the tissue 15602 and to release the adjunct 15600 when the tissue 15602 is engaged by the non-stapling end effector 15610. As illustrated in FIGS. 129A-129B, the first and second jaws 15612, 15614 can include approximately flat tissue contacting surfaces 15616, 15620 with a plurality of sockets 15622, 15624. The sockets 15622, 15624 are configured to receive corresponding barbed pins 15626, 15630. When the adjunct 15600 is positioned on the tissue contacting surfaces 15616, 15620, the barbed pins 15626, 15630 extend through the adjunct 15600, securing the adjunct 15600 thereto by frictional engagement. After the adjunct 15600 is positioned adjacent to the tissue 15602, the jaws 15612, 15614 can be compressed to engage the tissue 15602. The compressive force exerted by the jaws 15612, 15614 can drive a portion of the barbed pins 15626, 15630 into the tissue 15602. Thus, when the jaws 15612, 15614 are retracted from the tissue 15602, the barbed pins 15626, 15630 are retained in the tissue and the frictional engagement the barbed pins 15626, 15630 and the adjunct 15600 retains the adjunct 15600 in position on the tissue 15602 prior to stapling.

As shown, the adjunct 15600 can be formed from a single piece of material that includes a hinge 15632. This hinged configuration can allow a first adjunct portion 15600*a* on one side of the hinge 15632 to be retained on the first jaw 15612 by the barbed pins 15626 and a second adjunct portion 15600*b* on the other side of the hinge 15632 to be retained on the second jaw 15614 by the barbed pins 15630. Beneficially, because the first and second adjunct portions 15600*a*, 15600*b* are connected by the hinge 15632, the first and second adjunct portions 15600*a*, 15600*b* remain aligned when positioned on opposing sides of the tissue 15602. The adjunct 15600 and the barbed pins 15626 can be formed from bioabsorbable materials, as discussed above, so that they are absorbed by the body during healing.

Optionally, the first and second adjunct portions 15600*a*, 15600*b* can include a plurality of holes 15634 for receiving corresponding barbed pins 15626, 15630. The holes 15634 can possess a diameter smaller than a diameter the barbed pins 15626, 15630 to facilitate frictional engagement of the adjunct 15600 with the barbed pins 15626, 15630. Alternatively, the holes 15634 can be omitted and the barbed pins 15626, 15630 can puncture the adjunct 15600 for frictional engagement when positioned on the jaws 15612, 15614.

Following placement of the adjunct 15600 upon the tissue 15602 by the adjunct delivery device 15604, one or more staples 15636 can be delivered through the adjunct 15600 and into the tissue 15602. As illustrated in FIGS. 130A-130B, the end effector 30 of the stapler 10 can grasp the tissue 15602 at the location of the adjunct 15600 using the jaws 32, 34 and the firing system can be actuated to eject one or more staples 15636 into the clamped tissue 15602. As discussed above, the knife blade 36 (see FIG. 3) or other cutting element can be associated with the firing system to cut the tissue 15602 during the stapling procedure, after tissue fixation has started.

A person skilled in the art will appreciate that, while FIGS. 129A-130B illustrate the adjunct 15600 as a generally planar structure including the hinge 15632, the adjunct 15600 can adopt any desired shape. In one example (not shown), the hinge 15632 can be omitted and adjunct can be formed from two separate pieces that are secured to respective jaws 15612, 15614.

In another example, FIGS. 131A-131C illustrate a flanged adjunct 15800 configured to be positioned on a tissue 15802 by the adjunct delivery device 15604. The flanged adjunct 15800 includes flanges 15804 along lateral edges that, when mounted on the adjunct delivery device 15604, extend towards respective jaws 15612, 15614 upon which the flanged adjunct 15800 is mounted. When positioned on the tissue 15802, the flanges 15804 can be dimensioned to facilitate alignment of a stapler 10 with the flanged adjunct 15800 for delivery of one or more staples 15806 through the flanged adjunct 15800 and tissue 15802. Optionally, the flanged adjunct 15800 can be formed from a single, continuous piece with a hinge (not shown), as discussed above, to maintain alignment between respective portions of the flanged adjunct 15800. In either instance, the flanged adjunct 15800 can be delivered to tissue, and subsequently the flanges 15804 can guide the jaws 15612, 15614 into alignment with the flanged adjunct 15800 for staple delivery.

Another embodiment of an adjunct system 15900 configured for use with the stapler 10 is illustrated in FIGS. 132A-132B. The adjunct system 15900 includes an adjunct 15902 and a sheet of material 15904, different from the adjunct 15902. The adjunct 15902 can be configured to be attached to the first jaw 32 including the staple cartridge 40 containing a plurality of staples and the sheet of material 15904 can be configured to be attached to the second jaw 34. In certain embodiments, the adjunct 15902 is only attached to the first jaw 32 and not the second jaw 34. The first and second jaws 32, 34 can include one or more attachment mechanisms for securing the adjunct 15902 and the sheet of material 15904 thereto. Examples of attachment mechanisms can include, but not limited to, adhesives, protrusions, etc. The strength with which the attachment mechanism secures the adjunct 15902 and sheet of material 15904 to respective jaws 32, 34 can be sufficient to retain adjunct 15902 and sheet of material 15904 thereon during placement of the adjunct system 15900 on a tissue 15906 and to release the adjunct 15902 and the sheet of material 15904 when staples are deployed through the adjunct 15902. As an example, when the end effector 30 fires a plurality of staples 15910 through the adjunct 15902, the sheet of material 15904, and the tissue 15906, the staples 15910 can secure the adjunct 15902 to the tissue 15906 with sufficient force to retain the adjunct 15902 on the tissue 15906 when the end effector 30 is retracted from the tissue 15906 (FIG. 132B).

Terminology

It will be appreciated that the terms "proximal" and "distal" are used herein with reference to a user, such as a clinician, gripping a handle of an instrument. Other spatial terms such as "front" and "back" similarly correspond respectively to distal and proximal. It will be further appreciated that for convenience and clarity, spatial terms such as "vertical" and "horizontal" are used herein with respect to the drawings. However, surgical instruments are used in many orientations and positions, and these spatial terms are not intended to be limiting and absolute.

A person skilled in the art will appreciate that the present invention has application in conventional minimally-invasive and open surgical instrumentation as well application in robotic-assisted surgery. In some embodiments, the devices and methods described herein are provided for open surgical procedures, and in other embodiments, the devices and methods are provided for laparoscopic, endoscopic, and other minimally invasive surgical procedures. The devices may be fired directly by a human user or remotely under the direct control of a robot or similar manipulation tool. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

Furthermore, the devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed:

1. A surgical system, comprising:
    an adjunct including first and second layers attached together, the adjunct being configured to be released from an end effector of a surgical stapler and stapled to tissue, the first layer includes a compressible fibrous structure including a plurality of fibers, and the second layer includes a plurality of interconnected structures that each defines a hollow interior and that each has a hole formed therein providing access therethrough to the hollow interior; and
    a cartridge body with a plurality of staple cavities on a tissue-facing surface thereof, each staple cavity having a staple disposed therein that is configured to be deployed into tissue;
    wherein the second layer of the adjunct is disposed on the tissue-facing surface of the cartridge body;
    the hollow interior of each of the plurality of interconnected structures includes an air pocket in fluid communication with the hole; and
    the staples, when deployed, are configured to puncture the air pockets and thereby release suction from the air pockets.

2. The system of claim 1, wherein each of the interconnected structures is generally round in shape.

3. The system of claim 1, wherein each of the interconnected structures protrudes from a surface of the second layer in a direction away from the first layer.

4. The system of claim 1, wherein the fibrous structure is a fiber-based lattice formed from a synthetic material.

5. The system of claim 1, wherein the fibrous structure is formed from oxygenized regenerated cellulose (ORC).

6. The system of claim 1, wherein the fibrous structure is formed from a biologic material including at least one of collagen; gelatin; and a bioabsorbable gel film cross-linked with omega-3 fatty acids.

7. The system of claim 1, wherein the first and second layers are non-removably attached together.

8. The system of claim 1, further comprising the end effector;
    wherein the end effector includes a jaw, and the cartridge body is configured to be seated in the jaw.

9. A surgical system, comprising:
    a first jaw having a cartridge with a plurality of staple cavities configured to seat staples therein, the staple cavities opening on a tissue-facing surface of the cartridge;
    a second jaw having an anvil with a plurality of staple-forming cavities formed on a tissue-facing surface of the anvil, the first and second jaws being configured to clamp tissue therebetween; and
    an adjunct configured to be stapled to tissue with the staples, the adjunct including first and second layers attached together, the first layer including a compressible fibrous structure including a plurality of fibers, the second layer including a plurality of interconnected structures that each defines a hollow interior and that each has a hole formed therein providing access therethrough to the hollow interior, and the second layer being releasably attached to the tissue-facing surface of one of the cartridge and the anvil;
    the hollow interior of each of the plurality of interconnected structures includes an air pocket in fluid communication with the hole; and
    the staples, when deployed, are configured to puncture the air pockets and thereby release suction from the air pockets.

10. The system of claim 9, wherein each of the interconnected structures is generally round in shape.

11. The system of claim 9, wherein each of the interconnected structures protrudes from a surface of the second layer in a direction away from the first layer.

12. The system of claim 9, wherein the fibrous structure is a fiber-based lattice formed from a synthetic material.

13. The system of claim 9, wherein the fibrous structure is formed from oxygenized regenerated cellulose (ORC).

14. The system of claim 9, wherein the fibrous structure is formed from a biologic material including at least one of collagen; gelatin; and a bioabsorbable gel film cross-linked with omega-3 fatty acids.

15. The system of claim 9, wherein the first and second layers are non-removably attached together.

16. A surgical system comprising:
- an adjunct including first and second layers attached together, the adjunct being configured to be released from an end effector of a surgical stapler and stapled to tissue, the first layer includes a compressible fibrous structure including a plurality of fibers, and the second layer includes a plurality of interconnected structures that each defines a hollow interior and that each has a hole formed therein providing access therethrough to the hollow interior;
- an anvil with a plurality of staple forming cavities formed on a tissue-facing surface thereof; and
- a cartridge body with a plurality of staple cavities on a tissue-facing surface thereof, each staple cavity having a staple disposed therein that is configured to be deployed into tissue;
- wherein the second layer of the adjunct is disposed on the tissue-facing surface of the anvil;
- the hollow interior of each of the plurality of interconnected structures includes an air pocket in fluid communication with the hole; and
- the staples, when deployed, are configured to puncture the air pockets and thereby release suction from the air pockets.

* * * * *